(12) United States Patent
Raj et al.

(10) Patent No.: US 12,275,685 B2
(45) Date of Patent: Apr. 15, 2025

(54) OLIGO-BENZAMIDE ANALOGS AND THEIR USE IN CANCER TREATMENT

(71) Applicant: Board of Regents, The University of Texas System, Austin, TX (US)

(72) Inventors: Ganesh Raj, Plano, TX (US); Jung-Mo Ahn, Plano, TX (US); Ratna K. Vadlamudi, Helotes, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 931 days.

(21) Appl. No.: 17/337,830

(22) Filed: Jun. 3, 2021

(65) Prior Publication Data

US 2022/0017454 A1 Jan. 20, 2022

Related U.S. Application Data

(63) Continuation-in-part of application No. PCT/US2019/064073, filed on Dec. 2, 2019.

(60) Provisional application No. 62/774,671, filed on Dec. 3, 2018.

(51) Int. Cl.
| | |
|---|---|
| *C07C 235/56* | (2006.01) |
| *A61P 35/00* | (2006.01) |
| *C07D 215/38* | (2006.01) |
| *C07D 231/56* | (2006.01) |
| *C07D 233/88* | (2006.01) |

(52) U.S. Cl.
CPC ............ *C07C 235/56* (2013.01); *A61P 35/00* (2018.01); *C07D 215/38* (2013.01); *C07D 231/56* (2013.01); *C07D 233/88* (2013.01)

(58) Field of Classification Search
CPC ..... A61P 35/00; C07C 235/56; C07C 237/44; C07C 2601/14; C07D 215/38; C07D 231/40; C07D 231/56; C07D 233/88
See application file for complete search history.

(56) References Cited

U.S. PATENT DOCUMENTS

| 6,027,892 A | 2/2000 | Chang et al. |
| 6,126,943 A | 10/2000 | Cheruvanky et al. |
| 6,166,177 A | 12/2000 | Probst et al. |

(Continued)

FOREIGN PATENT DOCUMENTS

| AU | 2004231248 | 12/2004 |
| AU | 2005200246 | 2/2005 |

(Continued)

OTHER PUBLICATIONS

Kulikov et. al., Eur. J. Organic Chem., pp. 3433-3445, publ. 2013, and supporting information (Year: 2013).*

(Continued)

*Primary Examiner* — Sarah Pihonak
(74) *Attorney, Agent, or Firm* — Parker Highlander PLLC

(57) ABSTRACT

The present disclosure compounds of the formulae:

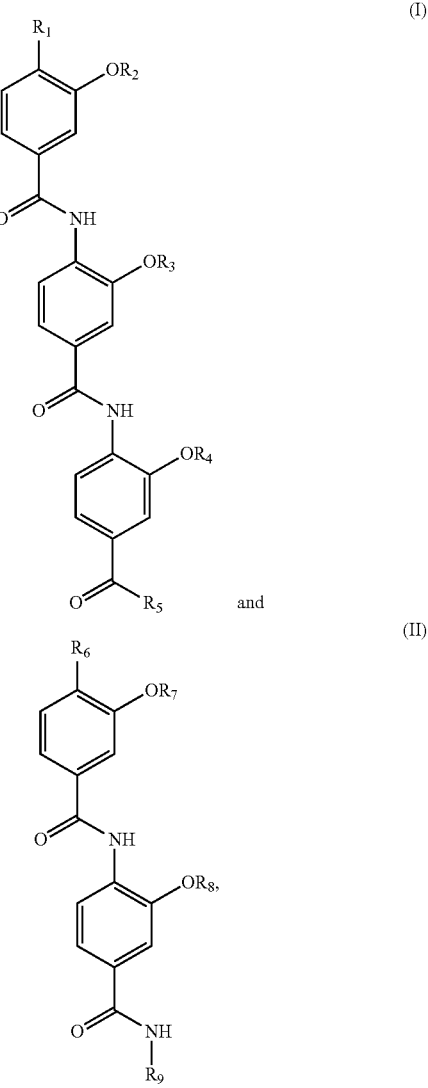

wherein the variables are defined herein, as well as pharmaceutical compositions thereof. The present disclosure also provides methods for the use of said compounds and/or pharmaceutical compositions, such as in the treatment of cancer.

33 Claims, 48 Drawing Sheets

Specification includes a Sequence Listing.

(56) References Cited

U.S. PATENT DOCUMENTS

| | | |
|---|---|---|
| 6,331,396 B1 | 12/2001 | Silverman et al. |
| 6,335,170 B1 | 1/2002 | Orntoft |
| 6,355,450 B1 | 3/2002 | Fleischmann et al. |
| 6,401,043 B1 | 6/2002 | Stanton, Jr. et al. |
| 6,465,502 B1 | 10/2002 | Bullock et al. |
| 6,727,063 B1 | 4/2004 | Lander et al. |
| 6,908,740 B2 | 6/2005 | Landekerckhove et al. |
| 6,962,989 B1 | 11/2005 | Pomejus et al. |
| 7,058,616 B1 | 6/2006 | Larder et al. |
| 7,074,559 B2 | 7/2006 | Kapur et al. |
| 7,122,373 B1 | 10/2006 | Williams et al. |
| 7,183,057 B2 | 2/2007 | Benson |
| 7,229,760 B2 | 6/2007 | Zohknhöfer et al. |
| 7,291,461 B2 | 11/2007 | Welch et al. |
| 7,323,466 B2 | 1/2008 | Bentley et al. |
| 7,422,848 B2 | 9/2008 | Bozdayi |
| 7,432,049 B2 | 10/2008 | Liew et al. |
| 7,479,276 B1 | 1/2009 | Xu et al. |
| 7,507,858 B2 | 3/2009 | Belvedere et al. |
| 7,588,767 B2 | 9/2009 | Szalay et al. |
| 7,629,141 B2 | 12/2009 | Bruce et al. |
| 7,668,659 B2 | 2/2010 | Shaighnessy et al. |
| 7,785,839 B2 | 8/2010 | Sznaidman et al. |
| 7,790,867 B2 | 9/2010 | Bentwich |
| 7,807,437 B2 | 10/2010 | Schildgen et al. |
| 7,888,064 B2 | 2/2011 | Berger et al. |
| 7,927,791 B2 | 4/2011 | Welch et al. |
| 7,943,306 B2 | 5/2011 | Chang et al. |
| 7,960,110 B2 | 6/2011 | Bastian et al. |
| 7,993,881 B2 | 8/2011 | Jeney et al. |
| 8,014,957 B2 | 9/2011 | Radich et al. |
| 8,043,837 B2 | 10/2011 | Burke et al. |
| 8,071,562 B2 | 12/2011 | Bader et al. |
| 8,158,360 B2 | 4/2012 | Heise et al. |
| 8,202,977 B2 | 6/2012 | Frost et al. |
| 8,229,673 B2 | 7/2012 | Palsson et al. |
| 8,236,983 B2 | 8/2012 | Ahn |
| 8,249,814 B2 | 8/2012 | Liew et al. |
| 8,304,398 B2 | 11/2012 | 't Hoen et al. |
| 8,420,103 B2 | 4/2013 | Baudin et al. |
| 8,461,310 B2 | 6/2013 | Uede et al. |
| 8,492,328 B2 | 7/2013 | Huang et al. |
| 8,546,118 B2 | 10/2013 | Weiner et al. |
| 8,618,324 B2 | 12/2013 | Ahn |
| 8,664,220 B2 | 3/2014 | Clark et al. |
| 8,741,861 B2 | 6/2014 | Mann |
| 8,754,124 B2 | 6/2014 | Ahn et al. |
| 8,758,764 B2 | 6/2014 | Masignani et al. |
| 8,969,000 B2 | 3/2015 | Roepman et al. |
| 9,040,464 B2 | 5/2015 | Jarvi et al. |
| 9,072,705 B2 | 7/2015 | Ahn et al. |
| 9,206,404 B2 | 12/2015 | Cui et al. |
| 9,221,891 B2 | 12/2015 | Bancel et al. |
| 9,315,860 B2 | 4/2016 | Becker et al. |
| 9,328,346 B2 | 5/2016 | Lee et al. |
| 9,434,771 B2 | 9/2016 | Li et al. |
| 9,435,001 B2 | 9/2016 | Switzer et al. |
| 9,493,840 B2 | 11/2016 | Hao et al. |
| 9,540,439 B2 | 1/2017 | Vignali et al. |
| 9,572,874 B2 | 2/2017 | Fotin-Mleczek et al. |
| 9,572,896 B2 | 2/2017 | Bancel et al. |
| 9,644,005 B2 | 5/2017 | Qian et al. |
| 9,683,233 B2 | 6/2017 | Paxton |
| 9,719,064 B2 | 8/2017 | Selber et al. |
| 9,939,443 B2 | 4/2018 | Spetzler et al. |
| 10,080,809 B2 | 9/2018 | Thess |
| 10,113,163 B2 | 10/2018 | Liu et al. |
| 10,167,457 B2 | 1/2019 | Liu et al. |
| 10,221,142 B2 | 3/2019 | Lapointe et al. |
| 10,279,018 B2 | 5/2019 | Vasserot et al. |
| 10,329,543 B2 | 6/2019 | Ostertag et al. |
| 10,493,167 B2 | 12/2019 | de Fougerolles et al. |
| 10,576,167 B2 | 3/2020 | Angel et al. |
| 10,597,696 B2 | 3/2020 | Haldar et al. |
| 10,683,344 B2 | 6/2020 | Corti |
| 10,821,086 B2 | 11/2020 | Choi et al. |
| 10,982,228 B2 | 4/2021 | Searia et al. |
| 11,040,958 B2 | 6/2021 | Tang et al. |
| 11,078,247 B2 | 8/2021 | Fotin-Mleczek et al. |
| 11,118,192 B2 | 9/2021 | Kirn et al. |
| 11,149,254 B2 | 10/2021 | Szalay et al. |
| 11,174,470 B2 | 11/2021 | Harrington et al. |
| 11,273,442 B1 | 3/2022 | Chen et al. |
| 2002/0032319 A1 | 3/2002 | Cargill et al. |
| 2002/0098511 A1 | 7/2002 | Heichman et al. |
| 2002/0119462 A1 | 8/2002 | Mendrick et al. |
| 2003/0119010 A1 | 6/2003 | Powell et al. |
| 2003/0154032 A1 | 8/2003 | Pittman et al. |
| 2003/0170678 A1 | 9/2003 | Tanzi et al. |
| 2003/0198970 A1 | 10/2003 | Roberts |
| 2003/0228618 A1 | 12/2003 | Levanon et al. |
| 2004/0005557 A1 | 1/2004 | Padigaru et al. |
| 2004/0005559 A1 | 1/2004 | Loring et al. |
| 2004/0014040 A1 | 1/2004 | Mendrick et al. |
| 2004/0048816 A1 | 3/2004 | Zohlnhöfer et al. |
| 2004/0138187 A1 | 7/2004 | Reading et al. |
| 2004/0209253 A1 | 10/2004 | Tam |
| 2004/0241088 A1 | 12/2004 | Chang et al. |
| 2005/0002998 A1 | 1/2005 | Chang et al. |
| 2005/0037395 A1 | 2/2005 | Van Sinderen |
| 2005/0043233 A1 | 2/2005 | Stefanic et al. |
| 2005/0058689 A1 | 3/2005 | McDaniel |
| 2005/0191685 A1 | 9/2005 | Vanmecheken et al. |
| 2005/0202451 A1 | 9/2005 | Burczynski et al. |
| 2005/0209181 A1 | 9/2005 | Akil et al. |
| 2005/0282207 A1 | 12/2005 | Rokutan et al. |
| 2006/0008803 A1 | 1/2006 | Brunner et al. |
| 2006/0018875 A1 | 1/2006 | Blatt et al. |
| 2006/0057582 A1 | 3/2006 | Rosen et al. |
| 2006/0068405 A1 | 3/2006 | Diber et al. |
| 2006/0194217 A1 | 8/2006 | Zoulim et al. |
| 2006/0210967 A1 | 9/2006 | Agan et al. |
| 2006/0246484 A1 | 11/2006 | Hare et al. |
| 2006/0247190 A1 | 11/2006 | Beach et al. |
| 2006/0251676 A1 | 11/2006 | Dubin et al. |
| 2006/0281091 A1 | 12/2006 | Lavedan |
| 2007/0004621 A1 | 1/2007 | Shridhar et al. |
| 2007/0014719 A1 | 1/2007 | Reading et al. |
| 2007/0026393 A1 | 2/2007 | Berlin et al. |
| 2007/0037144 A1 | 2/2007 | Wohlgemuth et al. |
| 2007/0048793 A1 | 3/2007 | Baynes |
| 2007/0065820 A1 | 3/2007 | Jiang et al. |
| 2007/0077553 A1 | 4/2007 | Bentwich |
| 2007/0082337 A1 | 4/2007 | Sorek et al. |
| 2007/0099209 A1 | 5/2007 | Clarke et al. |
| 2007/0172844 A1 | 7/2007 | Lancaster et al. |
| 2007/0238100 A1 | 10/2007 | McGlennen et al. |
| 2008/0057590 A1 | 3/2008 | Urdea et al. |
| 2008/0075696 A1 | 3/2008 | Parsons et al. |
| 2008/0131888 A1 | 6/2008 | Nuytinck |
| 2009/0010908 A1 | 1/2009 | Gow et al. |
| 2009/0053299 A1 | 2/2009 | Chang et al. |
| 2009/0227464 A1 | 9/2009 | Avigad et al. |
| 2009/0317392 A1 | 12/2009 | Nakamura et al. |
| 2010/0004253 A1 | 1/2010 | Aziz et al. |
| 2010/0028334 A1 | 2/2010 | Cottarel et al. |
| 2010/0035281 A1 | 2/2010 | Holt |
| 2010/0035963 A1 | 2/2010 | Chajut et al. |
| 2010/0040614 A1 | 2/2010 | Ahmed et al. |
| 2010/0055069 A1 | 3/2010 | Rooke et al. |
| 2010/0061957 A1 | 3/2010 | Rooke et al. |
| 2010/0119474 A1 | 5/2010 | Crystal et al. |
| 2010/0143372 A1 | 6/2010 | Yao et al. |
| 2010/0178324 A1 | 7/2010 | Ahn et al. |
| 2010/0184022 A1 | 7/2010 | Colau |
| 2010/0203076 A1 | 8/2010 | Fotin-Mleczek et al. |
| 2010/0227314 A1 | 9/2010 | Gryadunov et al. |
| 2010/0317002 A1 | 12/2010 | Daniely et al. |
| 2011/0071767 A1 | 3/2011 | Porter et al. |
| 2011/0091454 A1 | 4/2011 | Diber et al. |
| 2012/0178111 A1 | 7/2012 | Diamandis et al. |
| 2012/0258046 A1 | 10/2012 | Mutzke |
| 2012/0328719 A1 | 12/2012 | Iriyama et al. |
| 2013/0216557 A1 | 8/2013 | Bienkowska et al. |

(56) References Cited

U.S. PATENT DOCUMENTS

| | | |
|---|---|---|
| 2013/0231385 A1 | 9/2013 | Ahn et al. |
| 2013/0237454 A1 | 9/2013 | Schutzer |
| 2014/0170157 A1 | 6/2014 | Agarwal et al. |
| 2014/0243211 A1 | 8/2014 | Niculescu |
| 2014/0271644 A1 | 9/2014 | Scheinberg et al. |
| 2014/0304845 A1 | 10/2014 | Loboda et al. |
| 2014/0315929 A1 | 10/2014 | Chiosis |
| 2015/0086570 A1 | 3/2015 | Violette et al. |
| 2015/0133420 A1 | 5/2015 | Cheng et al. |
| 2015/0151004 A1 | 6/2015 | Xu et al. |
| 2015/0152474 A1 | 6/2015 | Pawlowski et al. |
| 2015/0291966 A1 | 10/2015 | Zhang et al. |
| 2015/0320754 A1 | 11/2015 | Kutok et al. |
| 2016/0031803 A1 | 2/2016 | Ahn et al. |
| 2016/0130217 A1 | 5/2016 | Ahn et al. |
| 2016/0220612 A1 | 8/2016 | Mazzolini et al. |
| 2016/0339022 A1 | 11/2016 | Tamang et al. |
| 2017/0087174 A1 | 3/2017 | Beumont et al. |
| 2017/0112861 A1 | 4/2017 | Takakura et al. |
| 2017/0356903 A1 | 12/2017 | Domenyuk et al. |
| 2018/0059115 A1 | 3/2018 | Gabrilovich et al. |
| 2018/0126003 A1 | 5/2018 | Hoerr |
| 2018/0258123 A1 | 9/2018 | Roberge et al. |
| 2018/0282692 A1 | 10/2018 | Rawlings et al. |
| 2019/0038773 A1 | 2/2019 | Esteves et al. |
| 2019/0076385 A1 | 3/2019 | Erti et al. |
| 2019/0119636 A1 | 4/2019 | Ostertag et al. |
| 2020/0071277 A1 | 3/2020 | Cravatt et al. |
| 2020/0143907 A1 | 5/2020 | Engreitz et al. |
| 2020/0149087 A1 | 5/2020 | M'Koma |
| 2020/0323964 A1 | 10/2020 | Desai et al. |
| 2020/0376022 A1 | 12/2020 | Domenyuk et al. |
| 2021/0032298 A1 | 2/2021 | Sharma et al. |
| 2021/0039557 A1 | 2/2021 | Choi |
| 2021/0098698 A1 | 4/2021 | Vega et al. |
| 2021/0104321 A1 | 4/2021 | Lipsky et al. |
| 2021/0107993 A1 | 4/2021 | Ostertag et al. |
| 2021/0115453 A1 | 4/2021 | Shedlock et al. |
| 2021/0130845 A1 | 5/2021 | Ostertag et al. |
| 2021/0254056 A1 | 8/2021 | Liu et al. |
| 2021/0255198 A1 | 8/2021 | Niculescu |
| 2021/0278417 A1 | 9/2021 | M'Koma et al. |
| 2021/0371866 A1 | 12/2021 | Aznarez |
| 2022/0017454 A1 | 1/2022 | Raj et al. |
| 2022/0025039 A1 | 1/2022 | Astarita et al. |
| 2022/0042083 A1 | 2/2022 | Glezer et al. |
| 2022/0042084 A1 | 2/2022 | Glezer |
| 2022/0049241 A1 | 2/2022 | Harrington et al. |
| 2022/0087950 A1 | 3/2022 | Chen et al. |

FOREIGN PATENT DOCUMENTS

| | | |
|---|---|---|
| AU | 2007203337 | 8/2007 |
| AU | 2017232121 | 10/2017 |
| AU | 2019202835 | 5/2019 |
| AU | 2020257150 | 11/2020 |
| BR | PI0903187 | 10/2011 |
| CN | 101186636 | 5/2015 |
| CY | 1117168 | 4/2017 |
| CZ | 303405 | 8/2012 |
| DE | 102005048828 | 4/2007 |
| EP | 1 278 892 | 1/2003 |
| EP | 1 309 723 | 5/2003 |
| EP | 1 713 900 | 10/2006 |
| EP | 2 703 496 | 3/2014 |
| EP | 2 816 351 | 12/2014 |
| EP | 1 423 406 | 11/2015 |
| EP | 2287305 | 11/2017 |
| EP | 3520820 | 8/2019 |
| GB | 2360284 | 9/2001 |
| GB | 2361238 | 10/2001 |
| JP | 2010088432 | 4/2010 |
| JP | 2020089313 | 6/2020 |
| KR | 20170062862 | 6/2017 |
| KR | 20210049684 | 5/2021 |
| MX | NL06000069 | 10/2008 |
| WO | WO 1999/64627 | 12/1999 |
| WO | WO 2001/92523 | 12/2001 |
| WO | WO 2002/068647 | 9/2002 |
| WO | WO 2002/079503 | 10/2002 |
| WO | WO 2002/081510 | 10/2002 |
| WO | WO 2004/080148 | 9/2004 |
| WO | WO 2004/101752 | 11/2004 |
| WO | WO 2005/071059 | 8/2005 |
| WO | WO 2006/035273 | 4/2006 |
| WO | WO 2008/112938 | 9/2008 |
| WO | WO 2008/112939 | 9/2008 |
| WO | WO 2008/112941 | 9/2008 |
| WO | WO 2010/083215 | 7/2010 |
| WO | WO 2011/050360 | 4/2011 |
| WO | WO 2011/150360 | 12/2011 |
| WO | WO 2013/078277 | 5/2013 |
| WO | WO 2013/078288 | 5/2013 |
| WO | WO 2013/151736 | 10/2013 |
| WO | WO 2020/051374 | 3/2020 |
| WO | WO 2020/117715 | 6/2020 |
| WO | WO2020/236777 | 11/2020 |
| WO | WO 2020/237391 | 12/2020 |
| WO | WO 2020/257356 | 12/2020 |
| WO | WO 2021/102250 | 5/2021 |
| WO | WO 2021/138678 | 7/2021 |
| WO | WO 2021/177896 | 9/2021 |
| WO | WO 2022/011037 | 1/2022 |
| WO | WO 2022/026478 | 2/2022 |
| WO | WO 2022/061166 | 3/2022 |

OTHER PUBLICATIONS

Adams et al., "Life-or-death decisions by the Bcl-2 protein family," *Trends Biochem. Sci*, 26:61-66, 2001.

Ahn et al., "A new approach to search the bioactive conformation of glucagon: positional cyclization scanning," *J. Med. Chem.*, 44:3109-3116, 2001.

Ahn et al., "Development of potent truncated glucagon antagonists," *J. Med. Chem.*, 44:1372-1379, 2001.

Ahn et al., "Facile synthesis of benzamides to mimic an α-helix," *Tetrahedron Letters*, 48:3543-3547, 2007.

Ahn et al., "Peptidomimetics and peptide backbone modifications," *Mini-Reviews in Medicinal Chemistry*, 2:463-473, 2002.

Bulotta et al., "A cultured pancreatic ductal cells undergo cell cycle re-distribution and beta-cell-like differentiation in response to glucagon-like peptide-1," *J. Mol. Endocrinol.*, 29:347-360, 2002.

Burgess et al., "Solid-phase syntheses of β-turn analogues to mimic or disrupt protein-protein interactions," *Acc. Chem. Res.*, 24:826-835, 2001.

Cavaghan et al., "Interactions between insulin resistance and insulin secretion in the development of glucose intolerance," *J. Clin. Invest.*, 106:329-333, 2000.

Chang et al., "Substituted imidazoles as glucagon receptor antagonists," *Bioorg. Med. Chem. Lett.*, 11:2549-2553, 2001.

Chapuis et al., "Shorter puromycin analog synthesis by means of an efficient Staudinger-Vilarrasa coupling," *Tetrahedron*, 62:12108-12115, 2006.

Chen et al., "A nonpeptidic agonist of glucagon-like peptide 1 receptors with efficacy in diabetic db/db mice," *Proc. Natl. Acad. Sci. USA*, 104:943-948, 2007.

Chittenden et al., "A conserved domain in Bak, distinct from BH1 and BH2, mediates cell death and protein binding functions," *EMBO J.*, 14:5589-5596, 1995.

Cochran, "Antagonists of protein-protein interactions," *Chem. Biol.*, 7:R85-R94, 2000.

Database CAPLUS on STN, Acc. No. 1937:30601, Izmail'skii et al., *Zhurnal Obshchei Khimii*, 7:80-83, 1937. (Abstract).

Database CAPLUS on STN, Acc. No. 1998:159344, Gambacorti-Passerini et al., "Inhibition of the ABL kinase activity blocks the proliferation of BCR/ABL+ leukemic cells and induces apoptosis," *Blood Cells, Molecules & Diseases*, 23(3):380-394, 1997 (Abstract).

Database CAPLUS on STN, Acc. No. 2006:237099, Lu et al., *Journal of Combinatorial Chemistry*, 8(3):315-325, 2006 (abstract only).

(56) References Cited

OTHER PUBLICATIONS

Database CAPLUS on STN, Acc. No. 2007:1424768, Plante et al., *Organic & Biomolecular Chemistry*, 6(1):138-146, 2008. (Abstract).
Database CAPLUS on STN, Acc. No. 2007:443215, Ahn et al., *Tetrahedron Letters*, 48(20):3543-3547, 2007. (Abstract).
Database CAPLUS on STN, Acc. No. 2008:1127781, Ahn, PCT International Application. (Abstract).
Database CAPLUS on STN, Acc. No. 2009:1006344, Plante et al., *Chemical Communications*, 34:5091-5093, 2009. (Abstract).
Database CAPLUS on STN, Acc. No. 2010:1318082, Han et al., *Advances in Experimental Medicine and Biology*, 611:119-120, 2009. (Abstract).
Defronzo et al., "Effects of exenatide (exendin-4) on glycemic control and weight over 30 weeks in metformin-treated patients with type 2 diabetes," *Diabetes Care*, 28:1092-1100, 2005.
Dehm, et al., "Selective role of an NH2-terminal WxxLF motif for aberrant androgen receptor activation in androgen depletion independent prostate cancer cells," *Cancer Res.*, 67:10067-77, 2007.
Drucker et al., "The incretin system: glucagon-like peptide-1 receptor agonists and dipeptidyl peptidase-4 inhibitors in type 2 diabetes," *Lancet*, 368:1696-1705, 2006.
Edwards et al., "Exendin-4 reduces fasting and postprandial glucose and decreases energy intake in healthy volunteers," *Am. J. Physiol. Endocrinol. Metab.*, 281:E155-E161, 2001.
Egan et al., "GLP-1 receptor antagonists are growth and differentiation factors for pancreatic islet beta cells," *Diabetes/Metab. Res. Rev.*, 19:115-123, 2003.
Elbrond et al., "Pharmacokinetics, pharmacodynamics, safety, and tolerability of a single-dose of NN2211, a long-acting glucagon-like peptide 1 derivative, in healthy male subjects," *Diabetes Care*, 25:1398-1404, 2002.
Ernst et al., "Design and application of an α-helixmimetic scaffold based on an oligoamide-foldamer strategy: antagonism of the Bak BH3/Bcl-xL complex," *Angew. Chem. Int. Ed.*, 42:535-539, 2003.
Gunther et al., "Alternative inhibition of androgen receptor signaling: peptidomimetic pyrimidines as direct androgen receptor/coactivator disruptors," *ACS Chem. Biol.*, 4:435-40, 2009.
Hoare et al., "Mechanisms of peptide and nonpepetide ligand binding to class B G-proteincoupled receptors," *Drug Discovery Today*, 10:417-427, 2005.
Hruby et al., "Design in topographical space of peptide and peptidomimetic ligands that affect behavior. A chemist's glimpse at the mind-body problem," *Acc. Chem. Res.*, 34(5):389-397, 2001.
Jacoby et al., "Biphenyls as potential mimetics of protein α-helix," *Bioorg. Med. Chem. Lett.*, 12:891-893, 2002.
Knudsen et al., "Glucagon-like peptide-1: the basis of a new class of treatment for type 2 diabetes," *J. Med. Chem.*, 47:4128-4134, 2004.
Knudsen et al., "Small-molecule agonists for the glucagon-like peptide 1 receptor," *Proc. Natl. Acad. Sci. U.S.A.*, 104:937-942, 2007.
Kolterman et al., "Synthetic exendin-4 (exenatide) significantly reduces postprandial and fasting plasma glucose in subjects with type 2 diabetes," *J. Clin. Endocrinol. Metab.*, 88:3082-3089, 2003.
Konig et al., "Solid-phase synthesis of oligo(p-benzamide) foldamers," *Organic Letters*, 8:1819-1822, 2006.
Konig et al., "Supramolecular PEG-co-Oligo(p-benzamide)s prepared on a peptide synthezier," *J. Am. Chem. Soc.*, 129:704-708, 2007. Published on Web Dec. 23, 2006.
Kussie et al., "Structure of the MDM2 oncoprotein bound to the p53 tumor suppressor transactivation domain," *Science*, 274:948-953, 1996.
Kutzki et al., "Development of a potent Bcl-xL antagonist based on α-helix mimicry," *J. Am. Chem. Soc.*, 124:11838-11839, 2002.
Ling et al., "Identification of alkylidene hydrazides as glucagon receptor antagonists," *J. Med. Chem.*, 44:3141-3149, 2001.
Madsen et al., "Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide," *J. Med. Chem.*, 45:5755-5775, 2002.
Mahato et al., "Emerging trends in oral delivery of peptide and protein drugs," *Critical Reviews in Therapeutic Drug Carrier Systems*, 20:153-214, 2003.
Marshall, et al., "A hierarchical approach to peptidomimetic design," *Tetrahedron*, 49:3547-3558, 1993.
Matias, et al., "Structural evidence for ligand specificity in the binding domain of the human androgen receptor" *J. Bio. Chem.*, 275:26164-71, 2000.
Murphy and Bloom, "Nonpeptidic glucagon-like peptide 1 receptor agonists: A magic bullet for diabetes," *Proc. Natl. Acad. Sci. U.S.A.*, 104:689-690, 2007.
Neidigh et al., "Exendin-4 and glucagon-likepeptide-1: NMR structural comparisons in the solution and micelle-associated states," *Biochemistry*, 40:13188-13200, 2001.
Peczuh et al., "Peptide and protein recognition by designed molecules," *Chem. Rev..*, 100:2479-2494, 2000.
Perry et al., "The glucagon-like peptides: a double-edged therapeutic sword," *Trends Pharmacol. Sci.*, 24:377-383, 2003.
Plante et al., "Synthesis of functionalised aromatic oligamide rods," *Organic & Biomolecular Chemistry*, 6:138-146, 2008.
Rickard et al., "Intermittend treatment with parathyroid hormone (PTH) as well as a non-petide small molecule agonist of the PTH1 receptor inhibits adipocyte differentiation in human bone marrow stromal cells," *Bone*, 39:1361-1372, 2006.
Runge et al., Different domains of the glucagon and glucagon-like peptide-1 receptors provide the critical determinants of ligand selectivity, *Br. J. Pharmacol.*, 138:787-794, 2003.
Saragoi et al., "Synthetic α-helix mimetics as agonists and antagonists of islet amyloid polypeptide aggregation," *Angewandte Chemie*, 49:736-739, 2010.
Sattler et al., "Structure of Bcl-xL-Bak peptide complex: Recognition between regulators of apoptosis," *Science*, 275:983-986, 1997.
Souers et al., "β-Turn mimetic library synthesis: scaffolds and applications," *Tetrahedron*, 57:7431-7448, 2001.
Stoffers et al., "Insulinotropics glucagon-like peptide 1 agonists stimulate expression of homeodomain protein IDX-1 and increase islet size in mouse pancreas," *Diabetes*, 49:741-749, 2000.
Tanatani et al., "Helical structures of N-alkylated poly(p-benzamide)s," *J. Am. Chem. Soc.*, 127:8553-8561, 2005.
Tibaduiza et al., "A small molecule ligand of the glucagon-like peptide 1 receptor targets its amino-terminal hormone binding domain," *J. Biol. Chem.*, 276:37787-37793, 2001.
Toft-Nielsen et al., "Determinants of the effectiveness of glucagon-like peptide-1 in type 2 diabetes," *J. Clin. Endocrinol. Metab.*, 86:3853-3860, 2001.
Vilsboll et al., "No reactive hypoglycaemia in type 2 diabetic patients after subcutaneous administration of GLP-1 and intravenous glucose," *Diabetic Med.*, 18:144-149, 2001.
Walensky et al., "Activation of apoptosis in vivo by a hydrocarbon-stapled BH3 helix," *Science*, 305:1466-1470, 2004.
Yin et al., "Terephthalamide derivatives as mimetics of helical peptides: Disruption of the Bcl-xL/Bak interaction," *J. Am. Chem. Soc.*, 127:5463-5468, 2005.
Yin et al., "Terphenyl-based Bak BH3 α-helical proteomimetics as low-molecular-weight antagonists of Bcl-xL," *J. Am. Chem. Soc.*, 127:10191-10196, 2005.
Yin et al., "Terphenyl-based helical mimetics that disrupt the p53/HDM2 interaction," *Angew. Chem. Int. Ed.*, 44:2704-2707, 2005.
Zander et al., "Effect of 6-week course of glucagon-like peptide 1 on glycaemic control, insulin sensitivity, and beta-cell function in type 2 diabetes: a parallel-group study," *Lancet*, 359:824-830, 2002.
Zhang et al., "New approaches in the treatment of type 2 diabetes," *Curr. Opin. Chem. Biol.*, 4:461-467, 2000.
Azzarito, Valeria, et al. "2-O-alkylated para-benzamide α-helix mimetics: The role of scaffold curvature." *Organic & Biomolecular Chemistry* 10.32 (2012): 6469-6472.
Karekar, Vaibhav V., Bapurao A. Bhoge, and Ishu Saraogi. "An expeditious synthetic route to proteomimetic foldamers." *New Journal of Chemistry* 43.2 (2019): 556-560.

(56) References Cited

OTHER PUBLICATIONS

Kulikov, Oleg V., and Andrew D. Hamilton. "Synthesis of the novel trimeric benzamides—potential inhibitors of protein-protein interactions." *Rsc Advances* 2.6 (2012): 2454-2461.
Oguri et al., "Design and synthesis of a trans-fused polycyclic ether skeleton as an a-helix mimetic scaffold," *Tetrahedron Lett.*, 46:2179-2183, 2005.
Orner et al., "Towards proteomimetics: Terphenyl derivatives as structural and functional mimics of extended regions of an α-helix," *J. Am. Chem. Soc.*, 123:5382-5383, 2001.
Partial Supplementary European Search Report issued in EP 19892172.8, dated Jul. 21, 2022.
Raj et al., "Estrogen receptor coregulator binding modulators (ERXs) effectively target estrogen receptor positive human breast cancers", eLife, 6:e26857, 2017.
Supplementary European Search Report for EP 19892172 dated Nov. 2, 2022, 19 pages.
English translation of Office Action issued in Japanese Patent Application No. 2021-531522, dated Dec. 5, 2023.
Registry: CAS registered RN 1373499-79-6, RN 1373499-44-5, RN 1373499-41-2, RN 1373499-38-7, RN 1373499-32-1, RN 1373499-29-6, RN 1373499-26-3, RN 1373499-23-0, dated May 14, 2012.
Burslem et al., "Synthesis of Highly Functionalized Oligobenzamide Proteomimetic Foldamers by Late Stage introductions of Sensitive Groups," *Org. Biomol. Chem.*, 14(15):3782-3786, 2016.
Elbronds et al., "Pharmacokinetics, pharmacodynamics, safety, and tolerability of a single-dose of NN2211, a long-acting glucagon-like peptide 1 derivative, in healthy male subjects," *Diabetes Care*, 25:1398-1404, 2002.
Ernst et al., "Design and application of an a-helixmimetic scaffold based on an oligoamide-foldamer strategy: antagonism of the Bak BH3/Bcl-xL complex," *Angew. Chem. Int. Ed.*, 42:535-539, 2003.
Fuller et al., "Configurational Preferences of arylamide α-helix mimetics via alchemical free energy calculations of relative binding affinities," *J. Phys. Chem. B.*, 116(35):10856-10869, 2012.
International Search Report and Written Opinion issued in International Application No. PCT/US2019/64073, mailed Dec. 3, 2018.
Jung et al., "Perturbation of the c-Myc-Max Protein-Protein Interaction via Synthetic α-Helix Mimetics," *J. Med. Chem.*, 58(7):3002-3024, 2015.
Kulikov et al., "Amphiphilic oligoamide α-helix peptidomimetics Inhibit Islet Amyloid Polypeptide Aggregation," *Tet. Lett.*, 56(23):3670-3673, 2015.
Kulikov et al., "Characterization of Aggregated Morphologies Derived from Mono- and Bis-arylbenzamides—potential alpha-helix mimetics," *New J. Chem.*, 41(15):7417-7423, 2017.
Kulikov et al., "Design and Synthesis of Oligoamide-Based Double α-Helix Mimetics," *Eur. J. of Org. Chem.*, 2013(17):3433-3445, 2013.
Murphy, "Nonpeptidic glucagon-like peptide 1 receptor agonists: A magic bullet for diabetes," *Proc. Natl. Acad. Sci. U.S.A.*, 104:689-690, 2007.
National Center for Biotechnology Information. "PubChem Compound Summary for CID 15932742, CID 15932742" *PubChem*, pubchem.ncbi.nlm.nih.gov/compound/15932742. (2007).
Plante et al., "Oligobenzamide Proteomimetic inhibitors of the p53-hDM2 protein-protein interaction," *Chem. Comm.*, 34:5091-5093, 2009. WO 2010/083215.
Ravindranathan et al., "Peptidomimetic Targeting of Critical Androgen Receptor-Coregulator Interactions in Prostate Cancer," *Nat. Comm.*, 4, 2013.
Shaginian et al., "Design, Synthesis, and Evaluation of an α-Helix Mimetic Library Targeting Protein-Protein Interactions," *J. Am. Chem. Soc.*, 131(15):5564-5572, 2009.
Yap et al., "Relaxation of the Rigid Backbone of an Oligoamide-foldamer-based α-helix Mimetic: Identification of Potent Bcl-XL Inhibitors," *Org. Biomol. Chem.*, 10(15):2928-2933, 2012.

\* cited by examiner

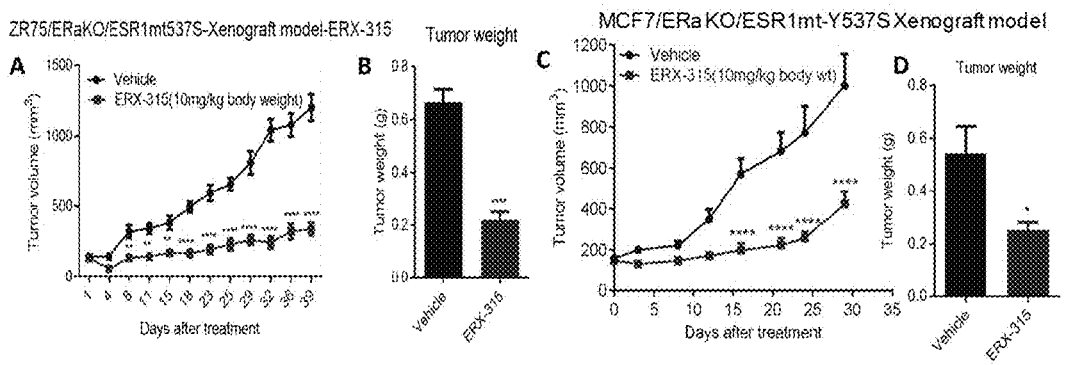
FIGS. 31A-D
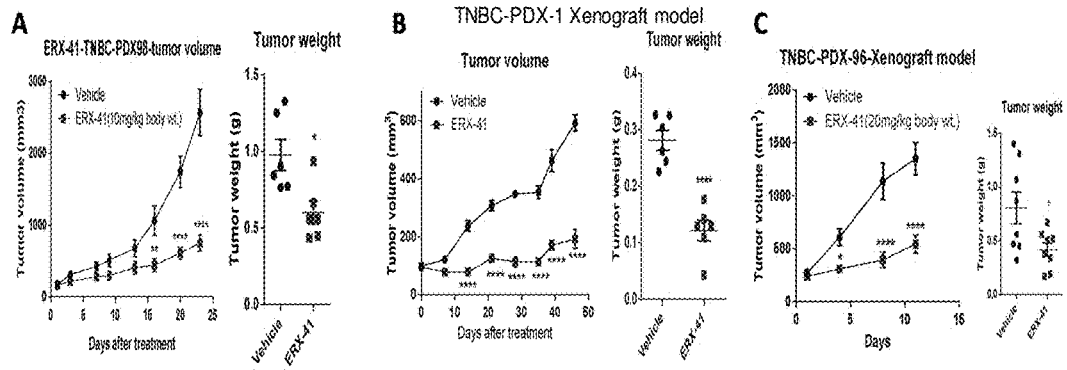
FIGS. 32A-C
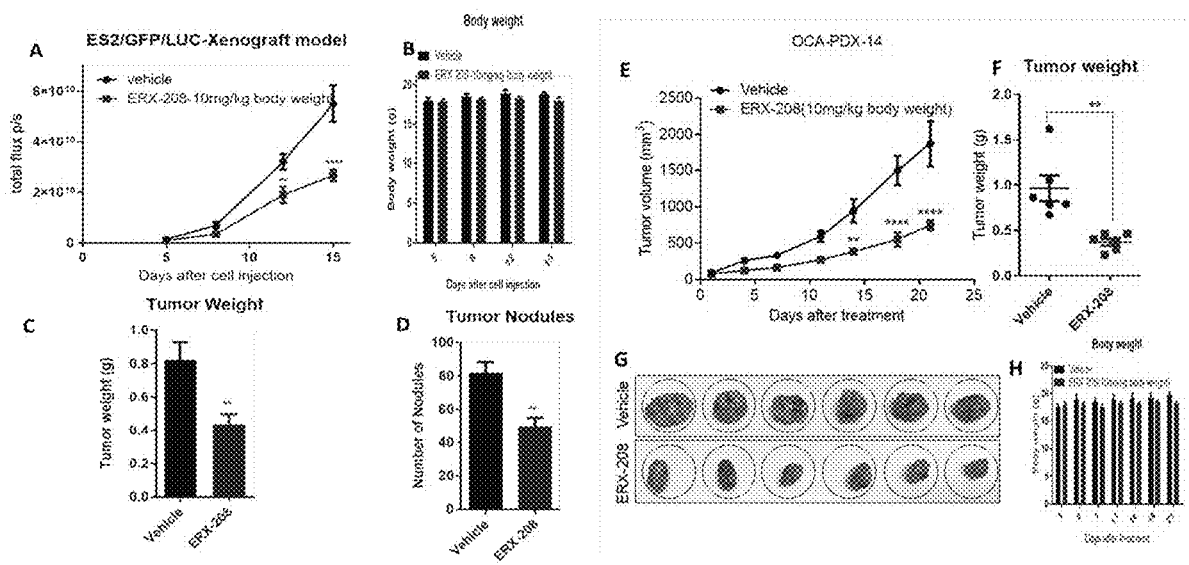
FIGS. 33A-H

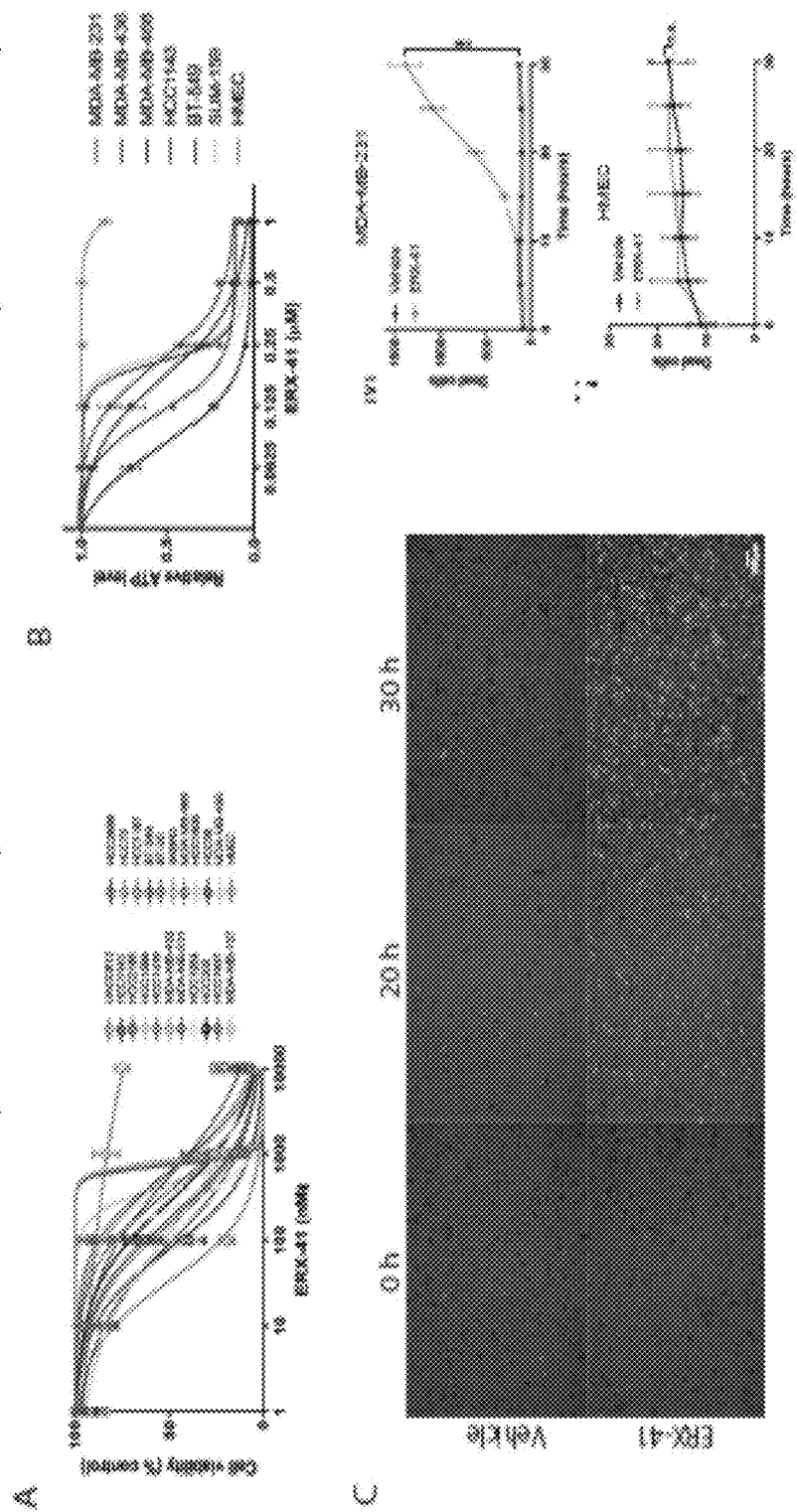
FIGS. 34A-C

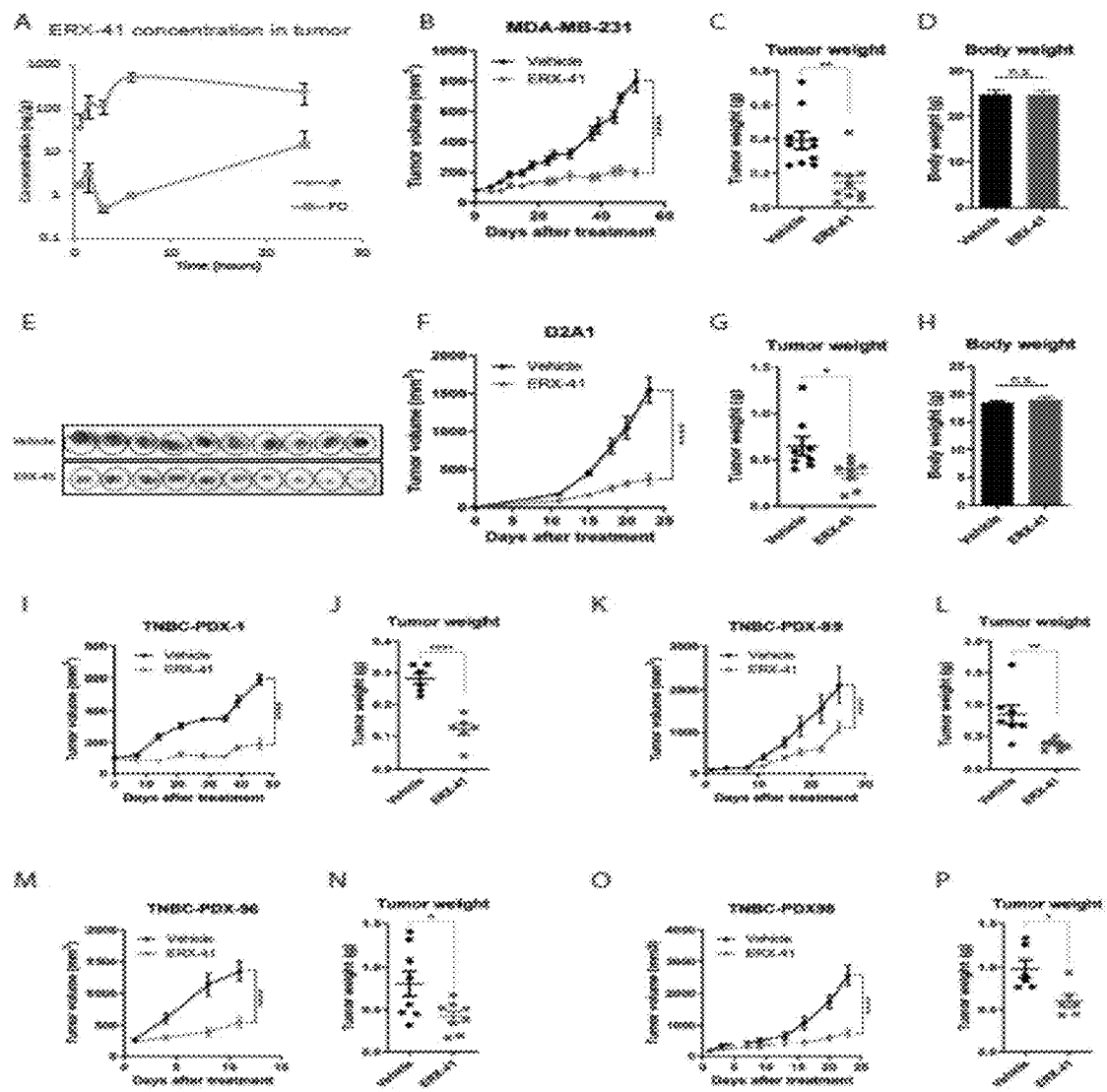
FIGS. 35A-P

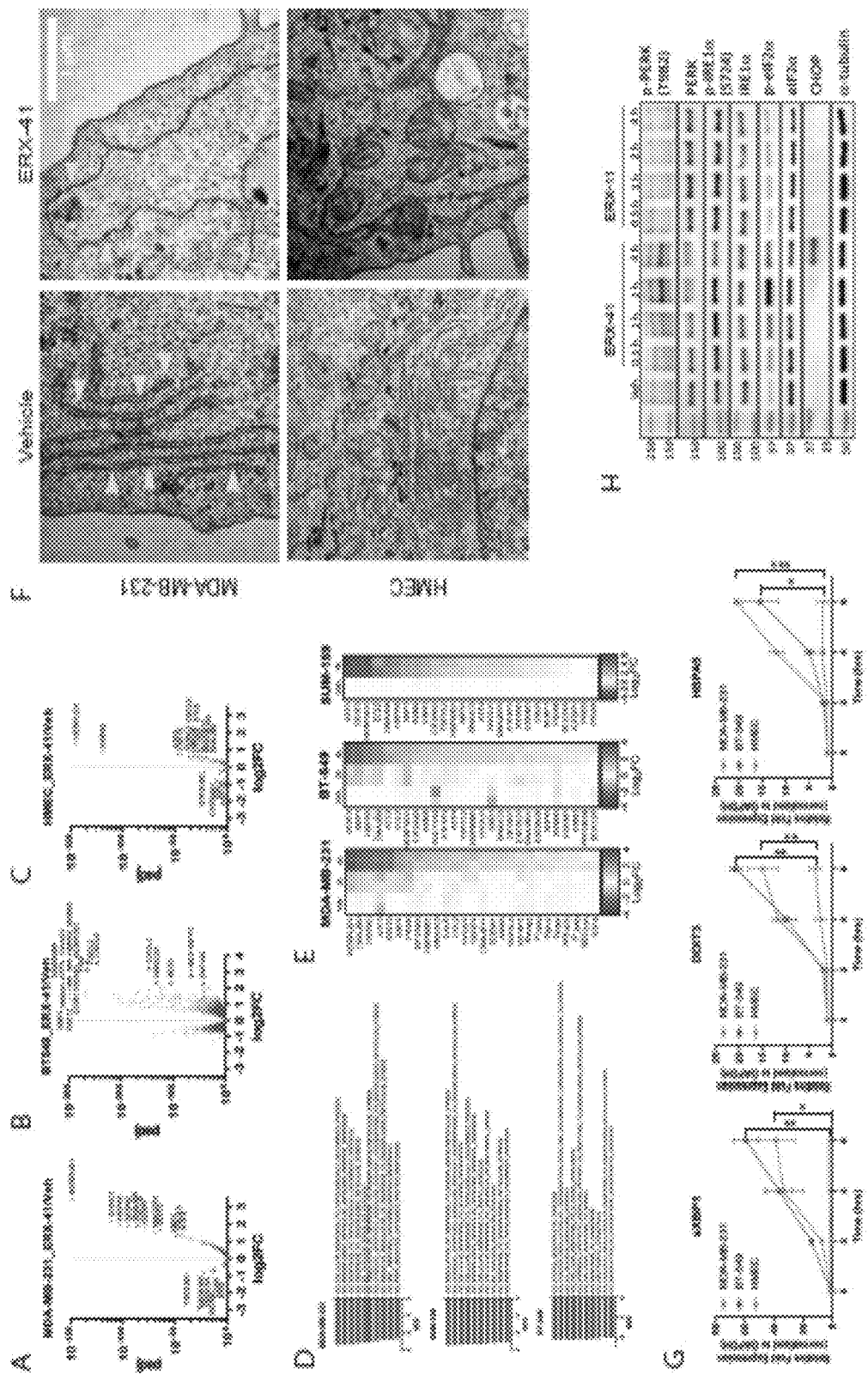
FIGS. 36A-H

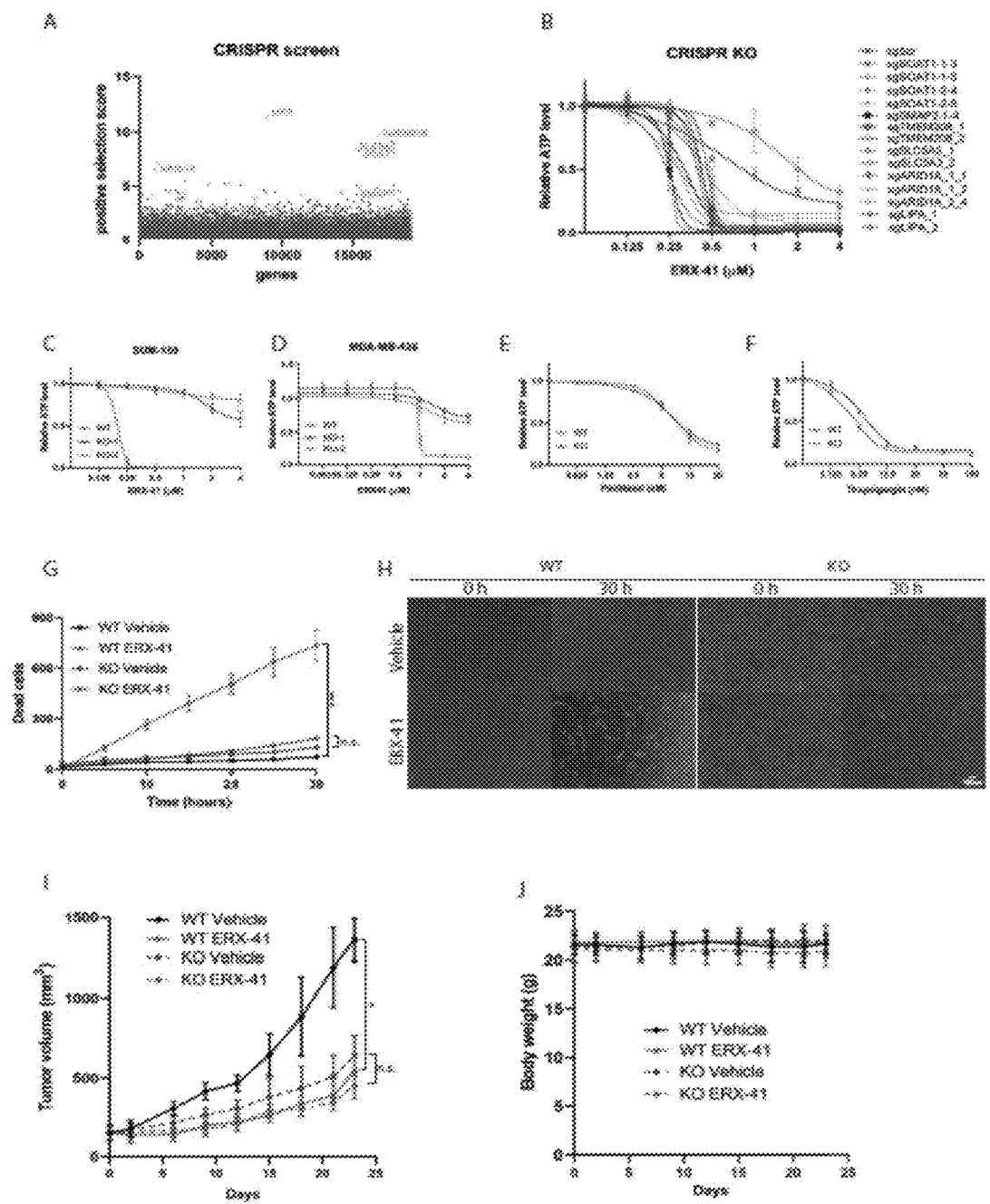
FIGS. 37A-J

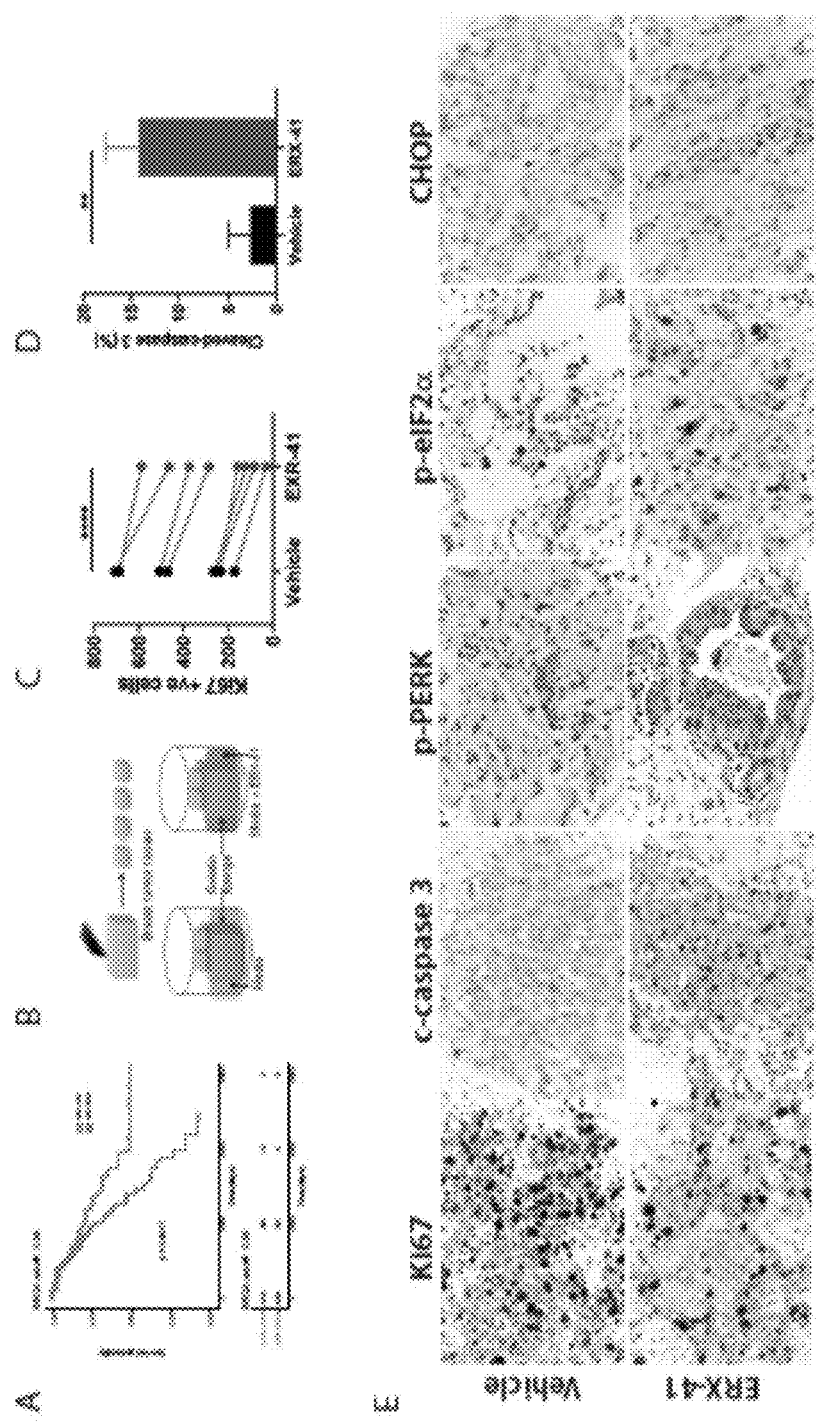
FIGS. 38A-E

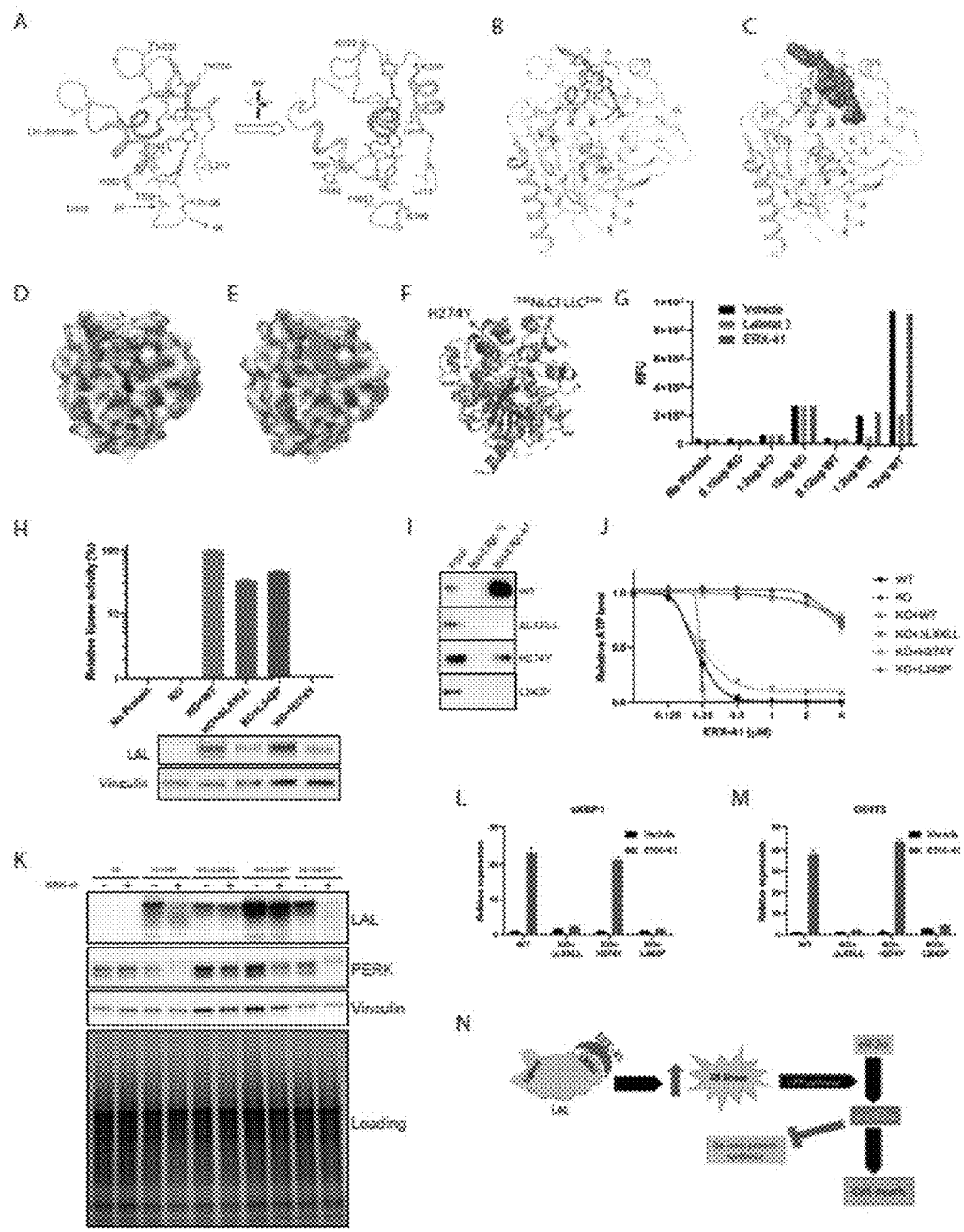
FIGS. 39A-N

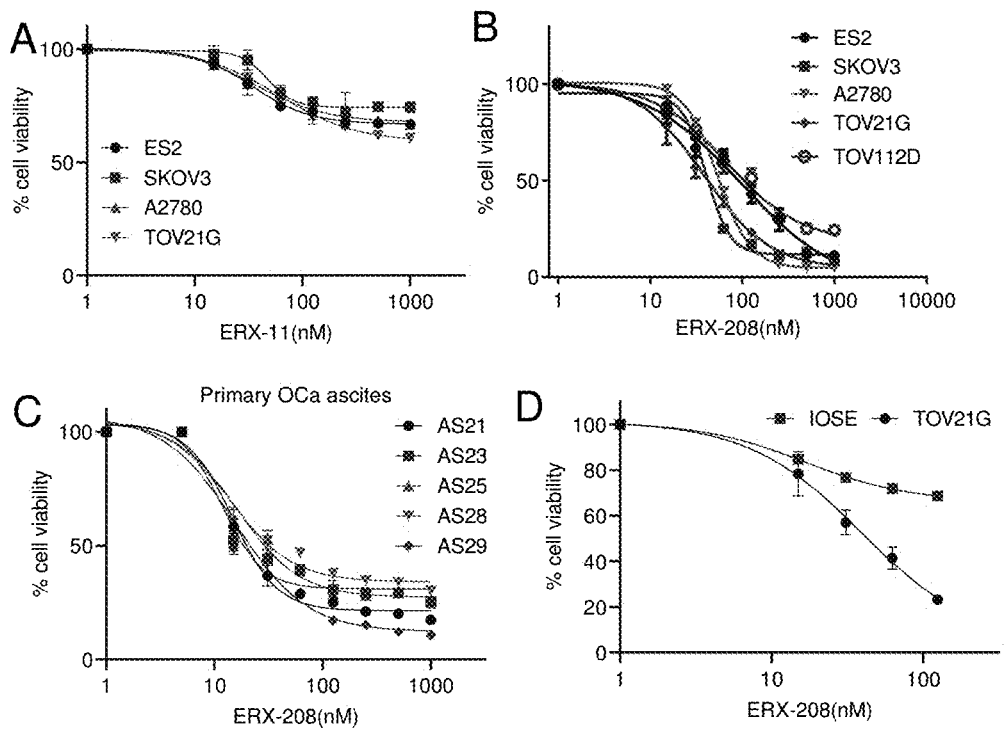
FIGS. 42A-D
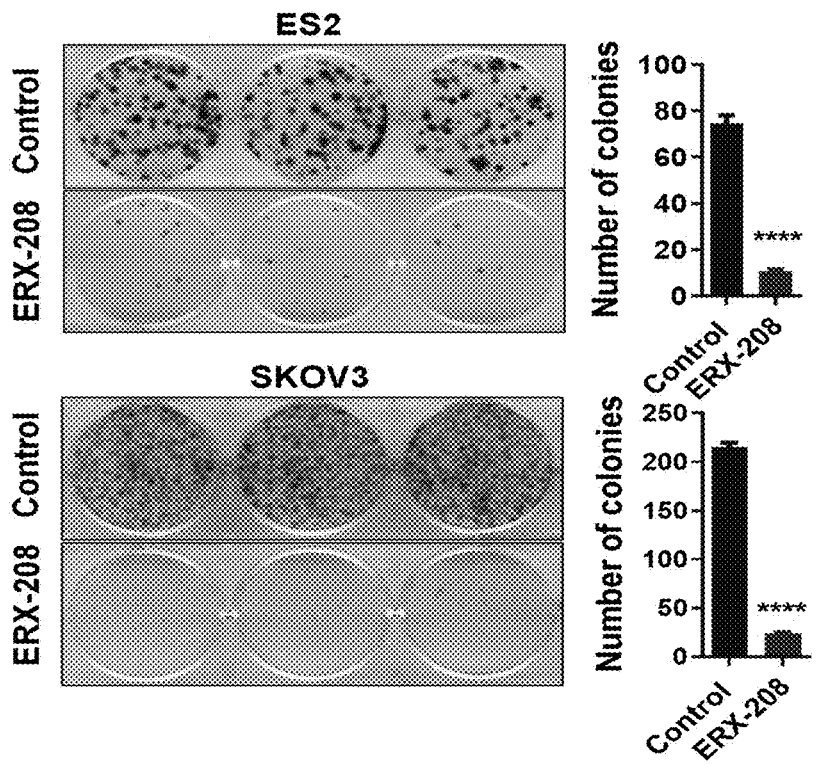
FIG. 43

FIGS. 46A-D

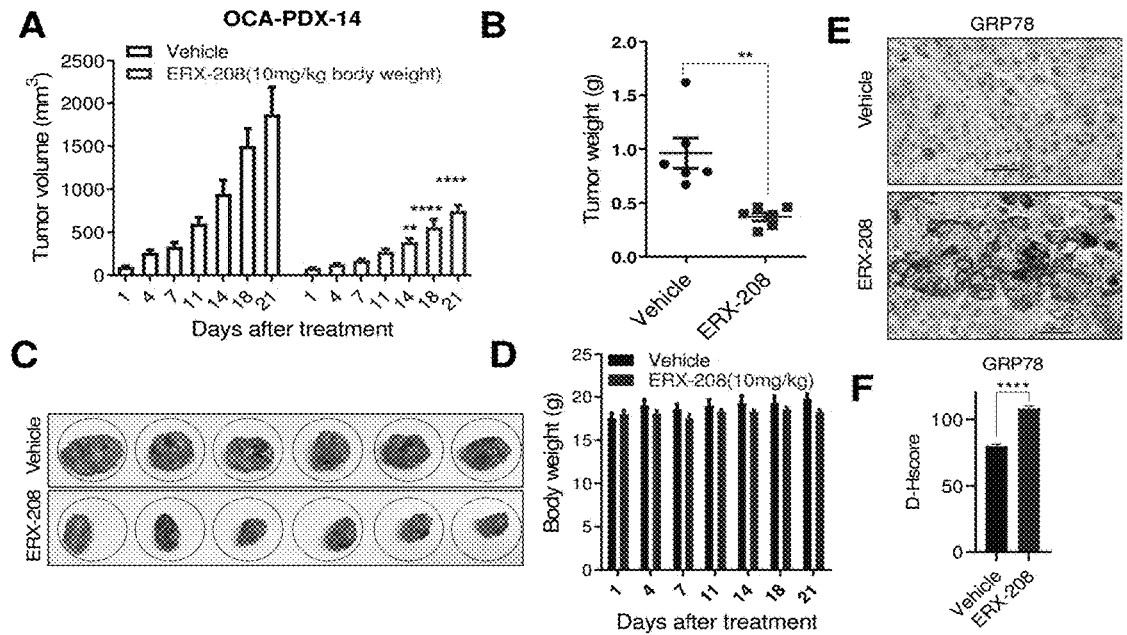
FIGS. 48A-F
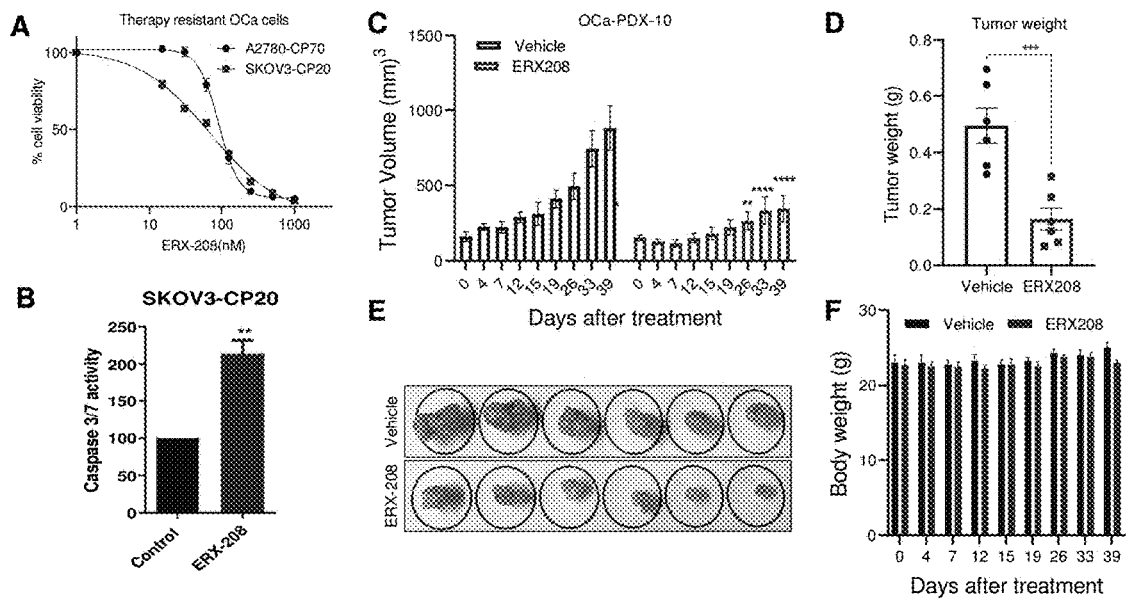
FIG. 49A-F

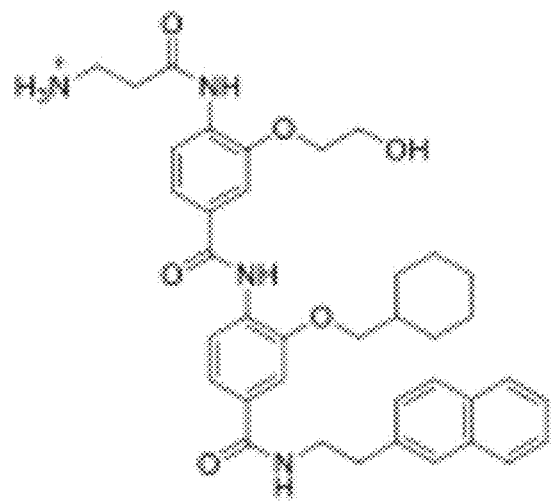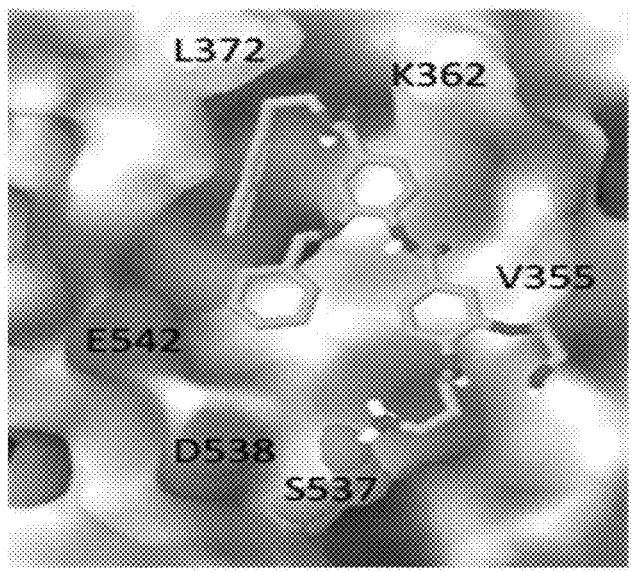
FIG. 51A FIG. 51B
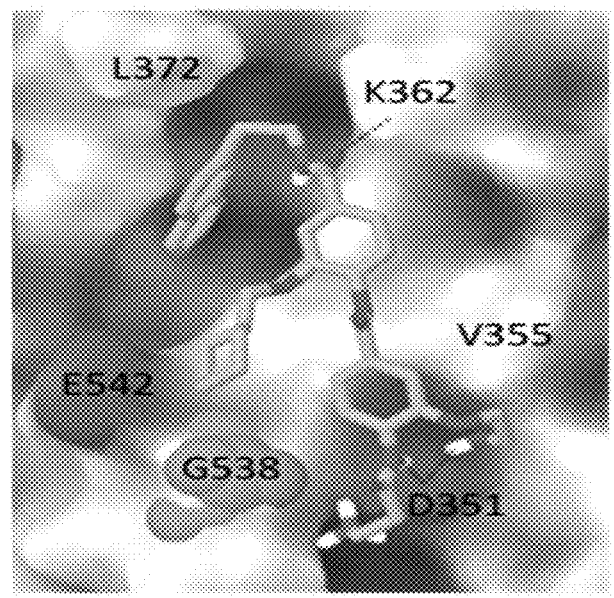
FIG. 51C

| Cell line | ERα | ERX-11 | TX-542 | Tam | ICI | GDC-0810 | AZD-9496 | RAD-001 | Palbo |
|---|---|---|---|---|---|---|---|---|---|
| ZR-75 WT | WT only | 280 | 25 | 500 | 400 | 50 | 100 | 50 | 100 |
| ZR-75 D538G MT | MT only | 320 | 20 | >5000 | 800 | 150 | 50 | 100 | 200 |
| ZR-75 Y537S MT | MT only | 260 | 20 | >5000 | 400 | 1000 | 100 | 100 | 200 |
| ZR-75 Y537N MT | MT only | 420 | 20 | 2500 | 500 | 150 | 300 | 100 | 250 |
| MCF-7 WT | WT only | 350 | 25 | 400 | 300 | 20 | 25 | 50 | 250 |
| MCF-7 D538G MT | WT/MT | 300 | 15 | >5000 | 1000 | 100 | 300 | 50 | 500 |
| MCF-7 Y537S MT | WT/MT | 380 | 15 | >5000 | 400 | 1500 | 500 | 500 | 250 |
| T47-D WT | WT only | 520 | 40 | 250 | 400 | 20 | 25 | 50 | 250 |
| T47-D D538G MT | MT only | 480 | 35 | >5000 | 1000 | 750 | 500 | 50 | 500 |
| T47-D Y537S MT | MT only | 600 | 10 | >5000 | 400 | 1000 | 25 | 500 | 500 |
| SUM-159 | none | >10µM | >10µM | na | >10µM | na | na | na | na |
| MDA-MB-231 | none | >10µM | >10µM | na | >10µM | na | na | na | na |

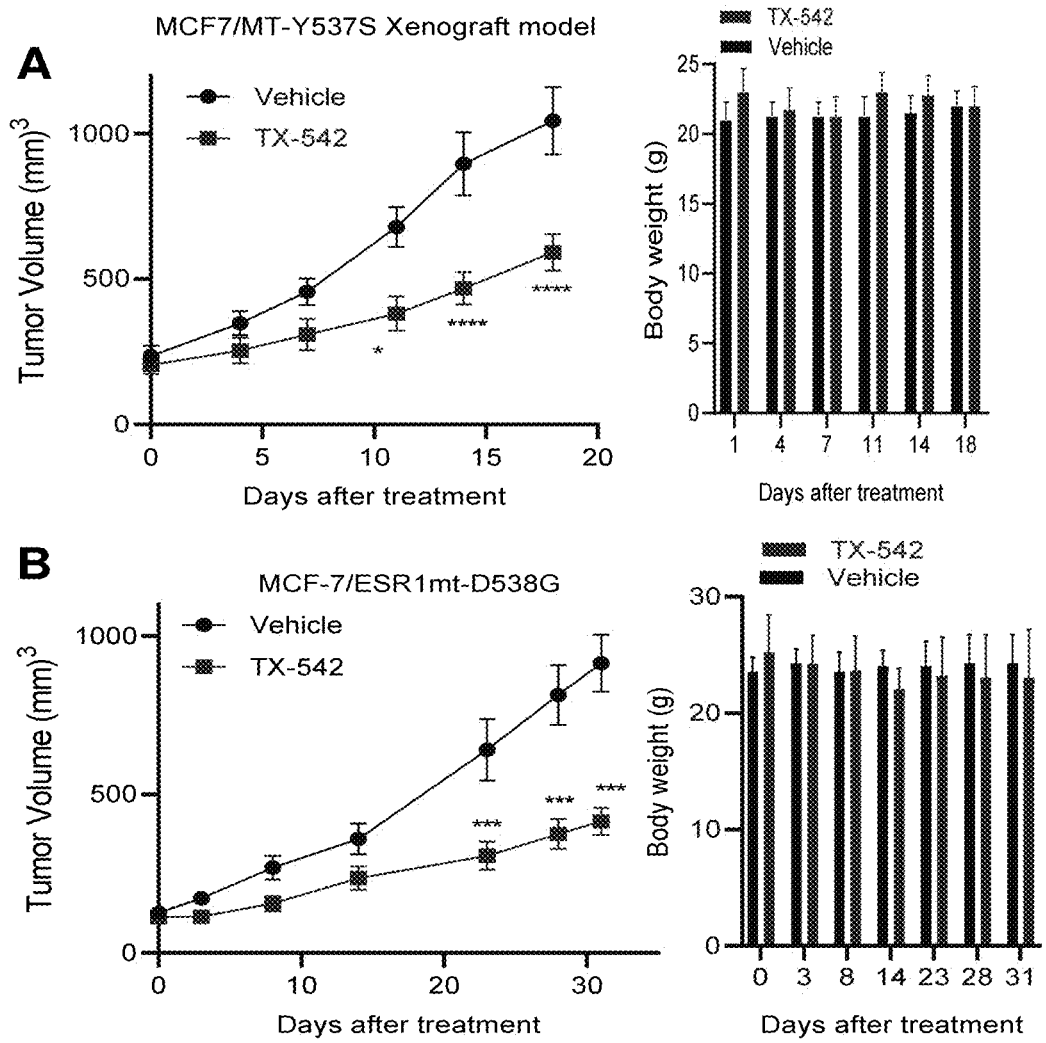
FIGS. 59A-B
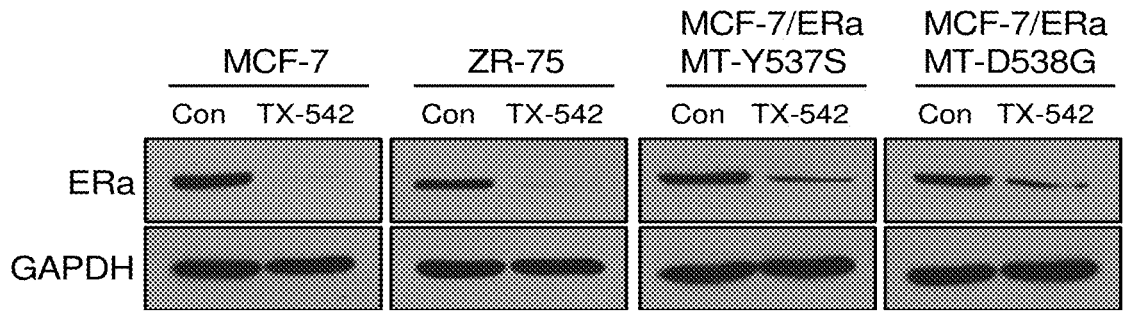
FIG. 60

FIGS. 65A-D

| Cell line | ERX-11 | ERX-315 | ERX-314 |
|---|---|---|---|
| ZR-75 WT | 280 | 30 | 1500 |
| ZR-75 D538G MT | 320 | 32 | 1500 |
| ZR-75 Y537S MT | 260 | 15 | 2500 |
| ZR-75 Y537N MT | 420 | 18 | 3000 |
| MCF-7 WT | 350 | 22 | 5000 |
| MCF-7 D538G MT | 300 | 26 | 3000 |
| MCF-7 Y537S MT | 380 | 24 | 2500 |

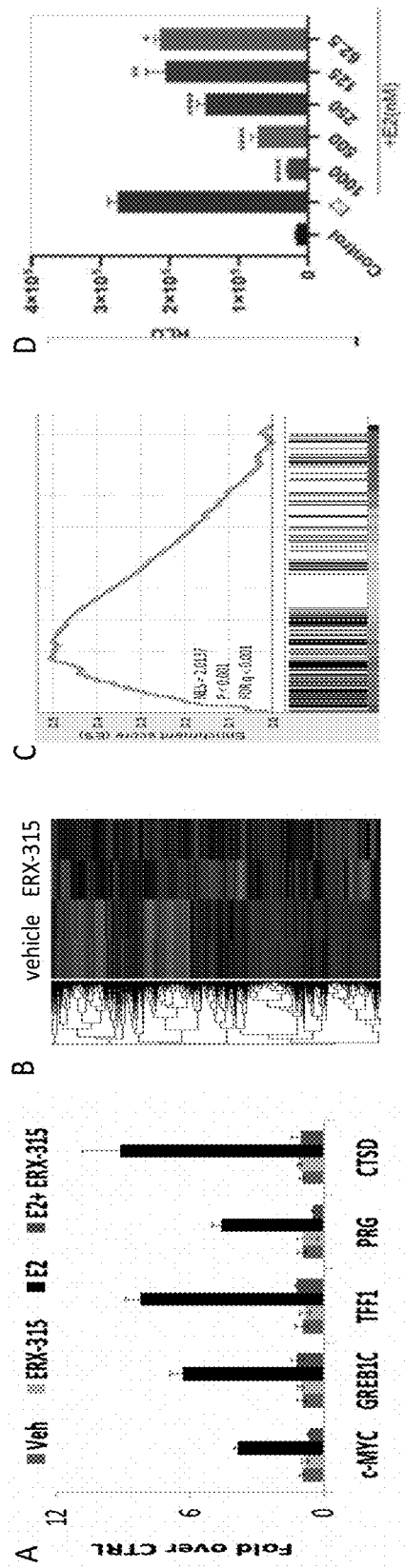
FIGS. 66A-D

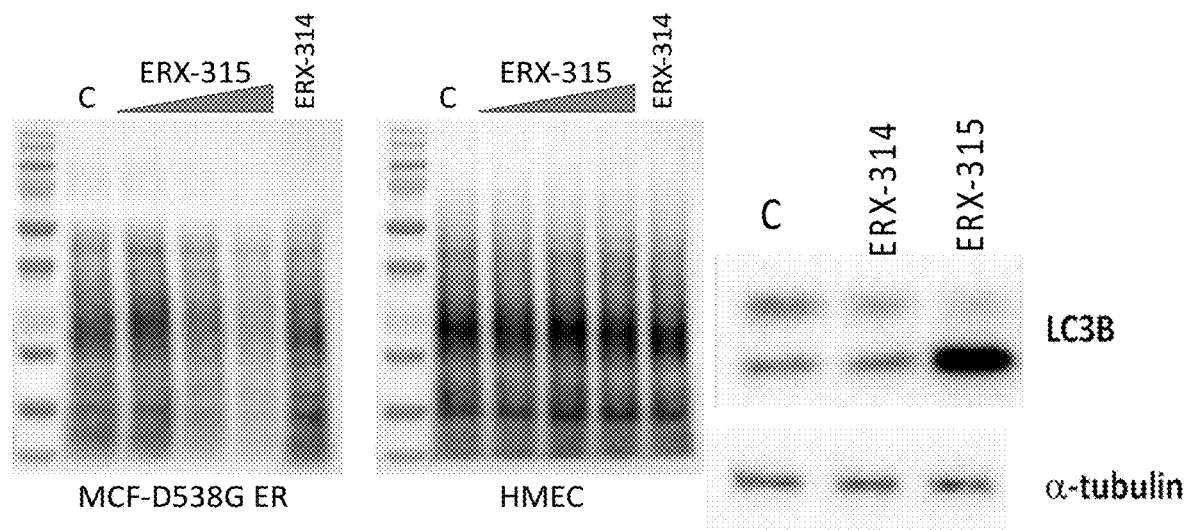
FIG. 67A  FIG. 67B
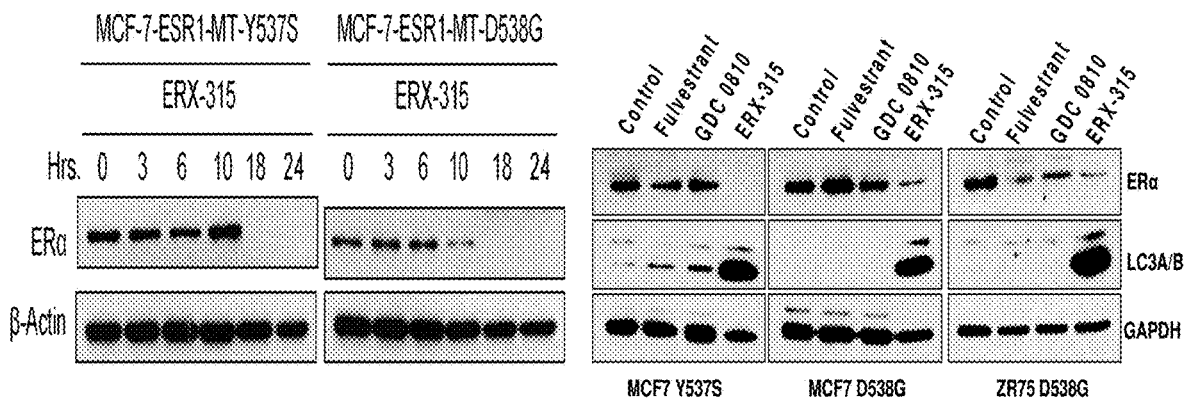
FIG. 67C  FIG. 67D

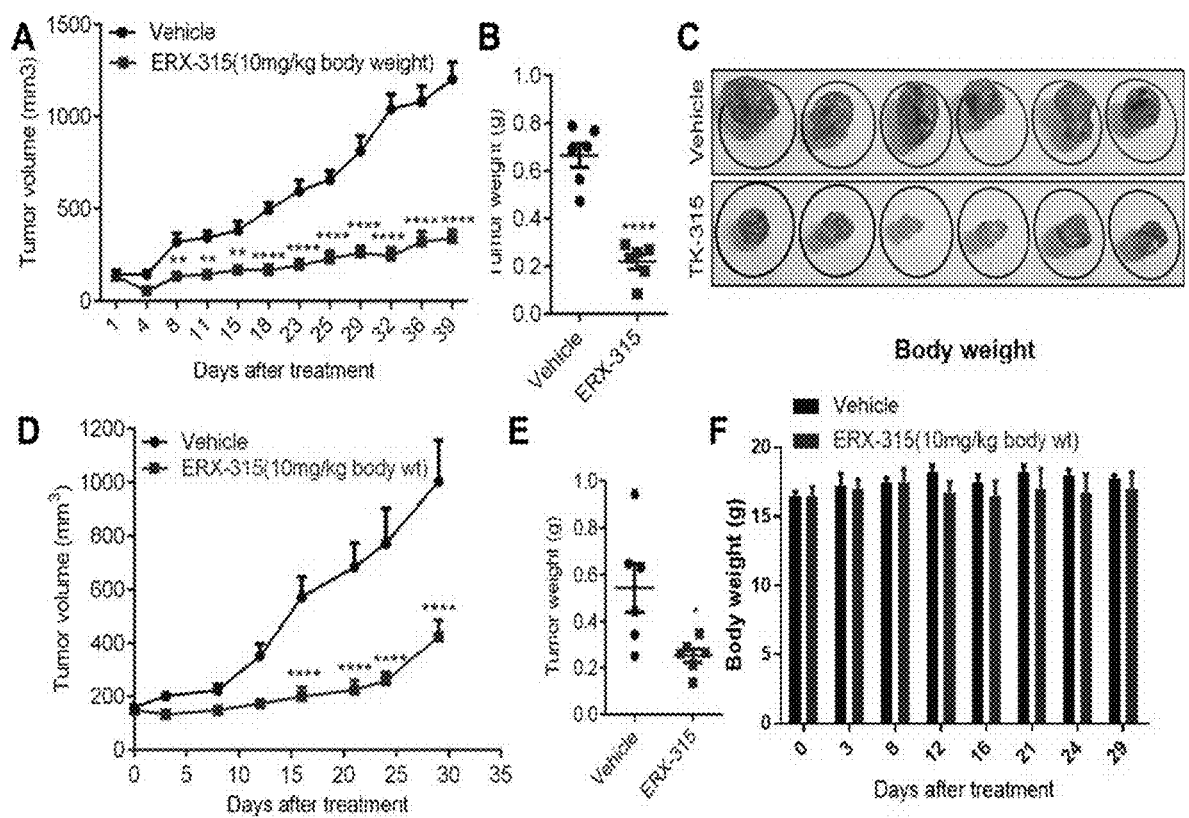
FIGS. 69A-F

OLIGO-BENZAMIDE ANALOGS AND THEIR USE IN CANCER TREATMENT

PRIORITY CLAIM

This application is a continuation in part of PCT/US2019/064073, filed Dec. 2, 2019, which in turn claims benefit of priority to U.S. Provisional Application Ser. No. 62/774,671, filed Dec. 3, 2018, the entire contents of each application being hereby incorporated by reference.

FEDERAL FUNDING STATEMENT

This invention was made with government support under Grant No. 1R01 CA223828-01 awarded by the National Institutes of Health. The government has certain rights in the invention.

INCORPORATION OF SEQUENCE LISTING

The sequence listing that is contained in the file named "UTSFP0142USCP1_ST25.txt", which is 1 KB (as measured in Microsoft Windows®) and was created on Jun. 3, 2021, is filed herewith by electronic submission and is incorporated by reference herein.

BACKGROUND

I. Field of the Invention

The present disclosure relates in general to the field of peptidomimetics and specifically to compositions of matter and methods of their use in medical indications, such as cancer.

II. Description of Related Art

Peptidomimetics (also known as peptide mimetics) are small organic molecules that do not possess the peptide backbone structure, however, still retain a capability to interact with the same target protein by arranging essential functional groups (i.e., pharmacophores) in a required three-dimensional pattern complimentary to a binding pocket in the protein. Since peptides and proteins adopt and utilize secondary structures (e.g., α-helix, β-sheet, and reverse turns) to make their global shapes and to recognize their binding partners, rational design of secondary structure mimetics is an important strategy in developing small molecule modulators for protein complex formation, compared to conventional high-throughput screening of a chemical library.

These compounds are known to bind to hormone receptors in cancer cells and are useful in treating these indications. Therefore, there remains a need to develop new and useful compounds which are useful in the treatment of cancers through the modulation of hormone receptors.

SUMMARY

The present disclosure provides oligo-benzamide peptidomimetic compounds for use in the treatment and/or prevention of cancer. These small molecules include α-helix mimetics that represent helical segments in the target molecules. The oligo-benzamide peptidomimetic compounds modulate protein-protein, protein-peptide, or protein-drug interaction to exert a variety of physiological consequences. The oligo-benzamide peptidomimetic compounds also cause significant endoplasmic reticulum stress in cancer cells and may effectively shut down de novo protein synthesis, leading to cell death.

In one aspect, the present disclosure provides compounds of the formula:

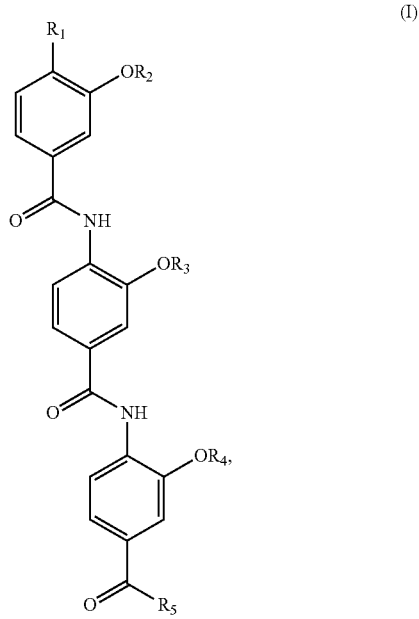

(I)

wherein:
R$_1$ is halo, —NO$_2$, alkyl$_{(C \leq 12)}$, substituted alkyl$_{(C \leq 12)}$, amido$_{(C \leq 12)}$, substituted amido$_{(C \leq 12)}$, or —NHC(O)CH(R$_{1a}$)NH$_2$, wherein:
R$_{1a}$ is aralkyl$_{(C \leq 18)}$, substituted aralkyl$_{(C \leq 18)}$, or the side chain of a canonical amino acid;
R$_2$, R$_3$, and R$_4$ are each independently alkyl$_{(C \leq 12)}$, substituted alkyl$_{(C \leq 12)}$, aralkyl$_{(C \leq 18)}$, or substituted aralkyl$_{(C \leq 18)}$; and
R$_5$ is —OR$_{5a}$ or —NHR$_{5b}$, wherein:
R$_{5a}$ is alkyl$_{(C \leq 12)}$ or substituted alkyl$_{(C \leq 12)}$;
R$_{5b}$ is hydrogen; or
cycloalkyl$_{(C \leq 12)}$, aryl$_{(C \leq 12)}$, aralkyl$_{(C \leq 18)}$, heteroaryl$_{(C \leq 12)}$, heteroaralkyl$_{(C \leq 18)}$, or a substituted version of any of these groups; or
a group of the formula:

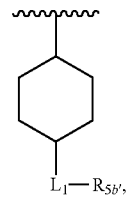

wherein:
L$_1$ is —CO$_2$— or —C(O)NR$_{L1}$—, wherein:
R$_{L1}$ hydrogen, alkyl$_{(C \leq 12)}$, or substituted alkyl$_{(C \leq 12)}$;
R$_{5b'}$ is aryl$_{(C \leq 12)}$, aralkyl$_{(C \leq 18)}$, heteroaryl$_{(C \leq 12)}$, heteroaralkyl$_{(C \leq 18)}$, or a substituted version of any of these groups;
provided R$_1$ is halo when R$_{5b}$ is hydrogen and provided R$_3$ is not alkyl$_{(C \leq 12)}$ when R$_{5a}$ is methyl; or compounds of the formula:

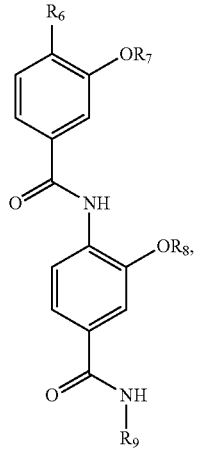

(II)

wherein:
- R$_6$ is halo, —NO$_2$, alkyl$_{(C \leq 12)}$, substituted alkyl$_{(C \leq 12)}$, amido$_{(C \leq 12)}$, substituted amido$_{(C \leq 12)}$, or —NHC(O)CH(R$_{6a}$)NH$_2$, wherein:
  - R$_{6a}$ is aralkyl$_{(C \leq 18)}$, substituted aralkyl$_{(C \leq 18)}$, or the side chain of a canonical amino acid;
- R$_7$ and R$_8$ are each independently alkyl$_{(C \leq 12)}$, -alkanediyl$_{(C \leq 12)}$-cycloalkyl$_{(C \leq 12)}$, aralkyl$_{(C \leq 18)}$, or a substituted version of any of these groups; and
- R$_9$ is cycloalkyl$_{(C \leq 12)}$, aryl$_{(C \leq 12)}$, aralkyl$_{(C \leq 18)}$, heteroaryl$_{(C \leq 12)}$, heteroaralkyl$_{(C \leq 18)}$, or a substituted version of any of these groups; or
- a group of the formula:

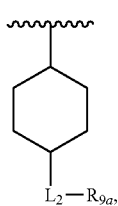

wherein:
- L$_2$ is —CO$_2$— or —C(O)NR$_{L2}$—, wherein:
  - R$_{L2}$ hydrogen, alkyl$_{(C \leq 12)}$, or substituted alkyl$_{(C \leq 12)}$;
- R$_{9a}$ is aryl$_{(C \leq 12)}$, aralkyl$_{(C \leq 18)}$, heteroaryl$_{(C \leq 12)}$, heteroaralkyl$_{(C \leq 18)}$, or a substituted version of any of these groups;

or a pharmaceutically acceptable salt of either of these formulae.

In some embodiments, the compounds are of formula (I). In further embodiments, the compounds are further defined as:

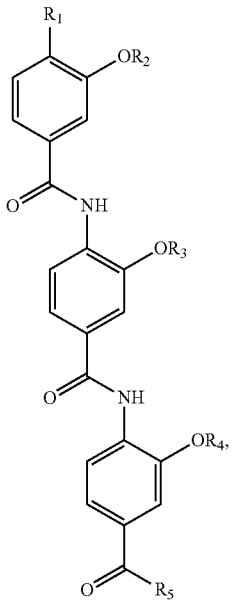

(I)

wherein:
- R$_1$ is halo, —NO$_2$, alkyl$_{(C \leq 12)}$, substituted alkyl$_{(C \leq 12)}$, amido$_{(C \leq 12)}$, substituted amido$_{(C \leq 12)}$, or —NHC(O)CH(R$_{1a}$)NH$_2$, wherein:
  - R$_{1a}$ is aralkyl$_{(C \leq 18)}$, substituted aralkyl$_{(C \leq 18)}$, or the side chain of a canonical amino acid;
- R$_2$, R$_3$, and R$_4$ are each independently alkyl$_{(C \leq 12)}$, substituted alkyl$_{(C \leq 12)}$, aralkyl$_{(C \leq 18)}$, or substituted aralkyl$_{(C \leq 18)}$; and
- R$_5$ is —OR$_{5a}$ or —NHR$_{5b}$, wherein:
  - R$_{5a}$ is alkyl$_{(C \leq 12)}$ or substituted alkyl$_{(C \leq 12)}$;
  - R$_{5b}$ is cycloalkyl$_{(C \leq 12)}$, aryl$_{(C \leq 12)}$, aralkyl$_{(C \leq 18)}$, heteroaryl$_{(C \leq 12)}$, heteroaralkyl$_{(C \leq 18)}$, or a substituted version of any of these groups; or
  - a group of the formula:

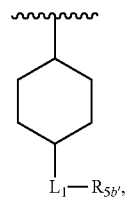

wherein:
- L$_1$ is —CO$_2$— or —C(O)NR$_{L1}$—, wherein:
  - R$_{L1}$ hydrogen, alkyl$_{(C \leq 12)}$, or substituted alkyl$_{(C \leq 12)}$;
- R$_{5b'}$ is aryl$_{(C \leq 12)}$, aralkyl$_{(C \leq 18)}$, heteroaryl$_{(C \leq 12)}$, heteroaralkyl$_{(C \leq 18)}$, or a substituted version of any of these groups;

or a pharmaceutically acceptable salt thereof.

In some embodiments, the compounds are further defined as:

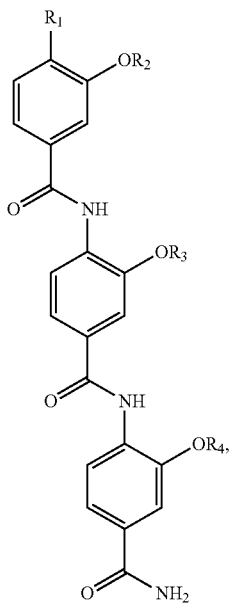

(III)

wherein:
R$_1$ is halo; and
R$_2$, R$_3$, and R$_4$ are each independently alkyl$_{(C\leq12)}$, substituted alkyl$_{(C\leq12)}$, aralkyl$_{(C\leq18)}$, or substituted aralkyl$_{(C\leq18)}$;
or a pharmaceutically acceptable salt thereof.

In some embodiments, the compounds are further defined as:

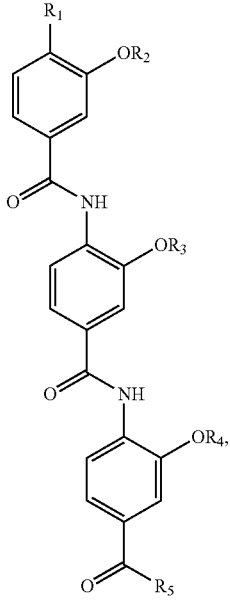

(IV)

wherein:
R$_1$ is halo, —NO$_2$, alkyl$_{(C\leq12)}$, substituted alkyl$_{(C\leq12)}$, amido$_{(C\leq12)}$, substituted amido$_{(C\leq12)}$, or —NHC(O)CH(R$_{1a}$)NH$_2$, wherein:
R$_{1a}$ is aralkyl$_{(C\leq18)}$, substituted aralkyl$_{(C\leq18)}$, or the side chain of a canonical amino acid;
R$_2$, R$_3$, and R$_4$ are each independently alkyl$_{(C\leq12)}$, substituted alkyl$_{(C\leq12)}$, aralkyl$_{(C\leq18)}$, or substituted aralkyl$_{(C\leq18)}$; and
R$_5$ is —OR$_{5a}$ or —NHR$_{5b}$, wherein:
R$_{5a}$ is alkyl$_{(C2-12)}$ or substituted alkyl$_{(C\leq12)}$;
R$_{5b}$ is hydrogen; or
cycloalkyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version of any of these groups; or
a group of the formula:

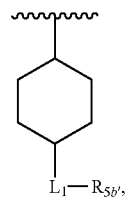

wherein:
L$_1$ is —CO$_2$— or —C(O)NR$_{L1}$—, wherein:
R$_{L1}$ hydrogen, alkyl$_{(C\leq12)}$, or substituted alkyl$_{(C\leq12)}$;
R$_{5b'}$ is aryl$_{(C\leq12)}$, aralkyl$_{(C\leq18)}$, heteroaryl$_{(C\leq12)}$, heteroaralkyl$_{(C\leq18)}$, or a substituted version of any of these groups;
or a pharmaceutically acceptable salt thereof.

In some embodiments, the compounds are further defined as:

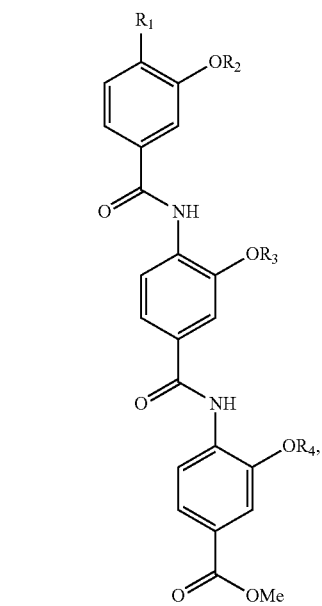

(V)

wherein:
R$_1$ is halo, —NO$_2$, alkyl$_{(C\leq12)}$, substituted alkyl$_{(C\leq12)}$, amido$_{(C\leq12)}$, substituted amido$_{(C\leq12)}$, or —NHC(O)CH(R$_{1a}$)NH$_2$, wherein:
R$_{1a}$ is aralkyl$_{(C\leq18)}$, substituted aralkyl$_{(C\leq18)}$, or the side chain of a canonical amino acid;
R$_2$ and R$_4$ are each independently alkyl$_{(C\leq12)}$, substituted alkyl$_{(C\leq12)}$, aralkyl$_{(C\leq18)}$, or substituted aralkyl$_{(C\leq18)}$; and $R_3$ is substituted alkyl$_{(C\leq12)}$, aralkyl$_{(C\leq18)}$, or substituted aralkyl$_{(C\leq18)}$;

or a pharmaceutically acceptable salt thereof.

In some embodiments, $R_{5b}$ is hydrogen. In some embodiments, $R_{5a}$ is methyl.

In some embodiments, the compounds are further defined as:

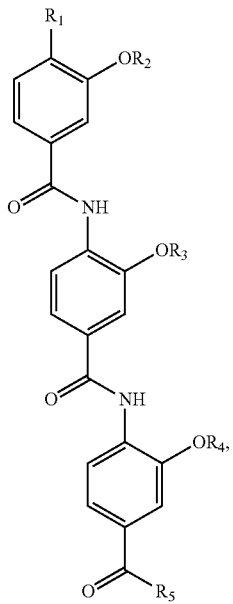

(VI)

wherein:
$R_1$ is halo, —NO$_2$, alkyl$_{(C\leq12)}$, substituted alkyl$_{(C\leq12)}$, amido$_{(C\leq12)}$, substituted amido$_{(C\leq12)}$, or —NHC(O)CH(R$_{1a}$)NH$_2$, wherein:
$R_{1a}$ is aralkyl$_{(C\leq18)}$, substituted aralkyl$_{(C\leq18)}$, or the side chain of a canonical amino acid;
$R_2$, $R_3$, and $R_4$ are each independently alkyl$_{(C\leq12)}$, substituted alkyl$_{(C\leq12)}$, aralkyl$_{(C\leq18)}$, or substituted aralkyl$_{(C\leq18)}$; and
$R_5$ is —NHR$_{5b}$, wherein:
$R_{5b}$ is cycloalkyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version of any of these groups; or
a group of the formula:

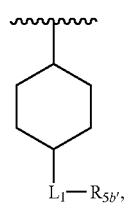

wherein:
$L_1$ is —CO$_2$— or —C(O)NR$_{L1}$—, wherein:
$R_{L1}$ hydrogen, alkyl$_{(C\leq12)}$, or substituted alkyl$_{(C\leq12)}$;
$R_{5b'}$ is aryl$_{(C\leq12)}$, aralkyl$_{(C\leq18)}$, heteroaryl$_{(C\leq12)}$, heteroaralkyl$_{(C\leq18)}$, or a substituted version of any of these groups;

or a pharmaceutically acceptable salt thereof.

In some embodiments, $R_2$ is aralkyl$_{(C\leq18)}$ or substituted aralkyl$_{(C\leq18)}$. In further embodiments, $R_2$ is substituted aralkyl$_{(C\leq18)}$, such as 4-hydroxyphenethyl. In other embodiments, $R_2$ is alkyl$_{(C\leq12)}$ or substituted alkyl$_{(C\leq12)}$. In further embodiments, $R_2$ is substituted alkyl$_{(C\leq12)}$, such as 1-hydroxyethyl. In some embodiments, $R_4$ is aralkyl$_{(C\leq18)}$ or substituted aralkyl$_{(C\leq18)}$. In further embodiments, $R_4$ is aralkyl$_{(C\leq18)}$, such as benzyl. In other embodiments, $R_4$ is alkyl$_{(C\leq12)}$ or substituted alkyl$_{(C\leq12)}$. In further embodiments, $R_4$ is alkyl$_{(C\leq12)}$, such as n-butyl or i-butyl. In some embodiments, $R_3$ is aralkyl$_{(C\leq18)}$ or substituted aralkyl$_{(C\leq18)}$. In further embodiments, $R_3$ is aralkyl$_{(C\leq18)}$, such as 2-(naphthalen-2-yl)ethyl. In other embodiments, $R_3$ is alkyl$_{(C\leq12)}$ or substituted alkyl$_{(C\leq12)}$. In further embodiments, $R_3$ is alkyl$_{(C\leq12)}$, such as methyl or i-butyl.

In some embodiments, $R_{5b}$ is aralkyl$_{(C\leq18)}$ or substituted aralkyl$_{(C\leq18)}$. In further embodiments, $R_{5b}$ is aralkyl$_{(C\leq18)}$, such as (naphthalen-2-yl)methyl. In other embodiments, $R_{5b}$ is heteroaryl$_{(C\leq12)}$ or substituted heteroaryl$_{(C\leq12)}$. In further embodiments, $R_{5b}$ is heteroaryl$_{(C\leq12)}$, such as 1H-imidazol-2-yl. In still other embodiments, $R_{5b}$ is cycloalkyl$_{(C\leq12)}$ or substituted cycloalkyl$_{(C\leq12)}$. In further embodiments, $R_{5b}$ is cycloalkyl$_{(C\leq12)}$, such as 4-methylcyclohexyl. In some embodiments, $L_1$ is —C(O)NR$_{L1}$—. In some embodiments, $R_{L1}$ is hydrogen. In some embodiments, $R_{5b'}$ is heteroaryl$_{(C\leq12)}$ or substituted heteroaryl$_{(C\leq12)}$. In further embodiments, $R_{5b'}$ is heteroaryl$_{(C\leq12)}$, such as quinolin-3-yl or 1H-indazol-7-yl.

In some embodiments, $R_1$ is —NO$_2$. In other embodiments, $R_1$ is alkyl$_{(C\leq12)}$ or substituted alkyl$_{(C\leq12)}$. In further embodiments, $R_1$ is alkyl$_{(C\leq12)}$, such as methyl. In still other embodiments, $R_1$ is halo, such as fluoro or iodo. In yet other embodiments, $R_1$ is amido$_{(C\leq12)}$ or substituted amido$_{(C\leq12)}$. In further embodiments, $R_1$ is substituted amido$_{(C\leq12)}$, such as 3-aminopropanamido. In some embodiments, $R_{1a}$ is aralkyl$_{(C\leq18)}$ or substituted aralkyl$_{(C\leq18)}$. In further embodiments, $R_{1a}$ is aralkyl$_{(C\leq18)}$, such as benzyl.

In other embodiments, the compounds are of formula (II). In some embodiments, $R_7$ is alkyl$_{(C\leq12)}$ or substituted alkyl$_{(C\leq12)}$. In further embodiments, $R_7$ is substituted alkyl$_{(C\leq12)}$, such as 1-hydroxyethyl. In some embodiments, $R_8$ is -alkanediyl$_{(C\leq12)}$-cycloalkyl$_{(C\leq12)}$ or substituted-alkanediyl$_{(C\leq12)}$-cycloalkyl$_{(C\leq12)}$. In further embodiments, $R_8$ is alkanediyl$_{(C\leq12)}$-cycloalkyl$_{(C\leq12)}$, such as (cyclohexyl)methyl. In some embodiments, $R_9$ is aralkyl$_{(C\leq18)}$ or substituted aralkyl$_{(C\leq18)}$. In further embodiments, $R_9$ is aralkyl$_{(C\leq18)}$, such as 2-(naphthalen-2-yl)ethyl. In some embodiments, $R_6$ is amido$_{(C\leq12)}$ or substituted amido$_{(C\leq12)}$. In further embodiments, $R_6$ is substituted amido$_{(C\leq12)}$, such as 3-aminopropanamido.

In some embodiments, the compound is further defined as:
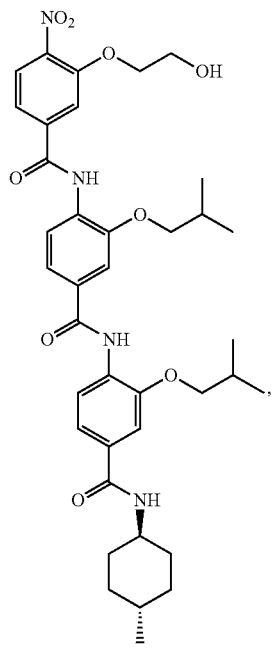
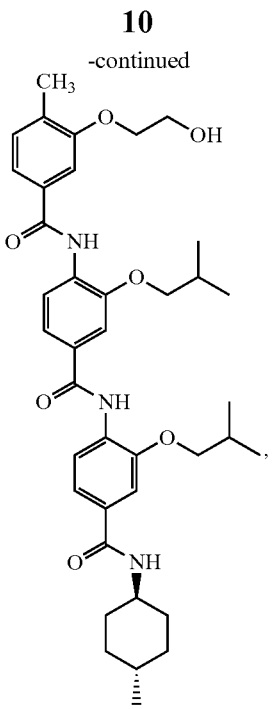
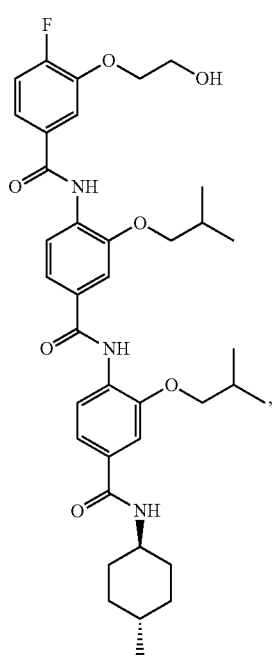
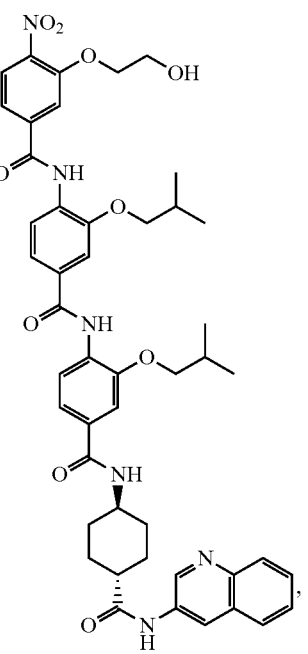

11
-continued
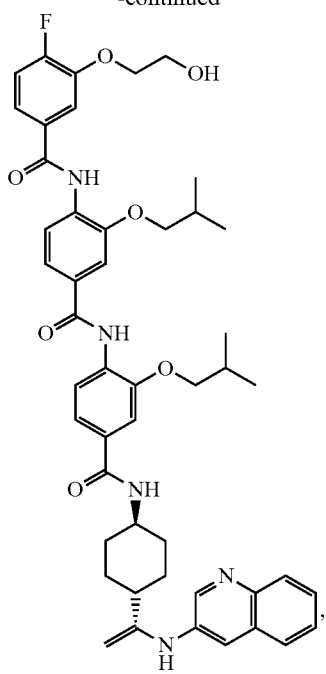
12
-continued
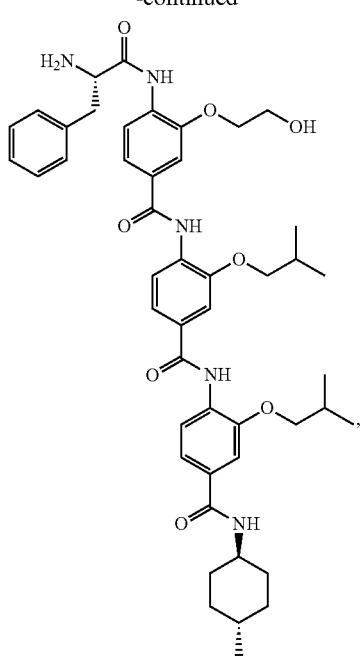
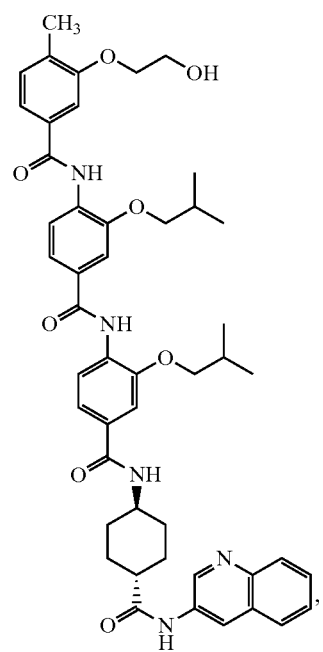
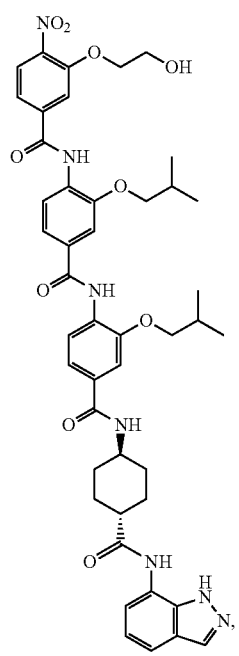

13
-continued
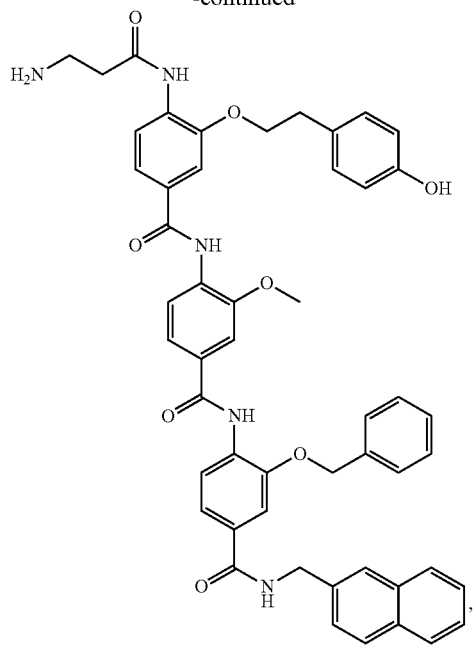
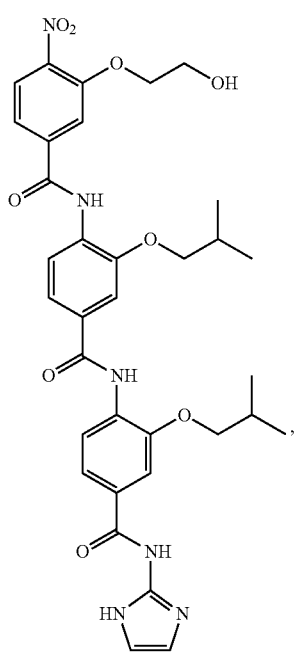
14
-continued
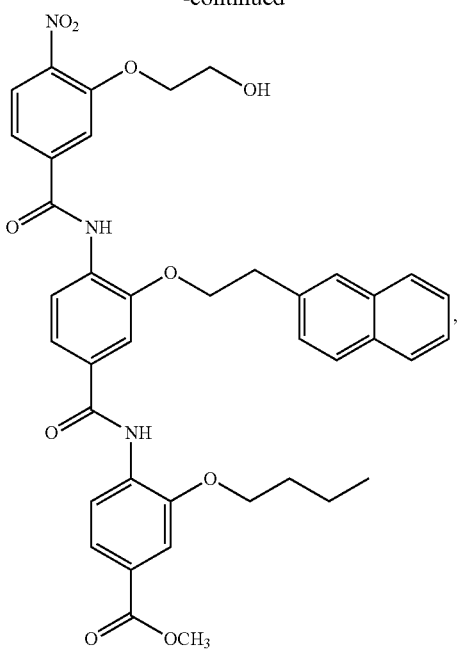
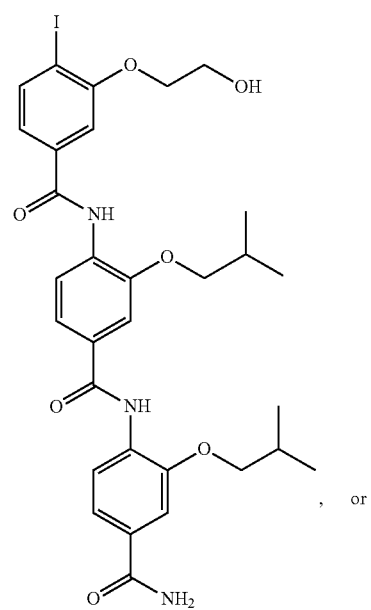
, or

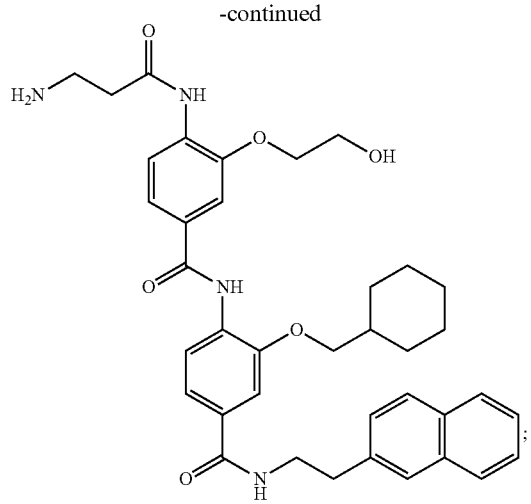
or a pharmaceutically acceptable salt thereof.
In some embodiments, the compound is further defined as:
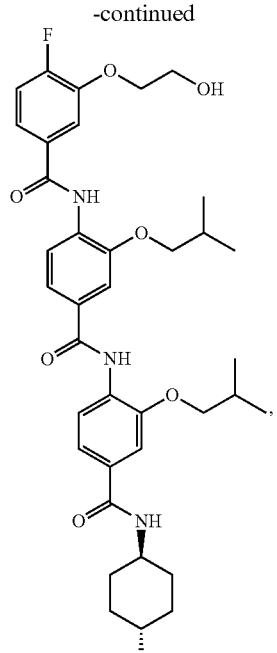
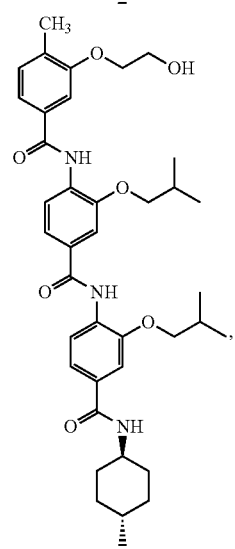
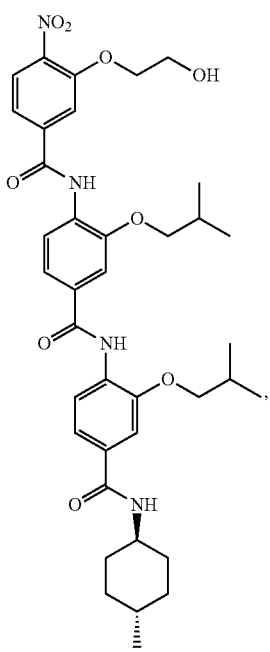
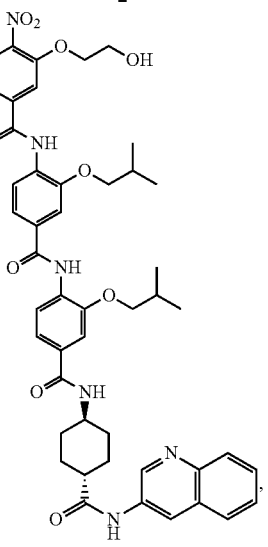

17
-continued
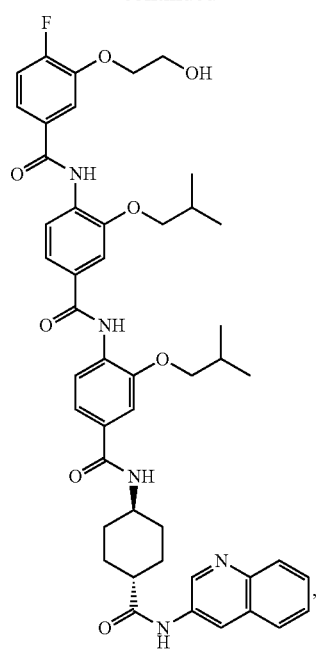
18
-continued
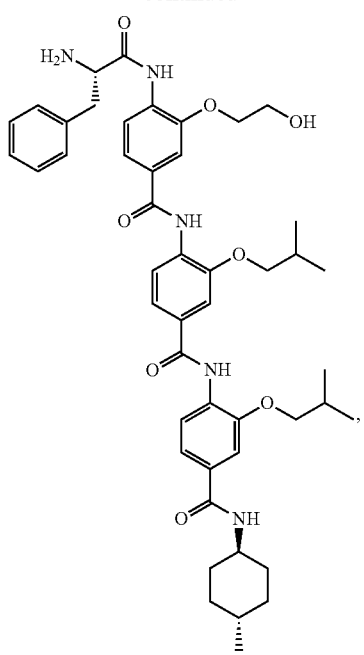
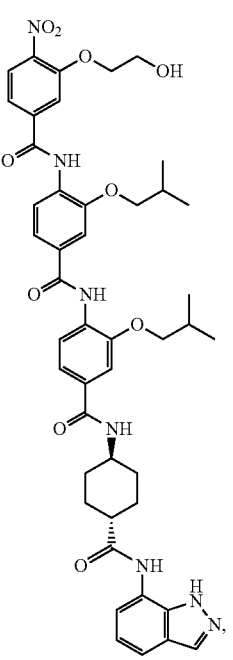

-continued
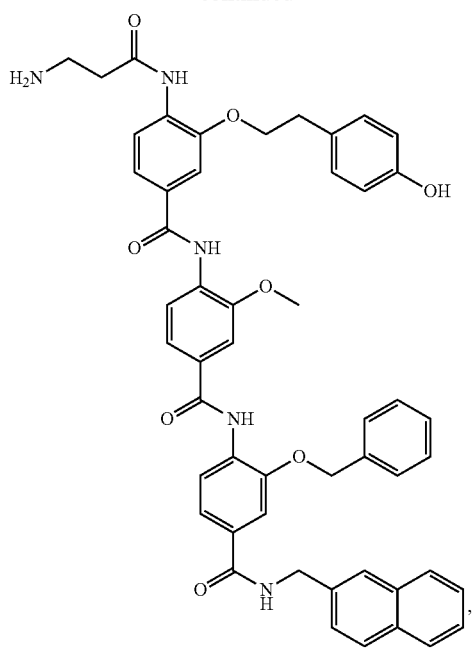
,
or a pharmaceutically acceptable salt thereof.
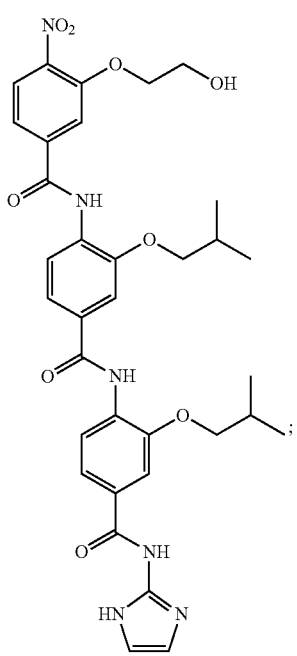
;
or a pharmaceutically acceptable salt thereof.
In some embodiments, the compound is further defined as:
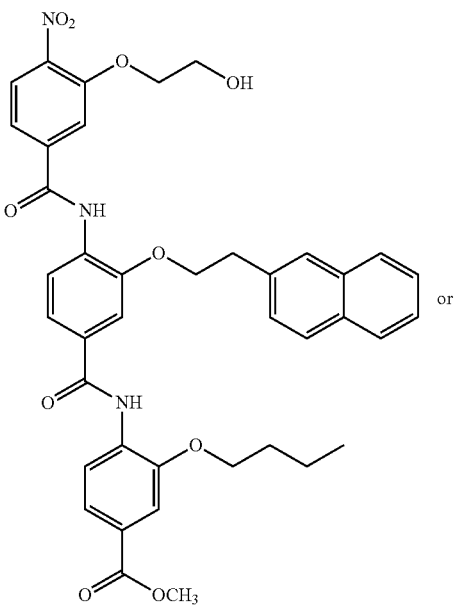 or
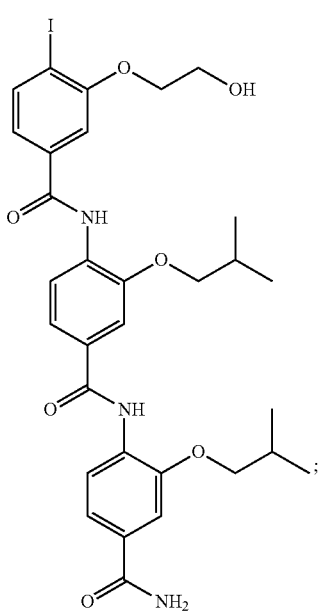
;
or a pharmaceutically acceptable salt thereof.

In some embodiments, the compound is further defined as:

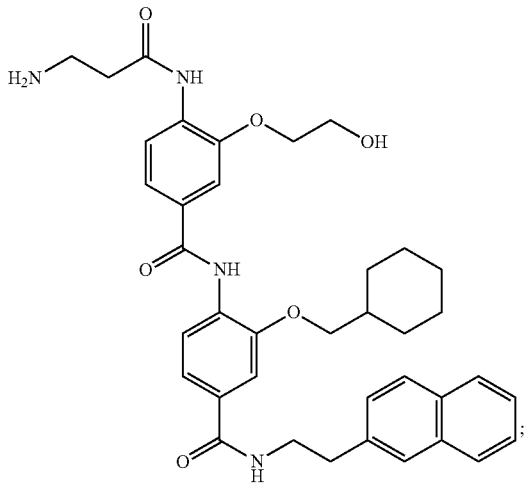 [SMILES: NCCC(=O)Nc1ccc(C(=O)Nc2ccc(C(=O)NCCc3ccc4ccccc4c3)cc2OCC2CCCCC2)cc1OCCO]

or a pharmaceutically acceptable salt thereof.

In another aspect, the present disclosure provides pharmaceutical compositions comprising:
a) a compound disclosed herein; and
b) an excipient and/or a pharmaceutically acceptable carrier.

In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In further embodiments, the composition is formulated for administration: orally, intraarterially, intratumorally, intravenously, locally, subcutaneously, topically, intraperitoneally, or via injection.

In still another aspect, the present disclosure provides methods of treating a disease or disorder in a patient in need thereof comprising administering to the patient a therapeutically effective amount of a compound or composition disclosed herein. In some embodiments, the patient is a mammal, such as a human. In some embodiments, the disease or disorder is cancer. In some embodiments, the cancer is a therapy resistant cancer. In some embodiments, the cancer is breast cancer, ovarian cancer, pancreatic cancer, or brain cancer. In further embodiments, the cancer is breast cancer, such as triple negative breast cancer. In other embodiments, the cancer is ovarian cancer. In still other embodiments, the cancer is pancreatic cancer. In yet other embodiments, the cancer is brain cancer, such as glioblastoma. In some embodiments, the cancer is an estrogen receptor-positive cancer. In other embodiments, the cancer is an estrogen receptor-negative cancer.

In some embodiments, administering comprises intravenous, intra-arterial, intra-tumoral, subcutaneous, topical or intraperitoneal administration. In some embodiments, administering comprises local, regional, systemic, or continual administration. In some embodiments, the methods further comprise providing to said subject a second anti-cancer therapy. In some embodiments, said second anti-cancer therapy is surgery, chemotherapy, radiotherapy, hormonal therapy, toxin therapy, immunotherapy, and cryotherapy. In some embodiments, said second anti-cancer therapy is provided prior to administering said compound. In other embodiments, said second anti-cancer therapy is provided after administering said compound. In still other embodiments, said second anti-cancer therapy is provided at the same time as said compound.

In some embodiments, said compound is administered daily. In some embodiments, said compound is administered daily for 7 days, 2 weeks, 3 weeks, 4 weeks, one month, 6 weeks, 8 weeks, two months, 12 weeks, or 3 months. In further embodiments, said compound is administered weekly. In some embodiments, said compound is administered weekly for 2 weeks, 3 weeks, 4 weeks, 6 weeks, 8 weeks, 10 weeks, or 12 weeks. In some embodiments, the compound or composition is administered in an amount sufficient to induce endoplasmic reticulum stress and/or shut down protein synthesis. In some embodiments, said compound acts via inducing endoplasmic reticulum stress within hours of administration and subsequently shuts down protein synthesis. In some embodiments, the level of basal endoplasmic reticulum stress or the compensatory unfolded protein response within a cell dictates the response to the drug.

The use of the word "a" or "an" when used in conjunction with the term "comprising" in the claims and/or the specification may mean "one," but it is also consistent with the meaning of "one or more," "at least one," and "one or more than one." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. The skilled artisan will understand that typically there is no limit on the number of items or terms in any combination, unless otherwise apparent from the context.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

For a more complete understanding of the features and advantages of the present disclosure, reference is now made to the detailed description of the disclosure along with the accompanying figures and in which:

FIG. 3A). Interaction with purified TLX protein was analyzed, following incubation with biotinylated-ERX-41, using avidin bead pull down (FIG. 3B). FIG. 3C shows GST-TLX was incubated with TNBC cellular lysates in the presence or absence of TK41 (1 µM) and TLX interaction with PELP1 was analyzed by GST pull down followed by westerns.

FIG. 7C) support that ERX-41 has activity against TNBC PDX tumors. *$p<0.05$; ****$p<0.001$.

FIG. 8B) support that ERX-41 has activity against ERMT tumors. *$p<0.05$; **$p<0.01$.

FIG. 10A shows the effect of TK208 against a variety of TNBC cell lines. FIG. 10B shows the effect of TK208 against a variety of ovarian cancer cell lines.

FIG. 11A shows the results of the cell viability assay. FIG. 11B shows the results of the caspase assay, demonstrating the effect of TK208 on apoptosis.

FIGS. 12A & 12C show TK208 promotes apoptosis both ovarian cancer cells. FIGS. 12B & 12D show TK208 reduces cell viability in both cancer cell lines.

FIGS. 31A-D show that oral administration of TK315 (ERX-315) decreased the growth and tumor weight of BC xenografts genetically engineered by CRISPR to express the Y537S ERα mutant in the ZR75 (FIGS. 31A-B) and MCF7 cells (FIGS. 31C-D). No change in body weight was noted.

FIGS. 32A-C show established breast PDX tumors treated either with vehicle (circles) or ERX-41 (squares). Tumor volume is graphed (left), distribution of tumor weights at necropsy (middle panel). *$p<0.05$; ****$p<0.001$.

FIGS. 33A-H. FIGS. 33A-D show ovarian cancer xenografts (ES2) treated with vehicle or TK208 (ERX-208). Tumor volume (FIG. 33A), body weight (FIG. 33B) distribution of tumor weights at necropsy (FIG. 33C) and nodules (FIG. 33D) were graphed. FIGS. 33E-H show ovarian PDX tumors were treated with vehicle or TK208 (ERX-208). Tumor volume (FIG. 33E), distribution of tumor weights at necropsy (FIG. 33F) and tumor images (FIG. 33G) and body weight (FIG. 33H) were graphed.

FIGS. 34A-C: Dose response curve of ERX-41 in multiple TNBC. cell lines using WST-1 assays (FIG. 34A) and CellTiter-Glo assays (FIG. 34B). (FIG. 34C) Time lapsed images of live cell imaging with SYTOX Green shows the effect of ERX-41 induced cell death in MDA-MB-231 at 0 h, 20 h and 30 h after treatment with either vehicle or ERX-41. Quantification of the number of dead cells over time seen with live cell imaging in MDAMB-231 and HMEC cells is shown.

FIGS. 35A-P: ERX-41 is potent against TNBC in vivo. (FIG. 35A) Following establishment of subcutaneous MDA-MB-231 xenograft tumors (200 mm$^3$), 10 mg/kg single dose ERX-41 was administered either by oral or intraperitoneal route. The tumor was harvested 0, 0, 5, 1, 5, 3, 6 and 24 h after drug administration and the drug levels assayed by LC-MS/MS and graphed. (FIGS. 35B-E) Following establishment of MDA-MB-231 xenografts in mammary fat pad in vivo (100 mm$^3$ size), daily administration of 10 mg/kg ERX-41 or vehicle control (N=8 each group) was initiated. Tumor volumes were measured using digital calipers and graphed (FIG. 35B). Tumor weights (FIG. 35C), body weights (FIG. 35D) and extirpated tumors (FIG. 35E) at end of study are also shown. (FIGS. 35F-H) Following establishment of D2A1 syngeneic xenografts in mammary fat pad in vivo (100 mm$^3$ size), daily administration of 10 mg/kg ERX-41 or vehicle control (N=8 each group) was initiated. Tumor volumes were measured using digital calipers and graphed (FIG. 35F) along with tumor weights (FIG. 35G) and body weights (FIG. 35H). (FIGS. 35I-P) Effect of ERX-41 on the growth (FIG. 35I, FIG. 35K, FIG. 35M, FIG. 35O) and tumor weights (FIG. 35J, FIG. 35L, FIG. 35N, FIG. 35P) of four distinct TNBC PDXs compared to vehicle. *p<0.05. p<0.01; *p<0.001.

FIGS. 36A-H: ERX-41 induces ER stress in TNBC. (FIGS. 36A-C) Volcano plots show the relative effect of 4 h treatment of 1 µM ERX-41 compared to vehicle in MDA-MB-231 (FIG. 36A), BT-549 (FIG. 36B) TNBC and HMEC (FIG. 36C) cell lines. (FIG. 36D) Gene ontology analyses show the top regulated pathways. (FIG. 36E) Heatmap of the top ER stress and UPR genes in these three TNBC cell lines after 2 h and 4 h treatment with 1 µM ERX-41 treatment. (FIG. 36F) Electron microscopy of MDA-MB-231 and HMEC cells shows the effect of ERX-41 on the ER (outlined with yellow arrowheads) at 4 h. (FIG. 36G) Time course of the effect of 1 µM ERX-41 on the mRNA expression of canonical ER stress genes, HSPA5 and DDIT3 and UPR stress sensor-sXBP1 in MDA-MB-231, BT-549 and HMEC cells. (FIG. 36H) Western blotting shows the time course of the effect of 1 µM ERX-41 or ERX-11 on the expression of UPR proteins in SUM-159 cells.

FIGS. 37A-J: The molecular target of ERX-41 in TNBC is LIPA. (FIG. 37A) Visualization of aCRISPR/Cas9 screen in MDA-MB-231 cells shows the genes associated with resistance to ERX-41. (FIG. 37B) Knockout clones of LIPA, ACACA, TMEM208, SOAT1 and ARID1A were generated in MDA-MB-231 cells and evaluated for response to ERX-41 using doseresponse curves using CellTiter-Glo assays in vitro. (FIGS. 37C-D) Effect of knockout of LIPA in SUM-159 (FIG. 37C) and MDA-MB436 (FIG. 37D) on dose response curve to ERX-41 using CellTiter-Glo assays in vitro. (FIGS. 37E-F) Dose response curves of SUM-159 parental cells and clones with LIPA KO to thapsigargin (FIG. 37E) and paclitaxel (FIG. 37F). (FIGS. 37G-H) Live cell imaging studies with SYTOX Green to examine ability of 1 µM ERX-41 to induce cell death in parental SUM-159 and SUM-159 clones with LIPA KO, with quantitation (FIG. 37G) and time-lapsed photomicrographs at 0 h and 30 h ((FIG. 37H). (FIGS. 37I-J) SCID mice were implanted with either parental SUM-159 or SUM-159 clones with LIPA KO (n=6, each group) and tumors were allowed to establish (150 mm$^3$). Following daily intraperitoneal administration of 10 mg/kg ERX-41, tumor sizes were measured and graphed (FIG. 37I), along with mice body weights (FIG. 37J). *p<0.05. p<0.01; *p<0.001.

FIGS. 38A-E: LIPA is a viable molecular target in TNBC. (FIG. 38A) Kaplan-Meier curves show the correlation between expression levels of LAL with survival outcomes using a TCGA dataset with numerical tabulation below. (FIGS. 38B-D) Following surgical extirpation, primary TNBC tumors were cultured ex vivo either with vehicle or 1 µM ERX-41, as shown by the schematic (FIG. 38B). The effect on proliferation index (ki67) (FIG. 38C) and apoptosis markers (cleaved caspase 3) (FIG. 38D) is graphed. Representative immunohistochemical images of the effect of ERX-41 on ki67, cleaved caspase 3 and UPR genes shown (FIG. 38E).

FIGS. 39A-N: (FIGS. 39A-E) Predicted binding mode of ERX-41 (colored in green) on the human lysosomal acid lipase (LAL, PDB code: 6V7N, LXXLL (SEQ ID NO: 1) domain colored in orange). (FIG. 39F) PDB structure of LAL protein showing relative positions of the catalytic domain (with $H_{274}Y$ MT) and the LXXLL (SEQ ID NO: 1) domain (L242P MT). (FIG. 39G) Evaluation of the effect of ERX-41 and lalistat (known lipase inhibitor) on lipase activity of parental SUM-159 (WT) and SUM-159 cells with LIPA KO. (FIG. 39H) Evaluation of basal lipase activity in parental SUM-159 (WT), SUM-159 cells with LIPA KO (KO), SUM-159 cells with LIPA KO and with reconstitution of either WT LIPA (KO+WT), $H_{274}Y$ MT-LIPA (KO+$H_{274}Y$), DLXXLL (SEQ ID NO: 2) MT-LIPA (KO+DLXXLL (SEQ ID NO: 2)) or L242P MT-LIPA (KO+L242P). Protein expression of LAL and control vinculin in these cells are shown below (FIG. 39I) Cellular lysates from described SUM-159 cells were incubated with biotinylated ERX-11 or biotinylated ERX-41 and then subject to a streptavidin column. Elutants were then evaluated for LIPA pulldown by western blotting. (FIG. 39J) Dose response curve to increasing concentrations of ERX-41 in described SUM-159 cells. (FIGS. 39K-M) Effect of vehicle or 1 µM ERX-41 on induction of UPR genes at the protein level (FIG. 39K) or RNA level (FIGS. 39L-M). (FIG. 39N) Model shows that ERX-41 binds to the LXXLL (SEQ ID NO: 1) domain of LAL protein and induces ER stress resulting in shut down of de novo protein synthesis and cell death. *p<0.05. p<0.01; *p<0.001.

FIGS. 42A-D: OCa cells were treated with ERX-11 (FIG. 42A) or ERX-208 (FIG. 42B). Primary OCa cells derived from ascites were treated with ERX-208 for 72 h (FIG. 42C) and cell viability by MTT assays. (FIG. 42D) Effect of ERX-208 on viability of IOSE cells was measured using MTT assays and TOV21G was used as +ve control.

FIG. 43: ES2 and SKOV3 cells were treated with ERX-208 and its effect on cell survival was measured using colony formation assays. ****$p<0.0001$.

FIGS. 48A-F: OCa PDX (n=6) tumors were established in the flanks of NSG mice. When the tumors reached 200 mm$^3$, treatment with vehicle or 10 mg/kg/day/i.p. ERX-208 was initiated. (FIG. 48A) Tumor volume, (FIG. 48B) tumor weight, (FIG. 48C) tumors picture, and
(FIG. 48D) body weight is shown. (FIGS. 48E-F) IHC analysis of GRP 78 as a marker of ER stress *$p<0.05$; $p<0.01$, **$p<0.0001$.

FIGS. 49A-F: (FIGS. 49A-B) Effect of ERX-208 on chemotherapy resistant OCa cells was measured by MTT and apoptosis assay. (FIGS. 49C-F) Platinum-resistant PDX tumors were treated with vehicle or ERX-208 (10 mg/kg/day/i.p). Tumor volume (FIG. 49C), weights (FIG. 49D), tumors picture (FIG. 49E), bodyweights (FIG. 49F) are shown.  $P<0.01$, *$p<0.001$ ****$p<0.0001$.

FIGS. 51A-51C: Structure of TX-542 (FIG. 51A) with modeled fit on Y537S MT-ERα (FIG. 51B) and D538G MT-ERα (FIG. 51C).

FIGS. 59A-B: MCF-7 MT-ERa D538G and Y537S xenograft tumors were injected into the mammary fat pad of nude mice. Once the tumors were established (100 mm$^3$), treatment with either vehicle or TX-542 (10 mg/kg/ip) was commenced and their effect on tumor growth and mice body weights were graphed (n=9 per group).

FIG. 60: Effect of 200 nM TX-542 on ER stability in multiple WT-ERα and MT-ERα BC cell lines at 24 h.

(FIG. 61A) Volcano plot shows that 1189 genes were upregulated (log 2FC>0.5, $p<0.010$ and 1029 genes were down regulated (log 2FC<−0.5, $p<0.01$). GSEA analyses indicate that TX-542 represses the expression of estradiol-induced genes (FIG. 61B-C), induces the expression of estradiol-repressed genes (FIG. 61D) and the expression of apoptotic genes (FIG. 61E). Effect of TX-542 on a luciferase reporter-driven by three copies of ERE in MCF-7 MT-ERα Y537S and D538G cells (FIG. 61F). Effect of TX-542 on MT-ERα DNA binding to progesterone (PGR) promoter 4 h after estradiol induction in MCF-7 MT-ERα Y537S cells using ChIP assays is shown.

FIGS. 65A-65E: A. Lead optimization strategy: ERX-11 (pink) interacts with Y537S MT-ERα (pdb: 6CBZ): following molecular modeling and simulation of >250,000 ERX-11 analogs, ~1000 analogs were synthesized and tested for activity in vitro. Modeled structure of the lead compound ERX-315 (blue) binding to Y537S MT-ERα LBD (FIG. 65A) and to the D538G MT-ERα LBD is shown (FIG. 65B). (FIG. 65C) Chemical structure of ERX-315. (FIG. 65D) Direct binding of ERX-315 to ERα LBD was determined using LanthaScreen® TR-FRET ERα coactivator assay using indicated dilution of ERX315 in the presence of 3.5 nM ER Alpha-LBD (GST), 250 nM Fluorescein-PGC1a LXXLL (SEQ ID NO: 1) peptide, 5 nM Tb anti-GST antibody, and 10 nM estradiol. 4-hydroxytamoxifen was used as a positive control. (FIG. 65E) Table 3 shows IC$_{50}$ of ERX-11 and its analogs ERX-314 and ERX-315 in vitro against MCF-7 and ZR-75 BC cell lines genetically engineered to express either Y537S ERa MT or the D538G ERα MT. ERX-314 has a methyl group instead of the fluoro group at the N-terminus of ERX-315.

FIGS. 66A-D: (FIG. 66A) Effect of ERX-315 on ERa DNA binding on the promoters of 5 canonical ERα-regulated genes with ERa ChIP in MCF-7 expressing D538G MT-ERα in the absence and presence of estradiol. (FIG. 66B) Heatmap shows the effect of ERX-315 on the transcriptional programme within MCF-7 expressing D538G MT-ERα, from RNA-sequencing studies. (FIG. 66C) Gene ontogeny analyses of the RNA-sequencing studies indicate that estrogen-upregulated genes are downregulated by ERX-315, (FIG. 66D) Effect of ERX-315 on ER transcriptional activity measured using ERE reporter assay in MCF-7 cells expressing D538G MT-ERα.

FIGS. 67A-67D: ERX-315 but not ERX-314 decreases global new protein synthesis at 16 h in MCF-7 expressing mutant D538G but not HMEC cells as shown by western blots for puromycin labeled nascent proteins (FIG. 67A). ERX-315 but not ERX-314 induces uncompensated UPR resulting in LC3B activation (FIG. 67B). ERX-315 decreases expression of ERα MCF-7 cells with MT-ERα, both the Y537S and D538G mutants (FIG. 67C), around 12-16 h (FIG. 67D). ERX-315 decease MT-ERa expression and induce ER stress as seen by induction of LC3 for the Y537S and D538G MT-ERa. In contrast, neither fulvestrant nor GDC-0810 consistently degrade MT-ERa nor induce LC3.

FIGS. 69A-F: Oral administration of ERX-315 in captisol decreased the growth of BC xenografts genetically engineered by CRISPR to express the Y537S MT-ERα in the ZR75 (FIG. 69A) and MCF7 cells (FIG. 69D). Following establishment of tumors, mice (n=6/group) were randomized and treated for 5 days/week with either 10 mg/kg/oral of ERX-315 or vehicle. Tumor sizes were substantially decreased with drug treatment (FIG. 69B, FIG. 69C and FIG. 69E), while no change in body weight was noted (FIG. 69F).

Figure 1:
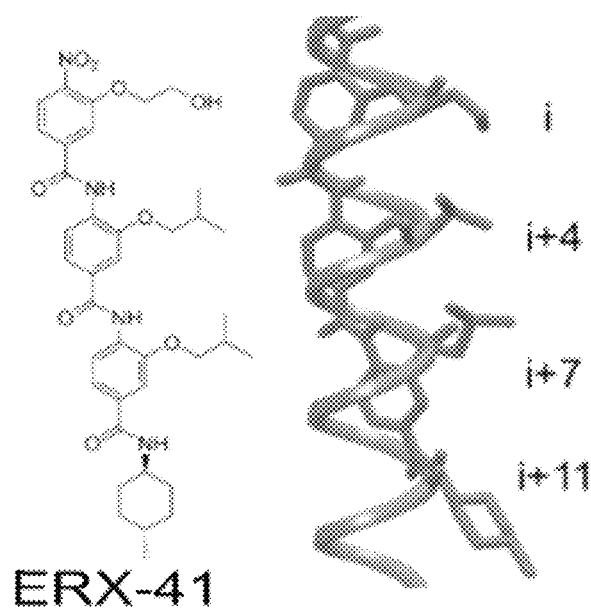
FIG. 1 shows primary TK41 (i.e., ERX-41) structure and low energy helical conformation.

70B) and CHOP (FIG. 70C) expression 24 h after a single oral 10 mg/kg ERX-315 dose, compared to tumors treated with DMSO.

DETAILED DESCRIPTION

The present disclosure relates oligo-benzamides which are modified with a cyclohexylamide group at the southern terminus of the compound. These compounds have been shown to binding to the hormone receptors in one or more cancer cells such as breast cancer. These compounds may show one or more preferential properties relative to those known in the art, such as improved efficiacy. In addition, the inventors found that ERX-41 and ERX-208 have a previously unknown molecular target (LIPA) and mechanism of action (induction of ER stress) and therefore should have utility in treating TNBC and ovarian cancers. Importantly, the expression of LIPA mRNA appears to be highest in renal, breast, pancreatic, ovarian, glioma and lung cancers (Human protein atlas). Preliminary studies indicate that multiple tumors, including breast, ovarian, pancreatic and glioblastoma, with high levels of LIPA expression are responsive to ERX-41 and the induction of ER stress. These data indicate that the ability of ERX-41 and ERX208 to target LIPA may extend its utility to multiple tumor types. Further, these studies showed that ERX-245 and ERX-315 are uniquely potent against tumors expressing the mutant estrogen receptor that are now being discovered in many hormone driven diseases including breast, endometrial, ovarian cancer and endometriosis.

These and other details are described below.

I. Compounds of the Present Disclosure

| Compoun ID | Structure |
|---|---|
| TK41 (ERX-41) | 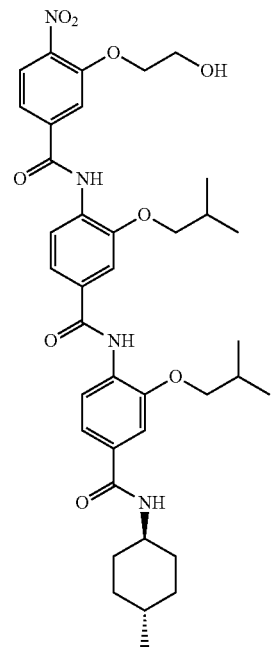 [SMILES: Cc1ccc(C(=O)Nc2ccc(C(=O)Nc3ccc(C(=O)N[C@H]4CC[C@H](C)CC4)cc3OCC(C)C)cc2OCC(C)C)cc1OCCO] |

| Compound ID | Structure |
|---|---|
| TK314 | |
| TK308 | |
| Compound ID | Structure |
|---|---|
| TK208 (ERX-208) | |
| TK315 (ERX-315) | |
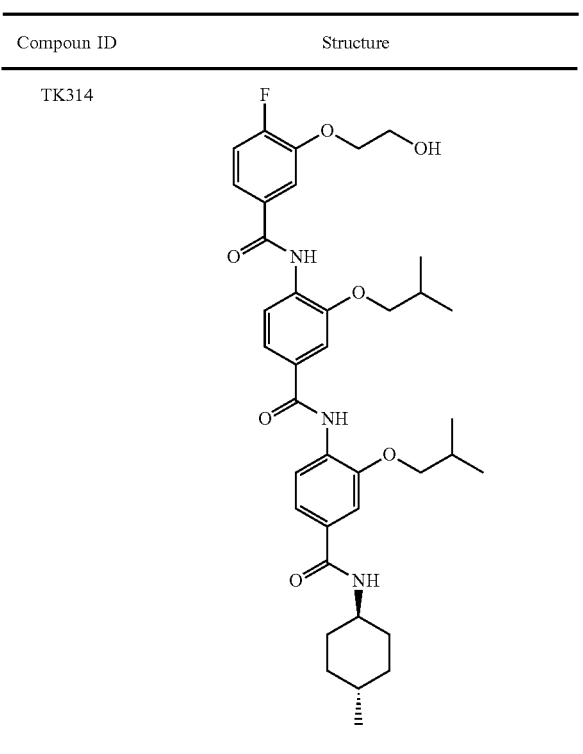
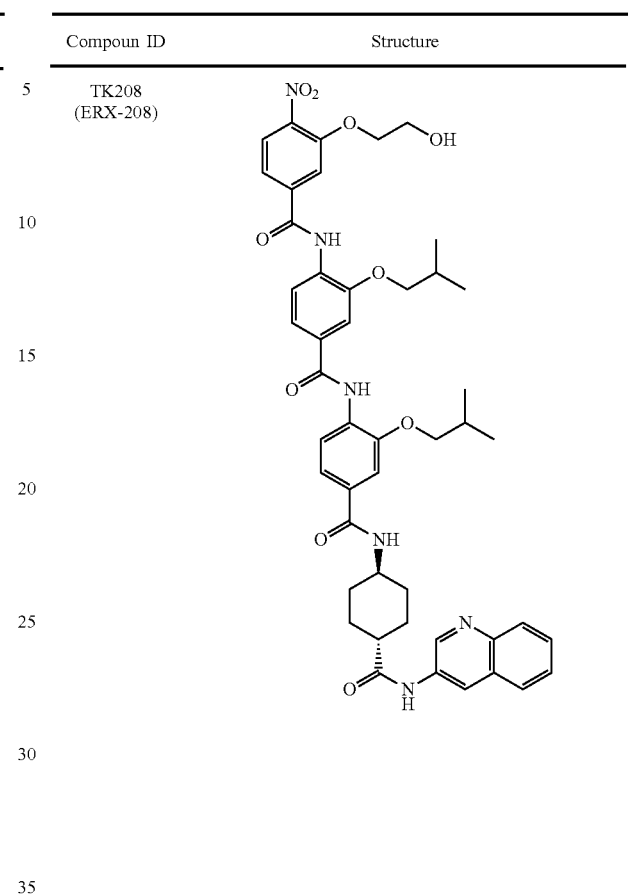

33
-continued

| Compoun ID | Structure |
|---|---|
| TK309 | 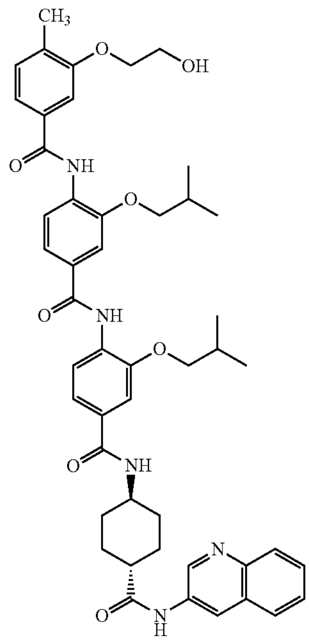 [SMILES: Cc1ccc(C(=O)Nc2ccc(C(=O)Nc3ccc(C(=O)N[C@H]4CC[C@H](C(=O)Nc5cnc6ccccc6c5)CC4)cc3OCC(C)C)cc2OCC(C)C)cc1OCCO] |
| TK207 | 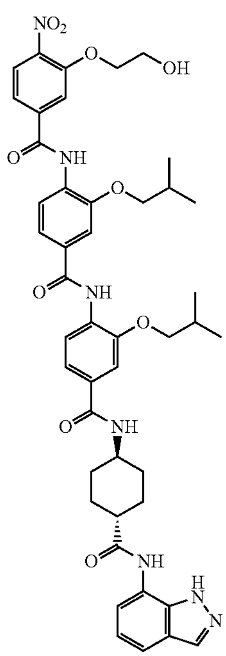 [SMILES: CC(C)COc1cc(C(=O)Nc2ccc(C(=O)N[C@H]3CC[C@H](C(=O)Nc4cccc5cn[nH]c45)CC3)cc2OCC(C)C)ccc1NC(=O)c1ccc([N+](=O)[O-])c(OCCO)c1] |

34
-continued

| Compoun ID | Structure |
|---|---|
| TK245 (TX-542) | 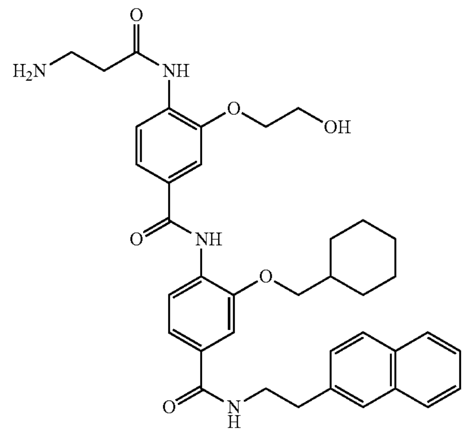 [SMILES: NCCC(=O)Nc1ccc(C(=O)Nc2ccc(C(=O)NCCc3ccc4ccccc4c3)cc2OCC2CCCCC2)cc1OCCO] |
| TK227 | 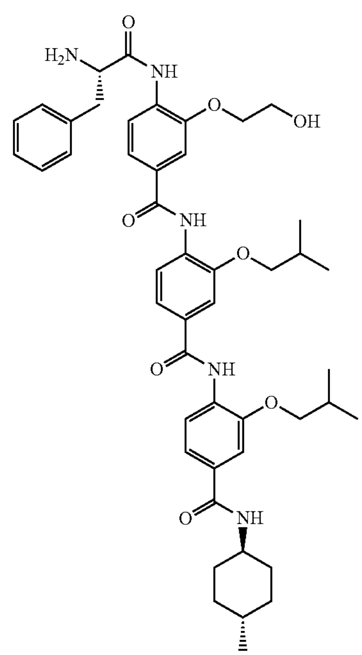 [SMILES: CC(C)COc1cc(C(=O)Nc2ccc(C(=O)N[C@H]3CC[C@H](C)CC3)cc2OCC(C)C)ccc1NC(=O)c1ccc(NC(=O)[C@@H](N)Cc2ccccc2)c(OCCO)c1] |

| Compoun ID | Structure |
|---|---|
| TK296 | 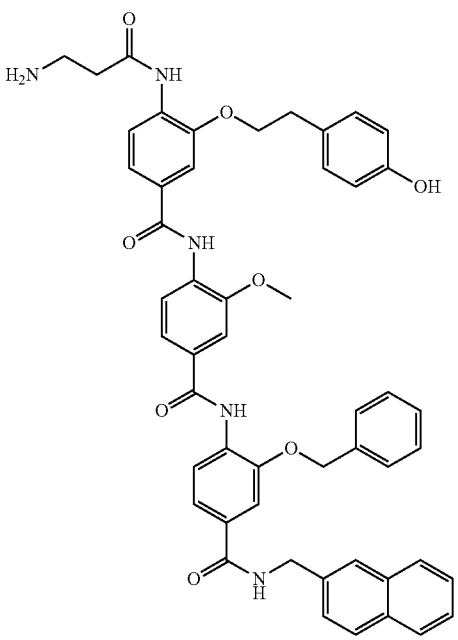 [SMILES: COc1cc(C(=O)Nc2ccc(C(=O)NCc3ccc4ccccc4c3)cc2OCc2ccccc2)ccc1NC(=O)c1ccc(NC(=O)CCN)c(OCCc2ccc(O)cc2)c1] |
| YL144 | 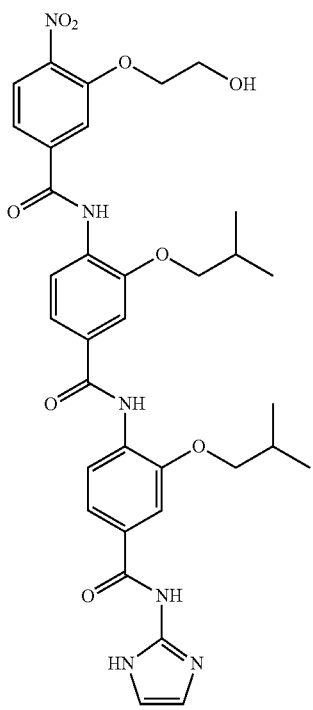 [SMILES: CC(C)COc1cc(C(=O)Nc2ncc[nH]2)ccc1NC(=O)c1ccc(NC(=O)c2ccc([N+](=O)[O-])c(OCCO)c2)c(OCC(C)C)c1] |
| YL1113 | 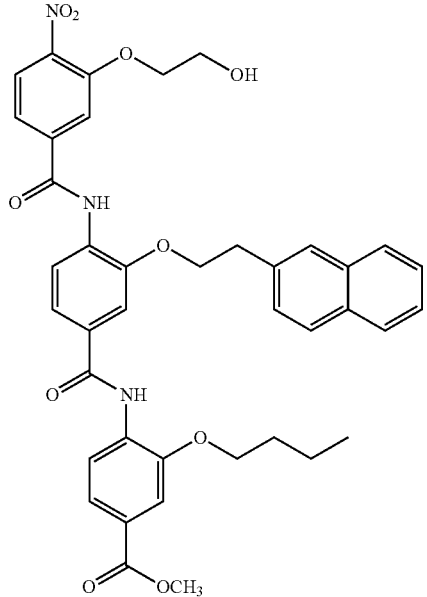 [SMILES: CCCCOc1cc(C(=O)OC)ccc1NC(=O)c1ccc(NC(=O)c2ccc([N+](=O)[O-])c(OCCO)c2)c(OCCc2ccc3ccccc3c2)c1] |
| YL1116 | 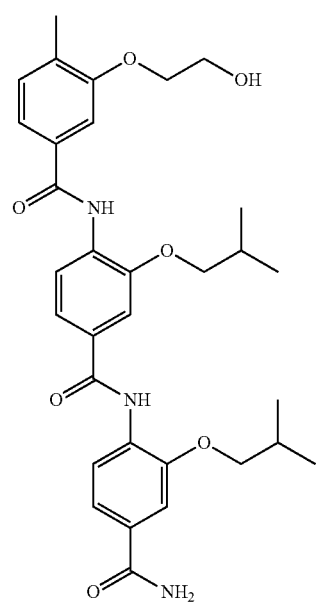 [SMILES: Cc1ccc(C(=O)Nc2ccc(C(=O)Nc3ccc(C(N)=O)cc3OCC(C)C)cc2OCC(C)C)cc1OCCO] |

The compounds of the present disclosure are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, isotopes of fluorine include $^{18}F$, and isotopes of carbon include $^{13}C$ and $^{14}C$.

In some embodiments, compounds of the present disclosure function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C+O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

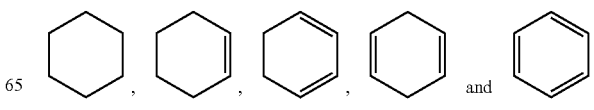

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ~~~ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol " ◂■ " means a single bond where the group attached to the thick end of the wedge is "out of the page." The symbol " ⦀⦀⦀ " means a single bond where the group attached to the thick end of the wedge is "into the page". The symbol " ~~~ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

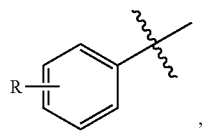

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

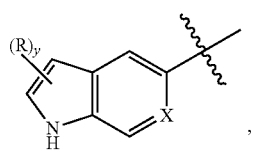

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/ groups, the carbon atoms can be joined together in straight chains, branched chains, or non-aromatic rings (alicyclic).

Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

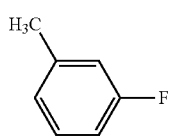

is also taken to refer to

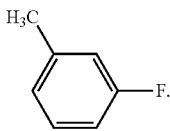

Aromatic compounds may also be depicted using a circle to represent the delocalized nature of the electrons in the fully conjugated cyclic π system, two non-limiting examples of which are shown below:

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

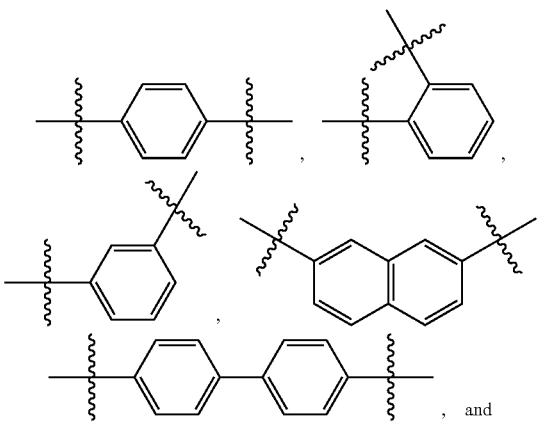

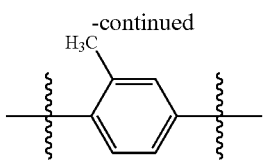

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heteroaralkyl" refers to the monovalent group -alkanediyl-heteroaryl, in which the terms alkanediyl and heteroaryl are each used in a manner consistent with the definitions provided above. Non-limiting examples are: pyridinylmethyl and 2-quinolinyl-ethyl. The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkylamino" refers to the group —NHR, in which R is an alkyl, as that term is defined above. Non-limiting examples include: —NHCH$_3$ and —NHCH$_2$CH$_3$. The term "dialkylamino" refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The terms "dicycloalkylamino", "dialkenylamino", "dialkynylamino", "diarylamino", "diaralkylamino", "diheteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)CH$_3$.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

III. Oligo-Benzamides and Methods of Synthesis

The present disclosure provides synthetic molecules which present the essential functionalities of corresponding peptide ligands in the proper three dimensional orientation that enables specific protein interactions, leading to either stimulation or inhibition of protein-mediated functions.

Peptidomimetics (also known as peptide mimetics) are small organic compounds which lack the peptide backbone of native peptides. Despite this modification, they still retain an ability to interact with corresponding receptors or enzymes by presenting essential chemical functionalities (i.e., pharmacophores) in characteristic three-dimensional patterns which are complimentary to the target proteins (Marshall, 1993; Ahn et al., 2002). Thereby, peptidomimetics potentially combine the advantages of peptides (e.g., high efficacy and selectivity, low side effects) and small organic molecules (e.g., high enzymatic stability and oral bioavailability).

To mimic α-helices, the present disclosure provides an oligo-benzamide scaffold that is rigid in structure and place and orient substituents as an α-helix does. Substitution on the rigid tris-benzamide, for instance, allowed easy placement of three functional groups ($R_{2-4}$) corresponding to the side chains of amino acids found at the i, i+4, and i+7 positions of an ideal α-helix. Furthermore, the present inventors have developed a facile synthetic route to prepare a number of tris-benzamides to represent α-helical segments of target proteins. U.S. Patent Publication 2009/0012141, incorporated herein by reference, discloses a variety of oligo-benzamide compounds and methods of synthesis therefor.

More specifically, the present disclosure provides an oligo-benzamide peptidomimetic compound as illustrated includes 2 or 3 optionally substituted benzamides—so called "bis" and "tris" benzamides. In addition, linkages between the optionally substituted benzamides may be varied as necessary including ester, thioester, thioamide, trans-ethylene, ethyl, methyloxy, methylamino, hydroxyethyl, carbamate, urea, imide, hydrozido, aminoxy, or other linkages known to the skilled artisan. And, the oligo-benzamide peptidomimetic compound may be attached to amino acids, oligopeptides, optionally substituted alkyl, or other structures known to the skilled artisan.

The substitution on the substituted benzamide is generally on a benzene ring and may be on the 2, 3, 4, 5, or 6 position of each of the benzene rings. The substitutions may be at the same position on each of the benzamide rings but may also be at different positions on each of the benzene rings. For example, the substitution is connected to the benzamide ring by a chemical linkage including ether, thioether, amine, amide, carbamate, urea, and carbon-carbon (single-, double-, and triple-) bonds, and the substitution comprises optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present disclosure also provides an oligo-benzamide peptidomimetic compound that includes at least two optionally substituted benzamides, with each of the substituted benzamides having one substitution on a benzene ring. The substitutions are individually attached to the benzene rings of the oligo-benzamide peptidomimetic compound by a chemical linkage including ether, thioether, amine, amide, carbamate, urea, and carbon-carbon (single-, double-, and triple-) bonds. The substitutions generally include optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

Figures 2A, 2B, 2C:
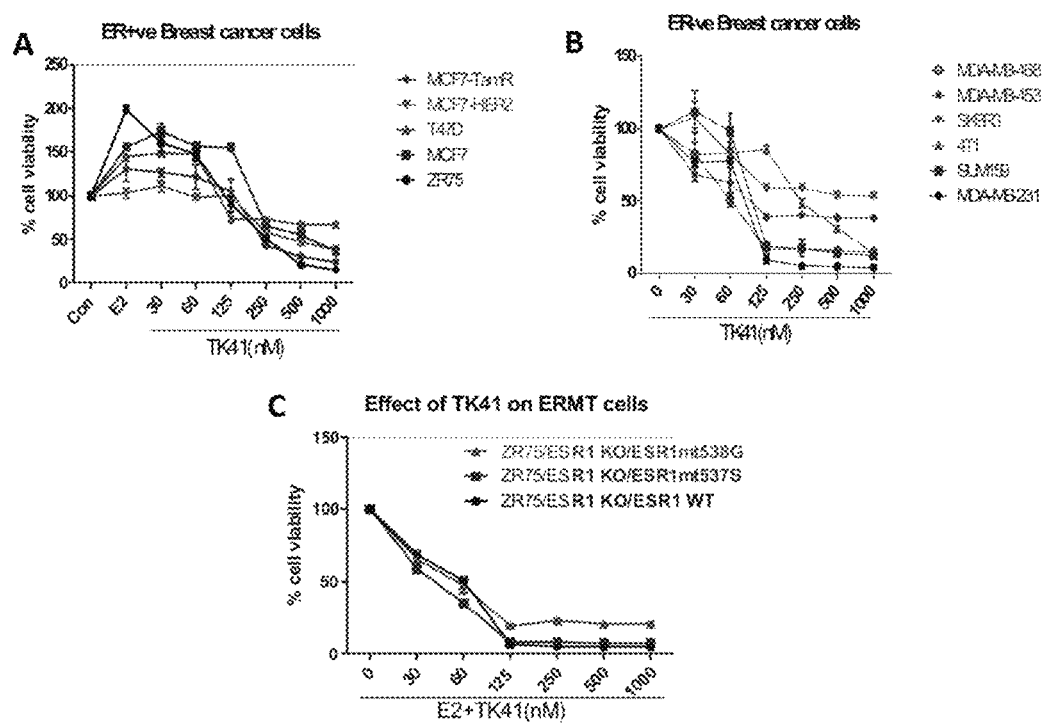
FIGS. 2A-2C show the potency of TK41 ($IC_{50}$ from 50-500 nM) on estrogen receptor-positive (FIG. 2A), estrogen receptor-negative (FIG. 2B) and therapy resistant ERMT (FIG. 2C) cells determined by MTT assay.
Figures 3A, 3B, 3C:
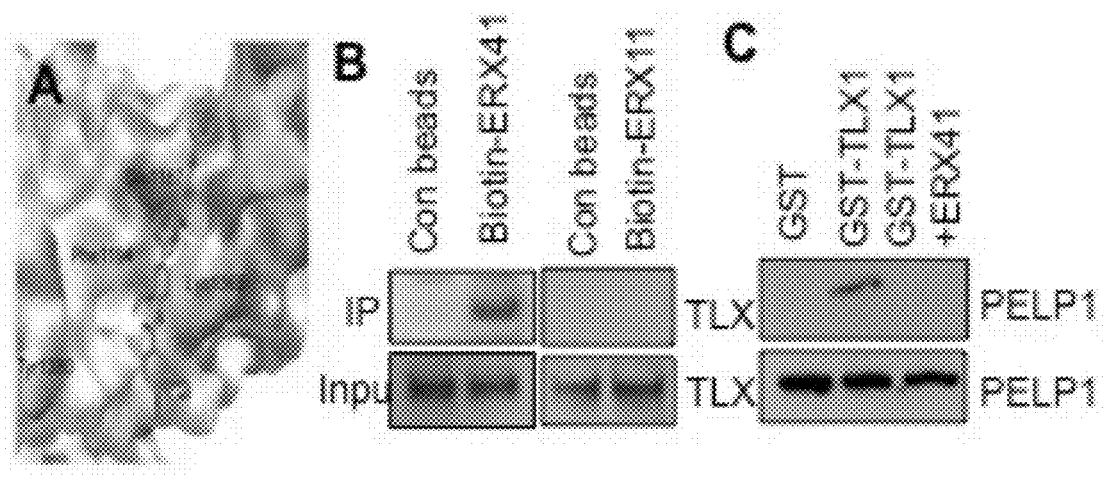
FIGS. 3A-3C show TK41 (i.e., ERX-41) docked on TLX (MacroModel and AutoDock.
Figures 4A, 4B, 4C:
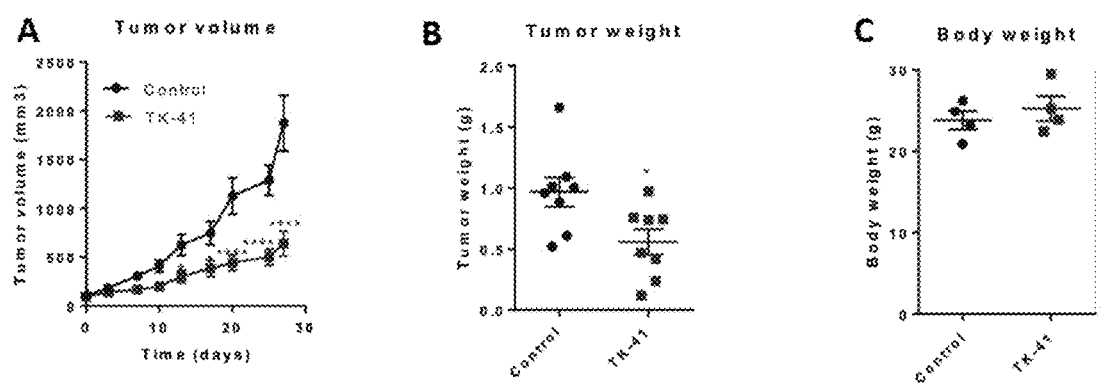
FIGS. 4A-4C show the effect of TK41 on estrogen receptor-positive (ER+ve) tumor growth. ZR75 (ER+ve; n=18) xenografts were established in nude mice and treated with either vehicle (circle markers) or 10 mg/kg/day TK41 (square markers) administered as an oral gavage in Captisol®. Effect on tumor volume is shown in FIG. 4A. Effect on tumor weight is shown in FIG. 4B. Comparison of mice body weights is shown in bar graphs (FIG. 4C). *$p<0.05$; ****$p<0.001$.
Figures 5A, 5B, 5C:
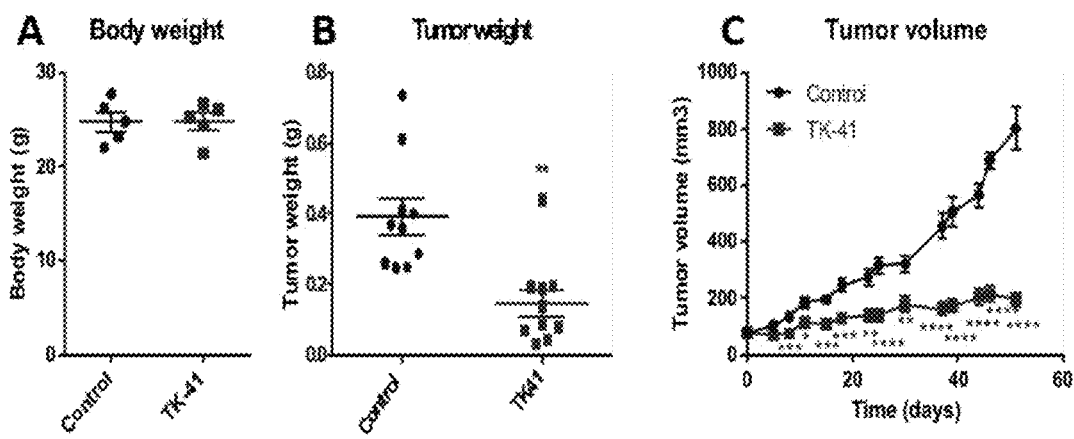
FIGS. 5A-5C show the effect of TK41 on triple negative breast cancer xenograft tumors. MDA-MB-231 (TNBC; n=10) xenografts were established in nude mice and treated with either vehicle (circle markers) or 10 mg/kg/day TK41 (square markers) administered as an oral gavage in Captisol®. Comparison of mice body weights is shown in bar graphs (FIG. 5A). Effect on tumor weight is shown in FIG. 5B. Effect on tumor volume is shown in FIG. 5C. Photographs of individual tumors at necropsy supports the effect of TK41 on TNBC. *$p<0.05$; ****$p<0.001$.
Figure 6:
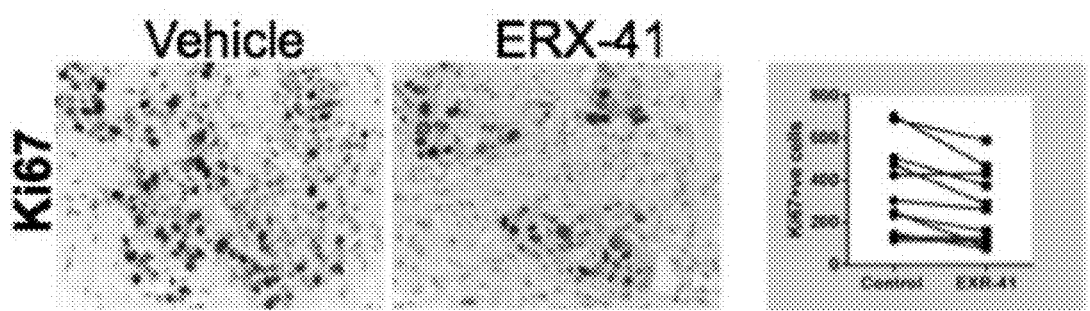
FIG. 6 shows the effect of ERX-41 (TK41) on proliferation of primary patient derived TNBC ex vivo culture tissues, as measured by ki67 staining. Cumulative series of n=11 experiments is shown.
Figures 7A, 7B, 7C:
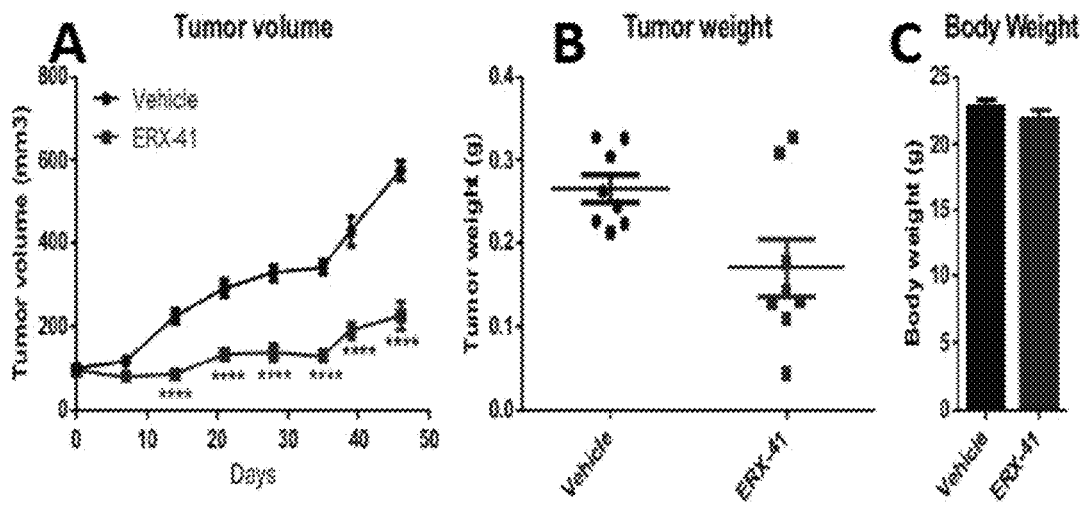
FIGS. 7A-7C show effect of TK41 in triple negative breast cancer in patient derived xenografts. TNBC patient derived xenografts (n=6) were established in nude mice and treated with vehicle (circle markers) or 10 mg/kg/day/oral ERX-41 (i.e., TK41; square markers). Tumor volume (FIG. 7A), distribution of tumor weights at necropsy (FIG. 7B), and mice body weights (bar graph.

U.S. Patent Publication 2009/0012141 provides synthesis schemes to prepare α-helix mimetic compounds of the present disclosure, for example, in FIG. 2 therein. A specific example in that document provides fifteen α-helix mimetic compounds made starting with a 4-amino-3-hydroxybenzoic acid compound 7, which was converted to an N—Ac protected methyl ester compound 8. Various alkyl groups were introduced to the hydroxyl group using a variety of alkyl halides and a base (e.g., NaOH) known to the skilled artisan. After the alkylation reaction, the methyl ester compound 9 was hydrolyzed using a base (like LiOH), and methyl 4-amino-3-hydroxybenzoate compound 10 was coupled to the free benzoic acid using a coupling reagent (like BOP), resulting in a benzamide compound 11 containing one alkyl group corresponding to the i position of a helix. These steps were repeated to synthesize oligo-benzamide compounds. Those of skill in the art would understand the broader applicability of such methods in the synthesis of other compounds such as those disclosed herein.

Additional peptidomimetics as well as methods for their manufacture are disclosed in Raj et al., 2017, which is incorporated herein by reference. One of skill in the art appreciates that the synthetic methods discosed in Raj et al., 2017 may be employed to contruct the compounds of the present disclosure.

IV. Pharmaceutical Formulations and Methods of Treatment

A. Formulations

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals.

In some embodiments, the human equivalent dose (HED) in mg/kg can be calculated in accordance with the following formula (see, e.g., Reagan-Shaw et al., *FASEB J.,* 22(3): 659-661, 2008, which is incorporated herein by reference):

$$HED(mg/kg) = \text{Animal Dose}(mg/kg) \times (\text{Animal } K_m / \text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the patient has eaten or will eat.

B. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the $HER_2$ mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy.

Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999; however, underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwise-healthy women for breast cancer in an attempt to achieve an earlier diagnosis. The assumption is that early detection will improve outcomes. A number of screening tests have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

C. Ovarian Cancer

Ovarian cancer is a cancerous growth arising from different parts of the ovary. Most (>90%) ovarian cancers are classified as "epithelial" and were believed to arise from the surface (epithelium) of the ovary. However, recent evidence suggests that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

In 2004, in the United States, 25,580 new cases were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid. Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer is classified according to the histology of the tumor, obtained in a pathology report. Histology dictates many aspects of clinical treatment, management, and prognosis. Surface epithelial-stromal tumour, also known as ovarian epithelial carcinoma, is the most common type of ovarian cancer. It includes serous tumour, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers, because most germ cell tumors are teratomas and most teratomas are benign (see Teratoma). Germ cell tumor tends to occur in young women and girls. The prognosis depends on the specific histology of germ cell tumor, but overall is favorable. Mixed tumors, containing elements of more than one of the above classes of tumor histology.

Ovarian cancer can also be a secondary cancer, the result of metastasis from a primary cancer elsewhere in the body. Seven percent of ovarian cancers are due to metastases while the rest are primary cancers. Common primary cancers are breast cancer and gastrointestinal cancer (a common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c).

This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body. The AJCC/TNM staging system also contains a Tx and a Nx sub-category which indicates that the extent of the tumor cannot be described because of insufficient data, respectively the involvement of the lymph nodes cannot be described because of the same reason.

Ovarian cancer, as well as any other type of cancer, is also graded, apart from staged. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

The signs and symptoms of ovarian cancer are most of the times absent, but when they exist they are nonspecific. In most cases, the symptoms persist for several months until the patient is diagnosed.

A prospective case-control study of 1,709 women visiting primary care clinics found that the combination of bloating, increased abdominal size, and urinary symptoms was found in 43% of those with ovarian cancer but in only 8% of those presenting to primary care clinics.

The exact cause is usually unknown. The risk of developing ovarian cancer appears to be affected by several factors. The more children a woman has, the lower her risk of ovarian cancer. Early age at first pregnancy, older age of final pregnancy and the use of low dose hormonal contraception have also been shown to have a protective effect. Ovarian cancer is reduced in women after tubal ligation.

The relationship between use of oral contraceptives and ovarian cancer was shown in a summary of results of 45 case-control and prospective studies. Cumulatively these studies show a protective effect for ovarian cancers. Women who used oral contraceptives for 10 years had about a 60% reduction in risk of ovarian cancer. (risk ratio 0.42 with statistical significant confidence intervals given the large study size, not unexpected). This means that if 250 women took oral contraceptives for 10 years, 1 ovarian cancer would be prevented. This is by far the largest epidemiological study to date on this subject (45 studies, over 20,000 women with ovarian cancer and about 80,000 controls).

The link to the use of fertility medication, such as Clomiphene citrate, has been controversial. An analysis in 1991 raised the possibility that use of drugs may increase the risk of ovarian cancer. Several cohort studies and case-control studies have been conducted since then without demonstrating conclusive evidence for such a link. It will remain a complex topic to study as the infertile population differs in parity from the "normal" population.

There is good evidence that in some women genetic factors are important. Carriers of certain mutations of the BRCA1 or the BRCA2 gene are notably at risk. The BRCA1 and BRCA2 genes account for 5%-13% of ovarian cancer-sand certain populations (e.g. Ashkenazi Jewish women) are at a higher risk of both breast cancer and ovarian cancer, often at an earlier age than the general population. Patients with a personal history of breast cancer or a family history of breast and/or ovarian cancer, especially if diagnosed at a young age, may have an elevated risk.

A strong family history of uterine cancer, colon cancer, or other gastrointestinal cancers may indicate the presence of a syndrome known as hereditary nonpolyposis colorectal cancer (HNPCC, also known as Lynch syndrome), which confers a higher risk for developing ovarian cancer. Patients with strong genetic risk for ovarian cancer may consider the use of prophylactic, i.e. preventative, oophorectomy after completion of childbearing. Australia being member of International Cancer Genome Consortium is leading efforts to map ovarian cancer's complete genome.

Ovarian cancer at its early stages(I/II) is difficult to diagnose until it spreads and advances to later stages (III/IV). This is because most symptoms are non-specific and thus of little use in diagnosis.

When an ovarian malignancy is included in the list of diagnostic possibilities, a limited number of laboratory tests are indicated. A complete blood count (CBC) and serum electrolyte test should be obtained in all patients.

The serum BHCG level should be measured in any female in whom pregnancy is a possibility. In addition, serum alpha-fetoprotein (AFP) and lactate dehydrogenase (LDH) should be measured in young girls and adolescents with suspected ovarian tumors because the younger the patient, the greater the likelihood of a malignant germ cell tumor.

A blood test called CA-125 is useful in differential diagnosis and in follow up of the disease, but it by itself has not been shown to be an effective method to screen for early-stage ovarian cancer due to its unacceptable low sensitivity and specificity. However, this is the only widely-used marker currently available.

Current research is looking at ways to combine tumor markers proteomics along with other indicators of disease (i.e., radiology and/or symptoms) to improve accuracy. The challenge in such an approach is that the very low population prevalence of ovarian cancer means that even testing with very high sensitivity and specificity will still lead to a number of false positive results (i.e., performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

To definitively diagnose ovarian cancer, a surgical procedure to take a look into the abdomen is required. This can be an open procedure (laparotomy, incision through the abdominal wall) or keyhole surgery (laparoscopy). During this procedure, suspicious areas will be removed and sent for microscopic analysis. Fluid from the abdominal cavity can also be analysed for cancerous cells. If there is cancer, this procedure can also determine its spread (which is a form of tumor staging).

Women who have had children are less likely to develop ovarian cancer than women who have not, and breastfeeding may also reduce the risk of certain types of ovarian cancer. Tubal ligation and hysterectomy reduce the risk and removal of both tubes and ovaries (bilateral salpingo-oophorectomy) dramatically reduces the risk of not only ovarian cancer but breast cancer also. The use of oral contraceptives (birth control pills) for five years or more decreases the risk of ovarian cancer in later life by 50%.

Tubal ligation is believed to decrease the chance of developing ovarian cancer by up to 67% while a hysterectomy may reduce the risk of getting ovarian cancer by about one-third. Moreover, according to some studies, analgesics such as acetaminophen and aspirin seem to reduce one's risks of developing ovarian cancer. Yet, the information is not consistent and more research needs to be carried on this matter.

Routine screening of women for ovarian cancer is not recommended by any professional society—this includes the U.S. Preventive Services Task Force, the American Cancer Society, the American College of Obstetricians and Gynecologists, and the National Comprehensive Cancer Network. This is because no trial has shown improved survival for women undergoing screening. Screening for any type of cancer must be accurate and reliable—it needs to accurately detect the disease and it must not give false positive results in people who do not have cancer. As yet there is no technique for ovarian screening that has been shown to fulfil these criteria. However, in some countries such as the UK, women who are likely to have an increased risk of ovarian cancer (for example if they have a family history of the disease) can be offered individual screening through their doctors, although this will not necessarily detect the disease at an early stage.

Researchers are assessing different ways to screen for ovarian cancer. Screening tests that could potentially be used alone or in combination for routine screening include the CA-125 marker and transvaginal ultrasound. Doctors can measure the levels of the CA-125 protein in a woman's blood—high levels could be a sign of ovarian cancer, but this is not always the case. And not all women with ovarian cancer have high CA-125 levels. Transvaginal ultrasound involves using an ultrasound probe to scan the ovaries from inside the vagina, giving a clearer image than scanning the abdomen. The UK Collaborative Trial of Ovarian Cancer Screening is testing a screening technique that combines CA-125 blood tests with transvaginal ultrasound.

The purpose of screening is to diagnose ovarian cancer at an early stage, when it is more likely to be treated successfully. However, the development of the disease is not fully understood, and it has been argued that early-stage cancers may not always develop into late-stage disease. With any screening technique there are risks and benefits that need to be carefully considered, and health authorities need to assess these before introducing any ovarian cancer screening programs.

The goal of ovarian cancer screening is to detect the disease at stage I. Several large studies are ongoing, but none have identified an effective technique. In 2009, however, early results from the UK Collaborative Trial of Ovarian Cancer Screening (UKCTOCS) showed that a technique combining annual CA-125 tests with ultrasound imaging did help to detect the disease at an early stage. However, it is not yet clear if this approach could actually help to save lives—the full results of the trial will be published in 2015.

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e., <1 cm in diameter of tumor is left behind ["optimal debulking"]), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery.

For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high "drop-out" rate, the group as a whole (including the patients that didn't complete IP chemotherapy treatment)

survived longer on average than patients who received intravenous chemotherapy alone.

Some specialists believe the toxicities and other complications of IP chemotherapy will be unnecessary with improved IV chemotherapy drugs currently being developed.

Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered. Radiation therapy is then commonly avoided in such stages as the vital organs may not be able to withstand the problems associated with these ovarian cancer treatments.

Ovarian cancer usually has a poor prognosis. It is disproportionately deadly because it lacks any clear early detection or screening test, meaning that most cases are not diagnosed until they have reached advanced stages. More than 60% of women presenting with this cancer already have stage III or stage IV cancer, when it has already spread beyond the ovaries. Ovarian cancers shed cells into the naturally occurring fluid within the abdominal cavity. These cells can then implant on other abdominal (peritoneal) structures, included the uterus, urinary bladder, bowel and the lining of the bowel wall omentum forming new tumor growths before cancer is even suspected.

The five-year survival rate for all stages of ovarian cancer is 45.5%. For cases where a diagnosis is made early in the disease, when the cancer is still confined to the primary site, the five-year survival rate is 92.7%.

D. Brain Cancer

A brain tumor is an intracranial solid neoplasm, a tumor (defined as an abnormal growth of cells) within the brain or the central spinal canal. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells), lymphatic tissue, blood vessels), in the cranial nerves, in the brain envelopes (meninges), skull, pituitary and pineal gland, or spread from cancers primarily located in other organs (metastatic tumors).

Any brain tumor is inherently serious and life-threatening because of its invasive and infiltrative character in the limited space of the intracranial cavity. However, brain tumors (even malignant ones) are not invariably fatal. Brain tumors or intracranial neoplasms can be cancerous (malignant) or non-cancerous (benign); however, the definitions of malignant or benign neoplasms differs from those commonly used in other types of cancerous or non-cancerous neoplasms in the body. Its threat level depends on the combination of factors like the type of tumor, its location, its size and its state of development. Because the brain is well protected by the skull, the early detection of a brain tumor only occurs when diagnostic tools are directed at the intracranial cavity. Usually detection occurs in advanced stages when the presence of the tumor has caused unexplained symptoms.

Primary (true) brain tumors are commonly located in the posterior cranial fossa in children and in the anterior two-thirds of the cerebral hemispheres in adults, although they can affect any part of the brain.

The prognosis of brain cancer varies based on the type of cancer. Medulloblastoma has a good prognosis with chemotherapy, radiotherapy, and surgical resection while glioblastoma multiforme has a median survival of only 12 months even with aggressive chemoradiotherapy and surgery. Brainstem gliomas have the poorest prognosis of any form of brain cancer, with most patients dying within one year, even with therapy that typically consists of radiation to the tumor along with cortico steroids. However, one type of brainstem glioma, a focal seems open to exceptional prognosis and long-term survival has frequently been reported.

Glioblastoma multiforme is the deadliest and most common form of malignant brain tumor. Even when aggressive multimodality therapy consisting of radiotherapy, chemotherapy, and surgical excision is used, median survival is only 12-17 months. Standard therapy for glioblastoma multiforme consists of maximal surgical resection of the tumor, followed by radiotherapy between two and four weeks after the surgical procedure to remove the cancer. This is followed by chemotherapy. Most patients with glioblastoma take a corticosteroid, typically dexamethasone, during their illness to palliate symptoms. Experimental treatments include gamma-knife radiosurgery, boron neutron capture therapy and gene transfer.

Oligodendroglioma is an incurable but slowly progressive malignant brain tumor. They can be treated with surgical resection, chemotherapy, and/or radiotherapy. For suspected low-grade oligodendrogliomas in select patients, some neuro-oncologists opt for a course of watchful waiting, with only symptomatic therapy. Tumors with the 1p/19q co-deletion have been found to be especially chemosensitive, and one source reports oligodendrogliomas to be among the most chemosensitive of human solid malignancies. A median survival of up to 16.7 years has been reported for low grade oligodendrogliomas.

Although there is no specific or singular clinical symptom or sign for any brain tumors, the presence of a combination of symptoms and the lack of corresponding clinical indications of infections or other causes can be an indicator to redirect diagnostic investigation towards the possibility of an intracranial neoplasm.

The diagnosis will often start with an interrogation of the patient to get a clear view of his medical antecedents, and his current symptoms. Clinical and laboratory investigations will serve to exclude infections as the cause of the symptoms. Examinations in this stage may include ophtamological, otolaryngological (or ENT) and/or electrophysiological exams. The use of electroencephalography (EEG) often plays a role in the diagnosis of brain tumors.

Swelling, or obstruction of the passage of cerebrospinal fluid (CSF) from the brain may cause (early) signs of increased intracranial pressure which translates clinically into headaches, vomiting, or an altered state of consciousness, and in children changes to the diameter of the skull and bulging of the fontanelles. More complex symptoms such as endocrine dysfunctions should alarm doctors not to exclude brain tumors.

A bilateral temporal visual field defect (due to compression of the optic chiasm) or dilatation of the pupil, and the occurrence of either slowly evolving or the sudden onset of focal neurologic symptoms, such as cognitive and behavioral impairment (including impaired judgment, memory loss, lack of recognition, spatial orientation disorders), personality or emotional changes, hemiparesis, hypoesthesia, aphasia, ataxia, visual field impairment, impaired sense of smell, impaired hearing, facial paralysis, double vision, or more severe symptoms such as tremors, paralysis on one side of the body hemiplegia, or (epileptic) seizures in a patient with a negative history for epilepsy, should raise the possibility of a brain tumor.

Imaging plays a central role in the diagnosis of brain tumors. Early imaging methods—invasive and sometimes dangerous—such as pneumoencephalography and cerebral angiography, have been abandoned in recent times in favor of non-invasive, high-resolution techniques, such as computed tomography (CT)-scans and especially magnetic resonance imaging (MRI). Neoplasms will often show as differently colored masses (also referred to as processes) in CT or MRI results.

Benign brain tumors often show up as hypodense (darker than brain tissue) mass lesions on cranial CT-scans. On MRI, they appear either hypo- (darker than brain tissue) or isointense (same intensity as brain tissue) on T1-weighted scans, or hyperintense (brighter than brain tissue) on T2-weighted MRI, although the appearance is variable.

Contrast agent uptake, sometimes in characteristic patterns, can be demonstrated on either CT or MRI-scans in most malignant primary and metastatic brain tumors. Perifocal edema, or pressure-areas, or where the brain tissue has been compressed by an invasive process also appears hyperintense on T2-weighted MRI might indicate the presence a diffuse neoplasm (unclear outline). This is because these tumors disrupt the normal functioning of the blood-brain barrier and lead to an increase in its permeability. However, it is not possible to diagnose high versus low grade gliomas based on enhancement pattern alone.

Glioblastoma multiforme and anaplastic astrocytoma have been associated with the genetic acute hepatic porphyrias (PCT, AIP, HCP and VP), including positive testing associated with drug refractory seizures. Unexplained complications associated with drug treatments with these tumors should alert physicians to an undiagnosed neurological porphyria.

The definitive diagnosis of brain tumor can only be confirmed by histological examination of tumor tissue samples obtained either by means of brain biopsy or open surgery. The histological examination is essential for determining the appropriate treatment and the correct prognosis. This examination, performed by a pathologist, typically has three stages: interoperative examination of fresh tissue, preliminary microscopic examination of prepared tissues, and followup examination of prepared tissues after immunohistochemical staining or genetic analysis.

When a brain tumor is diagnosed, a medical team will be formed to assess the treatment options presented by the leading surgeon to the patient and his/her family. Given the location of primary solid neoplasms of the brain in most cases a "do-nothing" option is usually not presented. Neurosurgeons take the time to observe the evolution of the neoplasm before proposing a management plan to the patient and his/her relatives. These various types of treatment are available depending on neoplasm type and location and may be combined to give the best chances of survival: surgery: complete or partial ressection of the tumor with the objective of removing as many tumor cells as possible; radiotherapy; and chemotherapy, with the aim of killing as many as possible of cancerous cells left behind after surgery and of putting remaining tumor cells into a nondividing, sleeping state for as long as possible.

Survival rates in primary brain tumors depend on the type of tumor, age, functional status of the patient, the extent of surgical tumor removal and other factors specific to each case.

The primary and most desired course of action described in medical literature is surgical removal (resection) via craniotomy. Minimally invasive techniques are being studied but are far from being common practice. The prime remediating objective of surgery is to remove as many tumor cells as possible, with complete removal being the best outcome and cytoreduction ("debulking") of the tumor otherwise. In some cases access to the tumor is impossible and impedes or prohibits surgery.

Many meningiomas, with the exception of some tumors located at the skull base, can be successfully removed surgically. Most pituitary adenomas can be removed surgically, often using a minimally invasive approach through the nasal cavity and skull base (trans-nasal, trans-sphenoidal approach). Large pituitary adenomas require a craniotomy (opening of the skull) for their removal. Radiotherapy, including stereotactic approaches, is reserved for inoperable cases.

Several current research studies aim to improve the surgical removal of brain tumors by labeling tumor cells with a chemical (5-aminolevulinic acid) that causes them to fluoresce. Post-operative radiotherapy and chemotherapy are integral parts of the therapeutic standard for malignant tumors. Radiotherapy may also be administered in cases of "low-grade" gliomas, when a significant tumor burden reduction could not be achieved surgically.

Any person undergoing brain surgery may suffer from epileptic seizures. Seizures can vary from absences to severe tonic-clonic attacks. Medication is prescribed and administered to minimize or eliminate the occurrence of seizures.

Multiple metastatic tumors are generally treated with radiotherapy and chemotherapy rather than surgery, the prognosis in such cases is determined by the primary tumor, but is generally poor.

The goal of radiation therapy is to selectively kill tumor cells while leaving normal brain tissue unharmed. In standard external beam radiation therapy, multiple treatments of standard-dose "fractions" of radiation are applied to the brain. This process is repeated for a total of 10 to 30 treatments, depending on the type of tumor. This additional treatment provides some patients with improved outcomes and longer survival rates.

Radiosurgery is a treatment method that uses computerized calculations to focus radiation at the site of the tumor while minimizing the radiation dose to the surrounding brain. Radiosurgery may be an adjunct to other treatments, or it may represent the primary treatment technique for some tumors.

Radiotherapy may be used following, or in some cases in place of, resection of the tumor. Forms of radiotherapy used for brain cancer include external beam radiation therapy, brachytherapy, and in more difficult cases, stereotactic radiosurgery, such as Gamma knife, Cyberknife or Novalis Tx radiosurgery.

Radiotherapy is the most common treatment for secondary brain tumors. The amount of radiotherapy depends on the size of the area of the brain affected by cancer. Conventional external beam 'whole brain radiotherapy treatment' (WBRT) or 'whole brain irradiation' may be suggested if there is a risk that other secondary tumors will develop in the future. Stereotactic radiotherapy is usually recommended in cases involving fewer than three small secondary brain tumors.

Patients undergoing chemotherapy are administered drugs designed to kill tumor cells. Although chemotherapy may improve overall survival in patients with the most malignant primary brain tumors, it does so in only about 20 percent of patients. Chemotherapy is often used in young children instead of radiation, as radiation may have negative effects on the developing brain. The decision to prescribe this treatment is based on a patient's overall health, type of tumor, and extent of the cancer. The toxicity and many side effects of the drugs, and the uncertain outcome of chemotherapy in brain tumors puts this treatment further down the line of treatment options with surgery and radiation therapy preferred.

A shunt is used not as a cure but to relieve symptoms by reducing hydrocephalus caused by blockage of cerebrospinal fluid.

Researchers are presently investigating a number of promising new treatments including gene therapy, highly focused radiation therapy, immunotherapy and novel chemotherapies. A variety of new treatments are being made available on an investigational basis at centers specializing in brain tumor therapies.

V. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results

Figures 8A, 8B:
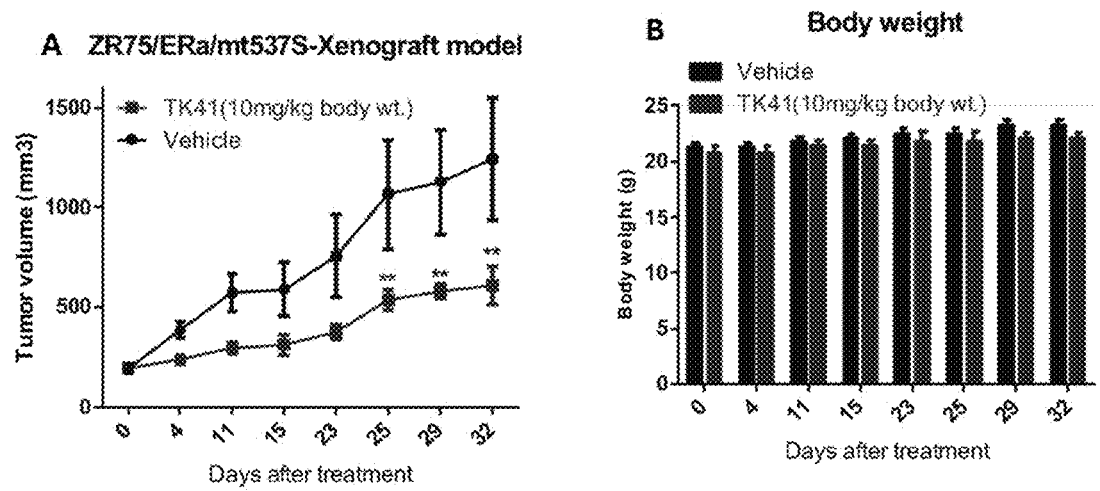
FIGS. 8A & 8B show the effect of TK41 (i.e., ERX-41) on therapy resistant cancer cells. ERMT (therapy resistant) xenografts (n=8) were established in nude mice and treated with vehicle (circle markers) or 10 mg/kg/day/oral ERX-41 (square markers). Tumor volume (FIG. 8A) and mice body weights (bar graph.

The present oligo-benzamide analogs are extremely potent and effective on various cancer cells including breast cancer, ovarian cancer, and pancreatic cancer. These compounds have a unique mode of action compared to existing therapeutic treatments to these diseases. The compounds are very potent with $IC_{50}$ values of 10-50 nM for growth inhibition. TK41 is a tris-benzamide analog and it inhibits nuclear receptor (NR) interaction with its coregulator proteins in cancer cells with high potency ($IC_{50}$ is approximately 100 nM; FIGS. 1-4). This compound was found to be very effective on endocrine therapy resistant breast cancer cells that are difficult to be treated by currently available endocrine and chemotherapy (FIG. 2 and FIG. 8).

Figure 9:
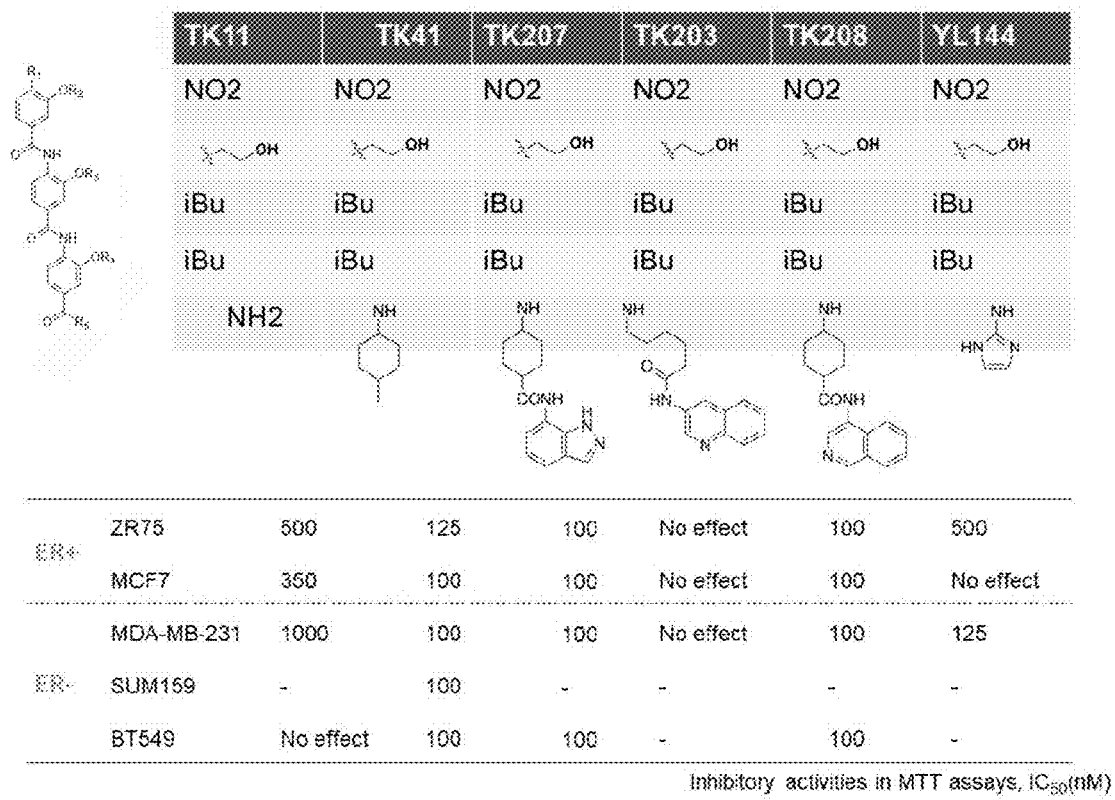
FIG. 9 shows structure activity relationship between TK11 (i.e., ERX-11; Raj et al., 2017), TK41, TK207, TK203, TK208, and YL144. Replacement of the $R_5$ amino group of TK11 with a substituted amino groups significantly increased activity against estrogen receptor-positive and estrogen receptor-negative cells lines.
Figures 10A, 10B:
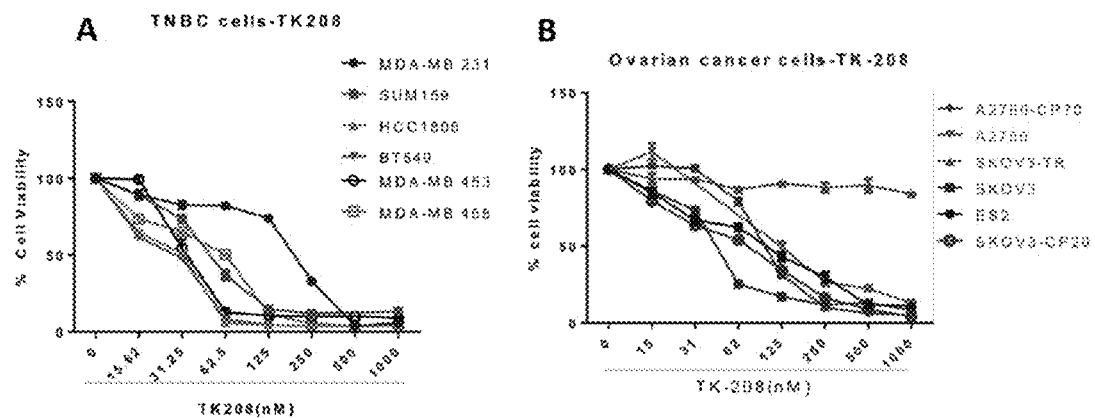
FIGS. 10A & 10B show effects of TK208 against cancer cells.
Figures 11A, 11B:
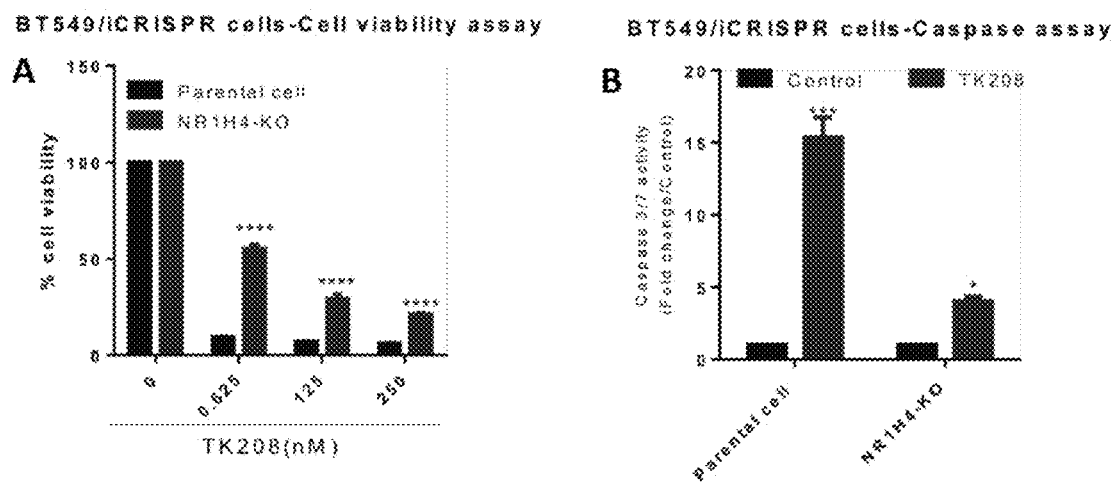
FIGS. 11A & 11B show the comparison of cytotoxic effects of TK208 in BT549 NR1H4 knockout cells versus the parental cell.
Figures 12A, 12B, 12C, 12D:
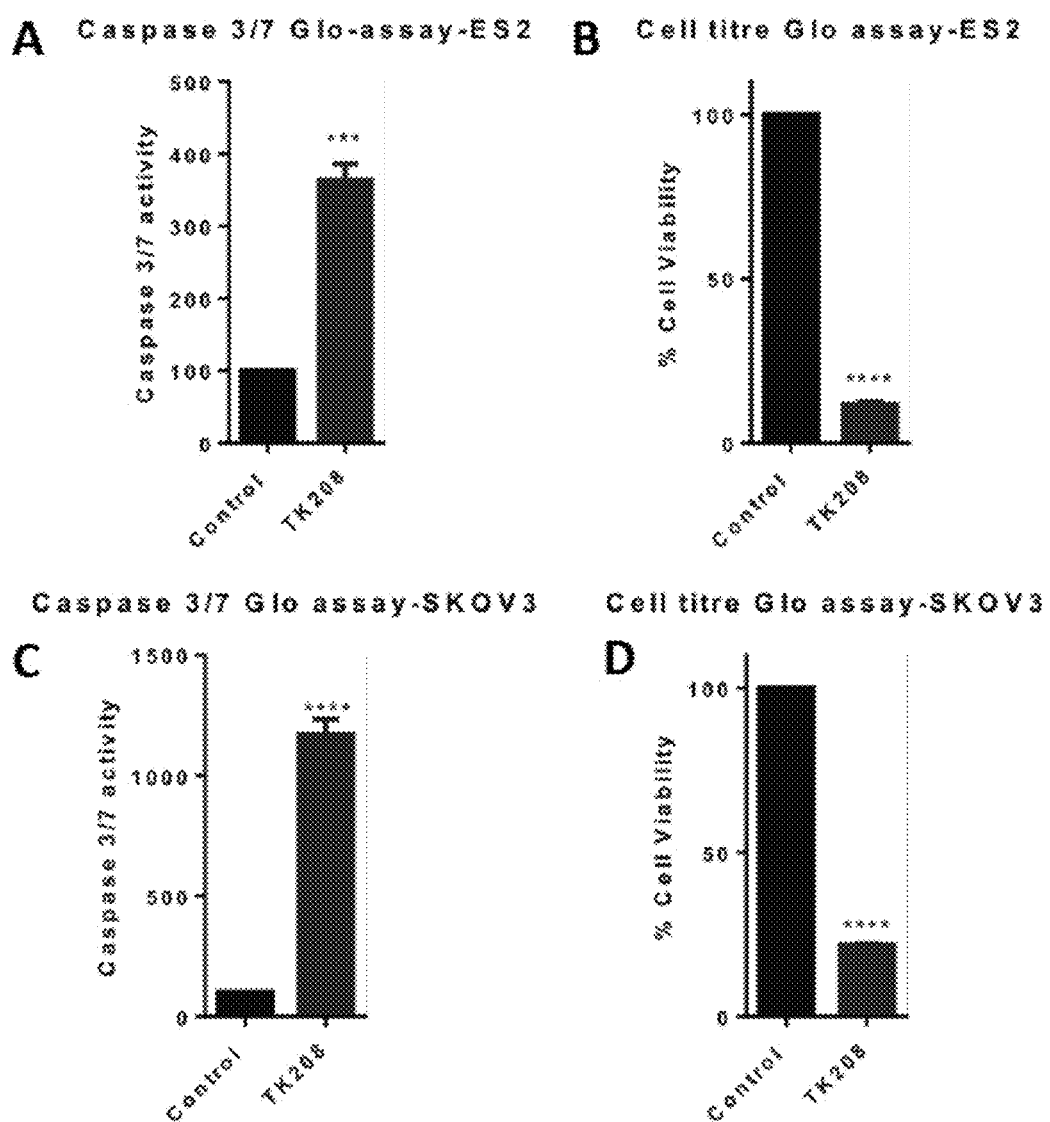
FIGS. 12A-12D show the effect of TK208 against ovarian cancer cell lines ES2 (FIGS. 12A & 12B) and SKOV3 (FIGS. 12C & 12D).
Figure 13:
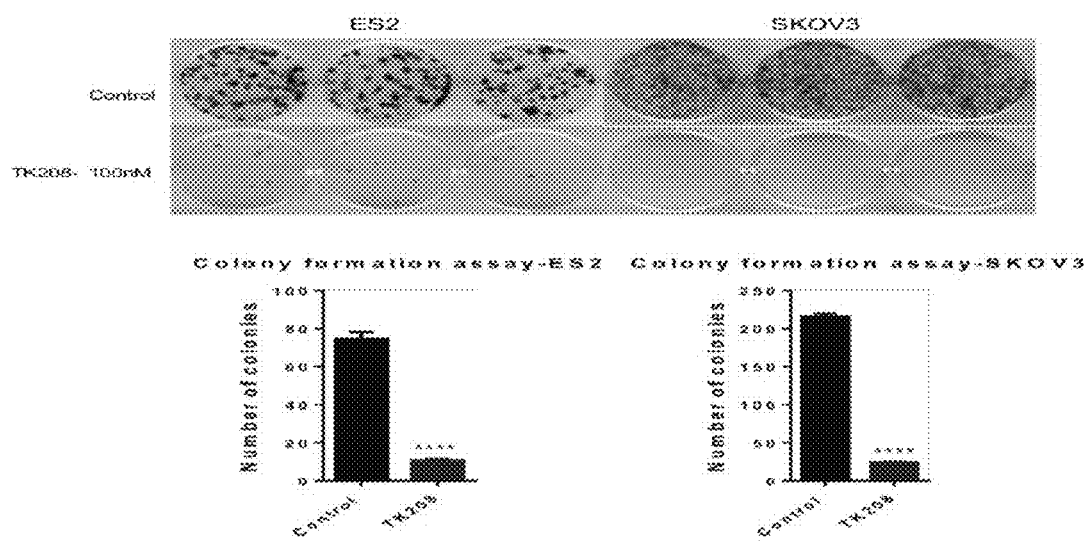
FIG. 13 shows TK208 reduces colony formation of ES2 and SKOV3 ovarian cancer cells.
Figure 14:
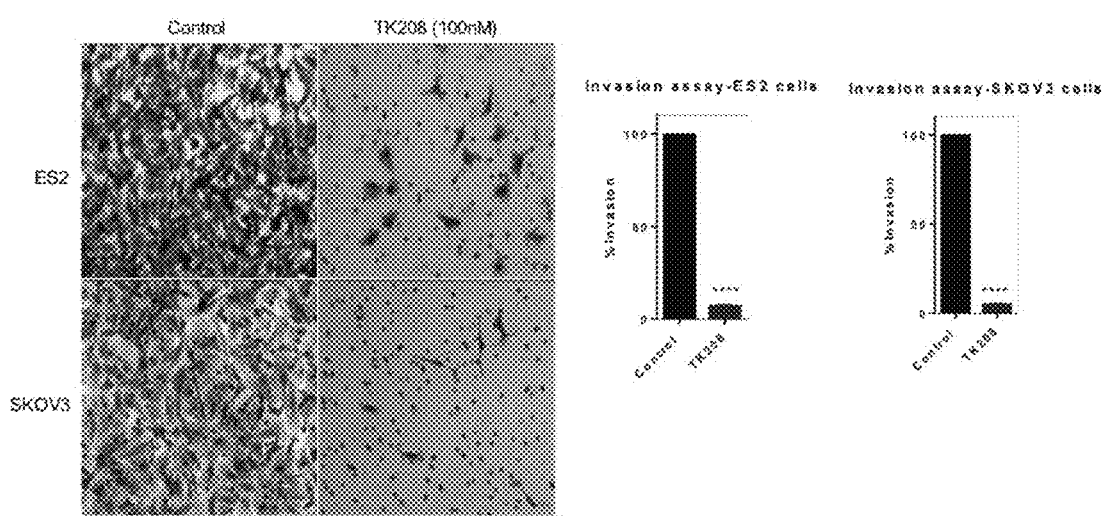
FIG. 14 shows TK208 reduces invasion of ES2 and SKOV3 ovarian cancer cells.
Figure 15:
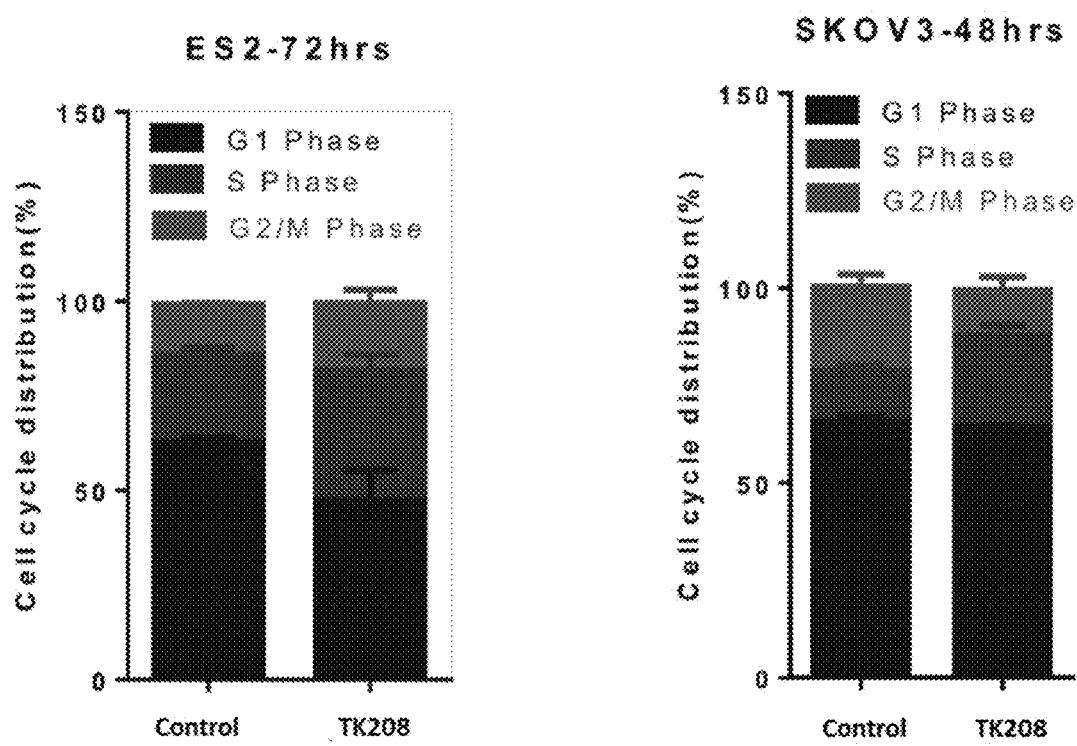
FIG. 15 shows TK208 promotes growth arrest of ES2 and SKOV3 ovarian cancer cells in S phase.

While TK41 was initially designed to target the estrogen receptor, it was found to also exhibit activity in triple negative breast cancer cells that are estrogen-receptor negative (FIG. 2 and FIGS. 5-7). This result was unexpected based on the performance of earlier benzamide compounds (see FIG. 9 for structure activity table). Indeed, TK41 shows remarkably strong growth inhibition of triple-negative breast cancer cells (TNBC) with the IC50 values below 100 nM. TNBC is difficult to be treated and currently there are no good drugs available in the market. Animal studies with TK41 not only showed outstanding tumor growth inhibition but also showed no apparent side effects or toxicity. TK41 is orally available and an excellent therapeutic candidate for a broad range of breast cancers.

Figure 21:
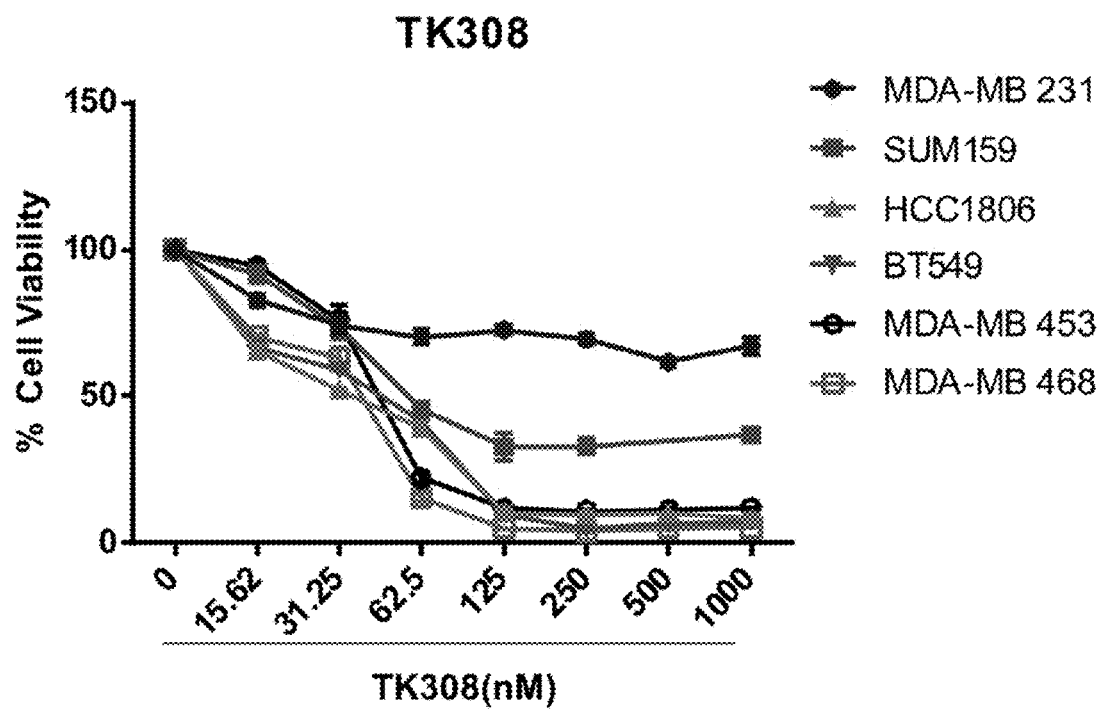
FIG. 21 shows the effect of TK308 on various cancer cell lines.
Figure 22:
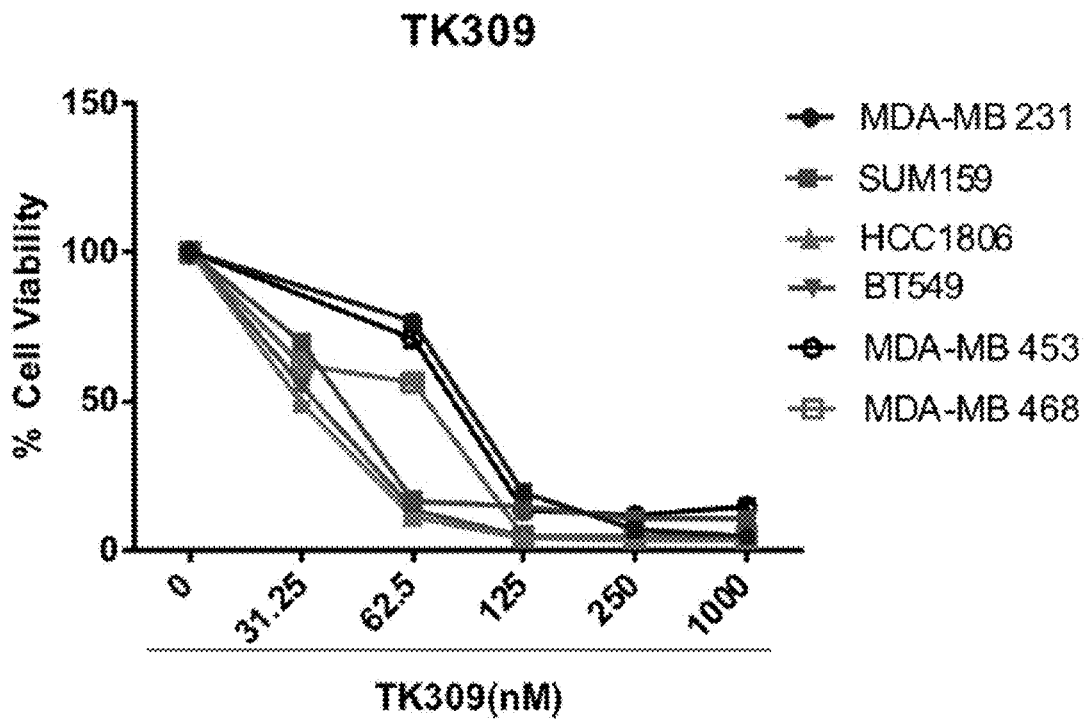
FIG. 22 shows the effect of TK309 on various cancer cell lines.
Figure 23:
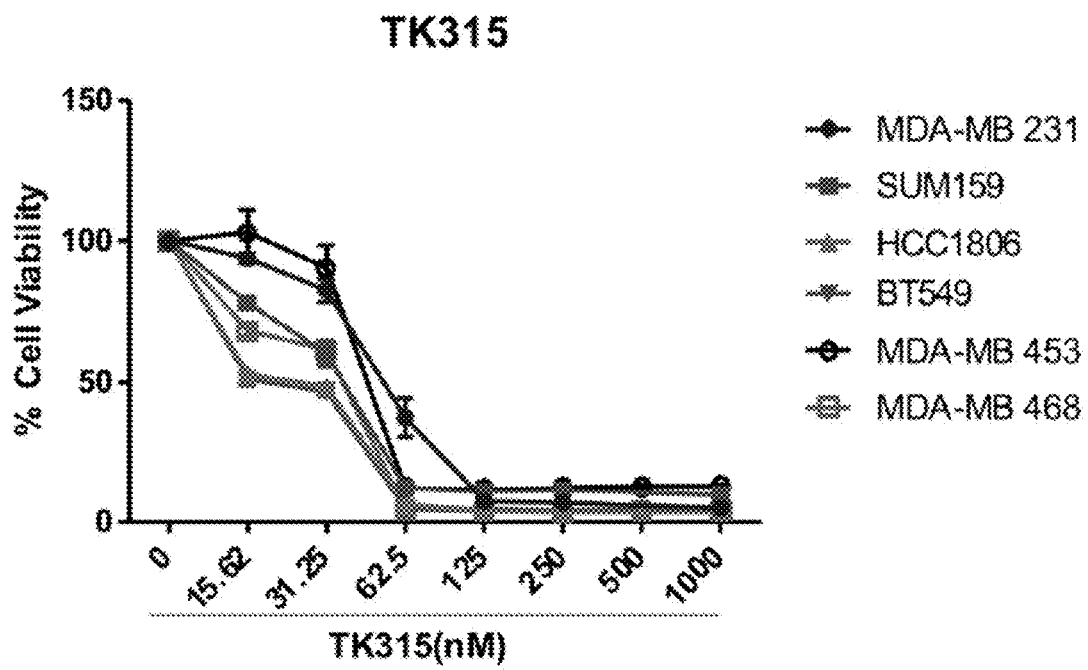
FIG. 23 shows the effect of TK315 on various cancer cell lines.
Figure 24:
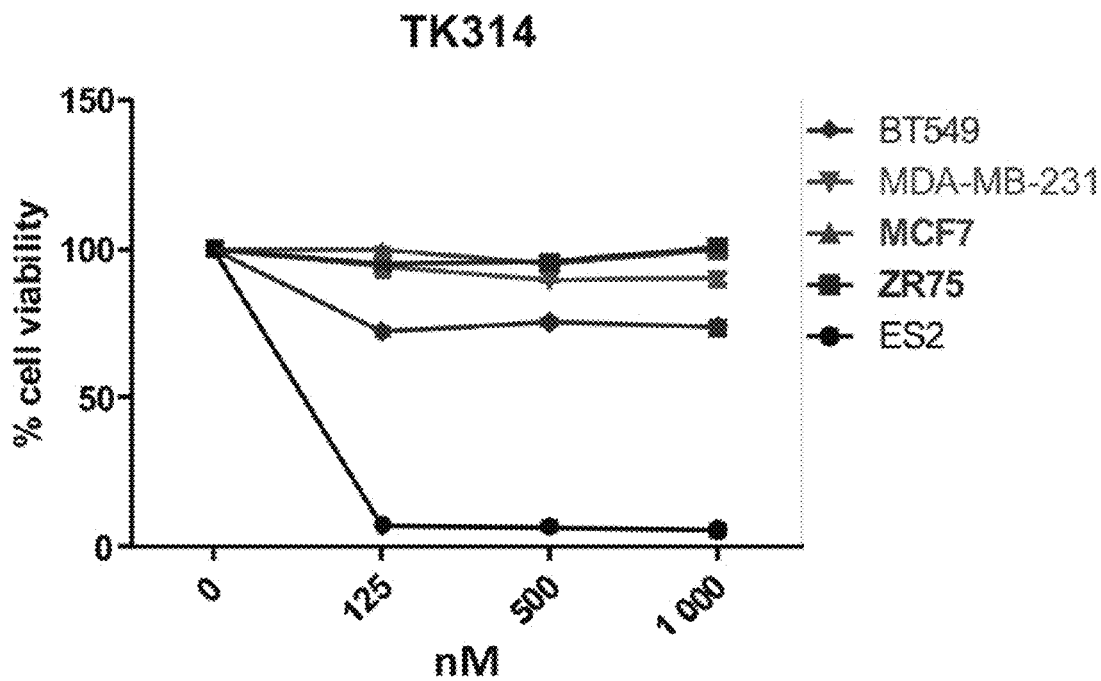
FIG. 24 shows the effect of TK314 on various cancer cell lines. TK314 exhibits unique activity against ovarian cancer cells with significantly less activity against breast cancer cells.

In addition, another tris-benzmaide compound TK208 was synthesized and tested against breast cancer and ovarian cancer cell lines (FIGS. 10-15). TK208 showed remarkably high potency in growth inhibition of TNBC and ovarian cancer cells with IC50 values from 10-100 nM. Additional tris-benzamide analogs, TK314 (FIG. 24) and TK315 (FIG. 23), were also prepared and exhibit even more potent activity against ovarian cancer cells and breast cancer cells, respectively, with $IC_{50}$ values of from 10-50 nM. These compounds (e.g., TK41, TK208, TK308 (FIG. 21), TK309 (FIG. 22), TK314, TK315) are extremely potent compounds that inhibit tumor growth and kill breast and ovarian cancer cells and as such, they are superb therapeutic candidates for such diseases.

Figure 16:
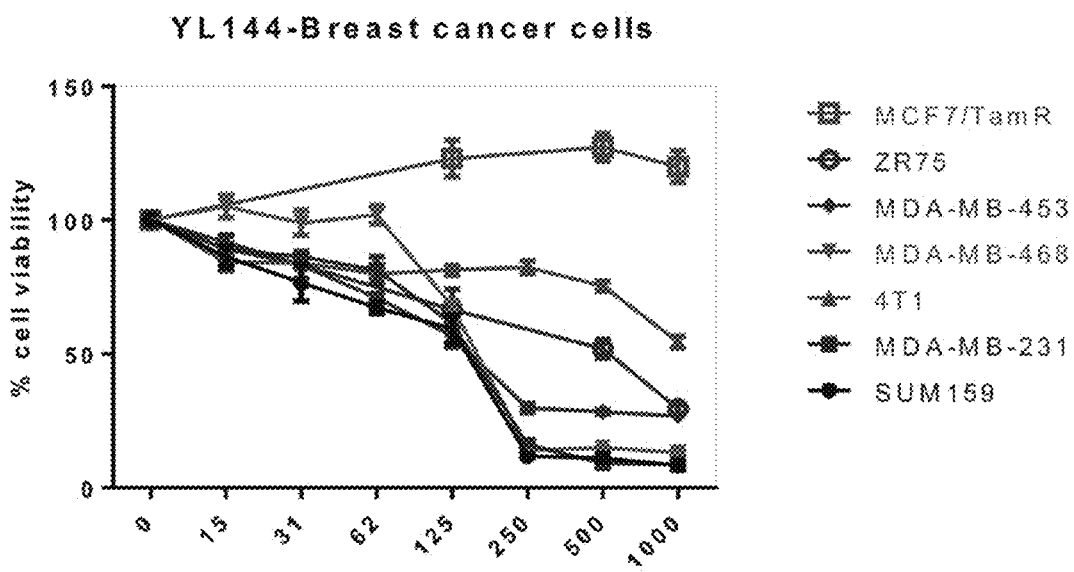
FIG. 16 shows the effect of YL144 on breast cancer cells from various cell lines.
Figure 17:
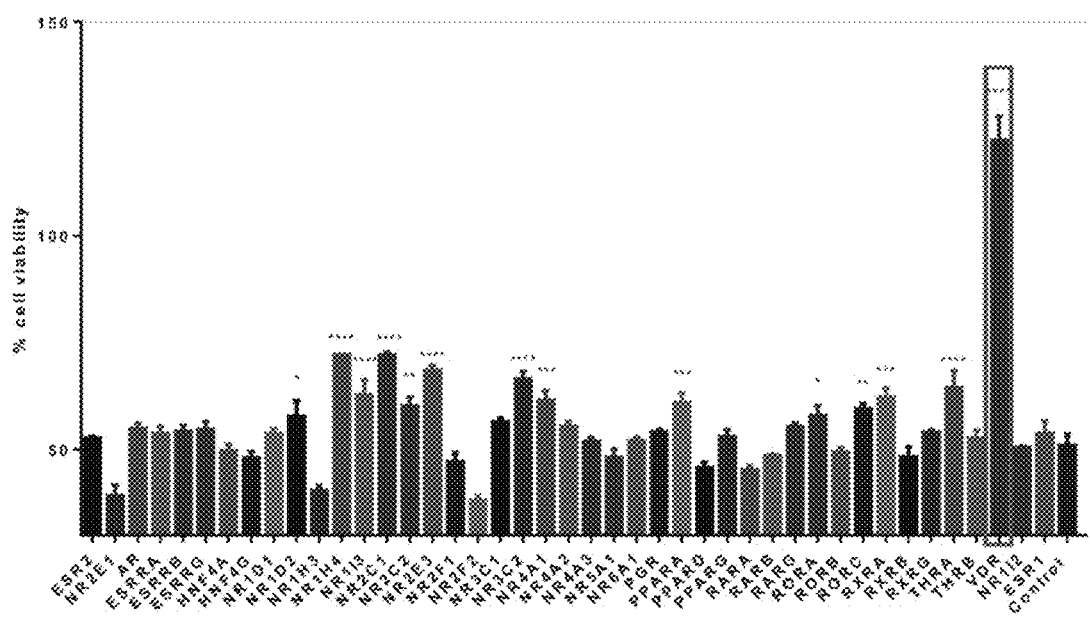
FIG. 17 shows the effect of YL144 on BT549/NR targeted knockout cells.
Figure 18:
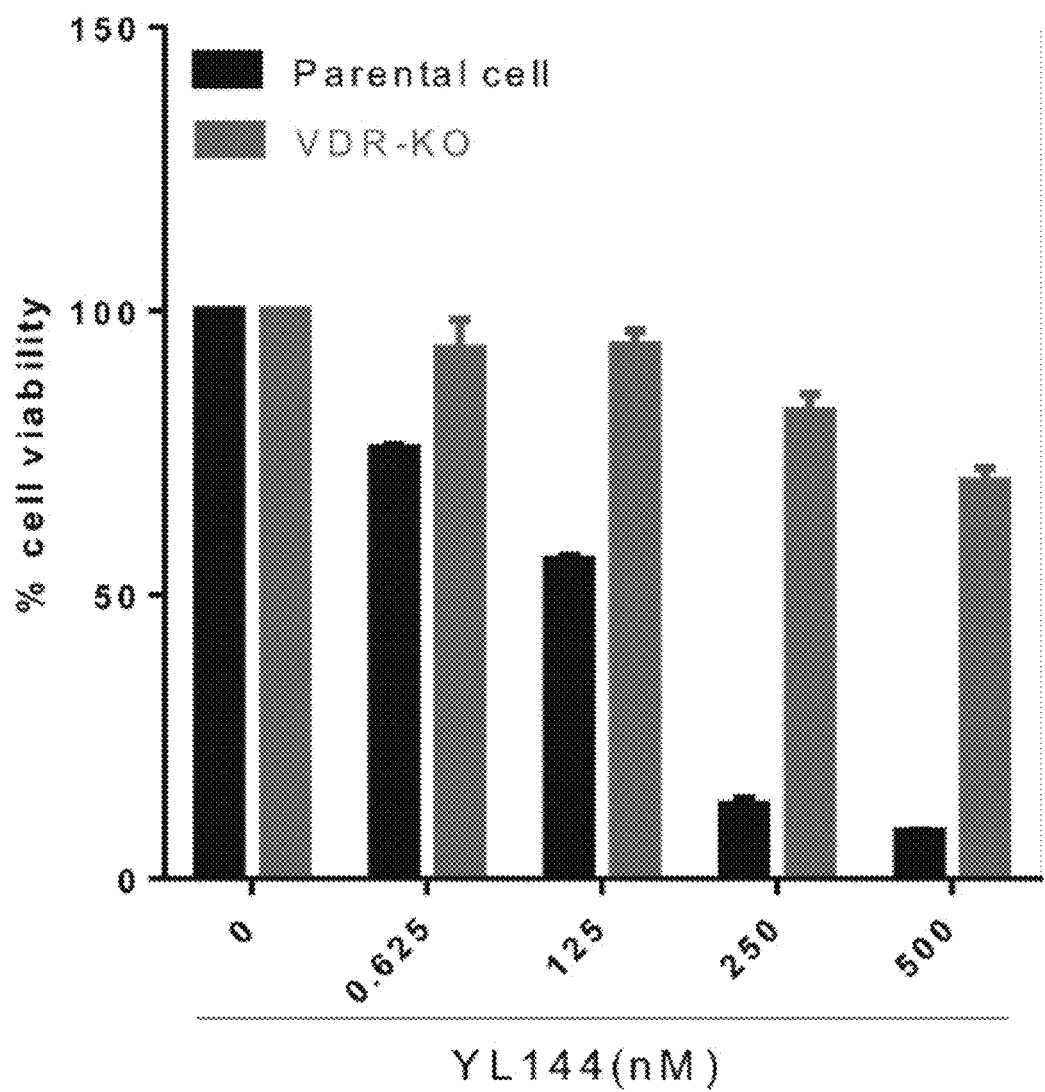
FIG. 18 shows the effect of YL144 on cell viability of VDR-CRISPR knockout cells.
Figures 19, 20:
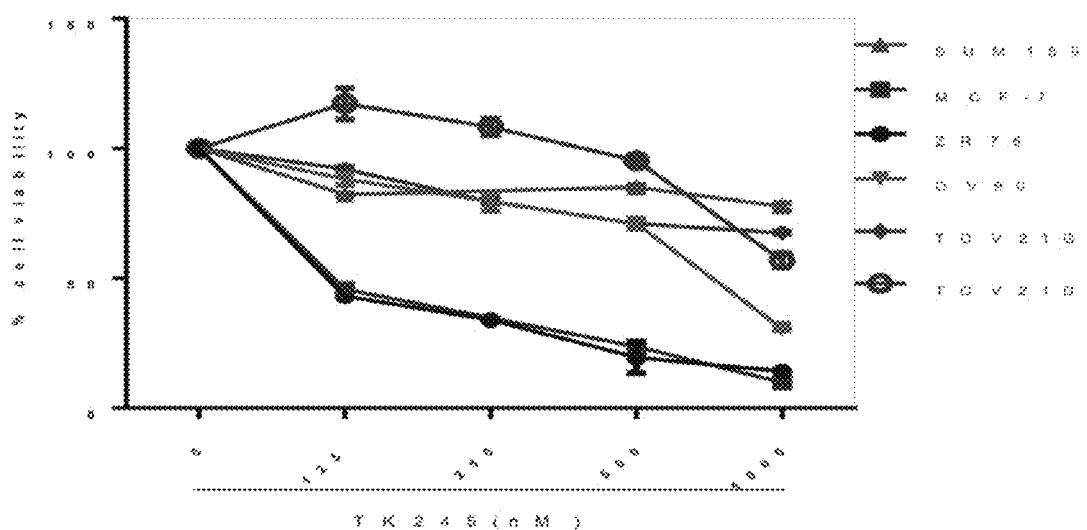
FIG. 19 shows structure activity relationship between TK11 (Raj et al., 2017), TK41, TK208, TK231, YL144, TK227, YL1113, and TK245.
FIG. 20 shows TK245 has high specificity for estrogen receptor-positive cells.

Tris-benzamide YL144 was also synthesized and was found to inhibit vitamin D receptor (VDR) with high potency and may be a useful therapeutic candidate for pancreatic cancer (FIGS. 16-18). Bis-benzamide TK245 is a unique compound showing strong growth inhibition of estrogen receptor-positive breast cancer (FIG. 19 and FIG. 20).

Figure 25:
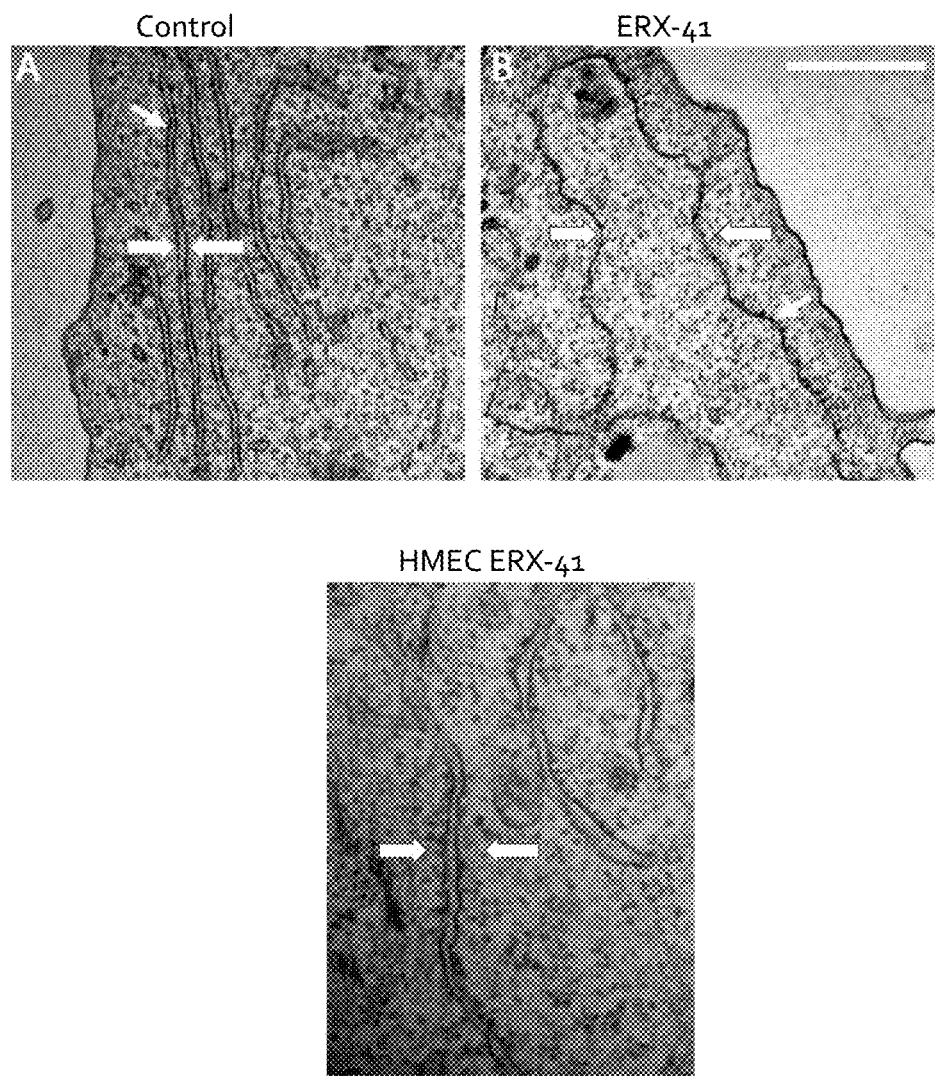
FIG. 25 shows the ability of TK41 to induce endoplasmic reticulum stress in TNBC MD-MBA-231 cells using electron microscopy. TK41 does not induce endoplasmic reticulum stress in HMEC cells (bottom panel)
Figure 26:
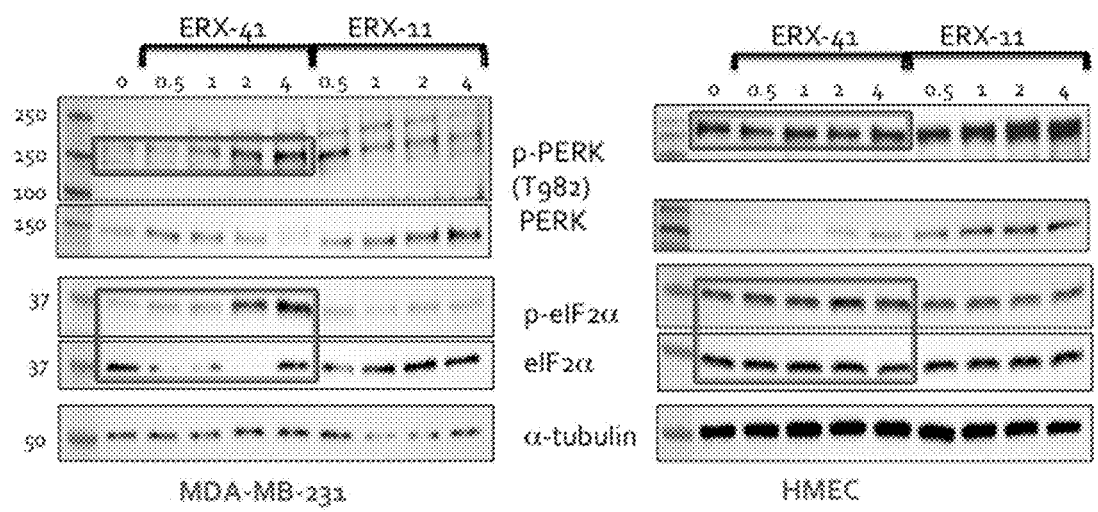
FIG. 26 shows the ability of TK41 to induce endoplasmic reticulum stress in MD-MBA-231 cell using western blots. TK41 does not induce endoplasmic reticulum stress in HMEC cells.
Figure 27:
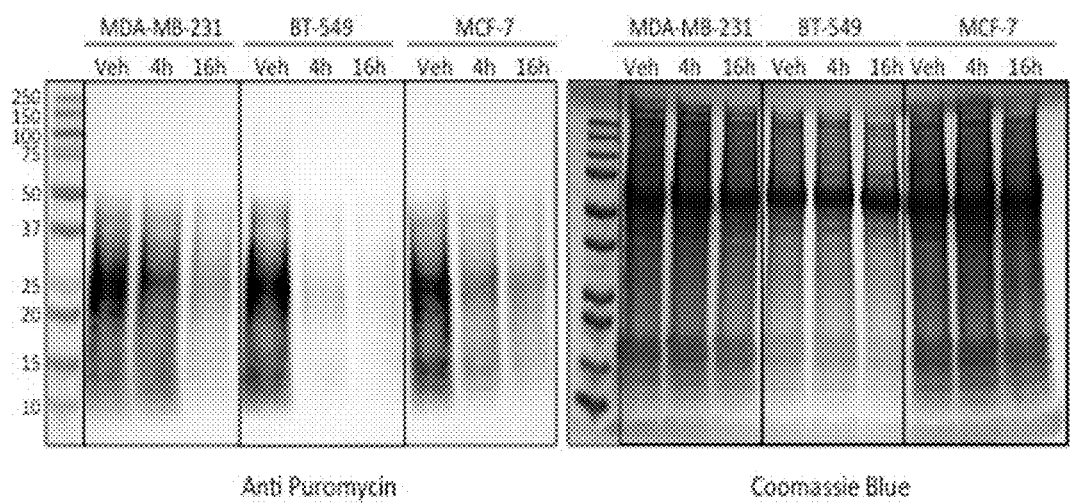
FIG. 27 shows the ability of TK41 to shut down de novo protein synthesis. TK-41 decreases global new protein synthesis at 4 h and 16 h in 3 TNBC cells as shown by western blots for puromycin labeled nascent proteins. Total protein is shown on right with coomassie blue staining.
Figure 28:
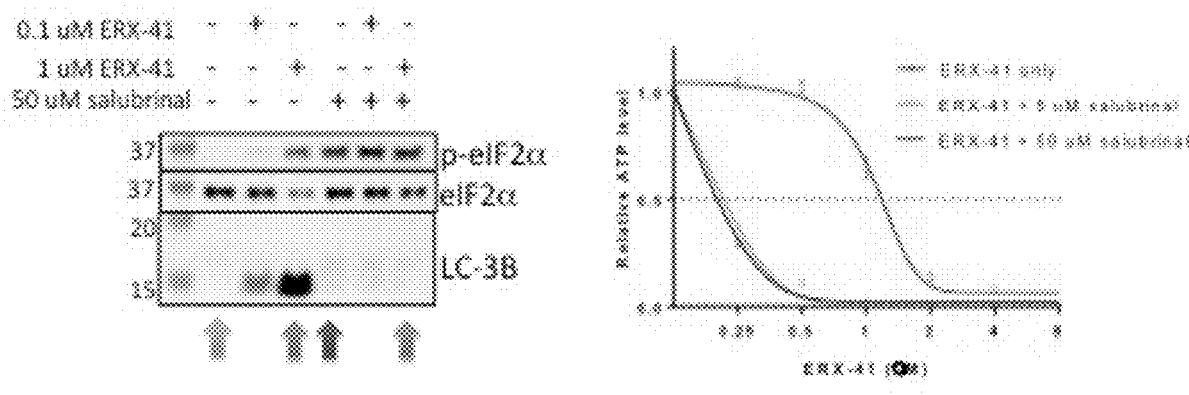
FIG. 28 shows that the basal level of expression of endoplasmic reticulum stress and unfolded protein response correlates with TK41 activity.
Figure 29:
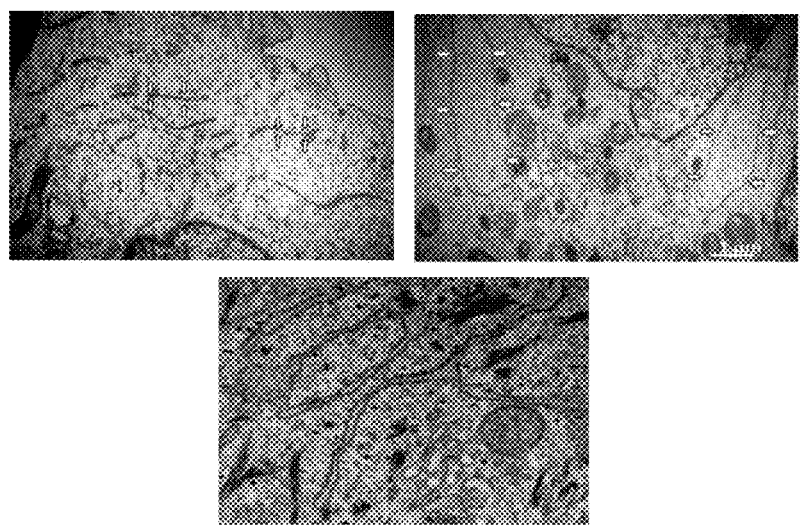
FIG. 29 shows the ability of TK41 to induce endoplasmic reticulum stress in pancreatic cancer MiaPaca cells using electron microscopy. TK41 does not induce endoplasmic reticulum stress in HMEC cells.
Figure 30:
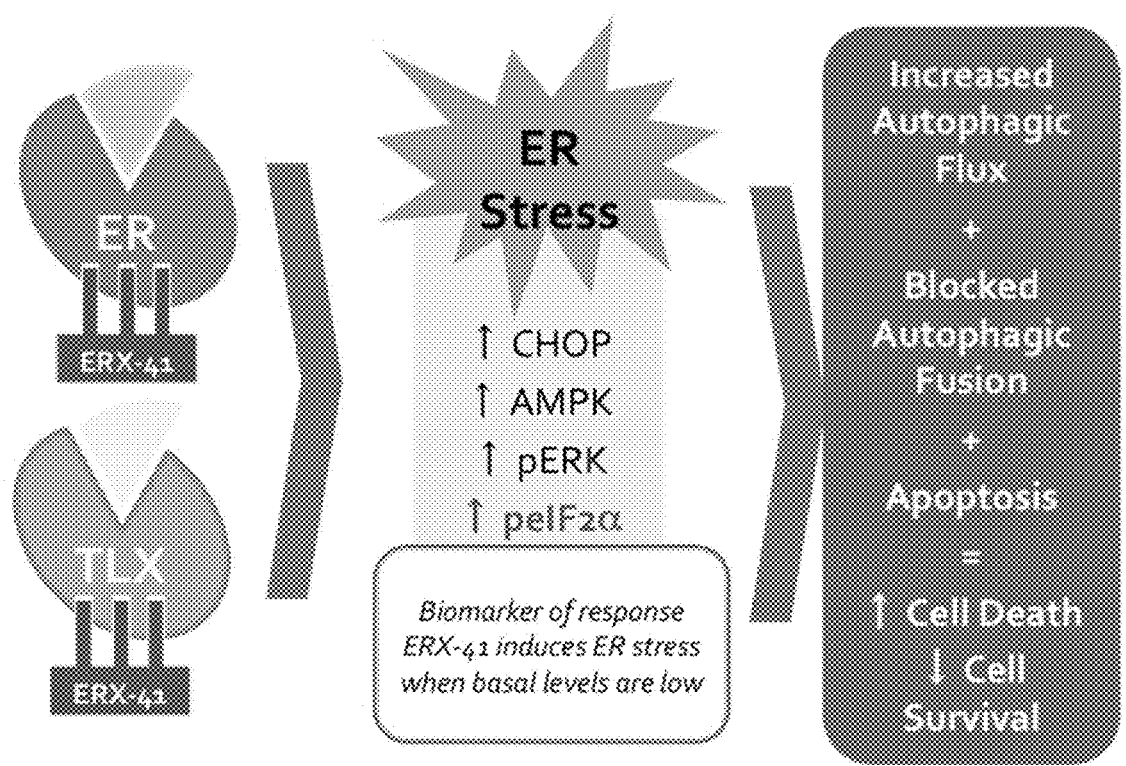
FIG. 30 shows the schematic that explains the mechanism of action of TK41 via targeting either ER or TLX and inducing Endoplasmic reticulum stress, subsequent apoptosis and blocking autophagic fusion.

TK41 was also shown to induce endoplasmic reticulum stress in TNBC MD-MBA-231 cells but does not induce endoplasmic reticulum stress in HMEC cells (FIG. 25 and FIG. 26). TK41 shuts down de novo protein synthesis in TNBC cells (FIG. 27). The basal level of expression of endoplasmic reticulum stress and unfolded protein response correlates with TK41 activity (FIG. 28). Modulation of the level of these stress proteins affects the activity of TK41. Thus, the basal level of expression of endoplasmic reticulum stress and unfolded protein response proteins may serve as a biomarker to predict response to TK41. Endoplasmic reticulum stress was also induced in pancreatic cancer MiaPaca cells upon exposure to TK41 but does not induce endoplasmic reticulum stress in HMEC cells (FIG. 29). Without wishing to be bound by any particular theory, the mechanism of action of TK41 may operate comprise targeting either ER or TLX and inducing endoplasmic reticulum stress, subsequent apoptosis, and blocking autophagic fusion (FIG. 30).

In summary, many oligo-benzamide analogs were developed and showed remarkably strong therapeutic potentials in treating breast cancer, ovarian cancer, and pancreatic cancer. Their mode of action and efficacy are unmatched by drugs currently available, and as such these are highly promising therapeutic candidates.

Example 2—Synthetic Methods

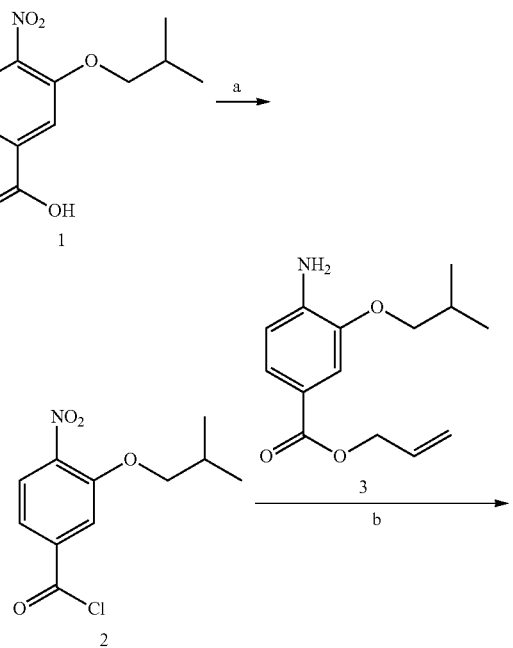

Scheme 1. Synthetic route to TK41.

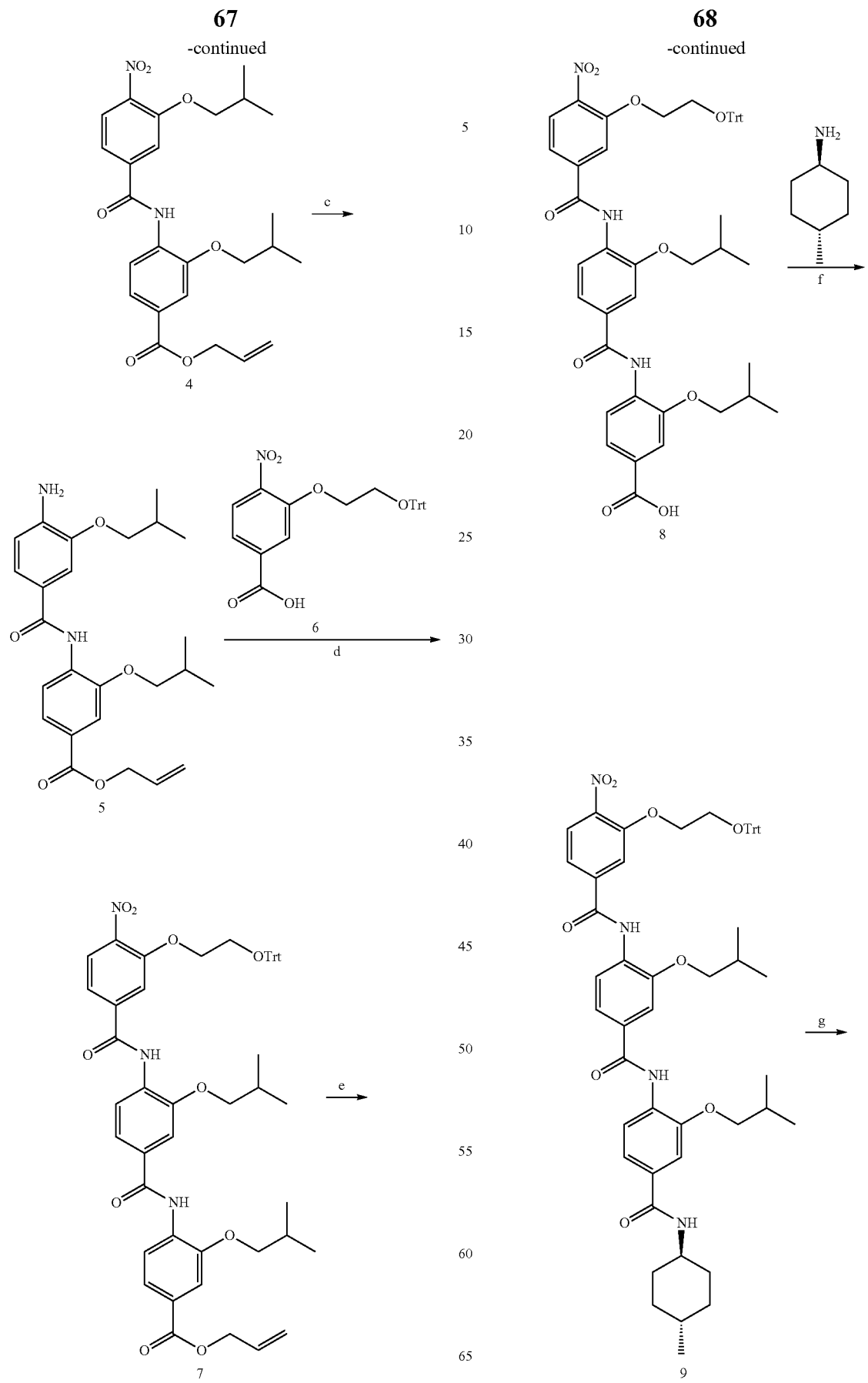

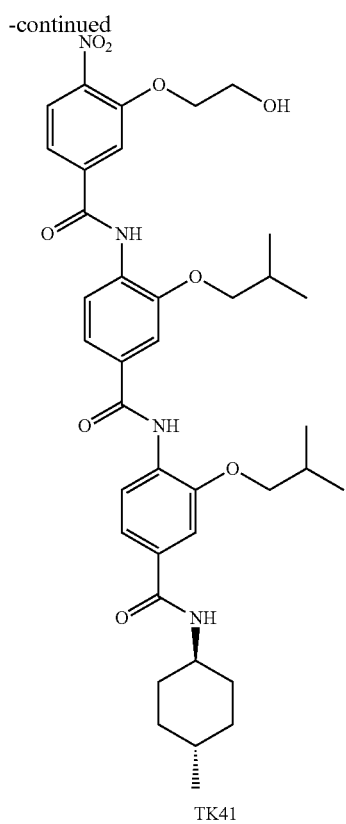

TK41

Reagents and conditions: (a) (COCl)$_2$, cat. DMF, DCM, rt, 2 h; (b) DIEA, DCM, rt, 24 h; (c) SnCl$_2$, DMF, rt, 12 h; (d) HATU, DIEA, DMF, rt, 24 h; (e) Pd(PPh$_3$)$_4$, PhSiH$_3$, THF, rt, 1 h; (f) HATU, DIEA, DMF, rt, 24 h; (g) conc. HCl, rt, 24 h.

Compound 4: A 250 mL round-bottomed flask was charged with compound 1 (5.45 g, 22.8 mmol), DCM (100 mL), oxalyl chloride (2.6 mL, 30.1 mmol) and 2 drops of DMF. The reaction mixture was stirred at room temperature for 2 h and then concentrated under reduced pressure. The resulting compound 2 was dissolved in DCM (20 mL) and slowly added to a solution of compound 3 (3.8 g, 15.2 mmol), DIEA (5.3 mL, 30.4 mmol) and DCM (100 mL). The reaction mixture was stirred at room temperature for 24 h, and then was washed with 1 N HCl (50 mL), saturated NaHCO$_3$ (50 mL) and brine (50 mL). The organic layer was dried over Na$_2$SO$_4$, filtered, and concentrated under reduced pressure to yield the crude product. Purification by crystallization from EtOAc/hexanes (1:4) gave compound 4 as a light yellow solid (5.1 g, 71%).

Compound 5: A 250 mL round-bottomed flask was charged with compound 4 (4.7 g, 10.0 mmol), DMF (100 mL), and SnCl$_2$.2H$_2$O (6.8 g, 30.0 mmol). The reaction mixture was stirred at room temperature for 12 h and then diluted with EtOAc (200 mL) and 1 N HCl (200 mL). The organic layer was separated and washed with 1 N HCl (100 mL) and brine (100 mL). The organic layer was dried over Na$_2$SO$_4$, filtered, and concentrated under reduced pressure to yield the crude product. Purification by flash chromatography (hexanes/EtOAc 4:1) gave the compound 5 as a light yellow solid (3.6 g, 82%).

Compound 7: A 250 mL round-bottomed flask was charged with compound 5 (3.6 g, 8.2 mmol), compound 6 (6.2 g, 13.2 mmol), HATU (6.7 g, 17.6 mmol), DMF (100 mL), and DIEA (4.6 mL, 26.4 mmol). The reaction mixture was stirred at room temperature for 24 h and then diluted with EtOAc (300 mL) and 0.5 N HCl (200 mL). The organic layer was separated and washed with 0.5 N HCl (100 mL) and brine (100 mL). The organic layer was concentrated under reduced pressure to yield the crude product. Purification by crystallization from EtOAc gave compound 7 as a light yellow solid (5.6 g, 77%).

Compound 8: A 250 mL round-bottomed flask was charged with compound 7 (5.3 g, 5.9 mmol) and THF (100 mL). Then, Pd(PPh$_3$)$_4$ (0.69 g, 0.60 mmol) and PhSiH$_3$ (1.5 mL, 12.2 mmol) were added to the reaction mixture. The reaction mixture was stirred at room temperature for 1 h. The resulting solid was filtered, washed with ether and dried in vacuo to give compound 8 as a white sold (4.9 g, 97%).

Compound 9: A 100 mL round-bottomed flask was charged with compound 8 (2.7 g, 3.2 mmol), HATU (1.4 g, 3.7 mmol), DMF (30 mL), trans-4-methylcyclohexylamine (0.73 g, 6.4 mmol), and DIEA (1.2 mL, 6.9 mmol). The reaction mixture was stirred at room temperature for 24 h and then diluted with EtOAc (100 mL) and 0.5 N HCl (50 mL). The organic layer was separated and washed with 0.5 N HCl (50 mL) and brine (50 mL). The resulting solid was filtered, washed with EtOAc and dried in vacuo to give compound 9 as a white sold (1.75 g). The product was used in the next reaction without further purification.

TK41: A 500 mL round-bottomed flask was charged with compound 9 (1.75 g), THF (300 mL) and conc. HCl (30 mL). The reaction mixture was stirred at room temperature for 24 h and then concentrated under reduced pressure. The resulting solid was filtered, washed with MeOH and dried in vacuo to give TK11-41 as a light yellow solid (1.3 g, 57% over 2 reaction steps).

Scheme 2. Synthetic route to TK296.

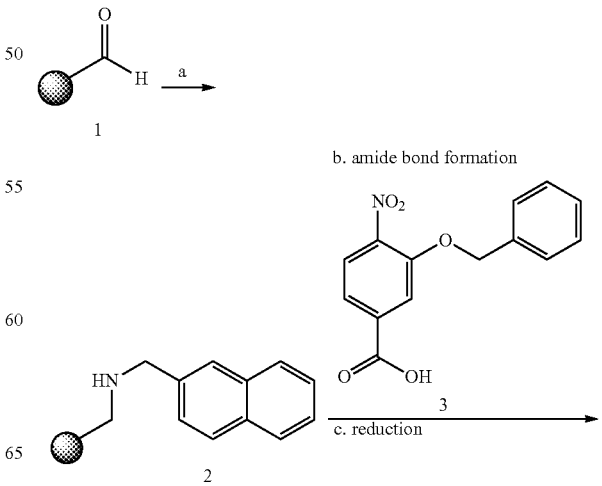

71
-continued
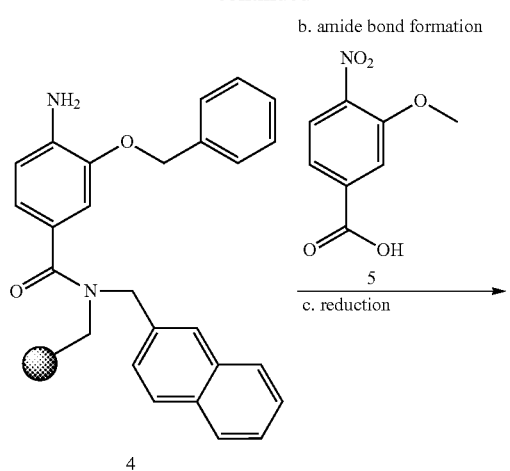
72
-continued
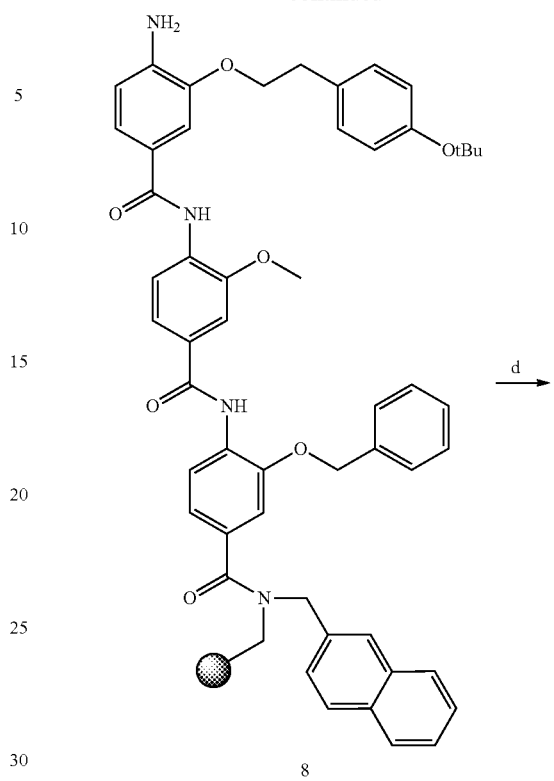
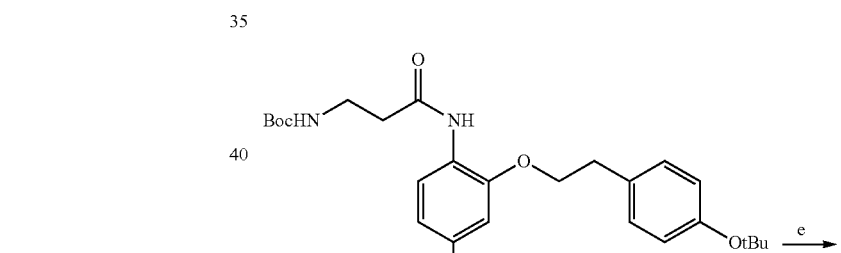
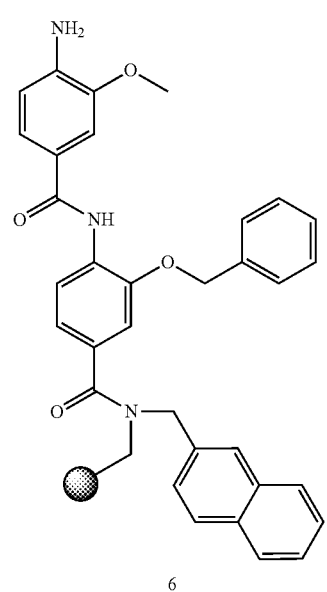
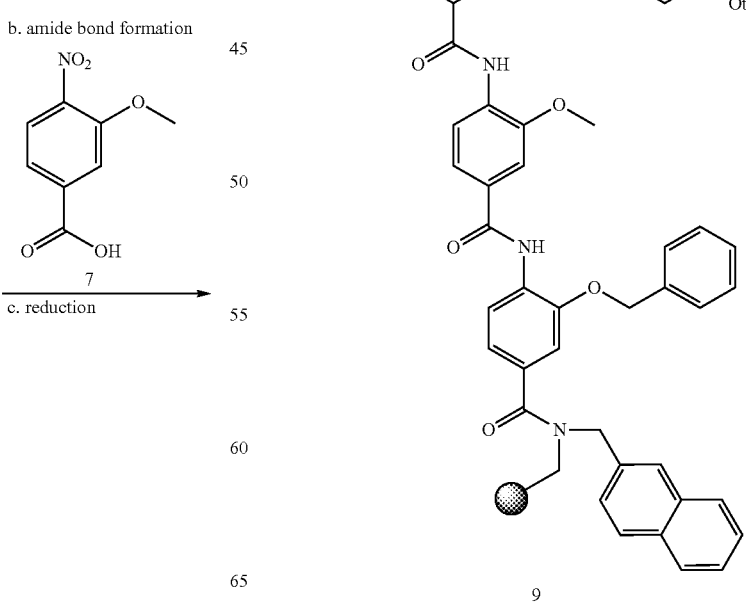

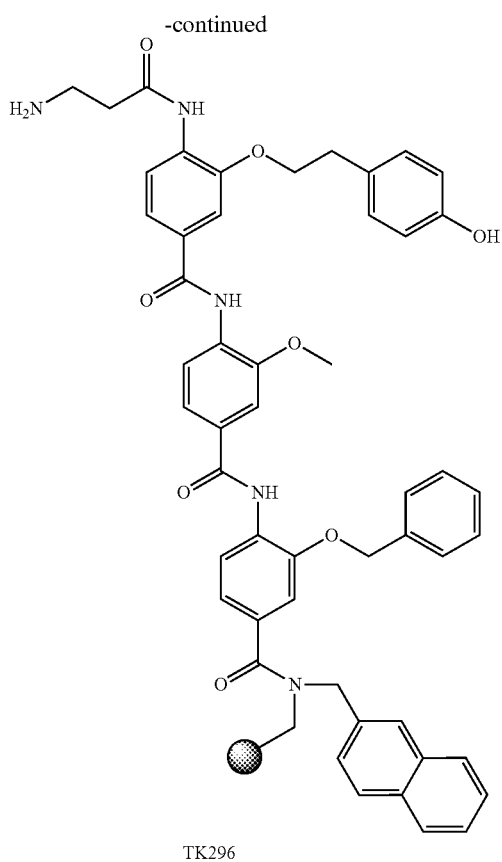

TK296

Reagents and conditions: (a) ), naphthalene-2-methaneamine hydrochloride, NaBH₃CN, 1% AcOH/DMF, rt, 24 h; (b) PyBroP, DIEA, DCM, rt, 24 h; (c) Na₂S₂O₄, 1,1'-di-n-octyl-4,4'-bipyridinium dibromide, K₂CO₃, H₂O/THF, rt, 24 h; (d) Boc-β-Ala-OH, DIC, DMF/DCM, rt, 24 h; (e) TFA, rt, 1 h.

Compound 1: AM PS resin (0.42 mmol/g, 3.0 g, 1.26 mmol) was swollen in DMF for 12 h and washed with DMF (3×1 min). A solution of BAL linker (676 mg, 2.52 mmol), PyBOP (1.44 g, 2.77 mmol) and DIEA (0.97 mL, 5.6 mmol) in DMF (25 mL) was added to the resin, shaken at room temperature for 24 h, and washed with DMF (3×1 min). The completion of the coupling reaction was confirmed by a negative Kaiser ninhydrin test.

Compound 2: A mixture of compound 1 (0.25 g, 0.11 mmol), naphthalene-2-methaneamine hydrochloride (85 mg, 0.44 mmol), NaBH₃CN (29 mg, 0.44 mmol) in 1% AcOH/DMF (5 mL) was shaken at room temperature for 24 h, and washed with DMF (3×1 min). The reaction was monitored using a positive chloranil test.

Compound 4:

1. Amide-bond formation: A solution of compound 3 (90 mg, 0.33 mmol), PyBroP (154 mg, 0.33 mmol) and DIEA (0.11 mL, 0.66 mmol) in DCM (6 mL) was shaken at room temperature for 1 h, and added to the compound 2. The reaction mixture was shaken at room temperature for 24 h, and washed with DMF (3×1 min). The completion of the reaction was confirmed by a negative chloranil test.

2. Reduction: A mixture of the resulting resin, Na₂S₂O₄ (113 mg, 0.55 mmol), 1,1'-di-n-octyl-4,4'-bipyridinium dibromide (6 mg, 0.01 mmol), K₂CO₃ (30 mg, 0.22 mmol) in 20% H₂O/THF (8 mL) was shaken at room temperature for 24 h, and washed with H₂O (3×1 min), 20% 1N HCl (aq)/THF (3×1 min), 20% H₂O/THF (3×1 min), DMF (3×1 min) to give compound 4.

Compound 6: This compound was prepared from compound 5 by using the same procedure as that for compound 4.

Compound 8: This compound was prepared from compound 7 by using the same procedure as that for compound 4.

Compound 9: A solution of Boc-β-Ala-OH (378 mg, 2.0 mmol), DIC (0.15 mL, 1.0 mmol) in 20% DMF/DCM (6 mL) was shaken at room temperature for 1 h, and added to the compound 6. The reaction mixture was shaken at room temperature for 24 h, and washed with DMF (3×1 min).

TK296: A mixture of compound 9 in 5% H₂O/TFA (5 mL) was shaken at room temperature for 2 h, and then the TFA solution was filtered, and the resin was washed with TFA (2 mL) and DCM (2 mL). The combined TFA solution was concentrated with a gentle stream of nitrogen, and a white solid was precipitated by adding cold diethyl ether (5 mL). The white solid was washed with ether and dried in vacuo to give TK296 (30 mg, 28%)

Scheme 3. Synthetic route to TK207.

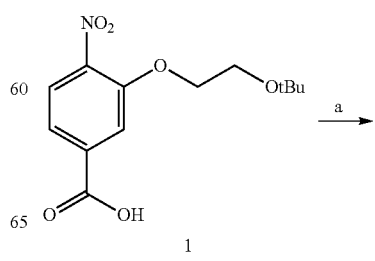

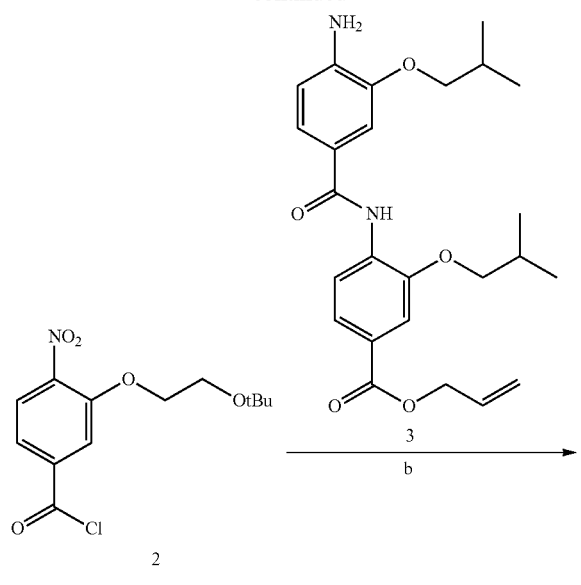
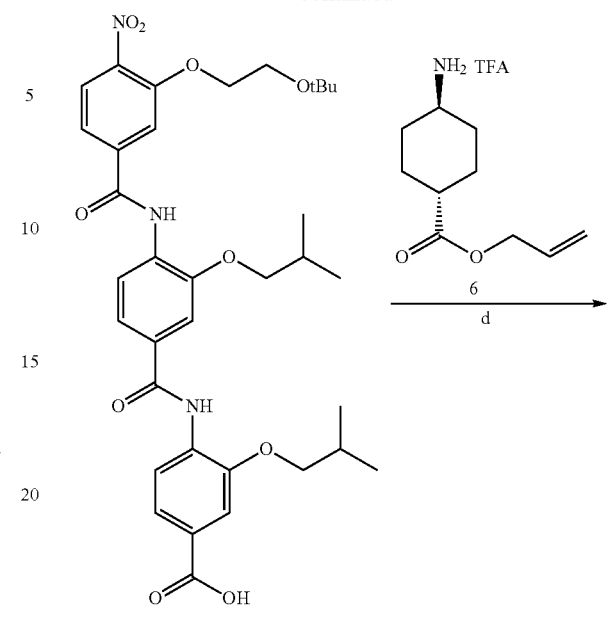

77

-continued

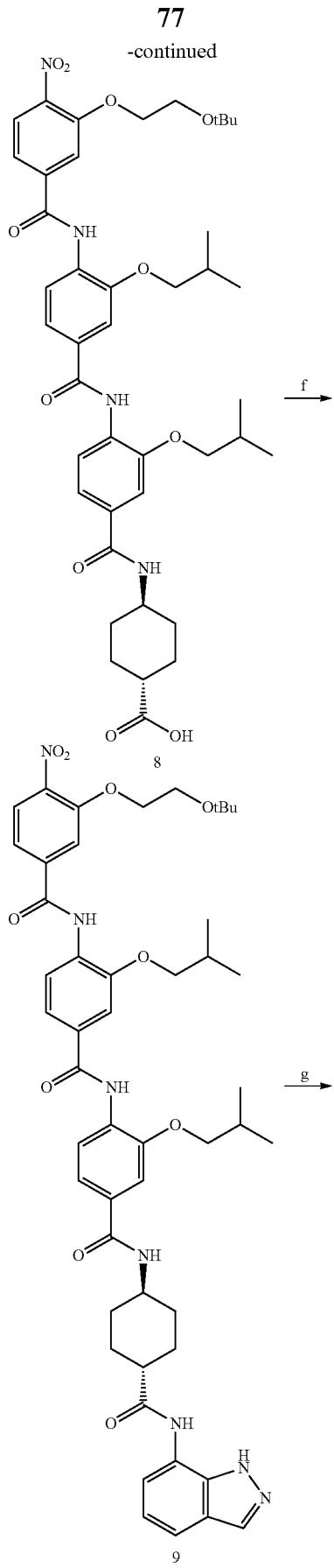

78

-continued

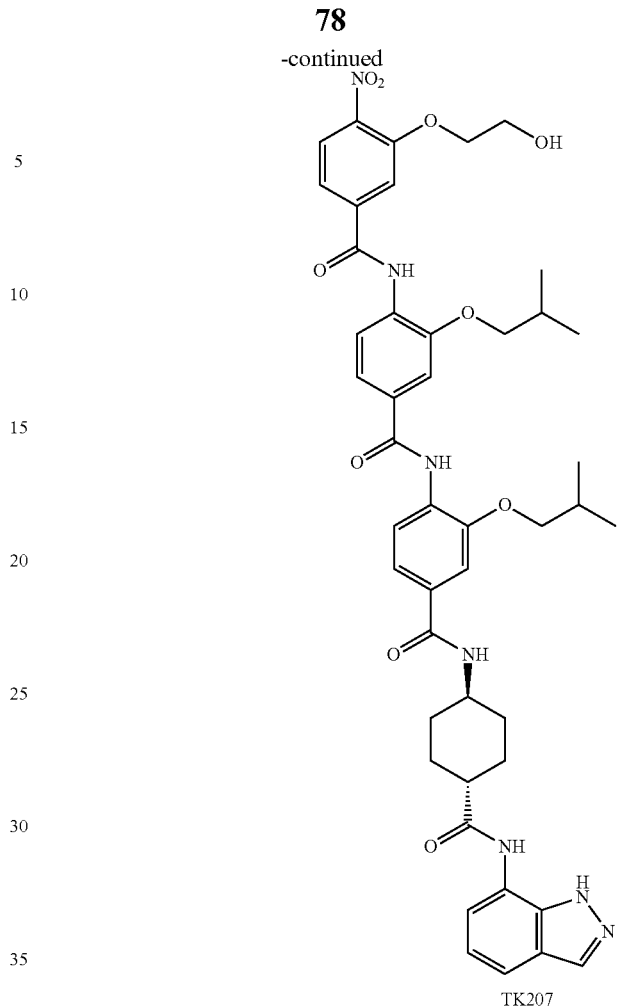

Reagents and conditions: (a) (COCl)₂, cat. DMF, DCM, rt, 2 h; (b) DIEA, DCM, rt, 24 h; (c) Pd(PPh₃)₄, PhSiH₃, THF, rt, 1 h; (d) PyBOP, DIEA, DMF, rt, 24 h; (e) Pd(PPh₃)₄, PhSiH₃, THF, rt, 1 h; (f) 7-amino-1H-indazole, HATU, DIEA, DMF, rt, 24 h; (g) TFA, rt, 1 h.

Compound 4: A 250 mL round-bottomed flask was charged with compound 1 (1.91 g, 6.75 mmol), DCM (50 mL), oxalyl chloride (1.2 mL, 13.5 mmol) and 2 drops of DMF. The reaction mixture was stirred at room temperature for 2 h and then concentrated under reduced pressure. The resulting compound 2 was dissolved in DCM (20 mL) and slowly added to a solution of compound 3 (2.0 g, 4.5 mmol), DIEA (1.6 mL, 9.0 mmol) and DCM (50 mL). The reaction mixture was stirred at room temperature for 24 h, and then was washed with 1 N HCl (50 mL), saturated NaHCO₃ (50 mL) and brine (50 mL). The organic layer was concentrated under reduced pressure to yield the crude product. Purification by crystallization from EtOAc/hexanes (1:2) gave compound 4 as a light yellow solid (2.7 g, 85%).

Compound 5: A 250 mL round-bottomed flask was charged with compound 4 (2.7 g, 3.83 mmol) and THF (100 mL). Then, Pd(PPh₃)₄ (0.59 g, 0.51 mmol) and PhSiH₃ (0.95 mL, 7.7 mmol) were added to the reaction mixture. The reaction mixture was stirred at room temperature for 1 h and then concentrated under reduced pressure. The resulting solid was washed with ether and dried in vacuo to give compound 5 as a light yellow sold (2.5 g, 98%).

Compound 7: A 100 mL round-bottomed flask was charged with compound 5 (0.60 g, 0.90 mmol), PyBOP (0.56 g, 1.1 mmol), DMF (30 mL), and DIEA (0.93 mL, 5.3 mmol), and the mixture was stirred at room temperature for 1 h. Compound 6 (0.80 g, 2.70 mmol) was then added to the reaction mixture and the resulting mixture was stirred at room temperature for 24 h. The reaction mixture was diluted with EtOAc (100 mL) and 1 N HCl (50 mL). The organic layer was separated and washed with 1 N HCl (50 mL) and brine (50 mL). The organic layer was concentrated under reduced pressure to yield the crude product. Purification by crystallization from EtOAc gave compound 7 as a light yellow solid (0.51 g, 68%).

Compound 8: A 250 mL round-bottomed flask was charged with compound 7 (0.49 g, 0.59 mmol) and THF (100 mL). Then, Pd(PPh$_3$)$_4$ (0.14 g, 0.12 mmol) and PhSiH$_3$ (0.30 mL, 0.24 mmol) were added to the reaction mixture. The reaction mixture was stirred at room temperature for 1 h and then concentrated under reduced pressure. The resulting solid was washed with ether and dried in vacuo to give compound 8 as a yellow sold (0.38 g, 81%).

TK207: A solution of compound 8 (40 mg, 0.051 mmol), HATU (25 mg, 0.066 mmol), and DIEA (27 µL, 0.16 mmol) in DMF (3 mL) was stirred at room temperature for 1 h. 7-Amino-1H-indazole (20 mg, 0.15 mmol) was then added to the reaction mixture and the resulting mixture was stirred at room temperature for 24 h. The reaction mixture was diluted with EtOAc (30 mL) and 1 N HCl (20 mL). The organic layer was separated and washed with 1 N HCl (20 mL) and brine (20 mL). The organic layer was concentrated under reduced pressure to yield the crude product. Purification by crystallization from EtOAc gave compound 9 as a yellow solid.

A solution of compound 9 in TFA (3 mL) was stirred at room temperature for 1 h and then concentrated under reduced pressure. The resulting solid was washed with ether and dried in vacuo to give TK207 as a yellow solid (16 mg, 37% over 2 reaction steps).

Scheme 4. Synthetic route to TK208.

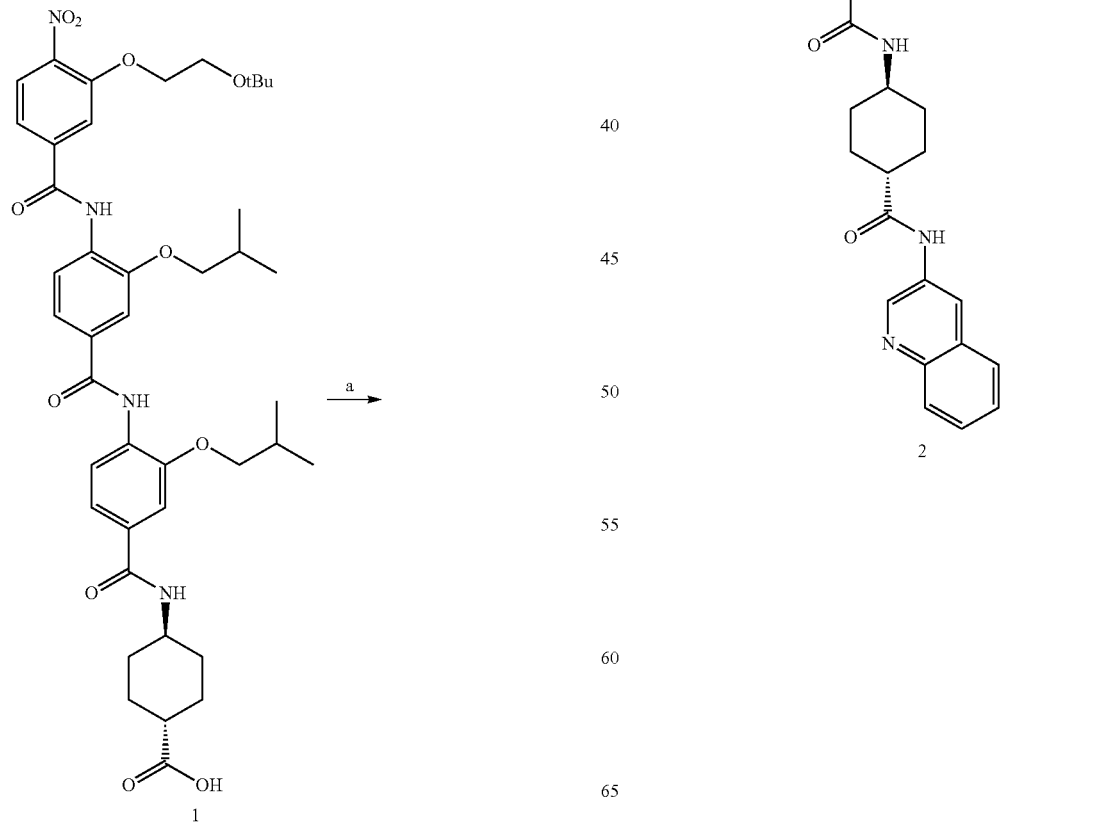

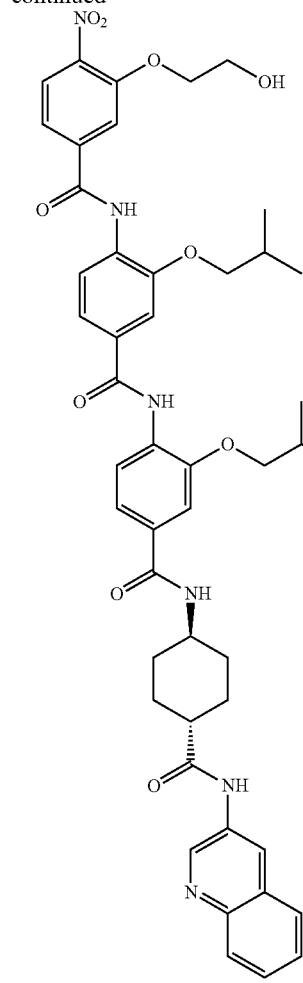

TK208

Reagents and conditions: (a) 3-aminoquinoline, HATU, DIEA, DMF, rt, 24 h; (b) TFA, rt, 1 h.

Compound 2: A solution of compound 1 (2.6 g, 3.3 mmol), HATU (1.5 g, 3.9 mmol), and DIEA (1.1 mL, 6.3 mmol) in DMF (50 mL) was stirred at room temperature for 1 h. 3-Aminoquinoline (1.4 g, 9.7 mmol) was then added to the reaction mixture and the resulting mixture was stirred at room temperature for 24 h. The reaction mixture was diluted with EtOAc (100 mL) and 1 N HCl (50 mL). The organic layer was separated and washed with 1 N HCl (50 mL) and brine (50 mL). The organic layer was concentrated under reduced pressure to yield the crude product. Purification by crystallization from EtOAc gave compound 2 as a yellow solid (2.6 g, 86%).

TK208: A solution of compound 9 (1.2 g, 1.31 mmol) in TFA (30 mL) was stirred at room temperature for 1 h and then concentrated under reduced pressure. The resulting solid was washed with ether and dried in vacuo to give TK208 as a yellow solid (0.67 g, 60%).

Scheme 5. Synthetic route to TK314.

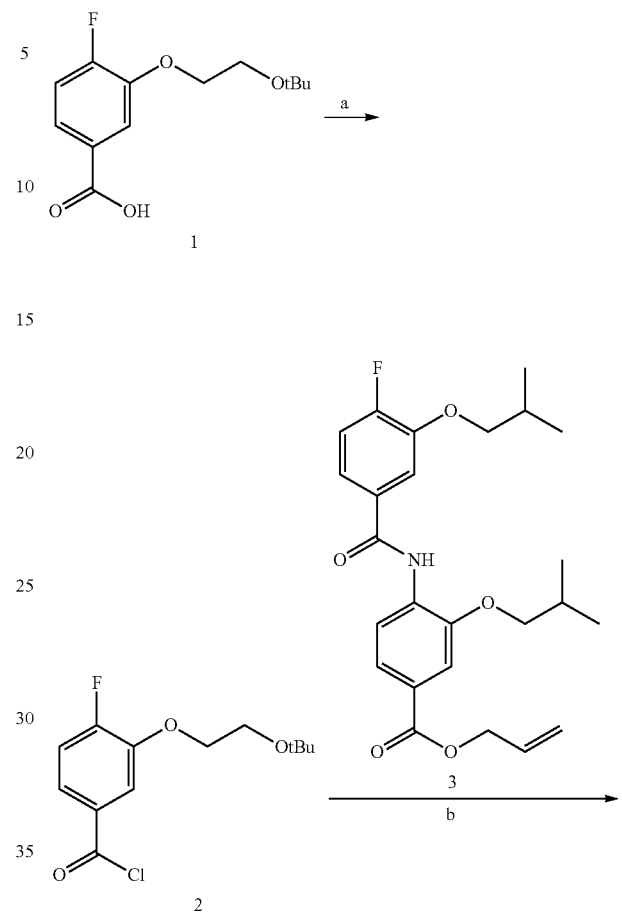

-continued

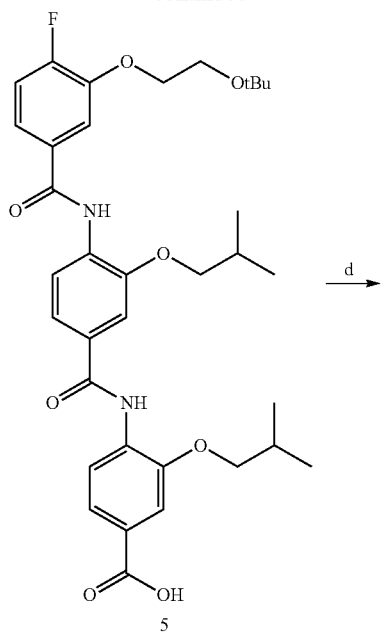

5

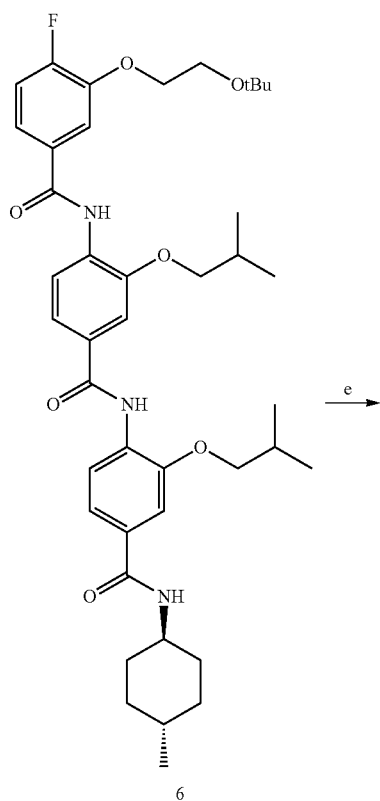

6

-continued

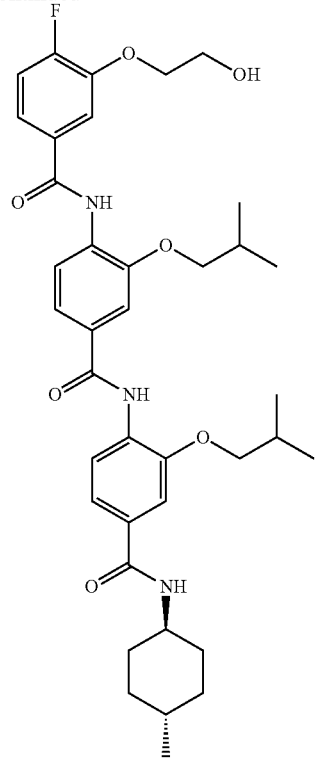

TK314

Reagents and conditions: (a) (COCl)₂, cat. DMF, DCM, rt, 2 h; (b) DIEA, DCM, rt, 24 h; (c) Pd(PPh₃)₄, PhSiH₃, THF, rt, 1 h; (d) trans-4-methylcyclohexylamine, HATU, DIEA, DMF, rt, 24 h; (e) TFA, rt, 1 h.

Compound 4: A solution of compound 1 (0.62 g, 2.4 mmol), oxalyl chloride (0.41 mL, 4.7 mmol) and 2 drops of DMF in DCM (30 mL) was stirred at room temperature for 2 h, and then concentrated under reduced pressure. The resulting compound 2 was dissolved in DCM (10 mL) and slowly added to a solution of compound 3 (0.70 g, 1.6 mmol), DIEA (0.55 mL, 3.2 mmol) and DCM (30 mL). The reaction mixture was stirred at room temperature for 24 h, and then was washed with 1 N HCl (50 mL), saturated NaHCO₃ (50 mL) and brine (50 mL). The organic layer was concentrated under reduced pressure to yield the crude product. Purification by crystallization from EtOAc/hexanes (1:2) gave compound 4 as a yellow solid (0.46 g, 42%).

Compound 5: A solution of compound 4 (0.40 g, 0.59 mmol), Pd(PPh₃)₄ (69 mg, 0.06 mmol) and PhSiH₃ (0.15 mL, 1.2 mmol) in THF (30 mL) was stirred at room temperature for 2 h, and then concentrated under reduced pressure. The resulting solid was washed with ether and dried in vacuo to give compound 5 as a yellow sold (0.37 g, 98%). TK314: A solution of compound 5 (50 mg, 0.078 mmol), HATU (39 mg, 0.10 mmol), DIEA (41 μL, 0.24 mmol) in DMF (4 mL) was stirred at room temperature for 1 h, and then trans-4-methylcyclohexylamine (45 mg, 0.40 mmol) was added to the reaction mixture. The resulting mixture was stirred at room temperature for 24 h and then diluted with EtOAc (20 mL) and 1 N HCl (10 mL). The organic layer was separated, washed with 1 N HCl (10 mL) and brine (10 mL), and concentrated under reduced pressure. The resulting solid was washed with EtOAc and dried in vacuo to give compound 6 as a yellow sold.

A solution of compound 6 in TFA (3 mL) was stirred at room temperature for 1 h and then concentrated under reduced pressure. The resulting solid was washed with ether and dried in vacuo to give TK314 as a yellow solid (42 mg, 79% over 2 reaction steps).

Scheme 6. Synthetic route ot TK315.

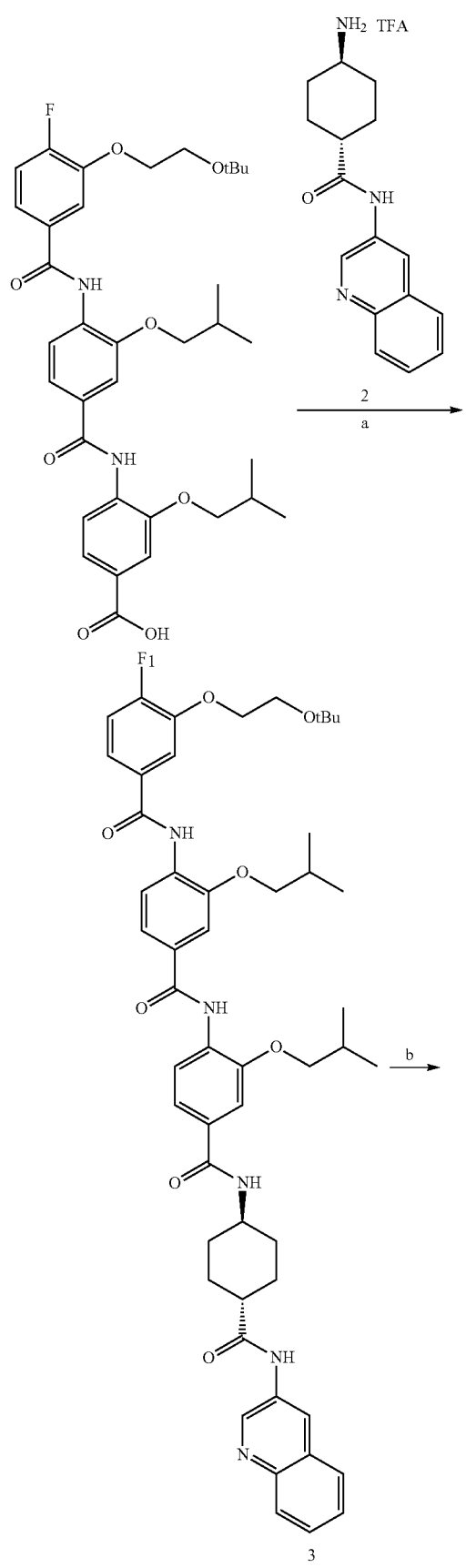

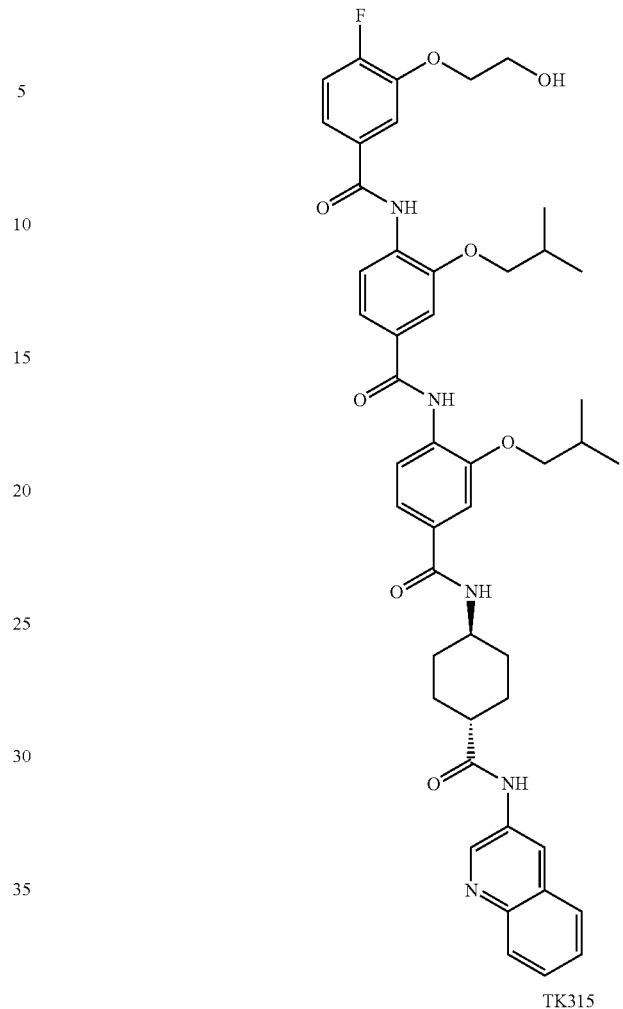

TK315

Reagents and condtitions: (a) HATU, DIEA, DMF, rt, 24 h; (b) TFA, rt, 1 h.

TK315: A solution of compound 1 (50 mg, 0.078 mmol), HATU (39 mg, 0.10 mmol), DIEA (41 μL, 0.24 mmol) in DMF (4 mL) was stirred at room temperature for 1 h, and then compound 2 (91 mg, 0.24 mmol) was added to the reaction mixture. The resulting mixture was stirred at room temperature for 24 h and then diluted with EtOAc (20 mL) and 1 N HCl (10 mL). The organic layer was separated, washed with 1 N HCl (10 mL) and brine (10 mL), and concentrated under reduced pressure. The resulting solid was washed with EtOAc and dried in vacuo to give compound 3 as a yellow sold.

A solution of compound 3 in TFA (3 mL) was stirred at room temperature for 1 h and then concentrated under reduced pressure. The resulting solid was washed with ether and dried in vacuo to give TK315 as a yellow solid (51 mg, 78% over 2 reaction steps).

Scheme 7. Synthetic route to TK308.
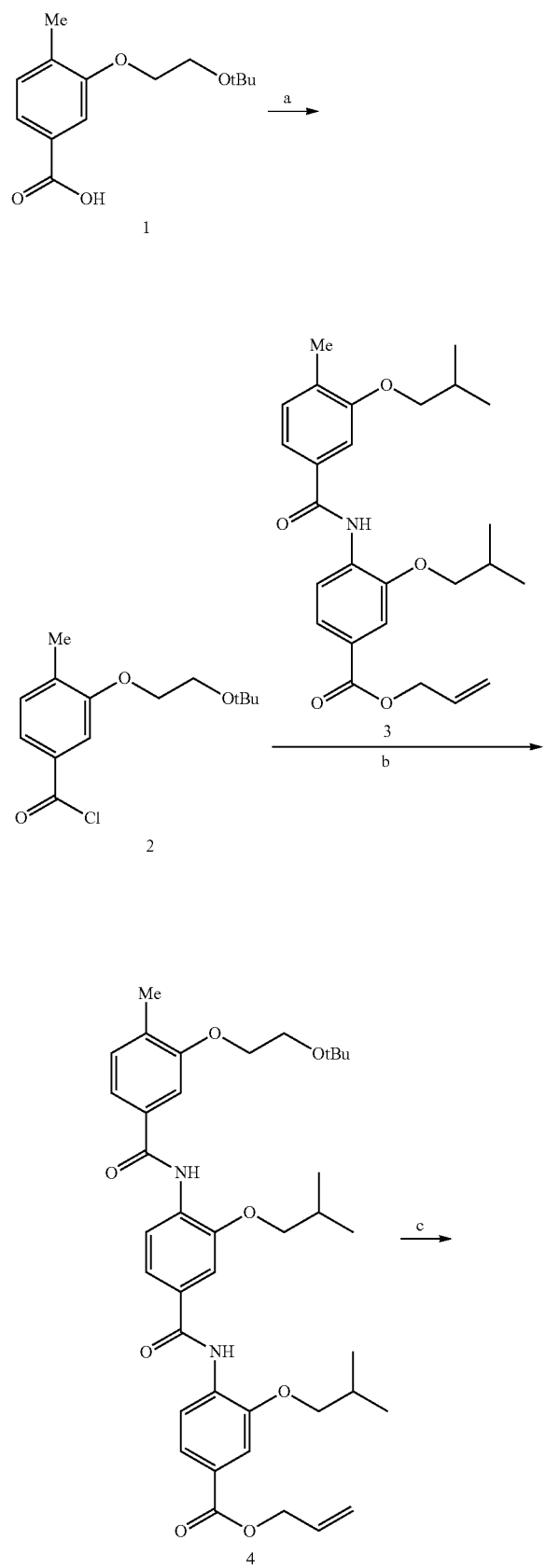
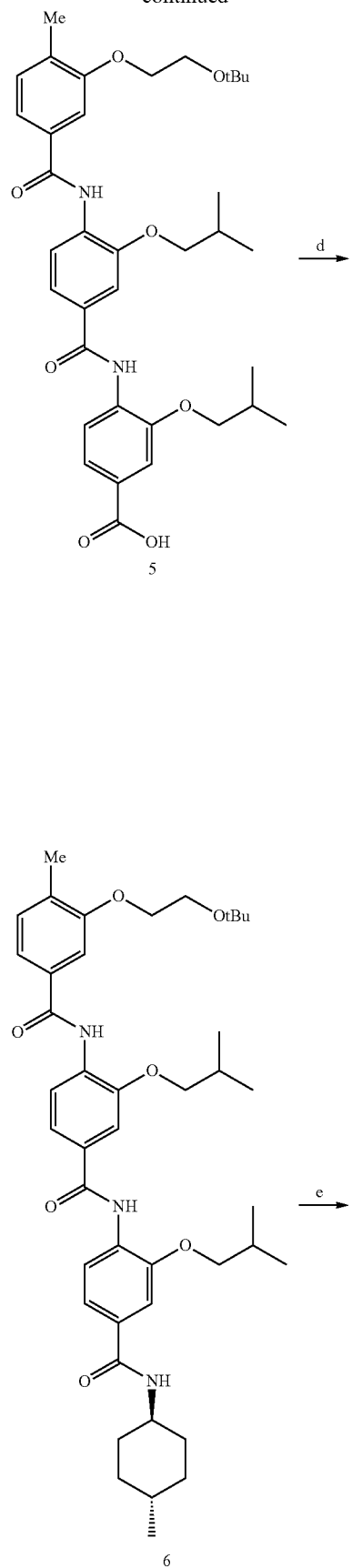
-continued

-continued

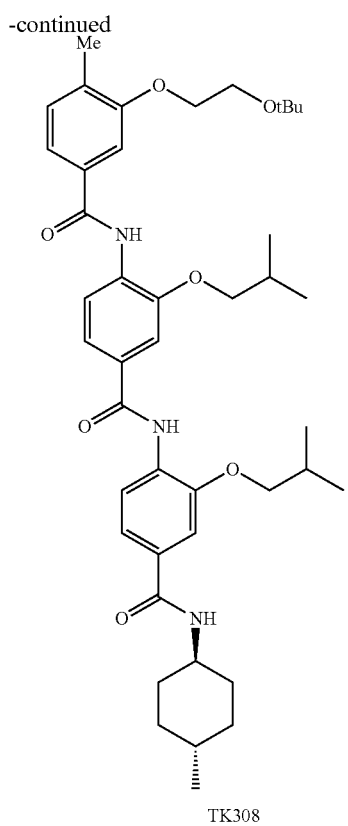

TK308

Reagents and conditions: (a) (COCl)₂, cat. DMF, DCM, rt, 2 h; (b) DIEA, DCM, rt, 24 h; (c) Pd(PPh₃)₄, PhSiH₃, THF, rt, 1 h; (d) trans-4-methylcyclohexyamine, HATU, DIEA, DMF, rt, 24 h; (e) TFA, rt, 1 h.

Compound 4: A solution of compound 1 (1.1 g, 4.4 mmol), oxalyl chloride (0.78 mL, 9.0 mmol) and 2 drops of DMF in DCM (30 mL) was stirred at room temperature for 2 h, and then concentrated under reduced pressure. The resulting compound 2 was dissolved in DCM (10 mL) and slowly added to a solution of compound 3 (1.3 g, 3.0 mmol), DIEA (1.0 mL, 5.7 mmol) and DCM (30 mL). The reaction mixture was stirred at room temperature for 24 h, and then was washed with 1 N HCl (50 mL), saturated NaHCO₃ (50 mL) and brine (50 mL). The organic layer was concentrated under reduced pressure to yield the crude product. Purification by crystallization from EtOAc/hexanes (1:2) gave compound 4 as a yellow solid (0.74 g, 37%).

Compound 5: A solution of compound 4 (0.70 g, 1.04 mmol), Pd(PPh₃)₄ (0.12 g, 0.10 mmol) and PhSiH₃ (0.26 mL, 2.1 mmol) in THF (30 mL) was stirred at room temperature for 2 h, and then concentrated under reduced pressure. The resulting solid was washed with ether and dried in vacuo to give compound 5 as a yellow sold (0.57 g, 86%).

TK308: A solution of compound 5 (50 mg, 0.079 mmol), HATU (39 mg, 0.10 mmol), DIEA (41 µL, 0.24 mmol) in DMF (4 mL) was stirred at room temperature for 1 h, and then trans-4-methylcyclohexylamine (45 mg, 0.40 mmol) was added to the reaction mixture. The resulting mixture was stirred at room temperature for 24 h and then diluted with EtOAc (20 mL) and 1 N HCl (10 mL). The organic layer was separated, washed with 1 N HCl (10 mL) and brine (10 mL), and concentrated under reduced pressure. The resulting solid was washed with EtOAc and dried in vacuo to give compound 6 as a yellow sold.

A solution of compound 6 in TFA (3 mL) was stirred at room temperature for 1 h and then concentrated under reduced pressure. The resulting solid was washed with ether and dried in vacuo to give TK308 as a yellow solid (40 mg, 75% over 2 reaction steps).

Scheme 8. Synthetic route ot TK309.

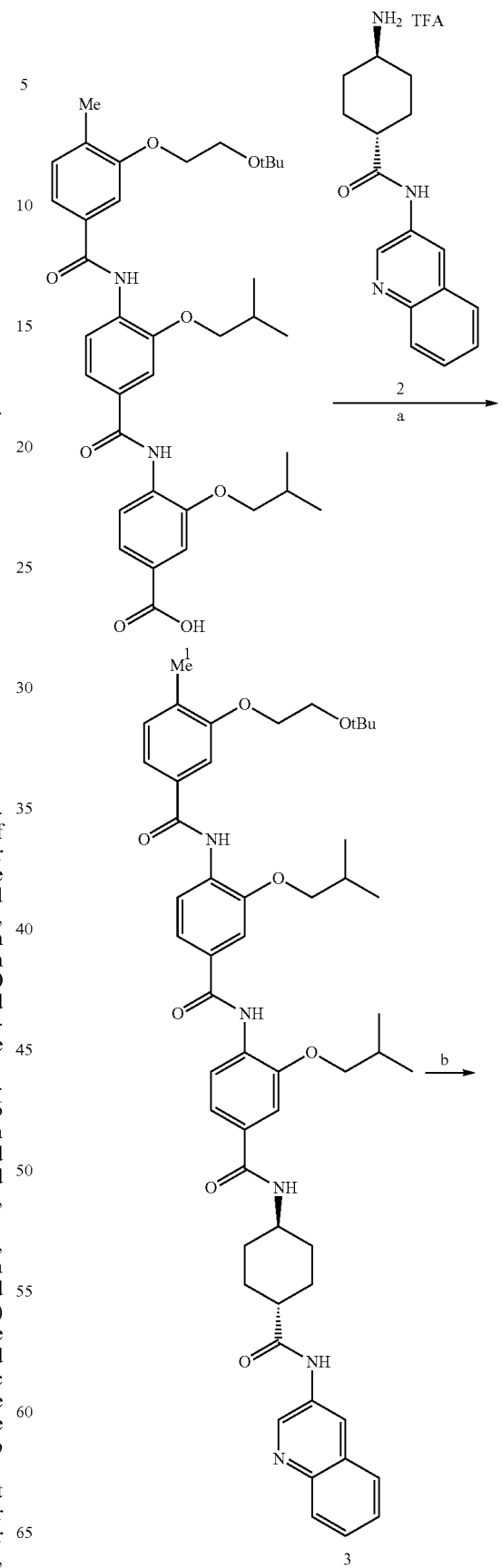

-continued

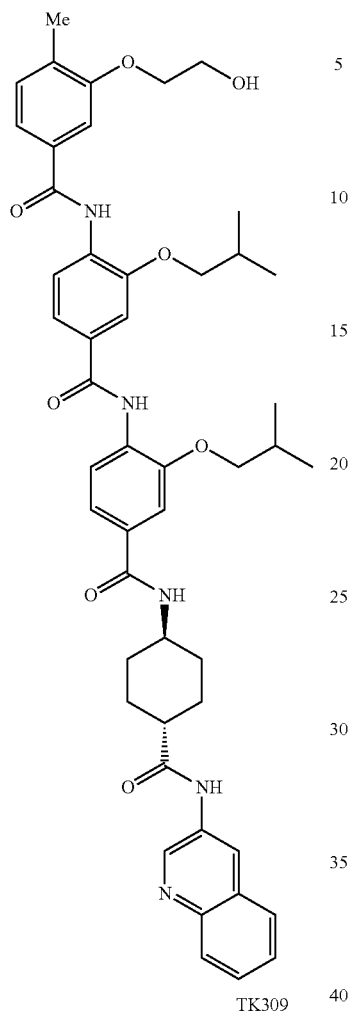

TK309

Reagents and conditions: (a) HATU, DIEA, DMF, rt, 24 h; (b) TFA, rt, 1 h.

TK309: A solution of compound 1 (50 mg, 0.079 mmol), HATU (39 mg, 0.10 mmol), DIEA (41 μL, 0.24 mmol) in DMF (4 mL) was stirred at room temperature for 1 h, and then compound 2 (91 mg, 0.24 mmol) was added to the reaction mixture. The resulting mixture was stirred at room temperature for 24 h and then diluted with EtOAc (20 mL) and 1 N HCl (10 mL). The organic layer was separated, washed with 1 N HCl (10 mL) and brine (10 mL), and concentrated under reduced pressure. The resulting solid was washed with EtOAc and dried in vacuo to give compound 3 as a yellow sold.

A solution of compound 3 in TFA (3 mL) was stirred at room temperature for 1 h and then concentrated under reduced pressure. The resulting solid was washed with ether and dried in vacuo to give TK309 as a yellow solid (55 mg, 84% over 2 reaction steps).

Scheme 9. Synthetic route to YL144.

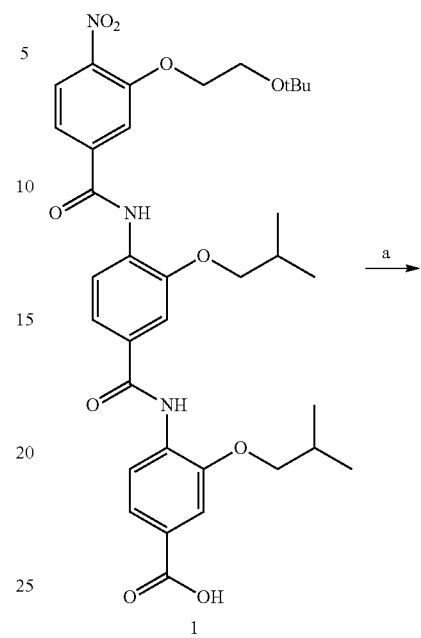

1

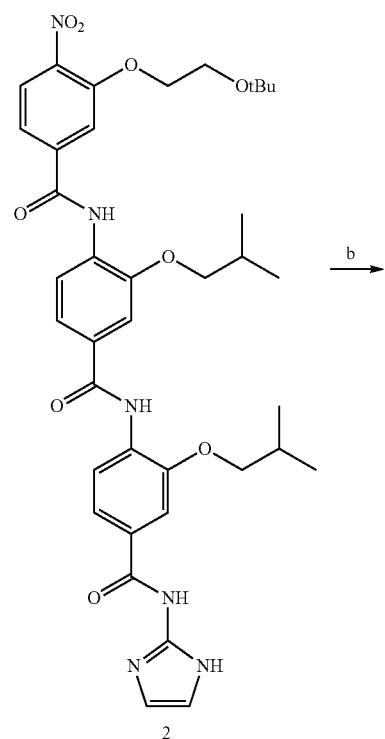

2

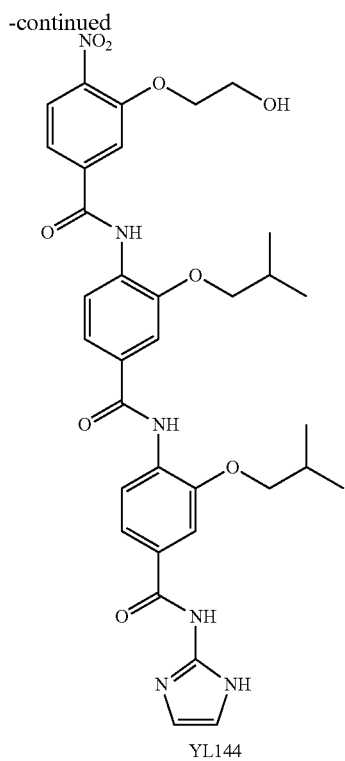

YL144

Reagents and conditions: (a) 2-aminoimidazole sulfate, HATU, DIEA, DMF, rt, 24 h; (b) TFA, rt, 1 h.

YL144: A mixture of compound 1 (0.20 g, 0.30 mmol), 2-aminoimidazole sulfate (79 mg, 0.60 mmol) and DIEA (0.42 mL, 2.4 mmol) in DMF (20 mL) was stirred at 60° C. for 1 h. HATU (0.15 g, 0.39 mmol) was then added to the reaction mixture and the resulting mixture was stirred at 60° C. for 24 h. The reaction mixture was cooled to room temperature and diluted with EtOAc (50 mL) and 1 N HCl (30 mL). The organic layer was separated and washed with 1 N HCl (30 mL) and brine (30 mL). The organic layer was concentrated under reduced pressure to yield the crude product. Purification by crystallization from EtOAc gave compound 2 as a yellow solid.

A solution of compound 2 in TFA (5 mL) was stirred at room temperature for 1 h and then concentrated under reduced pressure. The resulting solid was washed with ether and dried in vacuo to give YL144 as a yellow solid (0.12 g, 52%).

Example 3—Oligo Benzamide Analogs and Their Use in Cancer Treatment

The inventors have conducted several studies at UTHSCSA using preclinical murine Xenograft and Patient derived xenografts (PDX) examining the efficacy of new compounds TK41 (ERX-41), TK208 (ERX-208) and TK315 (ERX-315). The results are given below.

Oral administration of TK315 (ERX-315) in captisol formulation showed potent activity against both MCF7-MT ESR1 ZR-75 and ZR75-MT Y537S ERα expressing therapy resistant BC xenograft models but no effect on mouse liver or body weight (FIGS. 31A-C). Histologic evaluation of the tumors showed dramatically decreased Ki67 proliferation indices in these tumors. Importantly, the lack of immune antibody infiltrates in the spleen, lymph nodes, kidney, or liver of the syngeneic D2A1 tumors with treated with ERX-315 suggested that ERX-315 is potent, not immunogenic and can be safely administered orally.

PDX models recapitulate the structural complexity and individual heterogeneity of human BC (primary tumor samples), therefore, studies with these models will establish an incontrovertible basis for clinical translation. Three different TNBC PDX tumors were established in NSG mice by transplanting PDX tumor pieces into the mammary fat fad using established protocol in the inventors' lab. Results showed that TK41 (ERX-41) treatment significantly decreased the growth of all the three TNBC PDX tumors tested (FIGS. 32A-C).

The inventors have tested the in vivo activity of TK208 (ERX-208) using both ovarian xenograft and PDX models. Results showed that TK208 (ERX-208) has good efficacy in reducing the ovarian tumor volume with no effect on mouse body weight, suggesting lack of toxicity (FIGS. 33A-H).

Example 4—Biological Activities

ERX-41 has potent activity against TNBC cells in vitro. To evaluate the generalizability of the inventors' findings, they evaluated ERX-41 in a large number of TNBC and ERa-positive cell lines. In 22 human preclinical TNBC cell line models, representing all six molecular subtypes of TNBC, ERX-41 had potent antiproliferative activity with an $IC_{50}$<500 nM using WST assays and <250 nM using CellTiter-Glo cell viability assays (FIGS. 34A-B). ERX-41 did not have significant effect against normal human mammary epithelial cells (HMEC) at >1 µM with either the WST, MTT or CellTiter-Glo assays (FIGS. 34A-B). Live cell imaging studies indicated that ERX-41 significantly induced cell death in TNBC cells within 30 hours of treatment in a vast majority of the cells (>90%) compared to control (<1%). By contrast, ERX-41 did not significantly induce cell death in HMEC cells.

ERX-41 has potent activity against TNBC in vivo. Daily oral or intraperitoneal administration of ERX-41 up to 200 mg/kg doses were well tolerated by mice, with no clear evidence of toxicity. Pharmacokinetic studies indicated that ERX-41 was orally bioavailable, with peak detectable levels in the plasma at 4 h after oral administration (10 mg/kg single dose). Additionally, ERX-41 was detectable within 1.5 h in established subcutaneous MDA-MB-231 xenograft tumors after oral or intraperitoneal administration (FIG. 35A). The inventors demonstrated that oral administration of ERX-41 (10 mg/kg/day) significantly decreased the growth of established MDA-MB-231 TNBC xenografts in vivo (FIG. 35B). ERX-41 decreased tumor growth, as shown by extirpated tumor sizes at the end of study (FIG. 35C and FIG. 35E). Importantly, ERX-41 treatment did not show overt signs of toxicity, as evidenced by no alterations in mouse body weights in the treated mice (FIG. 35D). Further, ERX-41 was able to significantly reduce the growth of D2A1 xenografts in a syngeneic tumor model (FIGS. 35F-H). The inventors validated the activity of ERX-41 in four distinct TNBC PDXs established in the mammary fat pad (FIGS. 35I-P). In each of these tumors, daily oral administration of ERX-41 (10 mg/kg/day) significantly decreased the rates of growth of the tumors in vivo. These data support that ERX-41 has potent activity on TNBC both in vitro and in vivo, without any associated toxicity and anti-estrogenic activity.

ERX-41 induces endoplasmic reticulum stress in TNBC. To understand the mechanism of action of ERX-41 in TNBC, the inventors performed unbiased RNA sequencing studies in three TNBC (SUM-159, MDA-MB-231, and BT549) and normal HMEC cell lines (FIGS. 36A-C). Gene ontology analyses revealed that the top pathways upregulated at 4 h in the TNBC cells were related to induction of endoplasmic reticulum (ER) stress and its compensatory unfolded protein response (UPR) pathway (FIG. 36D). Heatmaps show the induction of ER stress and UPR genes in these three TNBC cell lines (FIG. 36E). Evaluation of ER stress induction was then performed with ultrastructural studies using electron microscopy (EM) studies. ERX-41 induced dramatic dilation of the ER within 4 h of treatment in TNBC cells (FIG. 36F, ER outlined by yellow arrowheads). In contrast, in normal HMEC cells, ERX-41 was unable to induce ER stress, as shown by the lack of dilation of ER on EM (FIG. 36F). The induction of ER stress was broadly noted in multiple TNBC cells but not in normal cells, indicating that ERX-41 was able to target a vulnerability to induce ER stress in these cancer cells. The inventors have biochemically validated that ERX-41 but not ERX-11 induces ER stress and downstream UPR pathways via induction of phosphorylated protein kinase R-like ER kinase (p-PERK), inositol-requiring enzyme 1a (IRE1a), eukaryotic translation initiation factor 2 subunit 1 (eiF2a), and expression of CCAAT-enhancer binding homologous-protein (CHOP) in TNBC cells (FIG. 36H).

The molecular target of ERX-41 in TNBC is LIPA. To identify the molecular target of ERX-41, the inventors performed an unbiased CRISPR/Cas9 KO screen in MDA-MB-231 cells. There was significant concordance between two biological replicates of the screen performed at two distinct concentrations of ERX-41 and the top 6 genes from the screen were subject to a secondary screen in MDA-MB-231 cells (FIG. 37A). Knockout clones of LIPA, SLC5A3, SMAP2, TMEM208, SOAT1 and ARID1A were generated in multiple TNBC cells and evaluated for response to ERX-41. Of these, only knockout (KO) of LIPA was able to consistently abrogate the cytotoxic response to ERX-41 (FIG. 37B). While these data do not rule out a role for the other identified ERX-41 targets, the inventors were able to show that KO of LIPA in multiple TNBC cell lines including SUM-159, MDA-MB436 and MDA-MB-231 was able to alter the response of TNBC cells to ERX-41 (FIGS. 37C-D) in CellTiter-Glo assays in vitro. The altered response of SUM-159 clones with LIPA KO was specific for ERX-41, as shown by similar responses of SUM-159 parental and LIPA KO clones to thapsigargin (ER stress inducer through its modulation of ER $Ca^{2+}$ levels) and paclitaxel (chemotherapeutic agent) (FIGS. 37E-F). Live cell imaging studies confirmed that KO of LIPA altered the response of SUM-159 cells to ERX-41 with dramatic decrease in cell death (quantitation in FIG. 37G, time lapsed pictures in FIG. 37H). The inventors then confirmed that xenografts of SUM-159 with LIPA KO did not respond to oral administration of ERX-41, in contrast to parental SUM-159 xenografts which responded significantly to ERX-41 in vivo (FIGS. 37I-J).

ERX-41 has activity on human TNBC tumors. To ascertain that ERX-41 would have activity against primary TNBC tumors, the inventors leveraged their prior significant experience with the ex vivo patient derived explant (PDE) cultures (FIG. 38A). The PDE cultures, maintains the native tissue architecture and better recapitulates the heterogeneity of human TNBC in a laboratory setting. The inventors have noted that ERX-41 had significant activity, as evidenced by decreased proliferation (ki67 staining) and increased apoptosis (cleaved caspase 3 staining) of TNBC PDEs (FIGS. 38C-D). Importantly, evaluation of these explants with immunohistochemical evaluation of UPR pathway markers shows enhanced pPERK, CHOP (protein product of DDIT3 gene) and peiF2a staining within 24 h after treatment with ERX-41 (FIG. 38E). These data further validate the on-target activity and potential utility of ERX-41, specifically in patients who would receive the drug.

ERX-41 interacts with LIPA through the LXXLL (SEQ ID NO: 1) motif and its activity is independent of LIPA lipase activity. LIPA is a lysosomal acid lipase (also known as cholesterol ester hydrolase) and is known to functions in the lysosome to catalyze the hydrolysis of cholesteryl esters and triglycerides (Li and Zhang, 2019). The lipase function of LIPA is critical to prevent accumulation of cholesteryl esters and triglycerides and can be fatal if deficient. To study how ERX-41 interacted with LAL, the inventors used in silico molecular docking simulation to evaluate potential binding sites of ERX-41 on LAL (FIGS. 39A-E). They noted that LIPA has a single 239LXXLL243 (SEQ ID NO: 1) motif and that ERX-41 (shown in green, FIGS. 39A-E) could potentially interact with this LXXLL (SEQ ID NO: 1) motif which was noted to be in the lid region of LAL (LXXLL (SEQ ID NO: 1) motif shown in orange, FIGS. 39A-E). Importantly, the critical domain of lipase activity of LIPA appeared to be spatially distinct from the LXXLL (SEQ ID NO: 1) motif: previous studies have identified a LIPA point mutation $H_{274}Y$ in LAL helix 13, that is known to abrogate LIPA lipase function (FIG. 39F). Further, ERX-41 showed no inhibition of lipase activity of LIPA, while lalistat (known lipase inhibitor) attenuated lipase activity in these assays (FIG. 39G). The inventors synthesized LIPA plasmid constructs under a constitutive promoter, including wild type LIPA (WT-LIPA), $H_{274}Y$ mutant LIPA ($H_{274}Y$ MT-LIPA), DLXXLL (SEQ ID NO: 2) mutant LIPA (deletion of the 238NLCFLLC244 cap), and the L242P mutant LIPA (point mutation of the second L in the LXXLL (SEQ ID NO: 1) motif). Evaluation of the lipase activity of these constructs revealed that the WT-LIPA, DLXXLL (SEQ ID NO: 2) MT-LIPA and L242P MT-LIPA had lipase activity while the $H_{274}Y$ MT-LIPA did not have lipase activity (FIG. 39H). The inventors confirmed direct interaction of ERX-41 with LIPA using biotinylated ERX-41 pulldown which indicated interaction between ERX-41 and proteins encoded by WT-LIPA and $H_{274}Y$ MT-LIPA but not DLXXLL (SEQ ID NO: 2) MT-LIPA or L242P MT-LIPA (FIG. 39I). Reconstitution of WT-LIPA (KO+WT) in SUM-159 cells with LIPA KO restored sensitivity to ERX-41, with an IC50 of 250 nM (FIG. 39J). Interestingly, reconstitution of the lipase-incompetent $H_{274}Y$ MT-LIPA (KO+$H_{274}Y$) also restored sensitivity to ERX-41 (FIG. 39J). These findings are further supported by the ability of WT-LIPA and $H_{274}Y$ MT-LIPA but not DLXXLL (SEQ ID NO: 2) MTLIPA or L242P MT-LIPA to restore the ability of ERX-41 to induce ER stress at the protein level (shown by activation of PERK in FIG. 39K) and UPR genes at the RNA level (sXBP1 and DDIT3 levels in FIGS. 39L-M) in SUM-159 cells with LIPA KO (FIGS. 39K-M). These data taken together indicate that ERX-41 interacts with LAL through its LXXLL (SEQ ID NO: 1) domain and its ability to induce ER stress and cell death in TNBC is independent of ability to induce ER stress and cell death in TNBC is independent of the lipase activity of LIPA.

Figure 40:
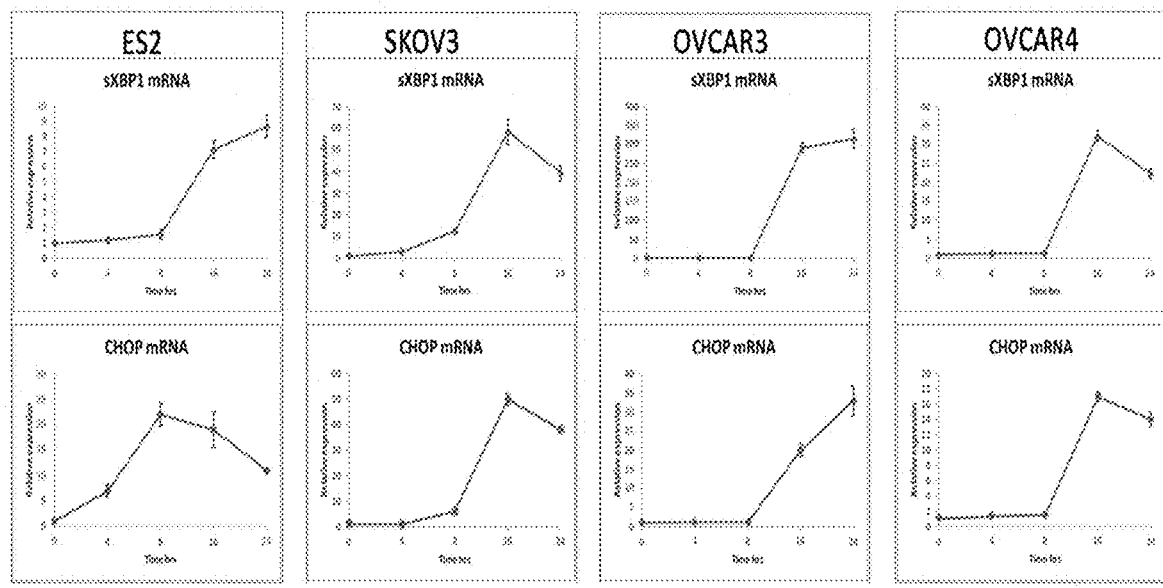
FIG. 40: Time course of induction of sXBP1 and CHOP mRNA in 4 OCa cell lines—ES2, SKOV3, OVCAR$_3$ and OVCAR$_4$ by ERX-208. Following treatment of OCa cell lines with 100 nM ERX-208, cells were harvested at various time points and lysates subjected to RT-PCR for both CHOP and sXBP1.
Figure 41:
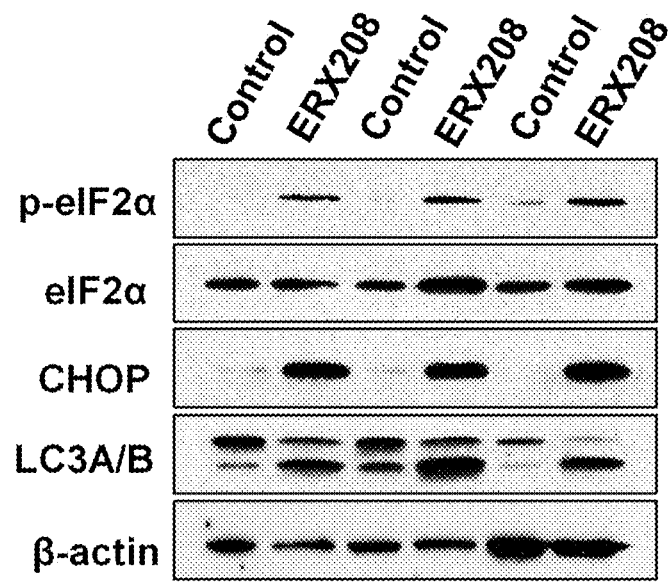
FIG. 41: OCa cells were treated with ERX-208 for 16 h and the status of UPR proteins were determined using western blotting.
Figure 44:
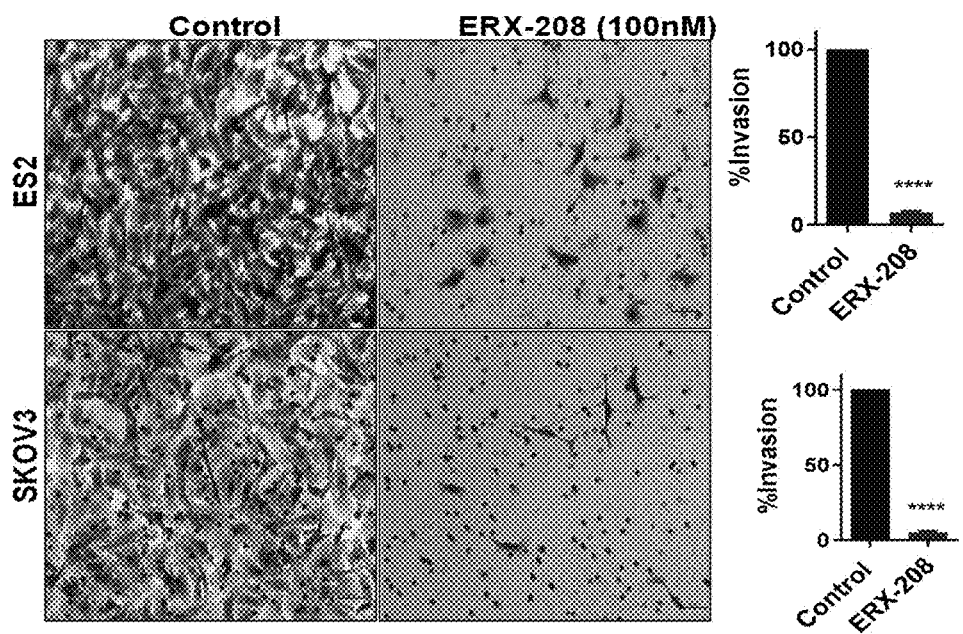
FIG. 44: ES2 and SKOV3 cells were treated with ERX-208 and its effect on invasion was measured using Matrigel invasion chamber assays. ****$p<0.0001$.
Figure 45:
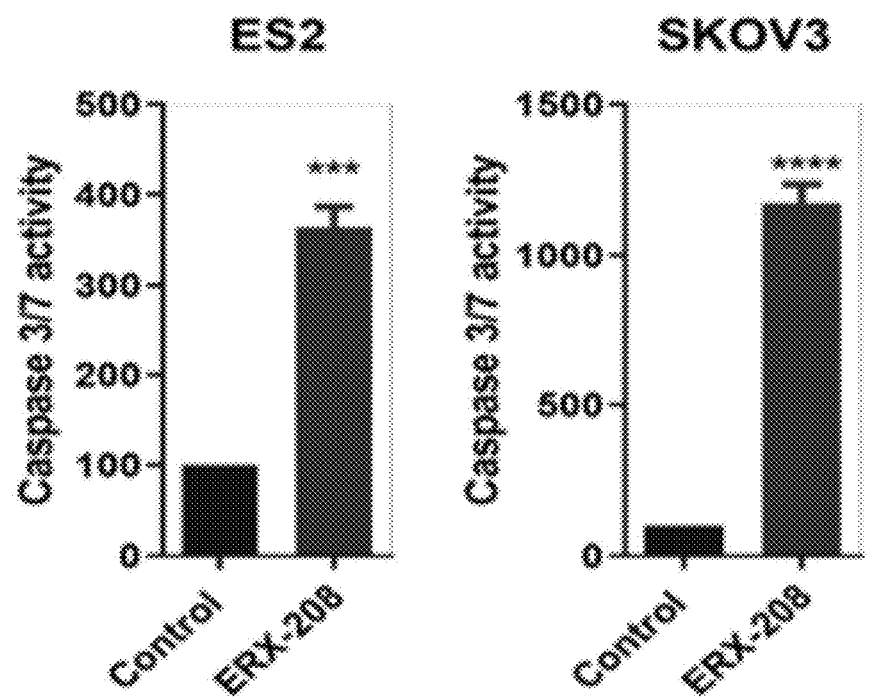
FIG. 45: ERX-208 effect on apoptosis of OCa cells was measured using Caspase-Glo® 3/7 Assays. ****$p<0.0001$.

ERX-208. ERX-208 as the most potent agent that consistently induced both ER stress (ERS) and apoptosis in OCa cells. The time course of induction of sXBP1 and CHOP mRNA in OCa cells shows a robust and consistent induction (>15-fold CHOP, >10 fold sXBP1) by ERX-208 within 24 h (FIG. 40). The inventors validated that ERX-208 was able to induce classic UPR components peIF2a, CHOP and LC3B at the protein level in multiple OCa cell lines (FIG. 41). Functionally, ERX-208 causes growth inhibition of OCa cells, as noted by MTT assays using five established OCa cells (ES2, SKOV3, A2780, TOV21G, TOV112D) and five primary OCa cells derived from HGSOC patient ascites (AS21, AS23, AS25, AS28, AS29) (FIGS. 42B-C). In contrast, ERX-11 has limited activity against OCa cells (FIG. 42A). Importantly, ERX-208 has limited activity in normal ovarian surface epithelial cells (IOSE) (FIG. 42D). The inventor noted an $IC_{50}$ of ~50-100 nM for ERX-208 both for inducing ERS and in reducing the growth of OCa cells. Importantly, ERX-208 treatment reduced colony formation (FIG. 43) and invasion (FIG. 11, using BD Biocoat Matrigel invasion assays) of SKOV3 and ES2 OCa cells. Further, results using Caspase-Glo® 3/7 Assay showed that ERX-208 promotes apoptosis of OCa cells (FIG. 40). Taken together, these data indicate that ERX-208 can induce ERS in OCa cells, reduce growth and induce apoptosis in OCa cells.

Figure 46:
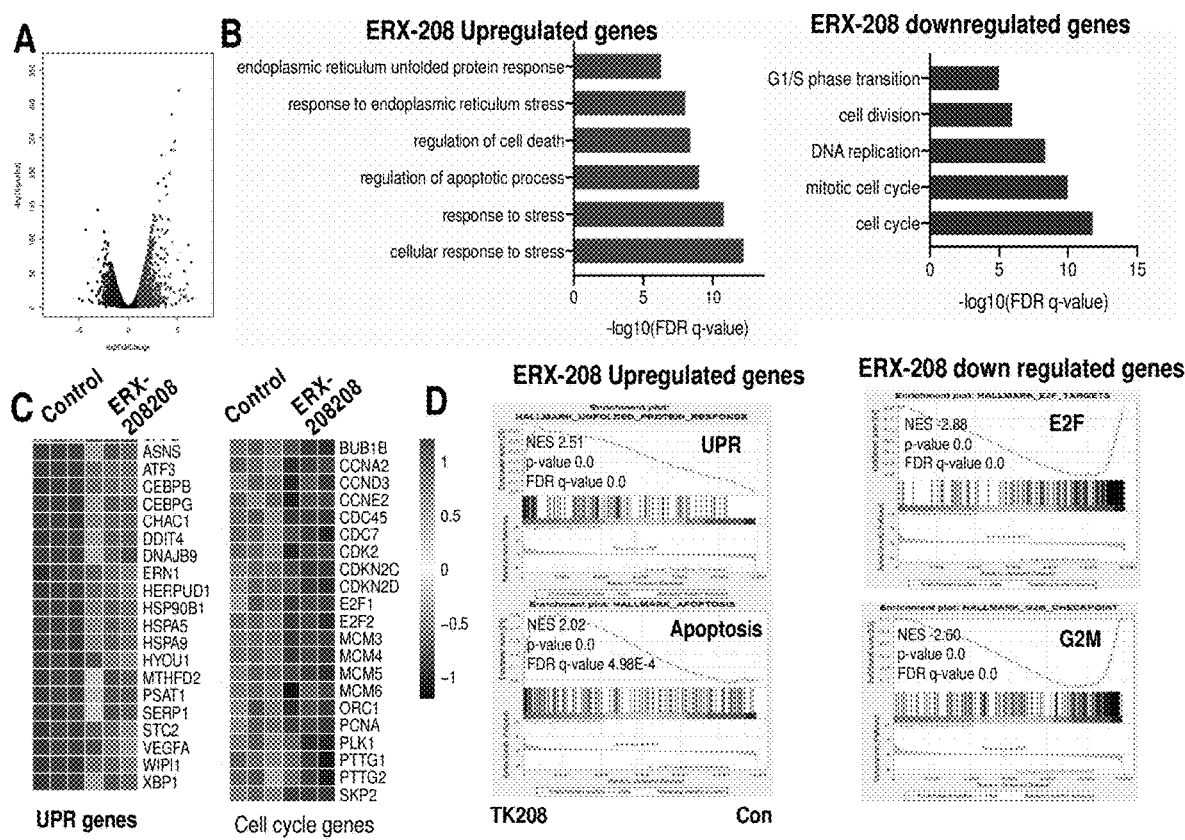
FIGS. 46A-D: SKOV3 cells were treated with ERX-208 for 48 h and RNA-seq analyses conducted using UT Health sequencing core.

Since UPR involves a coordinated transcriptional response, the inventors evaluated the transcriptional program in OCa cells following ERX-208 treatment. RNA-Seq studies showed that ERX-208 significantly upregulated expression of 1183 genes and down regulated 1018 genes. (FIG. 46A). Pathway analysis of upregulated genes validated that ERX-208 induces significant ERS, UPR and apoptosis (FIGS. 46B-D). In fact, all six of the top ERX-208 upregulated pathways in Gene set enrichment (GSEA) analysis involved either ERS, and apoptosis (FIG. 46B and FIG. 46D). Pathway analysis of downregulated genes identified that ERX-208 alters pathways involved in cell cycle. These data validate the inventors' prior findings that ERX-208 induces ERS and apoptosis in OCa cells.

Figure 47:
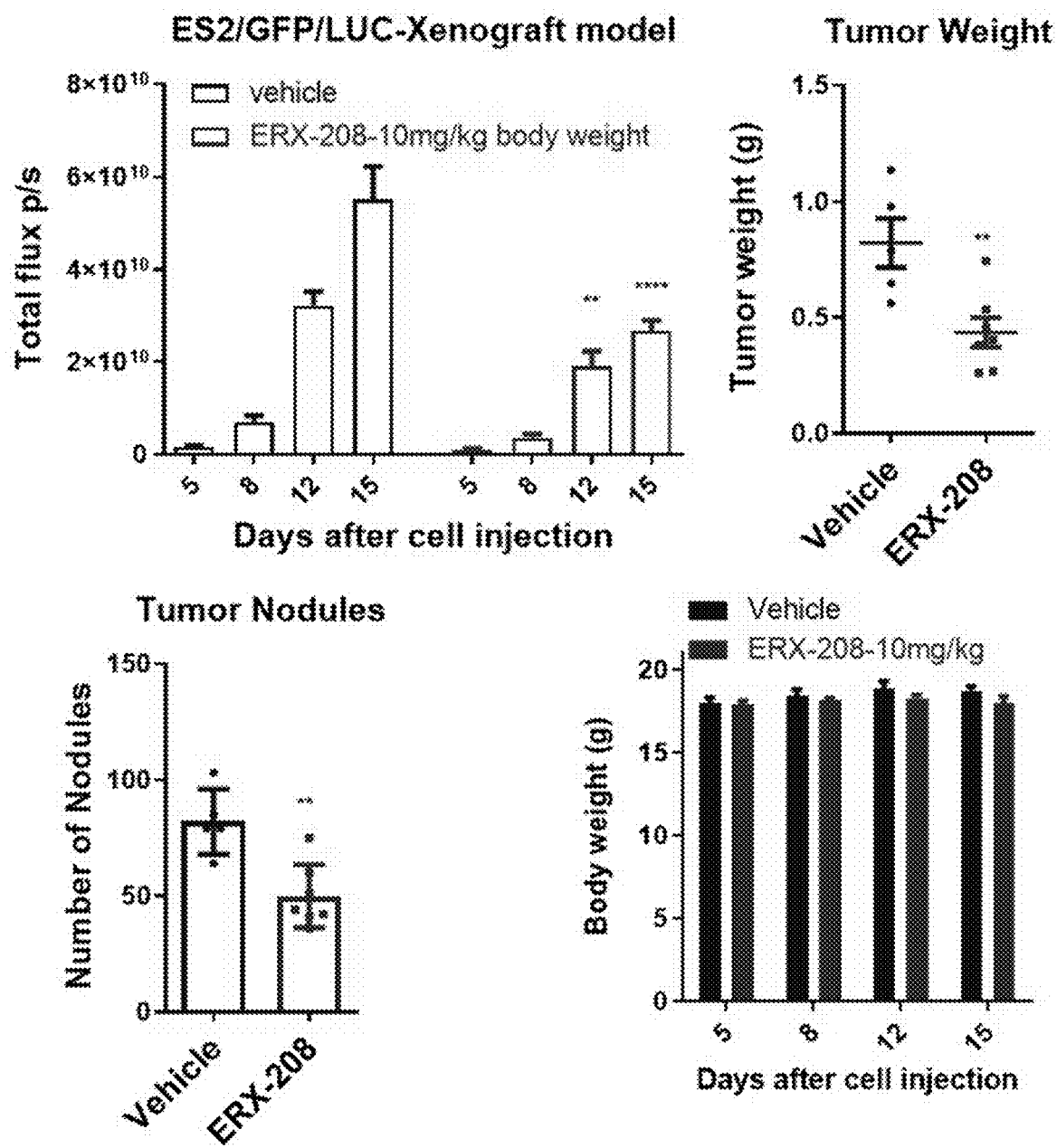
FIG. 47: ES2/GFP/LUC cells were injected i.p. and tumors established. Mice (n=5) were treated with vehicle or ERX-208 (10 mg/kg/day/i.p). Tumor volume, tumor weight, number of tumor nodules are shown. $p<0.01$, **$p<0.0001$.

ERX-208 suppressed growth of ES2 CDX tumors. ES2 cells stably labelled with GFP/LUC reporter ($2\times10^5$) were injected i.p. into nude mice. Following establishment of tumors, mice (n=5/group) were randomized and treated for 5 days/week with either 10 mg/kg/ip of ERX-208 or vehicle. Compared to vehicle, 15 days of ERX-208 treatment resulted in ~60% reduction of tumor volume measured by Xenogen-IVIS and ~50% reduction in tumor weight, tumor nodules with no significant change in body weight (FIG. 47). ERX-208 is effective in reducing growth of HGSOC PDX tumors. Following establishment of PDX tumors, NSG mice (n=6/group) were randomized and treated for 5 days/week with either 10 mg/kg/ip of ERX-208 or vehicle. Compared to vehicle, 21 days of ERX-208 treatment resulted in ~68% reduction of tumor volume measured and 60% reduction in tumor weight with no significant changes in body weight (FIGS. 48A-F). ERX-208 treatment induced expression of ER stress marker GRP78 (FIGS. 48E-F).

Figure 50:
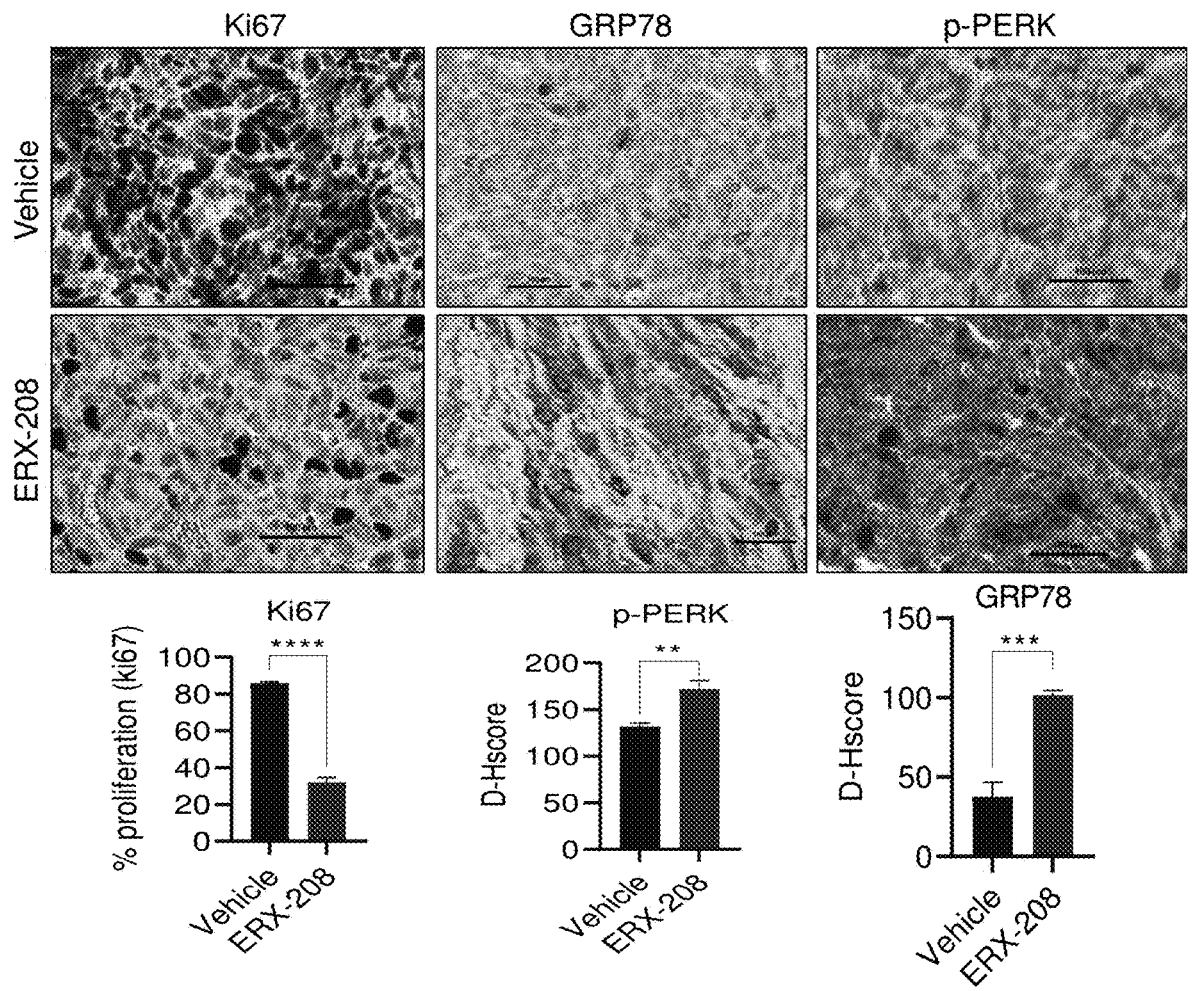
FIG. 50: IHC analyses of GRP78, pPERK and Ki67 of ERX-208 treated therapy-resistant HGSOC PDX tumors $p<0.01$; *$p<0.001$, ****$p<0.0001$.

ERX-208 is effective in reducing growth of chemotherapy resistant OCa. OCa initially responds to chemotherapy; however, majority will develop chemotherapy resistance. ERX-208 significantly reduced viability of carboplatin resistant OCa cells and promoted apoptosis (FIGS. 49A-B). The inventors conducted a proof of principle study using a therapy resistant HGSOC PDX model received from the UTHealth OBGYN PDX core. ERX-208 treatment resulted ~60% reduction in tumor volume (FIGS. 49C-F). IHC analyses showed increased activation of ERS markers such as GRP78, p-PERK and decreased proliferation measured by Ki67 (FIG. 50)

Figures 52, 53:
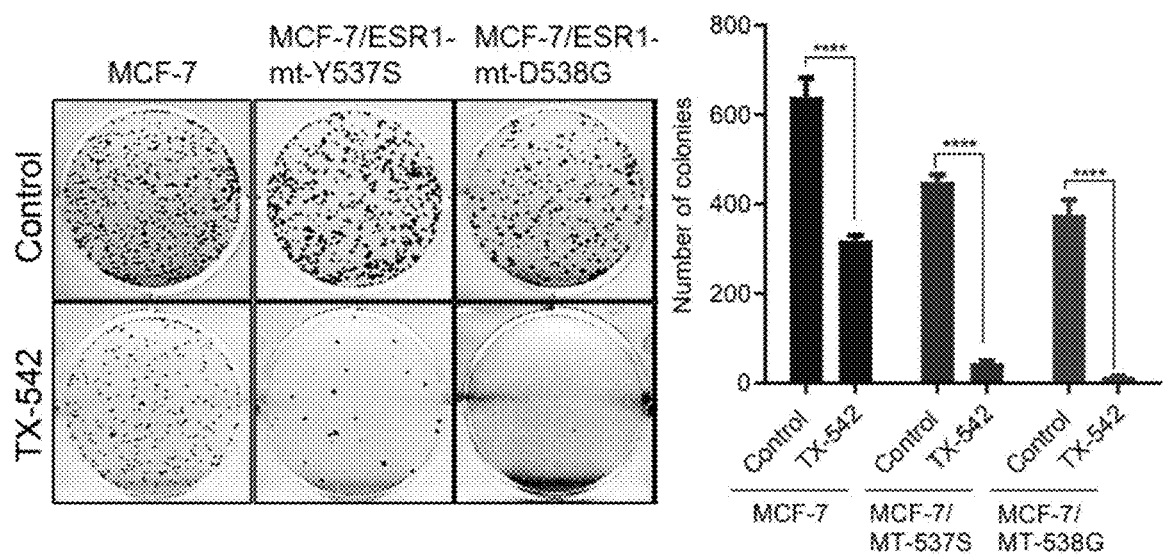
FIG. 52: Comparative efficacy of TX-542 and SERDs in BC cells expressing WT and/or MT ERα: Using CRISPR-Cas9, both copies of WT ERα genes were knocked out in ZR-75 and T47-D, while only one copy of WT Era was knocked out in MCF-7 cells. Following knockout of WT ERα clones with stable expression of either Y537S ERα MT or the D538G ERα MT were selected. Erα status in each cell line in the second column shows whether each parental and genetically engineered clone expresses the WT, MT or both forms of ERα. ERα-negative TNBC cells (SUM-159 and MDA-MB-231) were used as controls. Dose response curves were generated for ERX-11, TX-542 and SERDs using cell titer glo assays. IC50 values for each cell line and drug were calculated and tabulated. Tam=tamoxifen, ICI=fulvestrant, GDC-0810=Genentech SERD, AZD-9496 Astra Zeneca SERD, RAD-1901=Radius SERD, Palbo=Palbociclib. IC$_{50}$ values<50 nM are shown in red.
FIG. 53: Effect of 100 nM TX-542 on clonogenic survival of WT-ERα and MT-ERα BC cell lines.

TX-542. TX-542 structure and modeled fitting for WT-ERα and MT-ERα shown in FIG. 51. TX-542 was potent ($IC_{50}$~20-50 nM) as an antiproliferative agent against expressing MT-ERα, both in genetically modified MCF-7 cells with one WT-ERα allele and one MT-ERα allele introduced by CRISPR and genetically modified ZR-75 or T47-D cells in which both copies of WT-ERα alleles were replaced using CRISPR with MT-ERα. TX-542 had no activity against ER-null (SUM-159 or MDA-MB-231 cells) or non-tumorigenic breast epithelial cells, such as human mammary epithelial cells (HMEC). While several orally available SERDs (GDC-0810, AZD-9496) have shown some preclinical utility in treating ETR-BC tumors (Lai et al., 2015; Weir et al., 2016), their clinical development has been halted because of limitations with efficacy, bioavailability and toxicity. In addition, these agents are not able to consistently target all the MT-ERα forms in distinct genetic contexts, as shown in FIG. 52 and as reported by others. The inventors did find potent activity of these drugs against some cell lines expressing MT-ERα (for example, AZD-9496 aginst the T47-D Y537S MT) but not against others expressing the same mutation (AZD-9496 against the ZR-75 or MCF-7 Y537S MT). The inventors noted that only TX-542 had a consistent and potent activity effect against MT-ERα, with $IC_{50}$<50 nM in multiple models, including those with expression of MT-ERα alone (ZR-75 and T47-D) on in conjunction with the WT-ERa (MCF-7) (FIG. 53). Since TX-542 had favorable features for clinical translation, including enhanced solubility due to its polar groups (cLogP=2.7), and significantly less protein avidity (75% bound to proteins) than other synthesized analogs, the inventors decided to further evaluate the potential of TX-542 as a hit compound targeting MT-ERα.

Figure 54:
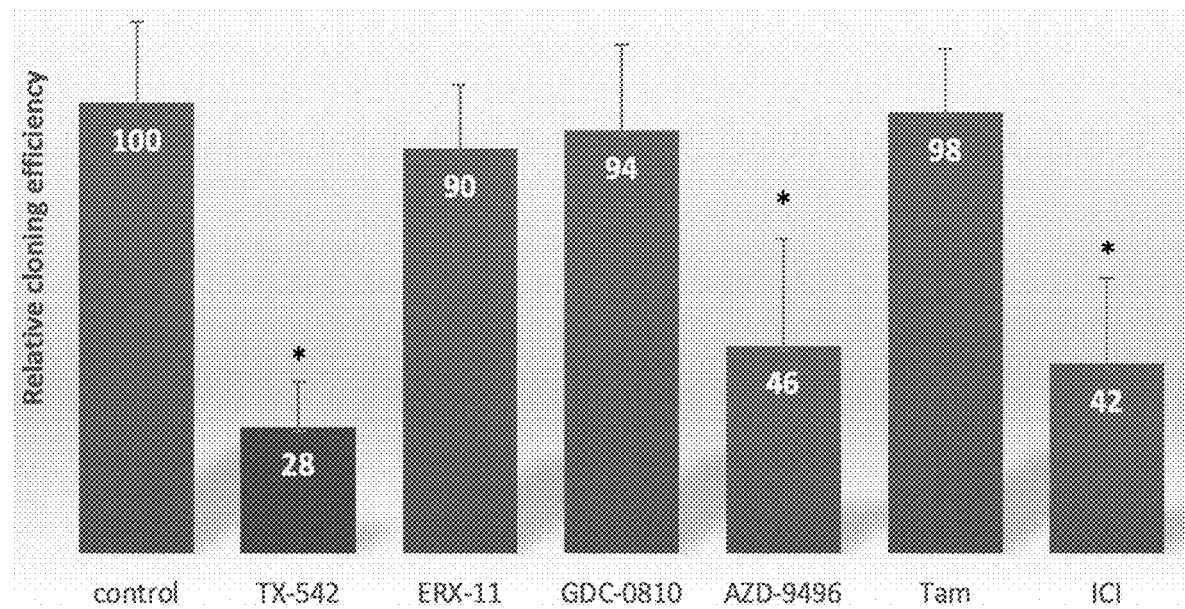
FIG. 54: Effect of 200 nM TX-542, SERMS and SERDs on soft agar colony formation by MCF-7 MT-ERα Y537S cells.
Figure 55:
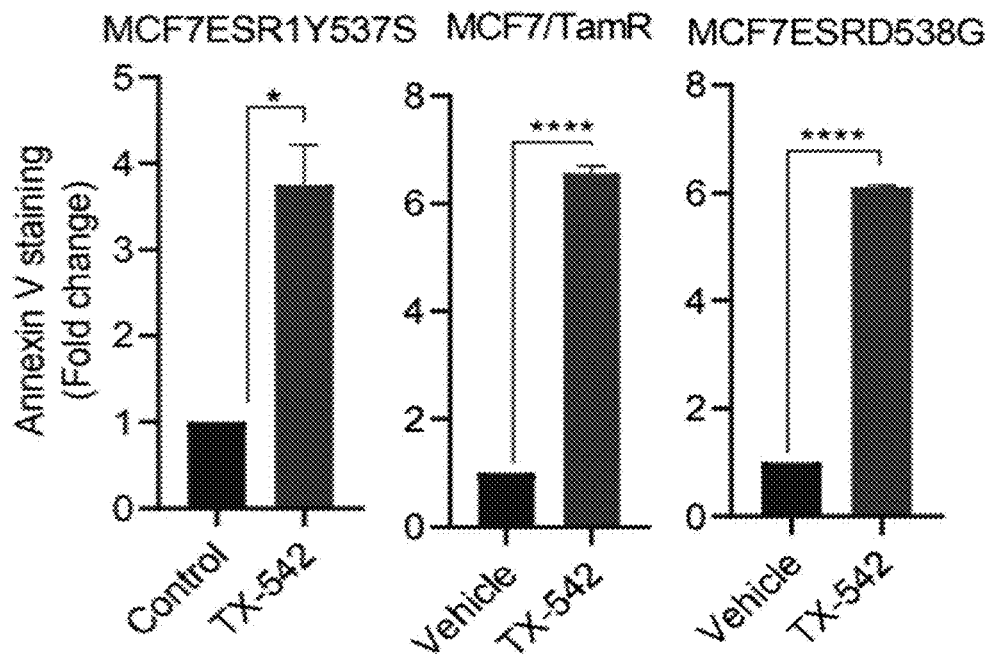
FIG. 55: Effect of 200 nM TX-542 on apoptosis of MT-ERα expressing BC cells.
Figure 56:
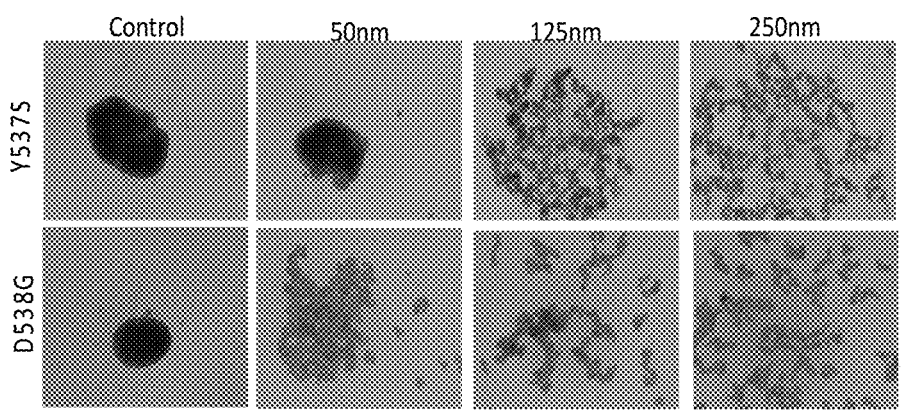
FIG. 56: Dose-dependent effect of TX-542 on spheroid formation in MCF-7 MT-ERα Y537S (top) and MCF-7 MT-ERα D538G (bottom) cells.
Figure 57:
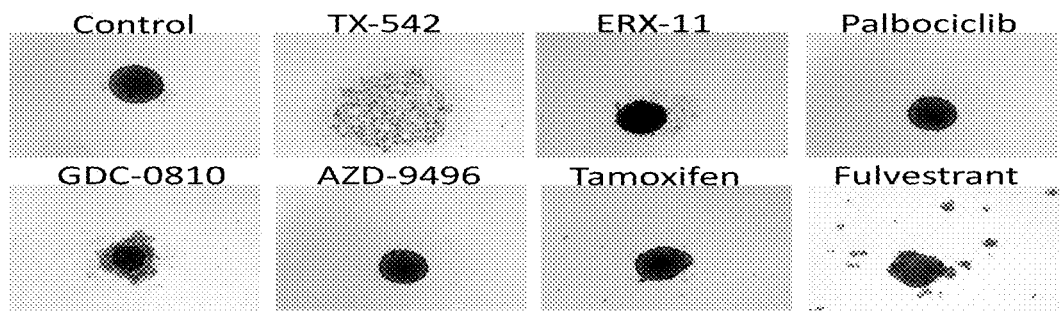
FIG. 57: Comparative effect of 200 nM tamoxifen, SERDs, fulvestrant and TX-542 on spheroid formation in MCF-7 MT-ERα Y537S cells.

The inventors then performed a number of validation studies, including clonogenic assays, where TX-542 significantly reduced the survival of BC cells expressing WT-ERα and MT-ERα (FIG. 54). While TX-542 potently reduced soft agar colony formation in MCF-7 MT-ER Y537S cells (FIG. 54), neither the parental ERX-11, tamoxifen nor GDC0810 SERD (at the same concentrations) had an effect on colony formation. While AZD-9496 and fulvestrant significantly affected colony formation in MCF-7 MT-ERα cells, their activity was not seen against the ZR-75 MT-ERα cells, suggesting that their effect could be partly attributed to the expression of WT-ERa in the MCF-7 cells (FIG. 54). The inventors then observed that TX-542 induced apoptotic cell death within 72 h after treatment, as evidenced by an increase in the number of apoptotic cells measured by annexin staining (FIG. 55). Finally, spheroid formation assays show a dramatic effect of TX-542 in both the MCF-7 MT-ERα Y537S and D538G cells, where low doses of TX-542 disrupted spheroid architecture (FIG. 56). In contrast, neither ERX-11, palbociclib, GDC-0810 nor AZD-9496, tamoxifen nor fulvestrant (at 200 nM) significantly disrupted spheroid size or architecture in MCF-7 MT-ERα Y537S cells (FIG. 57). The 200 nM dose for these drugs reflects the level at which each of these drugs has a significant effect on spheroid formation in the MCF-7 WT-ERa cells. Taken together, these studies indicate that TX-542 has significant activity against both WT-ERα and MT-ERα driven ERα+ BC cell lines and is a worthwhile candidate for further study.

Figure 58:
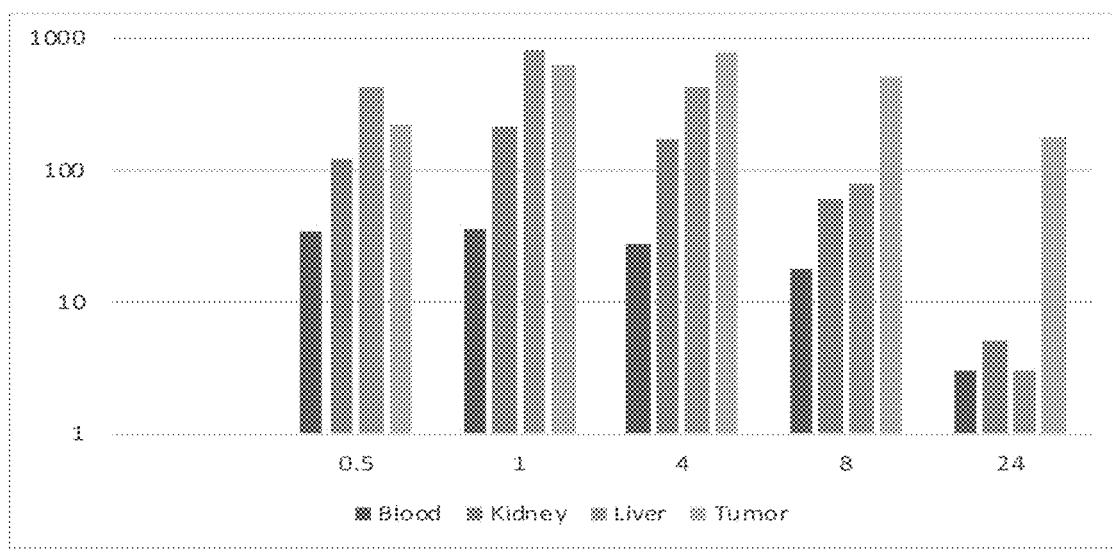
FIG. 58: PK properties of TX-542 indicate a half-life in plasma of 8 h and accumulation over time in tumor. Y-axis shows the relative drug levels in ng/g of tissue.

To establish the pharmacokinetic (PK) profile of TX-542, the inventors worked with the UTSW preclinical pharmacology core to characterize pharmacologic properties of TX-542 (FIG. 58). These studies indicated an 8-h half-life of TX-542 in the plasma, with drug detectable in both the liver and kidney after intraperitoneal (i.p.) administration. Importantly, evaluation of established MCF-Y537S xenografts showed that TX-542 levels reached a steady state after 5 days of daily i.p. 10 mg/kg dosing and remained detectable at >0.1 mg/g tumor tissue even 24 h after the last dose, correlating with >200 nM TX-542 which is above the therapeutic dose of TX-542. Thus, the inventors' initial studies suggest that once a day i.p. dosing of 10 mg/kg TX-542 is sufficient to maintain therapeutic drug levels in the tumor. These favorable PK parameters are complemented by a lack of change in renal and liver parameters or overt histopathological, clinical chemistry or drug-related deaths in treated animals. Importantly, TX-542 (10 mg/kg/ip) showed potent activity against growth of established WT-ERα ZR-75 or MT-ERα MCF-7 xenografts, but had no effect on mouse body weights (FIG. 59).

Figure 61A:
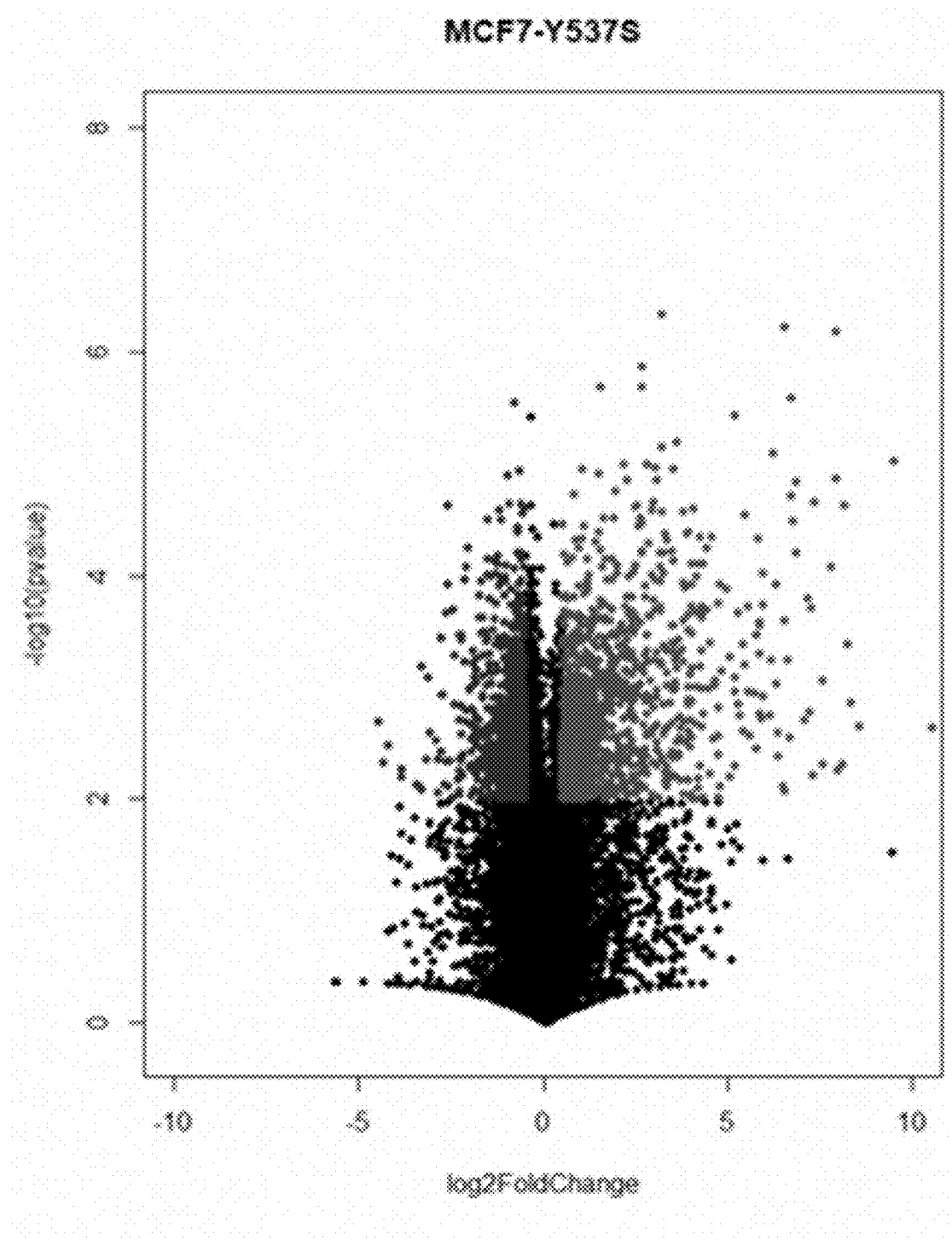
FIGS. 61A-61F: Effect of 200 nM TX-542 on the transcriptomic profile in MCF-7 MT-ERα Y537S cell line after 24 h of treatment.
Figure 61B:
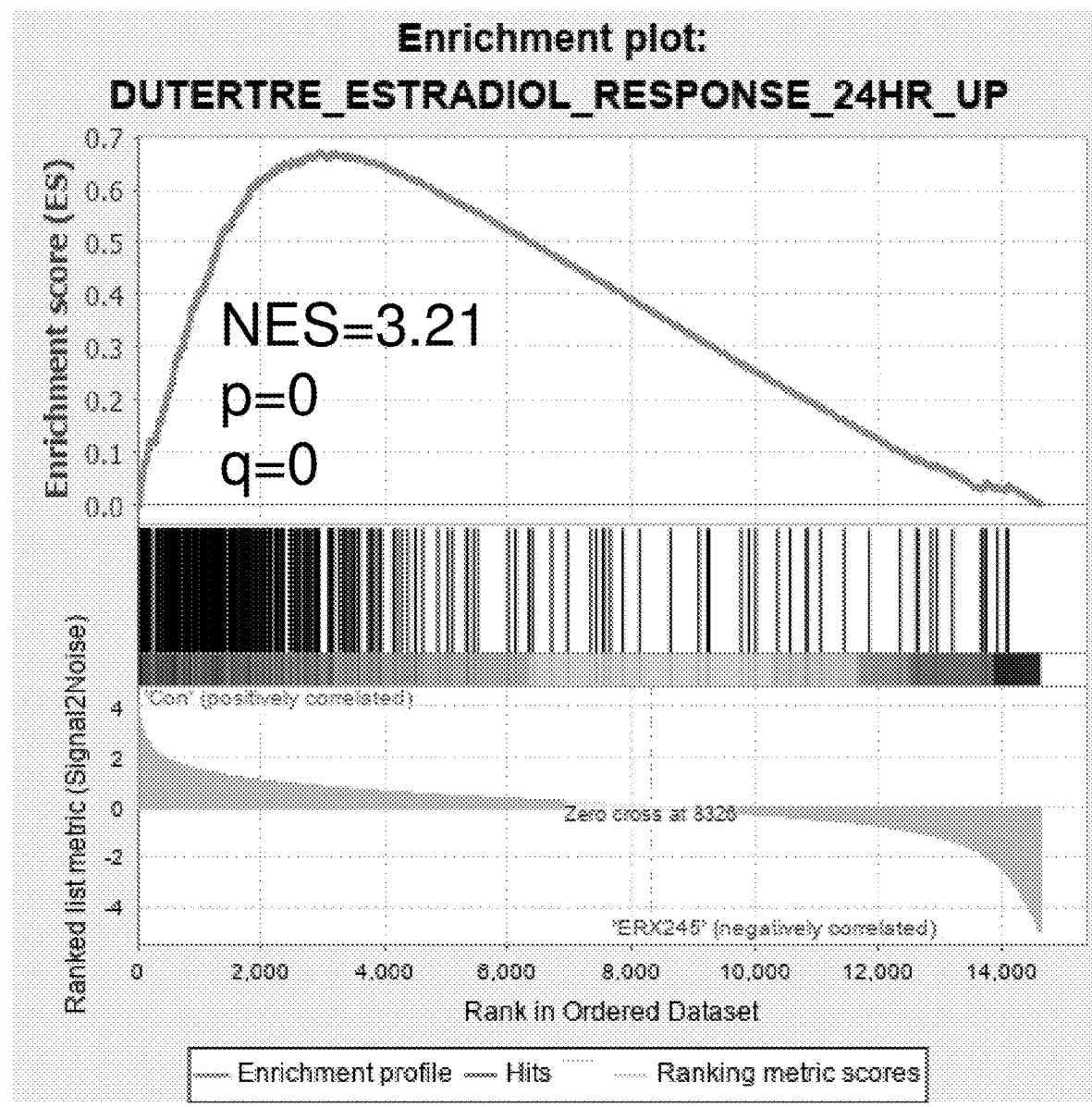
Figure 61C:
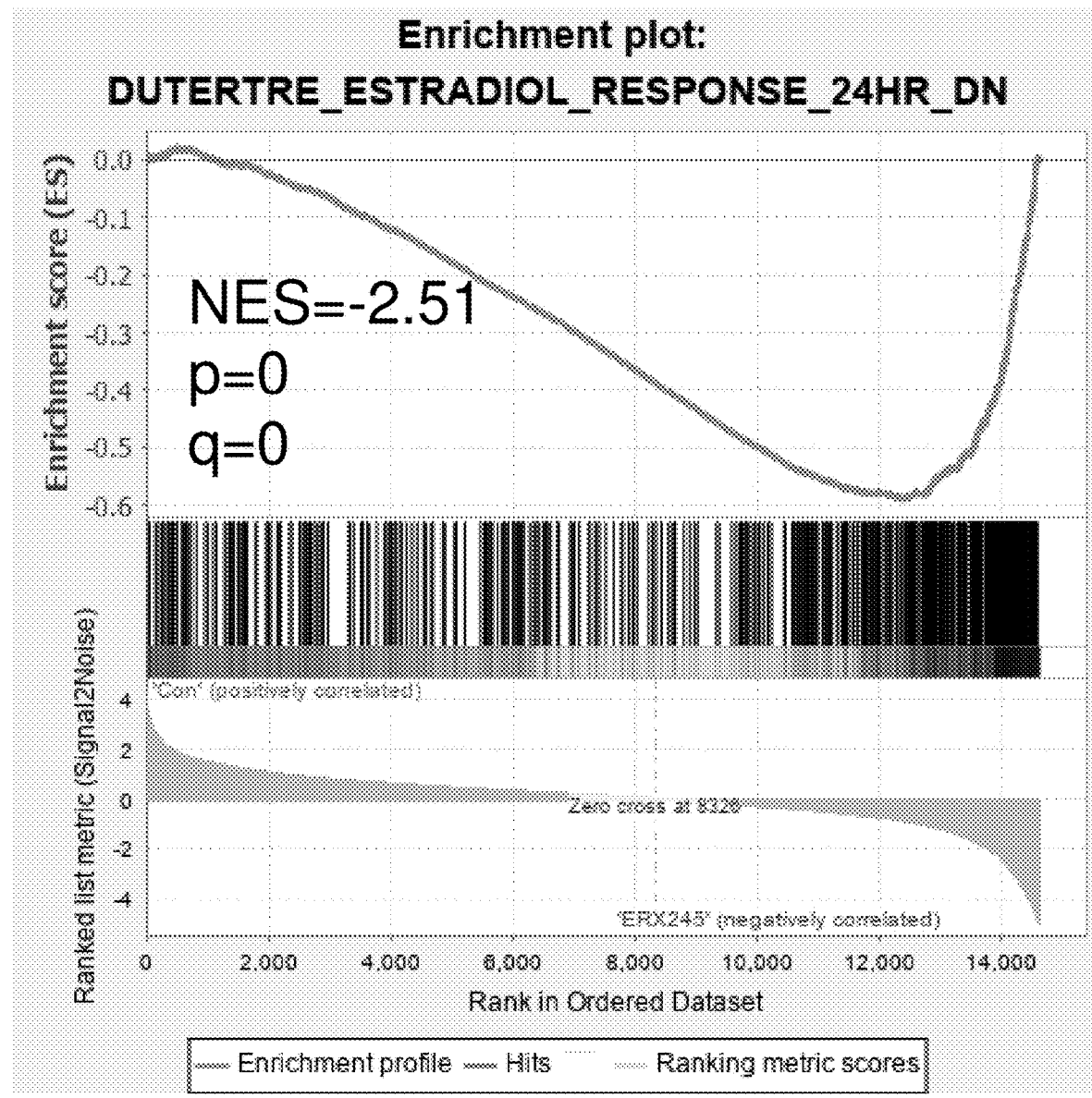
Figure 61D:
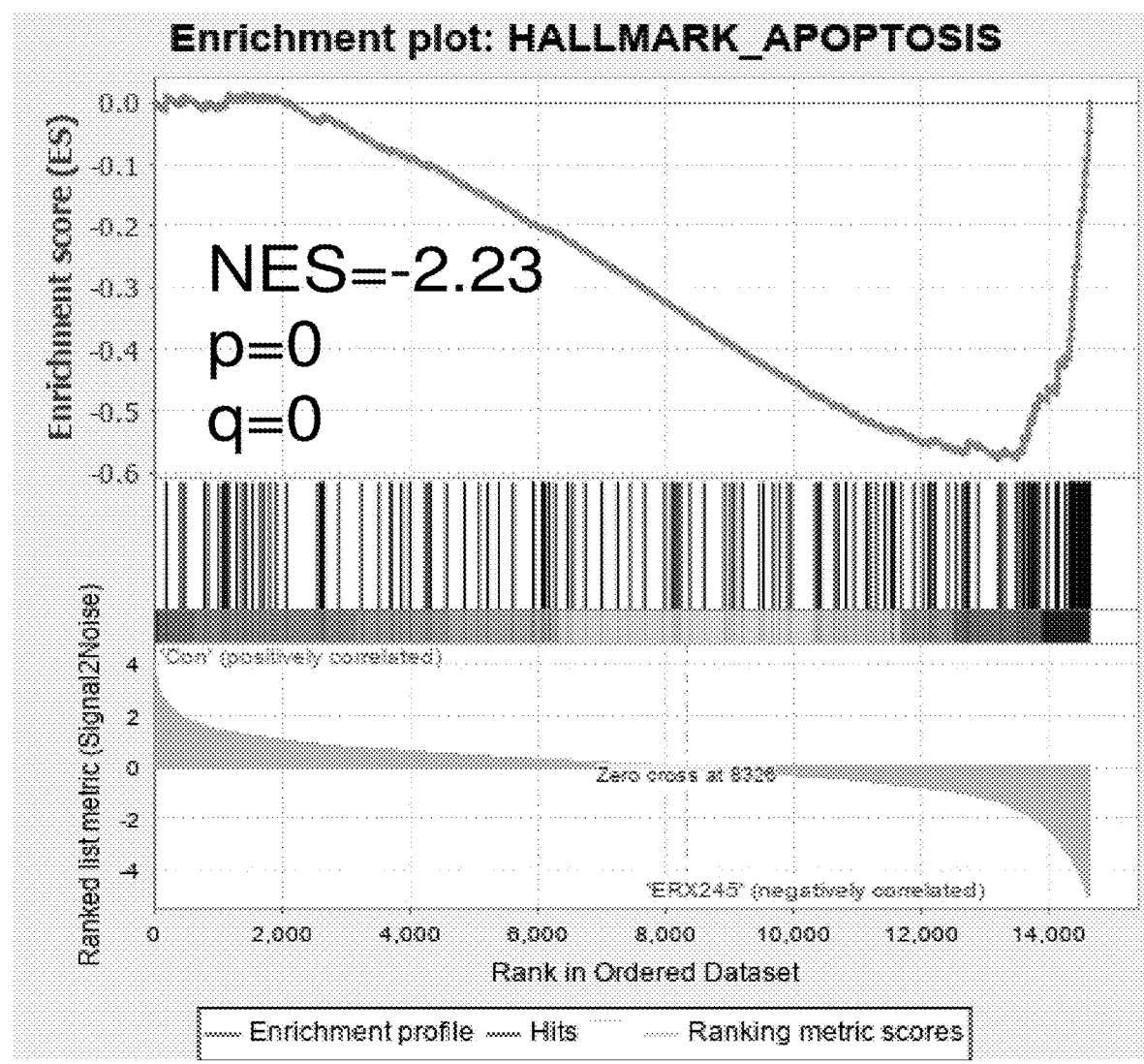
Figure 61E:
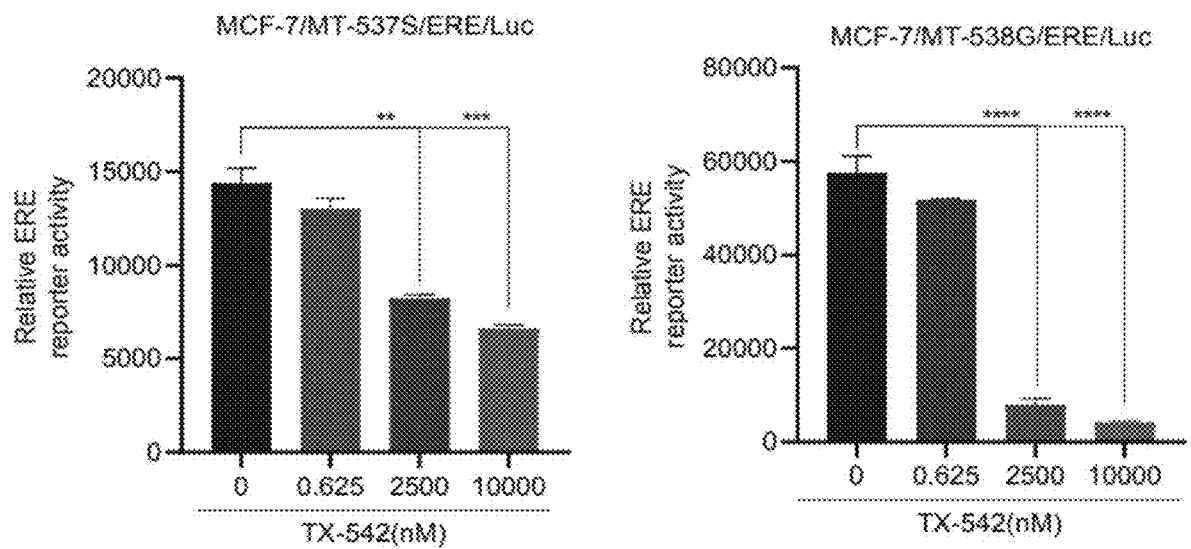
Figure 61F:
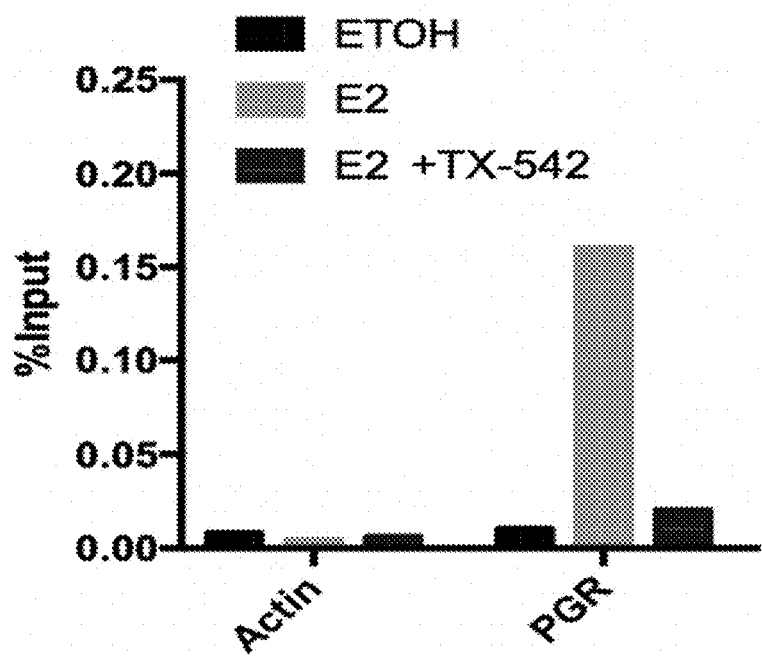

TX-542 functions like a slow-acting SERD and causes decreased ERα protein levels over time (FIG. 60). However, unlike fulvestrant, the kinetics of TX-542 mediated downregulation of ERα are much slower: fulvestrant causes WT-ERα degradation within 4 h, while the effect of TX-542 on MT-ERα levels is not noticeable until 24 h and more pronounced at 48 h. These data suggest that TX-542 causes decreased MT-ERa protein levels by blocking the MT-ERα-regulated transcriptional program, which includes autoregulation of ERa gene expression. Preliminary RNA-sequencing data suggests that TX-542 dramatically alters the transcription of ERα-regulated genes, with repression of canonical estradiol-upregulated and induction of estradiol-repressed genes (FIG. 61A-D). The ability of TX-542 to influence MT-ERα genomic signaling was validated by reporter gene assays, which indicate that TX-542 was able to decrease transcription driven by a minimal promoter with three copies of the ER-response element (ERE) (FIG. 61E) and by chromatin immunoprecipitation (ChIP) studies which show that TX-542 blocks both basal and estradiol-induced MT-ERα DNA binding (FIGS. 28A-D, shown for effect of TX-542 on estradiol-induced MT-ERα binding to progesterone receptor). Unbiased gene ontogeny (GO) analyses indicated that two of the top three pathways upregulated in TX-542 treated cells were related to apoptotic death (Table 1). In contrast, the top 3 downregulated pathways all involved cell cycle progression (Table 2).

Figure 62:
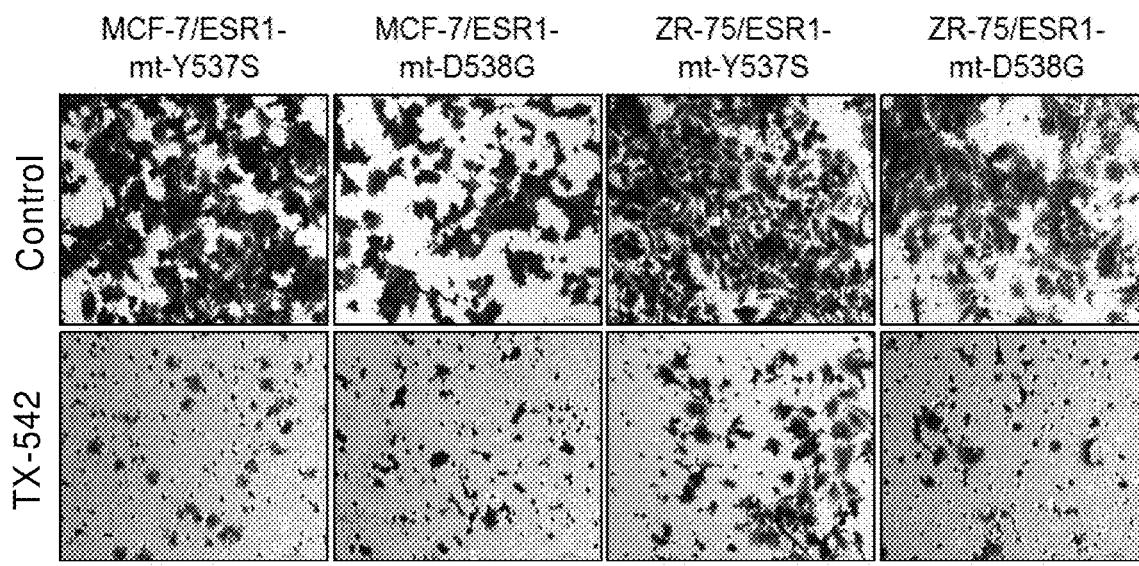
FIG. 62: Effect of TX-542 on invasiveness of BC cells expressing Erα mutants in a Boyden chamber assay.
Figure 63:
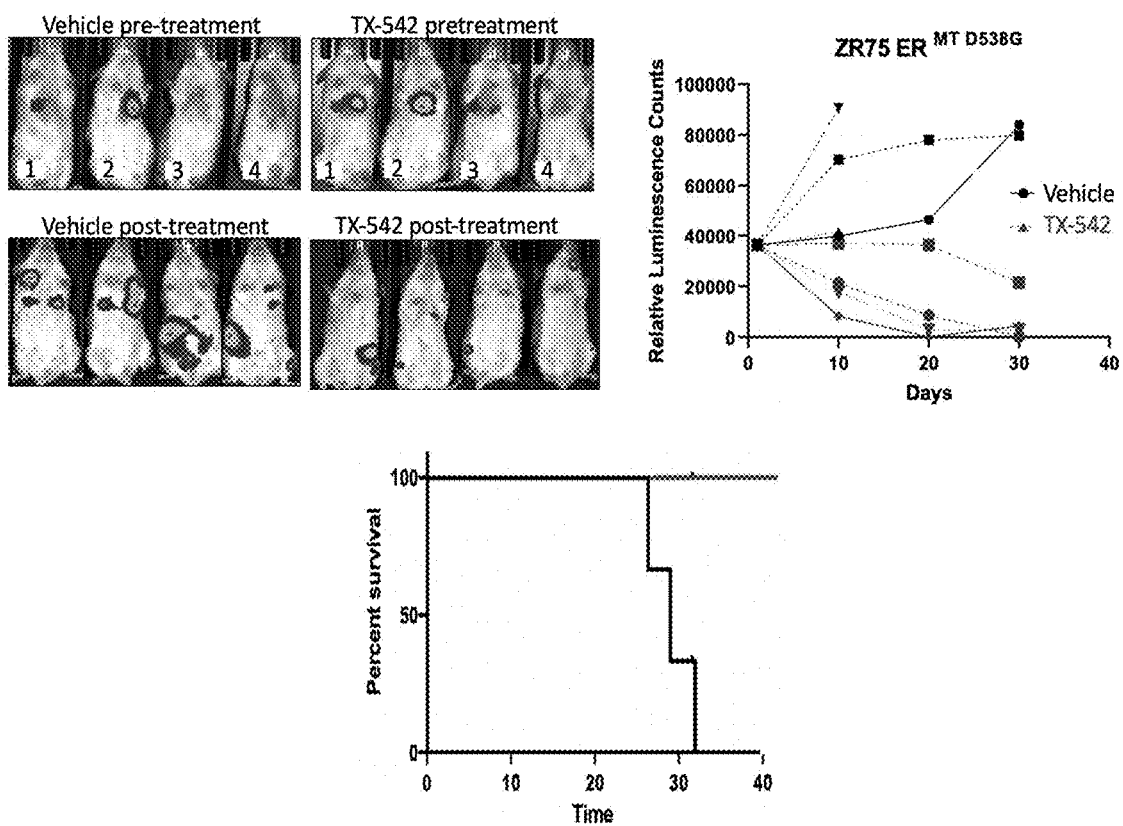
FIG. 63: Following intracardiac injection of luciferase-tagged ZR-75 MT-ERα Y537S tumors, mice are imaged five at a time under 2% isoflurane gas anesthesia. Each mouse is injected with D-Luciferin and imaged 10-15 minutes after the injection. BLI signal is quantified in regions of interest (ROIs) drawn around tumors, specific areas (for example cranial, thoracic or abdominal), whole body or tissues ex vivo and the signal is expressed as photons per second, representing the flux radiating omni-directionally from the user-defined region. Images are analyzed using Living Image 4.3.1 (PerkinElmer, Waltham, MA) software. Once the tumors were established (40,000 luminescence counts at 30 seconds exposure), mice were treated either with vehicle or TX-542. Bioluminescent imaging shows effect of vehicle (DMSO) or TX-542 (10 mg/kg/ip/day) treatment on the growth of the tumors in vivo (left panel) in the mice after 25 days of treatment. Relative luminescence counts are mapped (middle panel). Mice were sacrificed once symptomatic and the survival curves for vehicle treated (black) or TX-542 treated (red) are graphed (right panel) (n=6 in each group).
Figure 64:
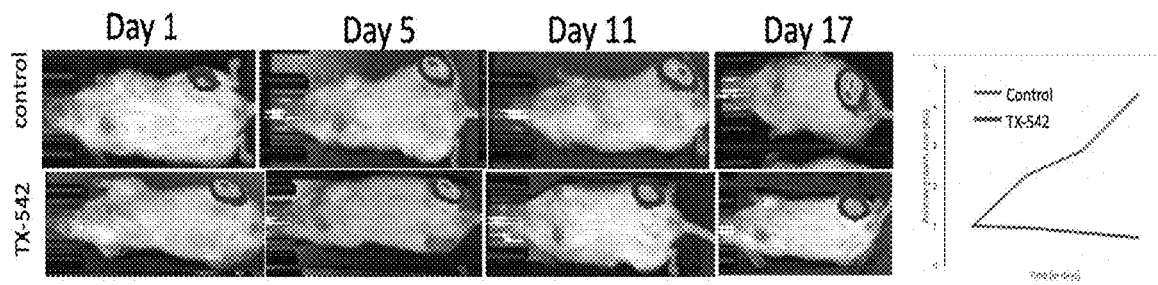
FIG. 64: Bioluminescent imaging shows luciferase-tagged ZR-75 MT-ERα Y537S tumors in the bone following intratibial injections. Once tumors were established, daily treatment of mice with either vehicle or TX-542 (10 mg/kg/ip) were performed. Results are shown and graphed (n=6).

These data indicate that TX-542 potently affects the invasion of multiple BC cells expressing MT-ERα (FIG. 62). Since MT-ERα is primarily expressed in metastases, the inventors used metastatic models to evaluate effect of TX-542 on the development and progression of metastasis. These studies showed that TX-542 could both dramatically decrease the formation of lung metastasis when started immediately after intracardiac injection (1/6 tumors treated with TX-542 formed mets within 4 weeks while 6/6 treated with vehicle had mets and had to be euthanized) (FIG. 63) and by data that TX-542 decrease the growth of lung metastasis (following intracardiac injection) and bone metastasis (following intratibial injection) of D538G MT-ERa expressing MCF-7 xenografts (FIG. 64, see graph, compare red (TX-542 treated) to blue lines (control).

TABLE 1

GO analyses of the top TX-542 up-regulated genes in MCF-7 MT-ERα Y537S cells after 24 h treatment

| GO Term | p-Value | FDR |
| --- | --- | --- |
| Response to cytokine | 6.82E−53 | 1.36E−49 |
| Programmed cell death | 3.45E−38 | 6.89E−35 |
| Apoptotic process | 1.74E−37 | 3.48E−34 |

TABLE 2

GO analyses of the top TX-542 down-regulated genes in MCF-7 MT-ERα Y537S cells after 24 h treatment.

| GO Term | p-Value | FDR |
| --- | --- | --- |
| Cell cycle | 3.20E−25 | 6.23E−22 |
| DNA replication | 1.51E−22 | 2.94E−19 |
| Cell cycle G1/S phase transition | 2.50E−13 | 4.88E−10 |

Figure 65E:
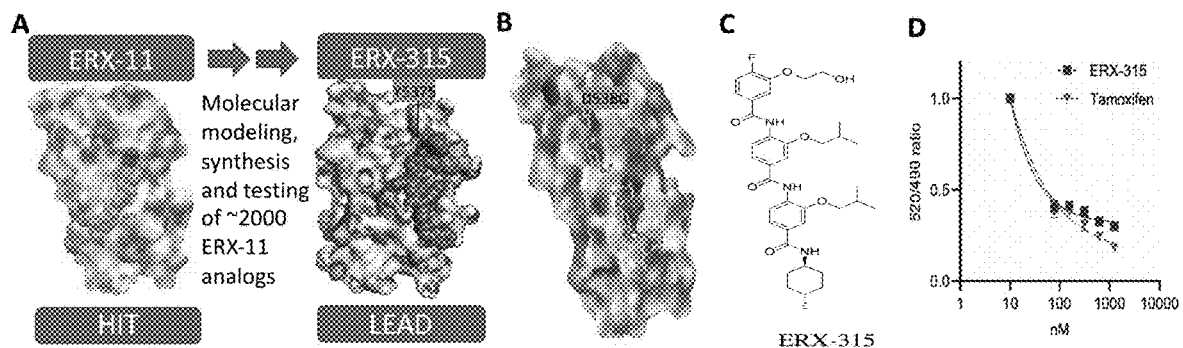

ERX-315. The binding of ERX-315 (structure shown in FIG. 65C) to ERα has been validated for WT ERα LBD using time-resolved FRET (TR-FRET)-ERα Coactivator assay (FIG. 65D: purified MT-ERα LBD is not available). Modeling studies identified that the binding of ERX-315 to the ERα LBD does not overlap with either the estradiol, or tamoxifen binding sites on ERα LBD Since the Y537 mutation is a surface mutation that alters the access to MT-ERα LBD, the ERα LBD pocket is largely conserved (Toy et al., 2017; Katzenellenbogen et al., 2018) and the hydrogen-bonding between Ser537 and Asp351 results in an altered conformation of the ERα helix 11-12 loop and likely contributes to both the constitutive activity of the Y537S MT-ERα and the lack of activity of tamoxifen. Importantly the in silico modeling suggests that ERX-315 may bind potently to the MT-ERα (predicted docking energy~5.9 kcal/mol). In contrast, ERX-314, which has a methyl group in place of the N-terminal fluoride of ERX-315, is modeled to bind less avidly to MT-ERα LBD (predicted docking energy~1.69 kcal/mol). Consequently, ERX-315 has potent anti-proliferative activity ($IC_{50}$~15-35 nM) against both WT- and MT-ERα-driven cell lines in vitro (FIG. 65E). ERX-315 had no activity against benign breast epithelial cells, shown for the human mammary epithelial cells (HMEC). In contrast, ERX-314 has dramatically lower potency ($IC_{50}$~1500-5000 nM) and serves an internal control for ERX-315. The inventors have performed most of the studies described below with three compounds-ERX-315 as the optimized lead, ERX-11 as the parental compound and ERX-314 as a negative control.

Prior studies have shown that MT-ERα drives a canonical ERα transcriptional programme, both in the absence and presence of estradiol. RNA sequencing studies indicate that ERX-315 alters the transcriptional heatmap in MCF-7 and ZR-75 cells expressing D538G and Y537S MT-ERα (FIG. 66B, data shown for MCF-7 cells expressing D538G MT-ERα). ERX-315 both decreased the expression of canonical ERα-upregulated genes and increased expression of ERα-downregulated genes (FIG. 66A), indicating that ERX-315 efficiently blocks the transcriptional programme mediated by MT-ERα. In contrast, neither tamoxifen nor ERX-314 is able to alter the ERα-regulated transcriptome in these cells. Reporter gene assays further validate that ERX-315 is able to attenuate transcription driven by ERa regulated elements (ERE) in MCF-7 cells expressing D538G MT-ERα (FIG. 66D). ERX-315 dramatically decreases MT-ERα binding to promoters of ERα-regulated genes, as shown by ERα Chromatin immunoprecipitation (ChIP) studies of D538G MT-ERα binding to canonical ERα-regulated genes (FIG. 66A). Taken together, these data indicate that ERX-315 blocks the transcriptional programme driven by MT-ERα by disrupting the MT-ERα transcriptional complex on the DNA.

Global shutdown of protein synthesis was seen, as evidenced by enhanced puromycin staining of BC cell lysates treated by ERX-315 but not ERX-314 (FIG. 67A). In contrast, no significant shutdown of protein synthesis is noted in HMEC cells (FIG. 67A). ERX-315 but not ERX-314 induced uncompensated UPR leading to LC3B activation and cell death (FIG. 67B).

To ascertain that the anti-proliferative effect of ERX-315 is directly related to its ability to induce ER stress and subsequent UPR, the inventors used a known eiF2α phosphatase inhibitor, salubrinal. Preincubation of MCF-7 cells with salubrinal induces peiF2α, which in turn shuts down de novo protein synthesis and alters the basal level of ER stress within the cell. They noted that pretreatment with salubrinal diminished the ability of ERX-315 to induce apoptosis and decrease proliferation of MCF-7 cells expressing the MT-ERα.

Figure 68A:
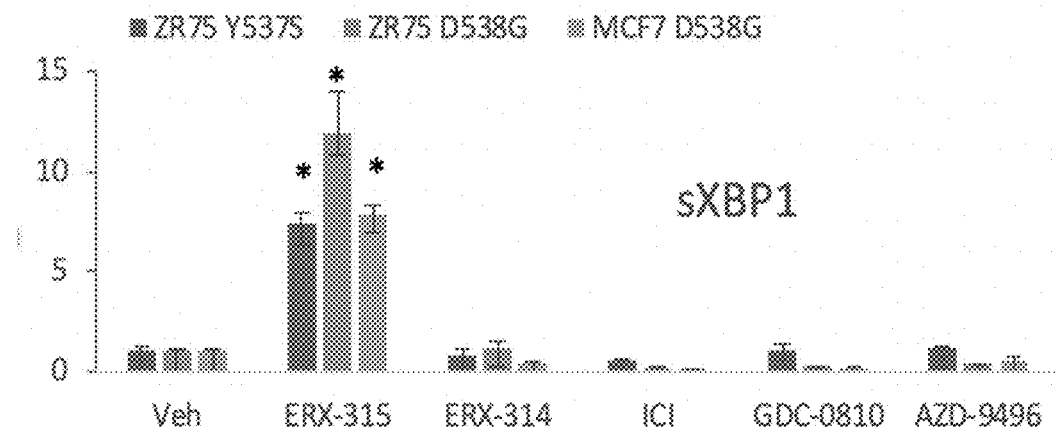
FIGS. 68A-68C: A) ERX-315 significantly enhances sXBP1 (FIG. 68A) and CHOP (FIG. 68B) mRNA levels and attenuates progesterone receptor (PGR) levels (FIG. 68C) in ZR-75 and MCF-7 cells that express Y537S and D538G MT-ERα. In contrast, neither ERX-314, fulvestrant (ICI), GDC-0810 nor AZD-9496 can induce CHOP nor sXBP1 mRNA or consistently repress PGR expression.
Figure 68B:
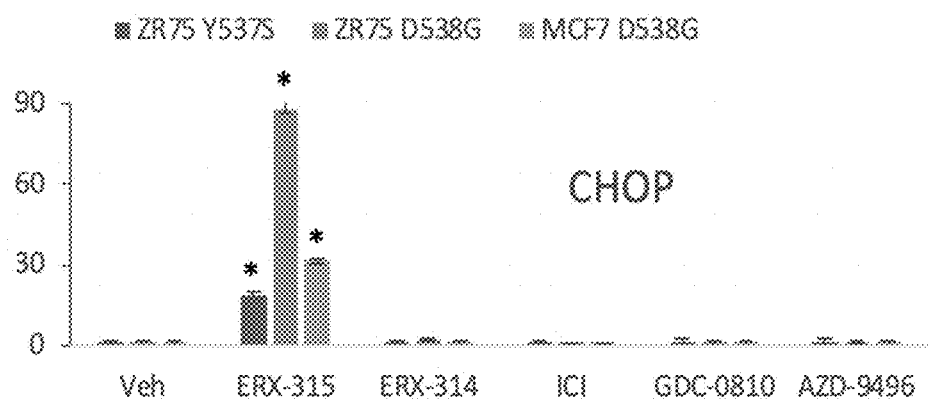
Figure 68C:
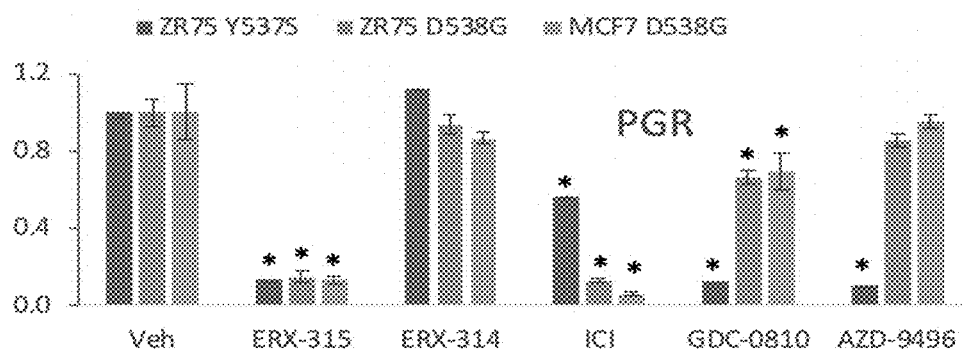

Since MT-ERα is a critical driver of these ETR-BCs, the inventors then evaluated the effect of ERX-315 on the expression of MT-ERα. Unlike fulvestrant and SERMs like GDC-0810, GDC-0927 and AZD9496 (Joseph et al., 2016), ERX-315 consistently decreases the protein levels of mutant Erα to <10% basal over 12-24 h time frame (FIG. 67C). In contrast, neither fulvestrant nor GDC-0810 were able to decrease MT-ERα protein levels (FIG. 67D) or induce ER stress or compensatory UPR in cells expressing MT-ERa as evidenced by evaluation at the protein level (FIG. 67D, see LC3A/B). Transcriptional evaluation indicates that ERX-315 but not ERX-314, fulvestrant (ICI), GDC-0810 or AZD-9496 was able to significantly enhance the expression of known UPR drivers such as sXBP1 and CHOP at the RNA level in three cell lines driven by MT-Erα (FIG. 68). The dramatic fold enhancement of UPR genes by ERX-315 causes uncompensated UPR leading to apoptotic cell death.

Taken together, these molecular studies indicate that ERX-315 treatment alters the MT-ERα transcriptional programme including that of the MT-ERα protein, induces the expression of genes involved in ER stress, shuts down de novo protein synthesis and induces uncompensated UPR pathway, leading to apoptotic cell death in BC cells expressing the MT-ERα. In contrast, ERX-315 does not induce ER stress, shut down protein synthesis or cause cell death in normal breast cells (FIG. 67A). These data suggest that ERX-315 functions in manner distinct from that of fulvestrant and other SERMs and is a first-in-class agent with activity against MT-ERα.

Pharmacokinetic studies indicated that ERX-315 was orally bioavailable in captisol formulation with half life in plasma ~4.5 hours (Table 3). At 24 h after oral administration, ERX-315 was still detectable in the plasma at >500 ng/mL. Importantly, evaluation of MCF-7 tumor xenograft tissue showed that after 2 weeks of daily oral dosing of 10 mg/kg ERX-315, ERX-315 levels reached a steady state and remained detectable at >0.1 µg/g tissue levels even 16 h after the last dose, correlating with >100 nM ERX-315, which is above the therapeutic dose of ERX-315. Thus, the inventors' initial studies indicate that once a day oral dosing of 10 mg/kg ERX-315 in captisol is sufficient to maintain therapeutic drug levels. These findings are congruent with prior studies with ERX-11 (Joseph et al., 2016) and since no significant toxicity was seen at this dose, further efficacy studies were conducted with 10 mg/kg daily ERX-315.

TABLE 3

Pharmacokinetic studies of ERX-315*

| Time (hr) | Blood (ng/mL) | Tumor (ng/mL) |
|---|---|---|
| 0.5 | 3437 ± 2317 | |
| 1 | 2396 ± 1462 | |
| 2 | 1845 ± 1289 | 1427 ± 631 |
| 4 | 15961 ± 394 | 1010 ± 850 |
| 8 | 823 ± 123 | 609 ± 404 |
| 16 | 427 ± 197 | 187 ± 238 |

*Mice were dosed once orally with 10 mg/kg ERX-315 in captisol and whole blood harvested at 0.5, 1, 2, 4, 8 and 16 h in duplicate, with an EDTA anticoagulant, and frozen. Another set of mice with orthotopic MCF7 xenograft tumors were treated with 10 mg/kh ERX-315 dosed orally 5 days/week for 10 days. Tumors were harvested 2, 4, 8 and 16 h after last dose, and snap frozen. Drug concentrations in the blood and tumor were determined following extraction with acetronitrile by HPLC/MS. A standard curve was generated for both blood and tumor by spiking known concentrations of the drug prior to evaluation by HPLC.

Figure 70A:
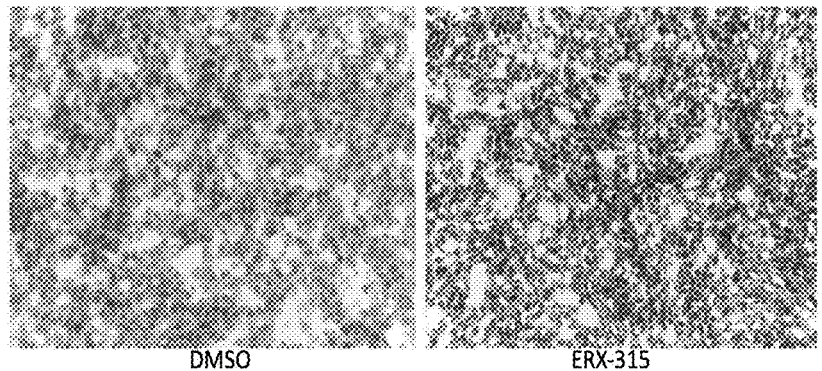
FIGS. 70A-70C: MCF-7 D538G MT-ERa xenograft tumors shows enhanced peIF2α (FIG. 70A), pPERK (FIG.
Figure 70B:
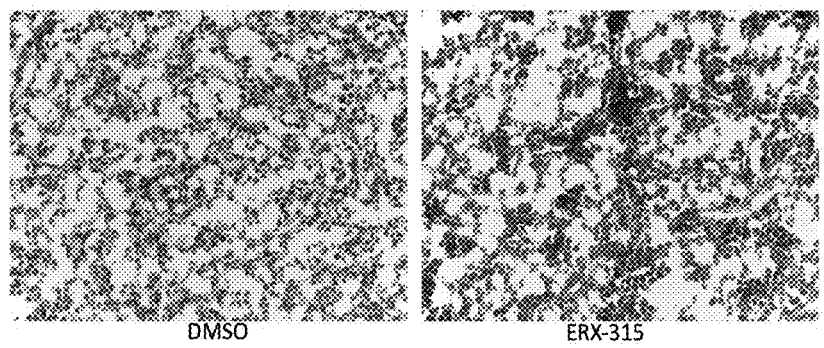
Figure 70C:
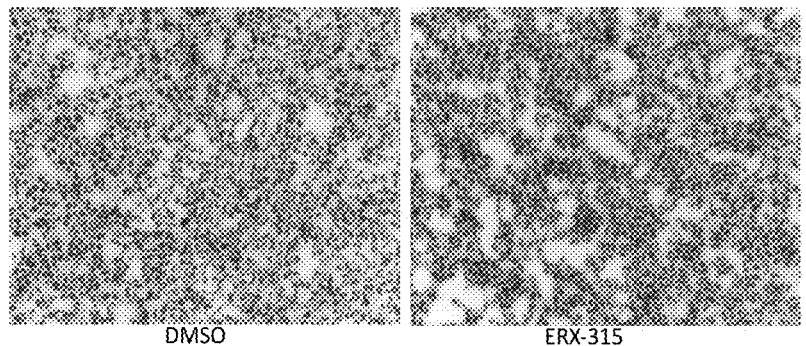

Oral administration of ERX-315 (10 mg/kg/day) showed potent activity against the growth of MT-ERα (ZR-75 and MCF-7 cells with MT Y537S ERα) driven xenograft models (FIGS. 69A-E). ERX-315 had no effect on mouse liver, uterus height or body weight (FIG. 36F). Immunohistochemical evaluation of xenograft tumors showed dramatically decreased Ki67 proliferation indices, and increased expression of UPR pathway proteins (especially pPERK, peIF2α and CHOP) following a single treatment with oral ERX-315 (FIGS. 70A-C).

Taken together, these data underscore that the anti-proliferative effect of ERX-315 is dependent on the induction of ER stress and suggest that the basal level and inducibility of peIF2α are associated with response to ERX-315. These findings indicate both potent nanomolar activity of ERX-315 and a favorable in vitro and in vivo therapeutic to toxicity profile of ERX-315 (due to induction of ER stress in BC but not in benign cells). The inventors' overarching hypothesis is that by targeting MT-ERα in BC, ERX-315 induces a significant ER stress response, leading to cell death and can overcome therapy resistance.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Anderson, *Practical Process Research & Development—A Guide for Organic Chemists*, $2^{nd}$ ed., Academic Press, New York, 2012.
Handbook of Pharmaceutical Salts: Properties, and Use, Stahl and Wermuth Eds., Verlag Helvetica Chimica Acta, 2002.
Reagan-Shaw et al., *FASEB J.*, 22(3):659-661, 2008.
Li & Zhang, *Arterioscler Thromb Vasc Biol* 39, 850-856, 2019.
Toy et al., *Cancer Discov.* 2017; 7:277-87.
Katzenellenbogen et al., *Nat Rev Cancer.* 2018; 18:377-88.
Joseph et al., *Elife* 2016, 5.
Smith, *March's Advanced Organic Chemistry: Reactions, Mechanisms, and Structure*, $7^{th}$ Ed., Wiley, 2013.
U.S. Patent Pub. 2009/0012141
Ahn et al., *Mini-Rev. Med. Chem.*, 2:463-473, 2002.
Marshall, *Tetrahedron*, 49:3547-3558, 1993.
Raj et al., *eLife*, 6:e26857, 2017.
Lai et al., *J Med Chem.* 58:4888-904, 2015.
Weir et al., *Cancer Res.* 76:3307-18, 2016.

The invention claimed is:

1. A compound of the formula:

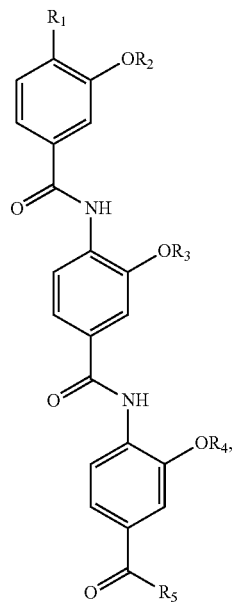

(I)

wherein:

$R_1$ is halo, $-NO_2$, alkyl$_{(C\leq 12)}$, substituted alkyl$_{(C\leq 12)}$, amido$_{(C\leq 12)}$, substituted amido$_{(C\leq 12)}$, or $-NHC(O)CH(R_{1a})NH_2$, wherein:

$R_{1a}$ is aralkyl$_{(C\leq 18)}$, substituted aralkyl$_{(C\leq 18)}$, or the side chain of a canonical amino acid;

$R_2$, $R_3$, and $R_4$ are each independently alkyl$_{(C\leq 12)}$, substituted alkyl$_{(C\leq 12)}$, aralkyl$_{(C\leq 18)}$, or substituted aralkyl$_{(C\leq 18)}$; and $R_5$ is $-NHR_{5b}$, wherein:

$R_{5b}$ is cycloalkyl$_{(C\leq 12)}$, or heteroaryl$_{(C\leq 12)}$, or a substituted version of these groups; or a group of the formula:

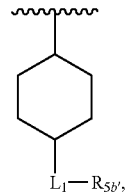

wherein:

$L_1$ is $-C(O)NR_{L1}-$, wherein:

$R_{L1}$ is hydrogen, alkyl$_{(C\leq 12)}$, or substituted alkyl$_{(C\leq 12)}$;

$R_{5b'}$ is aryl$_{(C\leq 12)}$, aralkyl$_{(C\leq 18)}$, heteroaryl$_{(C\leq 12)}$, heteroaralkyl$_{(C\leq 18)}$, or a substituted version of any of these groups;

or a pharmaceutically acceptable salt thereof.

2. The compound of claim 1, wherein the compound is further defined as:

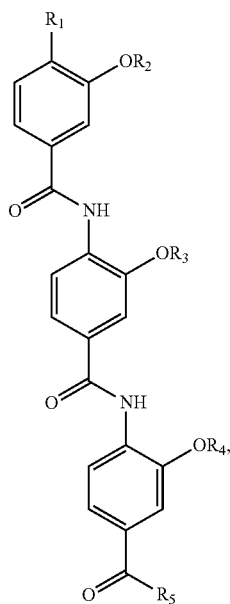

(I)

wherein:
R$_1$ is halo, —NO$_2$, alkyl$_{(C\leq12)}$, substituted alkyl$_{(C\leq12)}$, amido$_{(C\leq12)}$, substituted amido$_{(C\leq12)}$, or —NHC(O)CH(R$_{1a}$)NH$_2$, wherein:
R$_{1a}$ is aralkyl$_{(C\leq18)}$, substituted aralkyl$_{(C\leq18)}$, or the side chain of a canonical amino acid;
R$_2$, R$_3$, and R$_4$ are each independently alkyl$_{(C\leq12)}$, substituted alkyl$_{(C\leq12)}$, aralkyl$_{(C\leq18)}$, or substituted aralkyl$_{(C\leq18)}$; and
R$_5$ is —NHR$_{5b}$, wherein:
R$_{5b}$ is
a group of the formula:

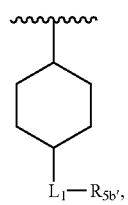

wherein:
L$_1$ is —C(O)NR$_{L1}$—, wherein:
R$_{L1}$ is hydrogen, alkyl$_{(C\leq12)}$, or substituted alkyl$_{(C\leq12)}$;
R$_{5b'}$ is aryl$_{(C\leq12)}$, aralkyl$_{(C\leq18)}$, heteroaryl$_{(C\leq12)}$, heteroaralkyl$_{(C\leq18)}$, or a substituted version of any of these groups;
or a pharmaceutically acceptable salt thereof.

3. The compound of claim 1, wherein the compound is further defined as:

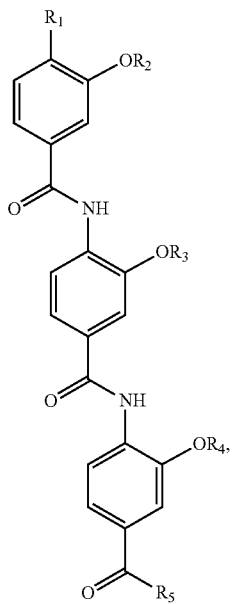

(IV)

wherein:
R$_1$ is halo, —NO$_2$, alkyl$_{(C\leq12)}$, substituted alkyl$_{(C\leq12)}$, amido$_{(C\leq12)}$, substituted amido$_{(C\leq12)}$, or —NHC(O)CH(R$_{1a}$)NH$_2$, wherein:
R$_{1a}$ is aralkyl$_{(C\leq18)}$, substituted aralkyl$_{(C\leq18)}$, or the side chain of a canonical amino acid;
R$_2$, R$_3$, and R$_4$ are each independently alkyl$_{(C\leq12)}$, substituted alkyl$_{(C\leq12)}$, aralkyl$_{(C\leq18)}$, or substituted aralkyl$_{(C\leq18)}$; and
R$_5$ is —NHR$_{5b}$, wherein:
R$_{5b}$ is
a group of the formula:

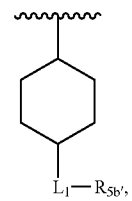

wherein:
L$_1$ is —C(O)NR$_{L1}$—, wherein:
R$_{L1}$ is hydrogen;
R$_{5b'}$ is aryl$_{(C\leq12)}$, aralkyl$_{(C\leq18)}$, heteroaryl$_{(C\leq12)}$, heteroaralkyl$_{(C\leq18)}$, or a substituted version of any of these groups;
or a pharmaceutically acceptable salt thereof.

4. The compound according to claim 1, wherein the compound is further defined as:

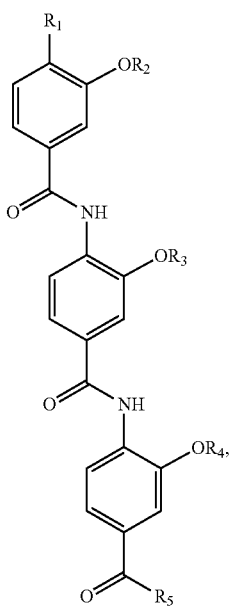

(VI)

wherein:
R$_1$ is halo, —NO$_2$, alkyl$_{(C\leq12)}$, substituted alkyl$_{(C\leq12)}$, amido$_{(C\leq12)}$, substituted amido$_{(C\leq12)}$, or —NHC(O)CH(R$_{1a}$)NH$_2$, wherein:
R$_{1a}$ is aralkyl$_{(C\leq18)}$, substituted aralkyl$_{(C\leq18)}$, or the side chain of a canonical amino acid;
R$_2$, R$_3$, and R$_4$ are each independently alkyl$_{(C\leq12)}$, substituted alkyl$_{(C\leq12)}$, aralkyl$_{(C\leq18)}$, or substituted aralkyl$_{(C\leq18)}$; and
R$_5$ is —NHR$_{5b}$, wherein:
R$_{5b}$ is
a group of the formula:

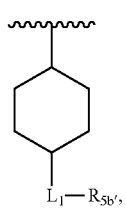

wherein:
L$_1$ is —C(O)NR$_{L1}$—, wherein:
R$_{L1}$ is hydrogen;
R$_{5b'}$ is aryl$_{(C\leq12)}$, aralkyl$_{(C\leq18)}$, or heteroaryl$_{(C\leq12)}$, or a substituted version of any of these groups;
or a pharmaceutically acceptable salt thereof.

5. The compound according to claim 1, wherein R$_2$ is aralkyl$_{(C\leq18)}$ or substituted aralkyl$_{(C\leq18)}$.

6. The compound according to claim 1, wherein R$_2$ is alkyl$_{(C\leq12)}$ or substituted alkyl$_{(C\leq12)}$.

7. The compound according to claim 1, wherein R$_2$ is 1-hydroxyethyl.

8. The compound according to claim 1, wherein R$_4$ is alkyl$_{(C\leq12)}$ or substituted alkyl$_{(C\leq12)}$.

9. The compound according to claim 1, wherein R$_4$ is i-butyl.

10. The compound according to claim 1, wherein R$_3$ is alkyl$_{(C\leq12)}$ or substituted alkyl$_{(C\leq12)}$.

11. The compound according to claim 1 wherein R$_3$ is i-butyl.

12. The compound according to claim 1, wherein R$_{5b}$ is heteroaryl$_{(C\leq12)}$ or substituted heteroaryl$_{(C\leq12)}$.

13. The compound according to claim 1, wherein R$_{5b}$ is heteroaryl$_{(C\leq12)}$.

14. The compound according to claim 1, wherein R$_{5b}$ is cycloalkyl$_{(C\leq12)}$ or substituted cycloalkyl$_{(C\leq12)}$.

15. The compound according to claim 1, wherein R$_{5b'}$ is heteroaryl$_{(C\leq12)}$ or substituted heteroaryl$_{(C\leq12)}$.

16. The compound according to claim 1, wherein R$_{5b}$ is heteroaryl$_{(C\leq12)}$.

17. The compound according to claim 1, wherein R$_{5b}$ is quinolin-3-yl.

18. The compound according to claim 1, wherein R$_1$ is —NO$_2$.

19. The compound according to claim 1, wherein R$_1$ is alkyl$_{(C\leq12)}$ or substituted alkyl$_{(C\leq12)}$.

20. The compound according to claim 1, wherein R$_1$ is halo.

21. The compound according to claim 1, wherein R$_1$ is fluoro.

22. The compound according to claim 1, wherein R$_1$ is amido$_{(C\leq12)}$ or substituted amido$_{(C\leq12)}$.

23. The compound according to claim 1, wherein R$_{1a}$ is aralkyl$_{(C\leq18)}$ or substituted aralkyl$_{(C\leq18)}$.

24. The compound according to claim 1, wherein the compound is further defined as:

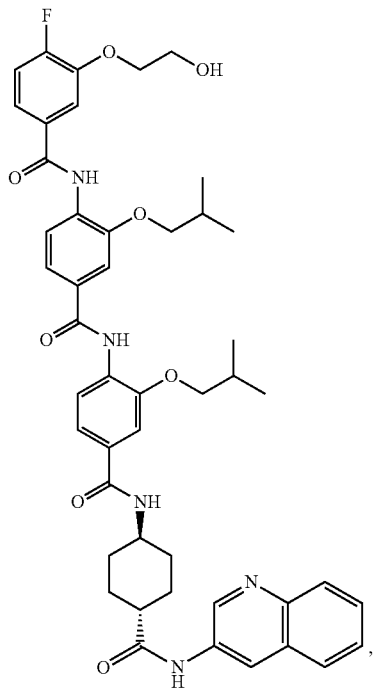 [SMILES: CC(C)COc1cc(C(=O)Nc2ccc(C(=O)N[C@H]3CC[C@H](C(=O)Nc4cnc5ccccc5c4)CC3)cc2OCC(C)C)ccc1NC(=O)c1ccc(F)c(OCCO)c1]

109
-continued
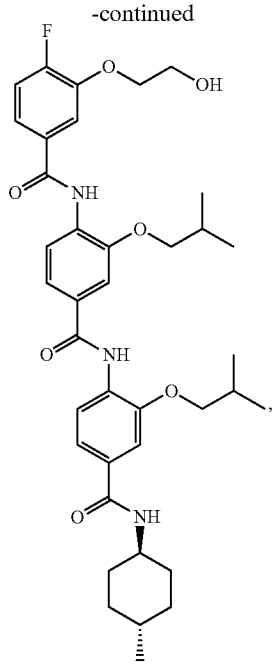
110
-continued
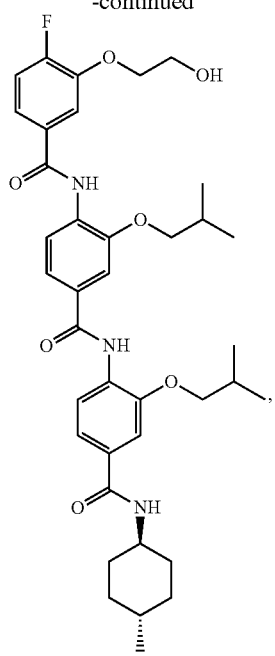
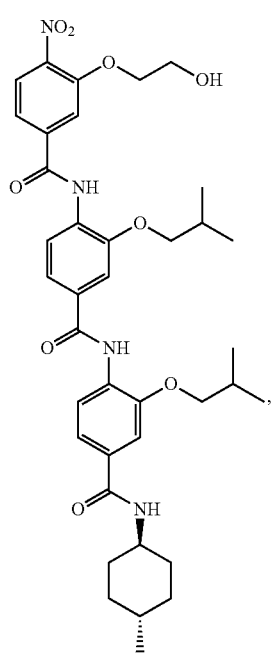 [SMILES: CC(C)COc1cc(C(=O)Nc2ccc(C(=O)N[C@H]3CC[C@H](C)CC3)cc2OCC(C)C)ccc1NC(=O)c1ccc([N+](=O)[O-])c(OCCO)c1]
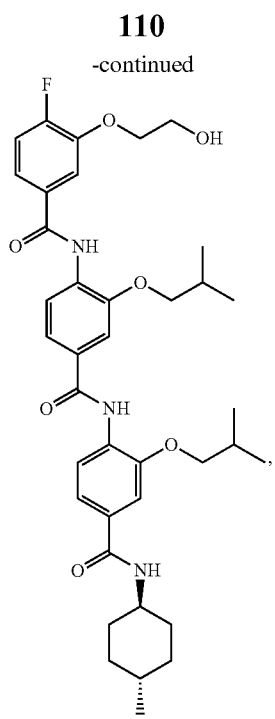

111
-continued
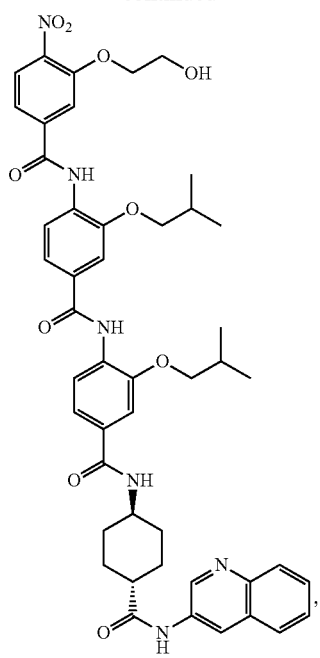
112
-continued
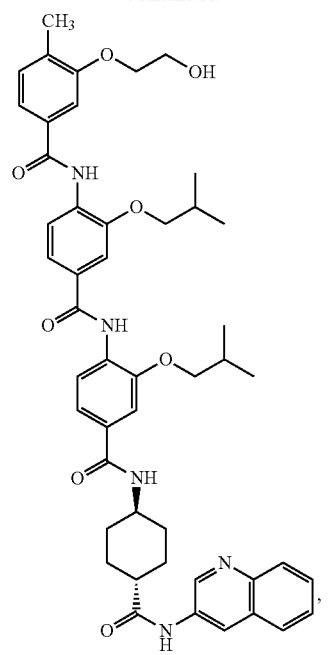
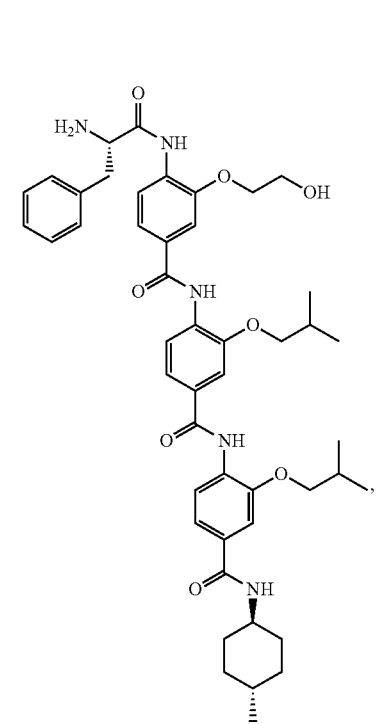

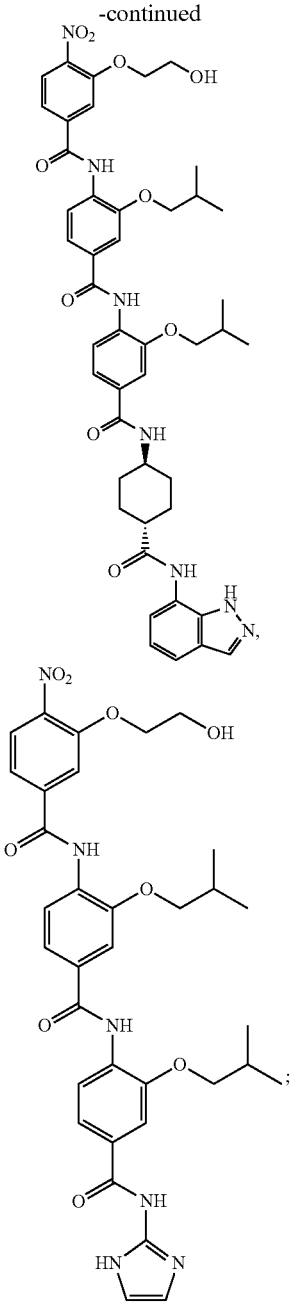

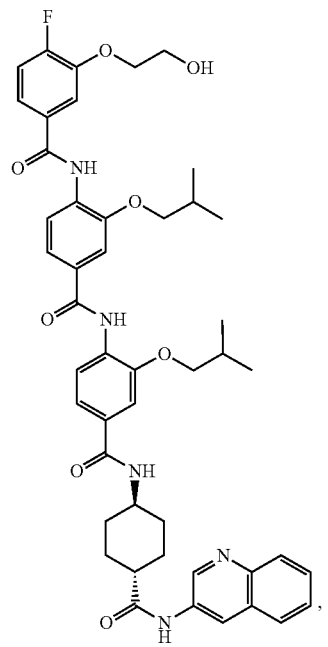

or a pharmaceutically acceptable salt thereof.

25. A pharmaceutical composition comprising:
a) a compound according to claim 1; and
b) an excipient and/or a pharmaceutically acceptable carrier.

26. A method of treating a disease or disorder in a patient in need thereof comprising administering to the patient a therapeutically effective amount of a compound according to claim 1, wherein the disease or disorder is breast cancer, ovarian cancer, pancreatic cancer, or brain cancer.

27. The method of claim 26, wherein the compound or composition is administered in an amount sufficient to induce endoplasmic reticulum stress and/or shut down protein synthesis.

28. The method according to claim 26, wherein the compound is further defined as:

115
-continued
116
-continued
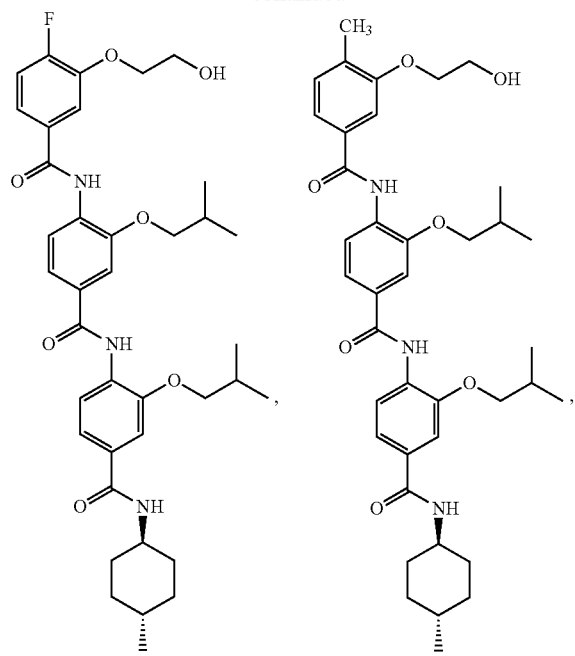
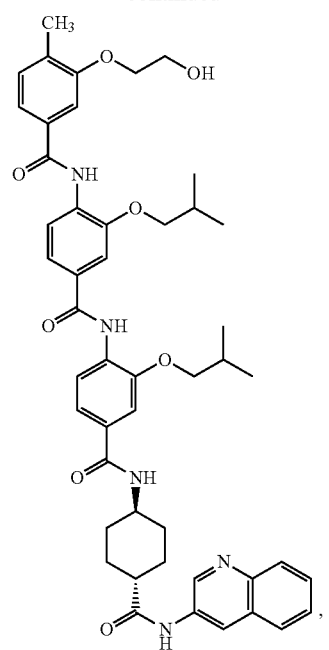
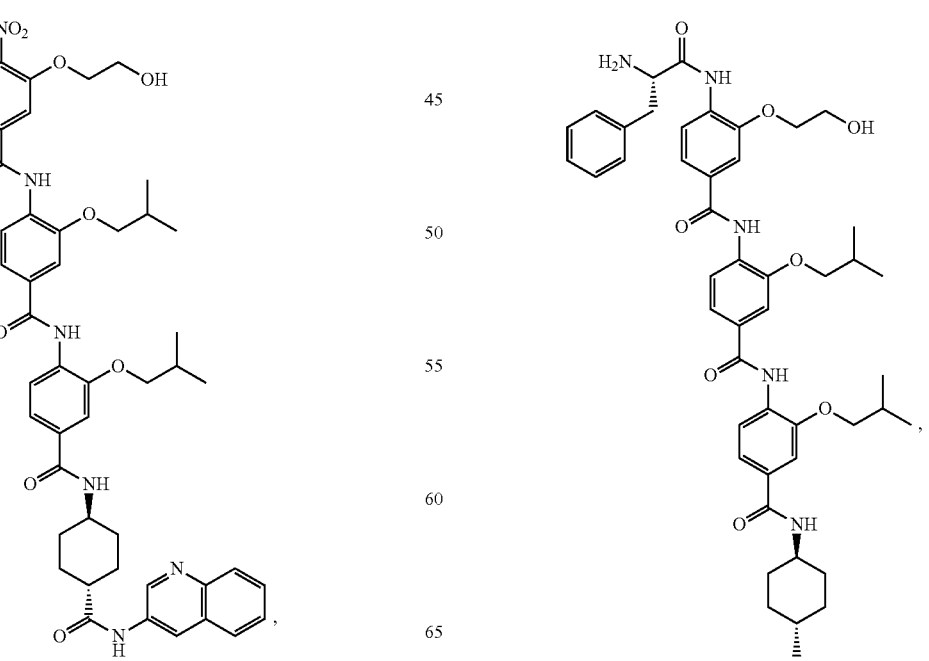

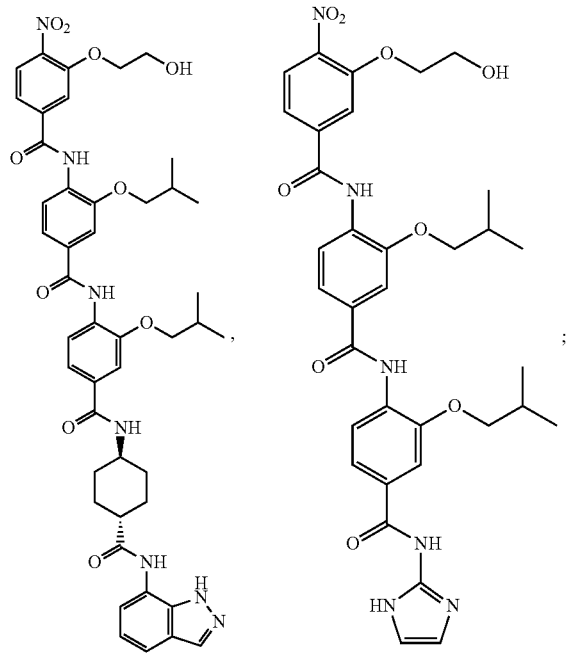
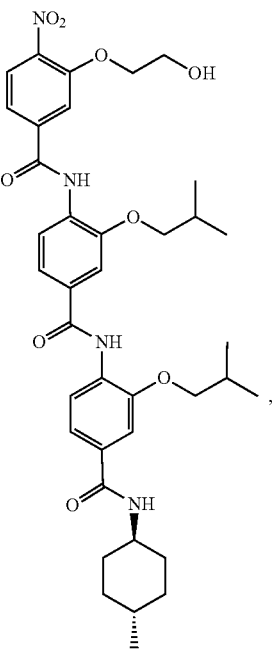
or a pharmaceutically acceptable salt thereof.
29. The pharmaceutical composition according to claim 25, wherein the compound is further defined as:
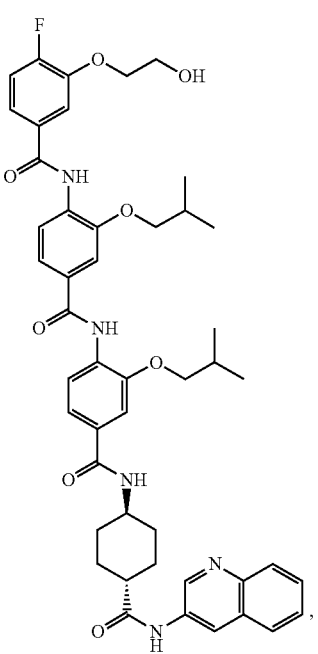
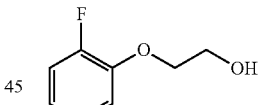
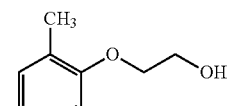
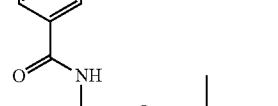
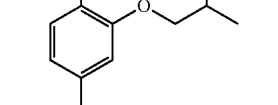
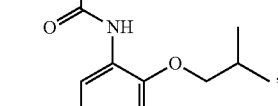
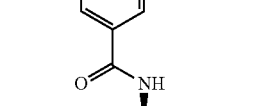
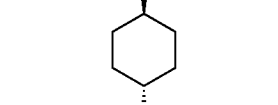

119
-continued
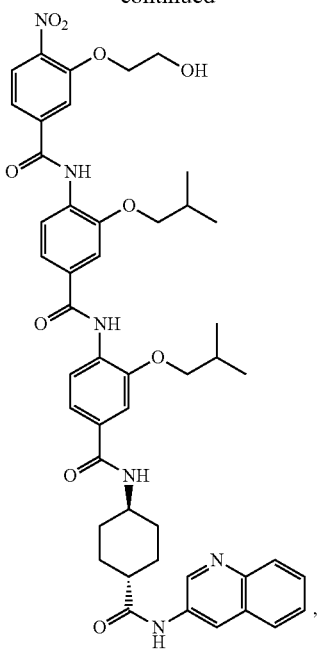
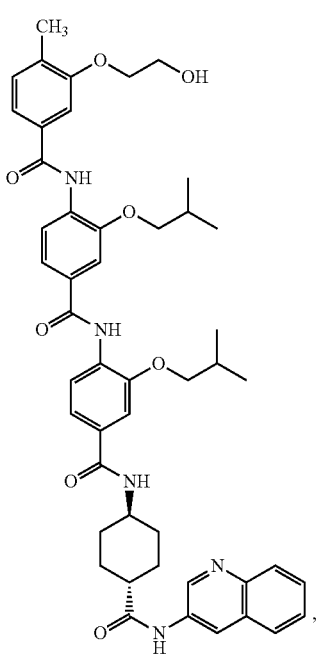
120
-continued
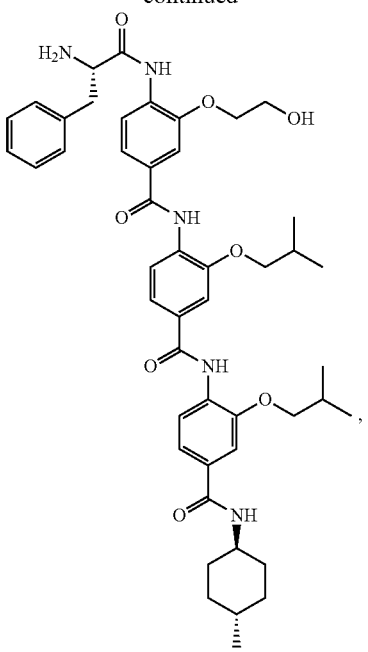
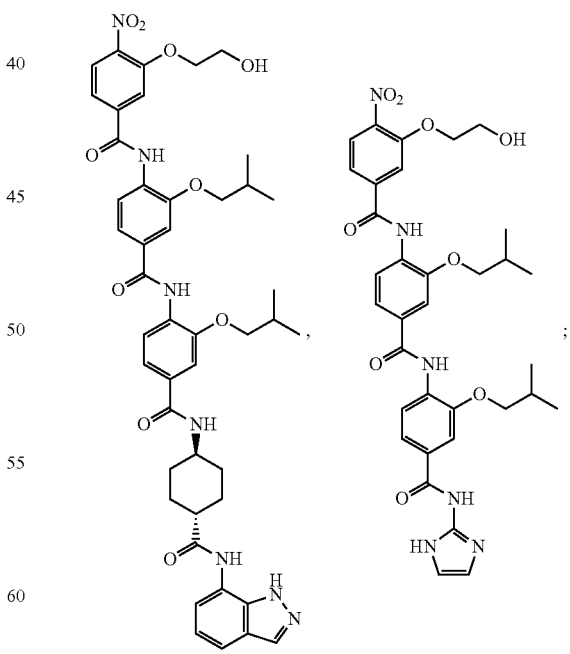
or a pharmaceutically acceptable salt thereof.
30. The method according to claim 27, wherein the compound is further defined as:

121
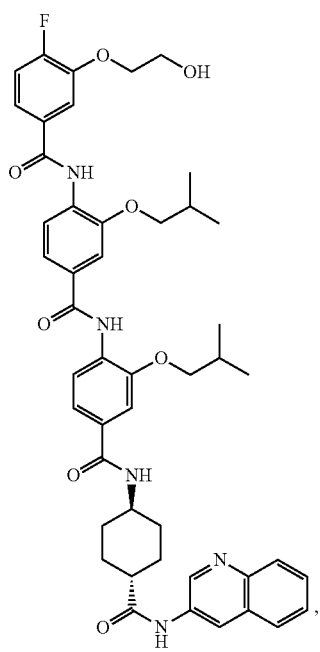
122
-continued
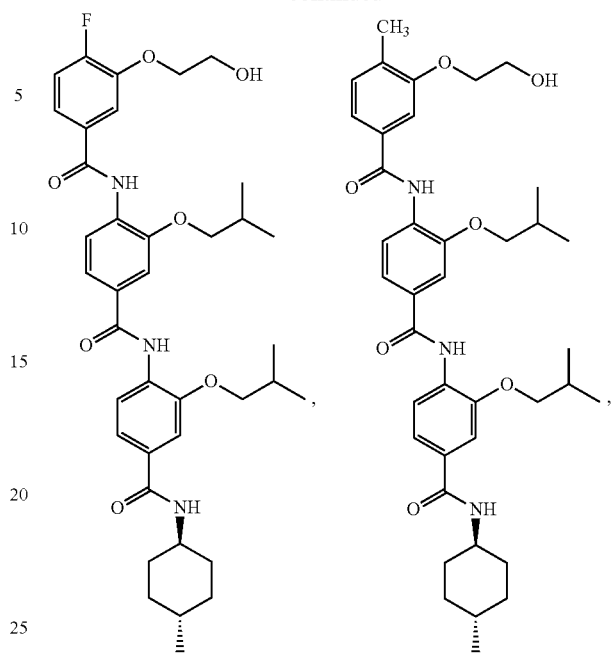
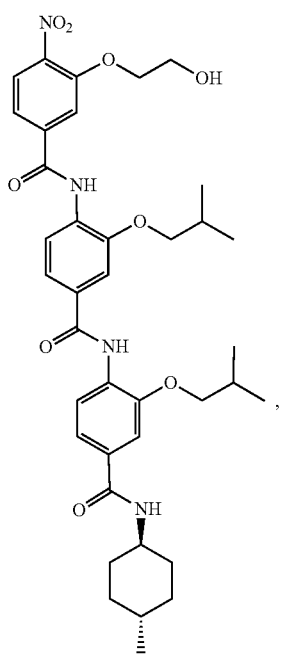
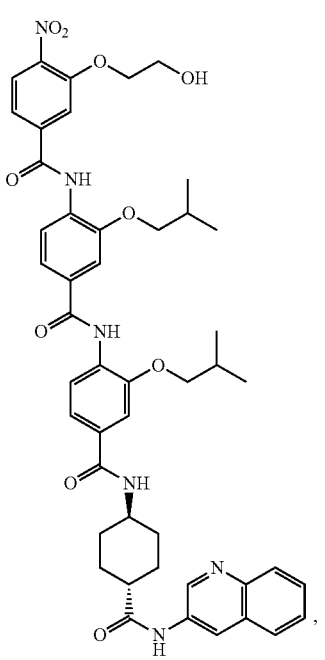

123
-continued
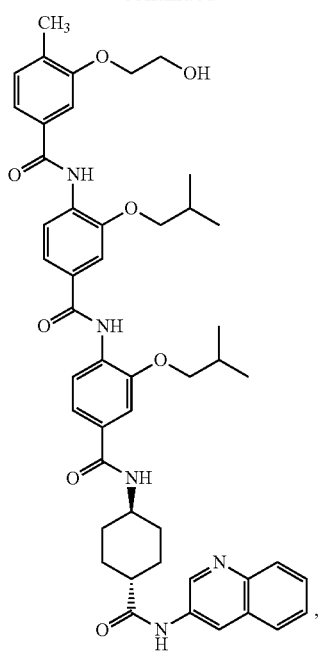
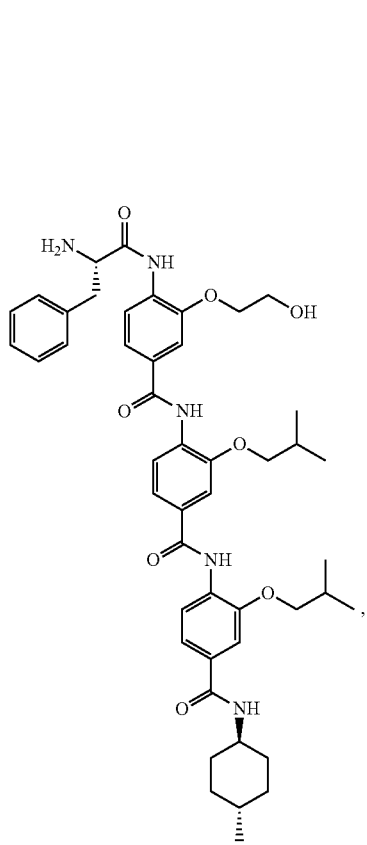
124
-continued
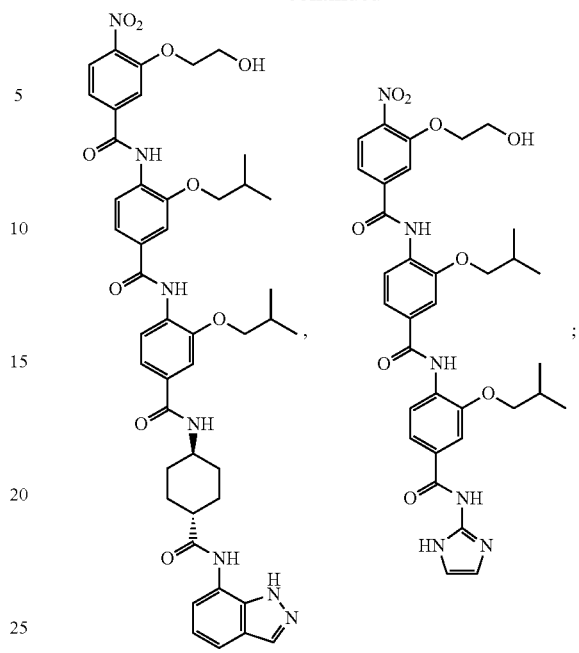
or a pharmaceutically acceptable salt thereof.
31. The compound according to claim 1, wherein the compound is:
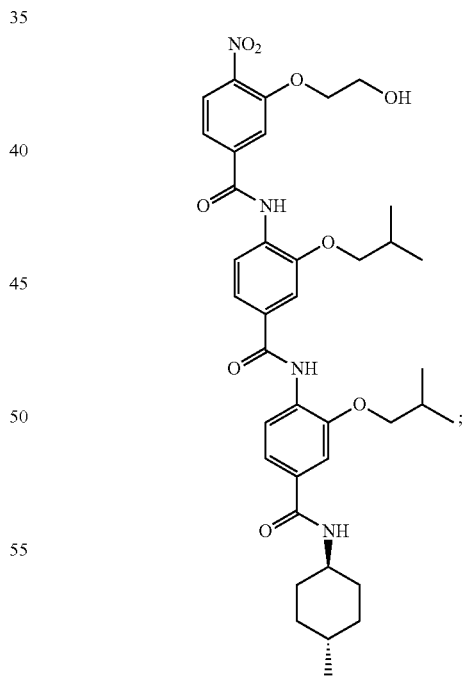
or a pharmaceutically acceptable salt thereof.
32. The compound according to claim 1, wherein the compound is:

125
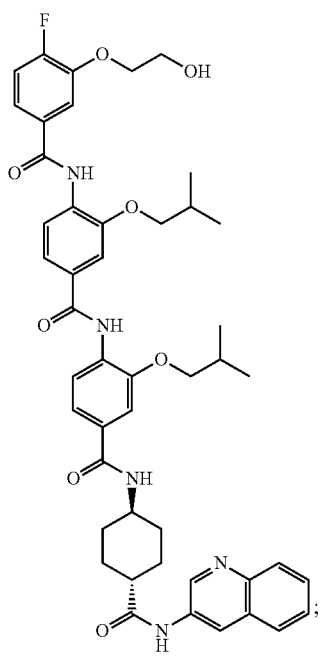 [SMILES: CC(C)COc1cc(C(=O)Nc2ccc(C(=O)N[C@H]3CC[C@H](C(=O)Nc4cnc5ccccc5c4)CC3)cc2OCC(C)C)ccc1NC(=O)c1ccc(F)c(OCCO)c1]
or a pharmaceutically acceptable salt thereof.
33. The compound according to claim 1, wherein the compound is:
126
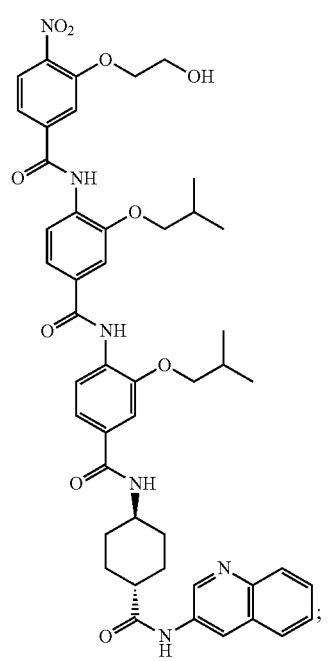
or a pharmaceutically acceptable salt thereof.
* * * * *

UNITED STATES PATENT AND TRADEMARK OFFICE
CERTIFICATE OF CORRECTION

PATENT NO. : 12,275,685 B2
APPLICATION NO. : 17/337830
DATED : April 15, 2025
INVENTOR(S) : Ganesh Raj et al.

Page 1 of 1

It is certified that error appears in the above-identified patent and that said Letters Patent is hereby corrected as shown below:

In the Claims

Column 108, Line 2, Claim 9, please delete "i-butyl." and insert --*i*-butyl-- therefor.

Column 108, Line 6, Claim 11, please delete "i-butyl." and insert --*i*-butyl-- therefor.

Column 109, Lines 1-25, Claim 24, please delete " 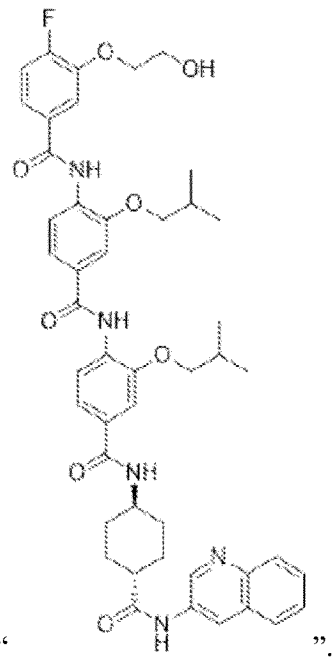 ".

Signed and Sealed this
Twenty-seventh Day of May, 2025

Coke Morgan Stewart
*Acting Director of the United States Patent and Trademark Office*

SEQUENCE LISTING

<160> NUMBER OF SEQ ID NOS: 2

<210> SEQ ID NO 1
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Leu Xaa Xaa Leu Leu
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 2

Asp Leu Xaa Xaa Leu Leu
1               5